US008822663B2

(12) United States Patent
Schrum et al.

(10) Patent No.: US 8,822,663 B2
(45) Date of Patent: Sep. 2, 2014

(54) ENGINEERED NUCLEIC ACIDS AND METHODS OF USE THEREOF

(75) Inventors: Jason P. Schrum, Somerville, MA (US); Stéphane Bancel, Cambridge, MA (US); Noubar B. Afeyan, Cambridge, MA (US)

(73) Assignee: Moderna Therapeutics, Inc., Cambridge, MA (US)

( * ) Notice: Subject to any disclaimer, the term of this patent is extended or adjusted under 35 U.S.C. 154(b) by 0 days.

(21) Appl. No.: 13/204,609

(22) Filed: Aug. 5, 2011

(65) Prior Publication Data

US 2012/0065252 A1 Mar. 15, 2012

Related U.S. Application Data

(60) Provisional application No. 61/401,052, filed on Aug. 6, 2010.

(51) Int. Cl.
*C07H 21/04* (2006.01)
*C12N 15/63* (2006.01)
*A61K 31/70* (2006.01)

(52) U.S. Cl.
USPC .......................................... 536/23.5; 435/455

(58) Field of Classification Search
USPC .......................................... 536/23.5; 435/455
See application file for complete search history.

(56) References Cited

U.S. PATENT DOCUMENTS

| | | |
|---|---|---|
| 3,737,524 A | 6/1973 | Ebel et al. |
| 3,906,092 A | 9/1975 | Hilleman et al. |
| 4,373,071 A | 2/1983 | Itakura |
| 4,399,210 A | 8/1983 | Nagano et al. |
| 4,401,796 A | 8/1983 | Itakura |
| 4,415,732 A | 11/1983 | Caruthers et al. |
| 4,458,066 A | 7/1984 | Caruthers et al. |
| 4,500,707 A | 2/1985 | Caruthers et al. |
| 4,579,849 A | 4/1986 | MacCoss et al. |
| 4,588,585 A | 5/1986 | Mark et al. |
| 4,668,777 A | 5/1987 | Caruthers et al. |
| 4,737,462 A | 4/1988 | Mark et al. |
| 4,816,567 A | 3/1989 | Cabilly et al. |
| 4,879,111 A | 11/1989 | Chong |
| 4,957,735 A | 9/1990 | Huang |
| 4,959,314 A | 9/1990 | Mark et al. |
| 4,973,679 A | 11/1990 | Caruthers et al. |
| 5,017,691 A | 5/1991 | Lee et al. |
| 5,021,335 A | 6/1991 | Tecott et al. |
| 5,047,524 A | 9/1991 | Andrus et al. |
| 5,116,943 A | 5/1992 | Koths et al. |
| 5,130,238 A | 7/1992 | Malek et al. |
| 5,132,418 A | 7/1992 | Caruthers et al. |
| 5,153,319 A | 10/1992 | Caruthers et al. |
| 5,168,038 A | 12/1992 | Tecott et al. |
| 5,169,766 A | 12/1992 | Schuster et al. |
| 5,194,370 A | 3/1993 | Berninger et al. |
| 5,262,530 A | 11/1993 | Andrus et al. |
| 5,298,422 A | 3/1994 | Schwartz et al. |
| 5,399,491 A | 3/1995 | Kacian et al. |
| 5,409,818 A | 4/1995 | Davey et al. |
| 5,437,990 A | 8/1995 | Burg et al. |
| 5,466,586 A | 11/1995 | Davey et al. |
| 5,514,545 A | 5/1996 | Eberwine |
| 5,545,522 A | 8/1996 | Van Gelder et al. |
| 5,554,517 A | 9/1996 | Davey et al. |
| 5,580,859 A | 12/1996 | Felgner et al. |
| 5,589,466 A | 12/1996 | Felgner et al. |
| 5,663,153 A | 9/1997 | Hutherson et al. |
| 5,665,545 A | 9/1997 | Malek et al. |
| 5,672,491 A | 9/1997 | Khosla et al. |
| 5,677,124 A | 10/1997 | DuBois et al. |
| 5,679,512 A | 10/1997 | Laney et al. |
| 5,693,622 A | 12/1997 | Wolff et al. |
| 5,700,642 A | 12/1997 | Monforte et al. |
| 5,703,055 A | 12/1997 | Felgner et al. |
| 5,712,127 A | 1/1998 | Malek et al. |
| 5,716,785 A | 2/1998 | Van Gelder et al. |
| 5,736,137 A | 4/1998 | Anderson et al. |
| 5,756,264 A | 5/1998 | Schwartz et al. |
| 5,807,707 A | 9/1998 | Andrews et al. |
| 5,824,497 A | 10/1998 | Andrews et al. |
| 5,849,546 A | 12/1998 | Sousa et al. |
| 5,851,829 A | 12/1998 | Marasco et al. |
| 5,861,501 A | 1/1999 | Benseler et al. |

(Continued)

FOREIGN PATENT DOCUMENTS

| | | |
|---|---|---|
| CA | 2473135 | 6/2003 |
| CA | 2376634 | 12/2004 |

(Continued)

OTHER PUBLICATIONS

Nagata S et al. Molecular cloning and expression of cDNA for human granulocyte colony-stimulating factor. Nature 319:415-418, 1986.*
Biocca et al. 1993. "Intracellular Expression of Anti-p21ras Single Chain Fv Fragments Inhibits Meiotic Maturation of *Xenopus oocytes*." Biochemical and Biophysical Research Communications. 197:422-427.
Capoccia, Benjamin J. "G-CSK and AMD3100 mobilize monocytes into the blood that stimulate angiogenesis in vivo through a paracrine mechanism." Stem Cells in Hematology, vol. 108, No. 7, Oct. 1, 2006.
Kormann et al. Expression of Therapeutic Proteins After Delivery of Chemically Modified rnRNA in Mice, Nature Biotechnology, Jan. 9, 2011, vol. 29, pp. 151-157.
Petit, et al. "G-CSF induces stem cell mobilization by decresing bone marrow SDF-I and up-regulating CXCR4" Nature Immunology, vol. 3 No. 1, Jul. 2002.

(Continued)

Primary Examiner — Quang Nguyen
(74) Attorney, Agent, or Firm — DT Ward, PC; Donna T. Ward; Jennifer F. Bryan

(57) ABSTRACT

Provided are compositions and methods for delivering biological moieties such as modified nucleic acids into cells to modulate protein expression. Such compositions and methods include the use of modified messenger RNAs, and are useful to treat or prevent diseases, disorders or conditions, or to improve a subject's heath or wellbeing.

4 Claims, 9 Drawing Sheets

(56) References Cited

U.S. PATENT DOCUMENTS

| | | |
|---|---|---|
| 5,869,230 A | 2/1999 | Sukhatme |
| 5,891,636 A | 4/1999 | Van Gelder et al. |
| 5,914,269 A | 6/1999 | Bennett et al. |
| 5,955,310 A | 9/1999 | Widner et al. |
| 5,958,688 A | 9/1999 | Eberwine et al. |
| 5,962,271 A | 10/1999 | Chenchik et al. |
| 5,962,272 A | 10/1999 | Chenchik et al. |
| 5,965,720 A | 10/1999 | Gryaznov et al. |
| 5,965,726 A | 10/1999 | Pavlakis et al. |
| 5,980,887 A | 11/1999 | Isner et al. |
| 5,989,911 A | 11/1999 | Fournier |
| 6,004,573 A | 12/1999 | Rathi et al. |
| 6,022,715 A | 2/2000 | Merenkova et al. |
| 6,057,494 A | 5/2000 | Koops et al. |
| 6,063,603 A | 5/2000 | Davey et al. |
| 6,090,591 A | 7/2000 | Burg et al. |
| 6,096,503 A | 8/2000 | Sutcliffe et al. |
| 6,100,024 A | 8/2000 | Hudson et al. |
| 6,124,091 A | 9/2000 | Petryshyn |
| 6,147,055 A | 11/2000 | Hobart et al. |
| 6,177,274 B1 | 1/2001 | Park et al. |
| 6,190,315 B1 | 2/2001 | Kost et al. |
| 6,214,804 B1 | 4/2001 | Felgner et al. |
| 6,217,912 B1 | 4/2001 | Park et al. |
| 6,228,640 B1 | 5/2001 | Cezayirli et al. |
| 6,234,990 B1 | 5/2001 | Rowe et al. |
| 6,239,116 B1 | 5/2001 | Krieg et al. |
| 6,251,665 B1 | 6/2001 | Cezayirli et al. |
| 6,255,076 B1 | 7/2001 | Widner et al. |
| 6,261,584 B1 | 7/2001 | Peery et al. |
| 6,265,387 B1 | 7/2001 | Wolff et al. |
| 6,265,389 B1 | 7/2001 | Burke |
| 6,267,987 B1 | 7/2001 | Park et al. |
| 6,291,170 B1 | 9/2001 | Van Gelder et al. |
| 6,300,484 B1 | 10/2001 | Duhl |
| 6,303,378 B1 | 10/2001 | Bridenbaugh et al. |
| 6,322,967 B1 | 11/2001 | Parkin |
| 6,326,174 B1 | 12/2001 | Joyce et al. |
| 6,376,248 B1 | 4/2002 | Hawley-Nelson et al. |
| 6,395,253 B2 | 5/2002 | Levy et al. |
| 6,406,705 B1 | 6/2002 | Davis et al. |
| 6,410,276 B1 | 6/2002 | Burg et al. |
| 6,413,942 B1 | 7/2002 | Felgner et al. |
| 6,433,155 B1 | 8/2002 | Umansky et al. |
| 6,491,657 B2 | 12/2002 | Rowe et al. |
| 6,500,419 B1 | 12/2002 | Hone et al. |
| 6,500,919 B1 | 12/2002 | Adema et al. |
| 6,514,948 B1 | 2/2003 | Raz et al. |
| 6,517,869 B1 | 2/2003 | Park et al. |
| 6,528,262 B1 | 3/2003 | Gilad et al. |
| 6,534,312 B1 | 3/2003 | Shiver et al. |
| 6,552,006 B2 | 4/2003 | Raz et al. |
| 6,555,525 B2 | 4/2003 | Burke |
| 6,586,524 B2 | 7/2003 | Sagara |
| 6,589,940 B1 | 7/2003 | Raz et al. |
| 6,610,661 B1 | 8/2003 | Carson et al. |
| 6,652,886 B2 | 11/2003 | Ahn et al. |
| 6,664,066 B2 | 12/2003 | Parks |
| 6,670,178 B1 | 12/2003 | Selden et al. |
| 6,676,938 B1 | 1/2004 | Teti et al. |
| 6,696,038 B1 | 2/2004 | Mahato et al. |
| 6,743,823 B1 | 6/2004 | Summar et al. |
| 6,777,187 B2 | 8/2004 | Makarov et al. |
| 6,808,888 B2 | 10/2004 | Zhang et al. |
| 6,818,421 B2 | 11/2004 | Kossmann et al. |
| 6,835,393 B2 | 12/2004 | Hoffman et al. |
| 6,900,302 B2 | 5/2005 | Teti et al. |
| 6,924,365 B1 | 8/2005 | Miller et al. |
| 7,001,890 B1 | 2/2006 | Wagner et al. |
| 7,052,891 B2 | 5/2006 | Leung et al. |
| 7,074,596 B2 | 7/2006 | Darzynkiewicz et al. |
| 7,169,750 B2 * | 1/2007 | Bridger et al. ............... 424/85.1 |
| 7,198,899 B2 | 4/2007 | Schleyer et al. |
| 7,202,226 B2 | 4/2007 | Murray et al. |
| 7,208,478 B2 | 4/2007 | Carson et al. |
| 7,268,120 B1 | 9/2007 | Horton et al. |
| 7,276,489 B2 | 10/2007 | Agrawal et al. |
| 7,316,925 B2 | 1/2008 | Draghia-Akli et al. |
| 7,329,741 B2 | 2/2008 | Duhl |
| 7,335,471 B2 | 2/2008 | Guillerez et al. |
| 7,354,742 B2 | 4/2008 | Kamme et al. |
| 7,371,404 B2 | 5/2008 | Panzner et al. |
| 7,374,778 B2 | 5/2008 | Hoffman et al. |
| 7,374,930 B2 | 5/2008 | Oh et al. |
| 7,476,506 B2 | 1/2009 | Schleyer et al. |
| 7,550,264 B2 | 6/2009 | Getts et al. |
| 7,709,452 B2 | 5/2010 | Pitard |
| 7,737,108 B1 | 6/2010 | Hoffman et al. |
| 7,745,391 B2 | 6/2010 | Mintz et al. |
| 7,776,523 B2 | 8/2010 | Garcia et al. |
| 7,846,895 B2 | 12/2010 | Eckert et al. |
| 7,964,571 B2 | 6/2011 | Fewell et al. |
| 8,003,129 B2 | 8/2011 | Hoffman et al. |
| 8,039,214 B2 | 10/2011 | Dahl et al. |
| 8,048,999 B2 | 11/2011 | Yamanaka et al. |
| 8,057,821 B2 | 11/2011 | Slobodkin et al. |
| 8,058,069 B2 | 11/2011 | Yaworski et al. |
| 8,101,385 B2 | 1/2012 | Cload et al. |
| 8,158,360 B2 | 4/2012 | Heise et al. |
| 8,158,601 B2 | 4/2012 | Chen et al. |
| 8,178,660 B2 | 5/2012 | Weiner et al. |
| 8,183,345 B2 | 5/2012 | Fay et al. |
| 8,183,352 B2 | 5/2012 | Ayyavoo et al. |
| 8,217,016 B2 | 7/2012 | Hoerr et al. |
| 8,242,087 B2 | 8/2012 | Adelfinskaya et al. |
| 8,278,036 B2 | 10/2012 | Kariko et al. |
| 8,304,183 B2 | 11/2012 | Sooknanan |
| 8,329,887 B2 | 12/2012 | Dahl et al. |
| 8,333,799 B2 | 12/2012 | Bales, Jr. et al. |
| 8,367,631 B2 | 2/2013 | Pitard |
| 8,383,340 B2 | 2/2013 | Ketterer et al. |
| 8,399,007 B2 | 3/2013 | Taft et al. |
| 8,404,222 B2 | 3/2013 | Harris |
| 8,404,799 B2 | 3/2013 | Podobinski et al. |
| 8,414,927 B2 | 4/2013 | Richard |
| 8,415,325 B2 | 4/2013 | Kiick et al. |
| 8,420,123 B2 | 4/2013 | Troiano et al. |
| 8,420,605 B2 | 4/2013 | Ulijn et al. |
| 8,431,160 B2 | 4/2013 | O'Hagan et al. |
| 8,435,504 B2 | 5/2013 | Kozlowski et al. |
| 8,440,231 B2 | 5/2013 | Smyth et al. |
| 8,440,614 B2 | 5/2013 | Castor |
| 8,444,992 B2 | 5/2013 | Borkowski et al. |
| 8,449,916 B1 | 5/2013 | Bellaire et al. |
| 8,450,298 B2 | 5/2013 | Mahon et al. |
| 8,454,946 B2 | 6/2013 | Shen |
| 8,454,948 B2 | 6/2013 | Pearlman et al. |
| 8,460,696 B2 | 6/2013 | Slobodkin et al. |
| 8,460,709 B2 | 6/2013 | Ausborn et al. |
| 8,461,132 B2 | 6/2013 | Cohen et al. |
| 8,466,122 B2 | 6/2013 | Heyes et al. |
| 8,470,560 B2 | 6/2013 | Bergmann-Leitner et al. |
| 8,470,771 B2 | 6/2013 | Gao et al. |
| 8,476,234 B2 | 7/2013 | Fima et al. |
| 8,506,966 B2 | 8/2013 | Podda et al. |
| 8,529,538 B2 | 9/2013 | Pang et al. |
| 8,529,939 B2 | 9/2013 | Masters et al. |
| 8,530,625 B2 | 9/2013 | Kaplan et al. |
| 8,535,655 B2 | 9/2013 | O'Shea et al. |
| 8,535,701 B2 | 9/2013 | Peery et al. |
| 8,535,702 B2 | 9/2013 | Richard et al. |
| 8,557,231 B2 | 10/2013 | Langer et al. |
| 8,563,041 B2 | 10/2013 | Grayson et al. |
| 8,568,784 B2 | 10/2013 | Lillard et al. |
| 8,569,256 B2 | 10/2013 | Heyes et al. |
| 8,580,297 B2 | 11/2013 | Essler et al. |
| 8,603,499 B2 | 12/2013 | Zale et al. |
| 8,603,500 B2 | 12/2013 | Zale et al. |
| 8,603,501 B2 | 12/2013 | Zale et al. |
| 8,603,534 B2 | 12/2013 | Zale et al. |
| 8,603,535 B2 | 12/2013 | Troiano et al. |
| 8,609,142 B2 | 12/2013 | Troiano et al. |
| 8,613,951 B2 | 12/2013 | Zale et al. |
| 8,613,954 B2 | 12/2013 | Zale et al. |

(56) References Cited

U.S. PATENT DOCUMENTS

| | | |
|---|---|---|
| 8,617,608 B2 | 12/2013 | Zale et al. |
| 8,618,240 B2 | 12/2013 | Podobinski et al. |
| 8,623,367 B2 | 1/2014 | Momm et al. |
| 8,628,801 B2 | 1/2014 | Garreta et al. |
| 8,636,696 B2 | 1/2014 | Ross et al. |
| 8,636,994 B2 | 1/2014 | Bossard et al. |
| 8,637,028 B2 | 1/2014 | Alexis et al. |
| 8,637,083 B2 | 1/2014 | Troiano et al. |
| 8,642,076 B2 | 2/2014 | Manoharan et al. |
| 8,652,487 B2 | 2/2014 | Maldonado |
| 8,652,528 B2 | 2/2014 | Troiano et al. |
| 2001/0001066 A1 | 5/2001 | Cezayirli et al. |
| 2001/0005506 A1 | 6/2001 | Cezayirli et al. |
| 2002/0001842 A1 | 1/2002 | Chapman et al. |
| 2002/0064517 A1 | 5/2002 | Cederholm-Williams |
| 2002/0099323 A1 | 7/2002 | Dev et al. |
| 2002/0111471 A1 | 8/2002 | Lo et al. |
| 2002/0123099 A1 | 9/2002 | Weiner et al. |
| 2002/0127592 A1 | 9/2002 | Ichihara et al. |
| 2002/0130430 A1 | 9/2002 | Castor et al. |
| 2002/0132788 A1 | 9/2002 | Lewis et al. |
| 2002/0143204 A1 | 10/2002 | Evain et al. |
| 2003/0026841 A1 | 2/2003 | Trubetskoy et al. |
| 2003/0032615 A1 | 2/2003 | Felgner et al. |
| 2003/0050468 A1 | 3/2003 | Shiver et al. |
| 2003/0073619 A1 | 4/2003 | Mahato et al. |
| 2003/0077604 A1 | 4/2003 | Sun et al. |
| 2003/0083272 A1 | 5/2003 | Wiederholt et al. |
| 2003/0138419 A1 | 7/2003 | Radic et al. |
| 2003/0143743 A1 | 7/2003 | Schuler et al. |
| 2003/0153735 A1 | 8/2003 | Breece et al. |
| 2003/0158133 A1 | 8/2003 | Movsesian |
| 2003/0170273 A1 | 9/2003 | O'Hagan et al. |
| 2003/0171253 A1 | 9/2003 | Ma et al. |
| 2003/0186237 A1 | 10/2003 | Ginsberg et al. |
| 2003/0225016 A1 | 12/2003 | Fearon et al. |
| 2004/0005667 A1 | 1/2004 | Ratti et al. |
| 2004/0018525 A1 | 1/2004 | Wirtz et al. |
| 2004/0106567 A1 | 6/2004 | Hagstrom et al. |
| 2004/0110191 A1 | 6/2004 | Winkler et al. |
| 2004/0122216 A1 | 6/2004 | Nielsen et al. |
| 2004/0142474 A1 | 7/2004 | Mahato et al. |
| 2004/0147027 A1 | 7/2004 | Troy et al. |
| 2004/0167090 A1 | 8/2004 | Monahan et al. |
| 2004/0171041 A1 | 9/2004 | Dahl et al. |
| 2004/0171980 A1 | 9/2004 | Mitragotri et al. |
| 2004/0197802 A1 | 10/2004 | Dahl et al. |
| 2004/0209274 A2 | 10/2004 | Daly |
| 2004/0236268 A1 | 11/2004 | Mitragotri et al. |
| 2004/0259081 A1 | 12/2004 | Watzele et al. |
| 2005/0032730 A1 | 2/2005 | Von Der Mulbe et al. |
| 2005/0037494 A1 | 2/2005 | Hecker et al. |
| 2005/0054026 A1 | 3/2005 | Atsushi et al. |
| 2005/0059624 A1 | 3/2005 | Hoerr et al. |
| 2005/0064596 A1 | 3/2005 | Riemen et al. |
| 2005/0089913 A1 | 4/2005 | Williams |
| 2005/0112141 A1 | 5/2005 | Terman et al. |
| 2005/0137155 A1 | 6/2005 | McSwiggen et al. |
| 2005/0153333 A1 | 7/2005 | Sooknanan |
| 2005/0181016 A1 | 8/2005 | Freyman et al. |
| 2005/0250723 A1 | 11/2005 | Hoerr et al. |
| 2006/0008910 A1 | 1/2006 | MacLachlan et al. |
| 2006/0018971 A1 | 1/2006 | Scott et al. |
| 2006/0035226 A1 | 2/2006 | Scheinert et al. |
| 2006/0083780 A1 | 4/2006 | Heyes et al. |
| 2006/0172003 A1 | 8/2006 | Meers et al. |
| 2006/0172966 A1 | 8/2006 | Lipford et al. |
| 2006/0188490 A1 | 8/2006 | Hoerr et al. |
| 2006/0204566 A1 | 9/2006 | Smyth-Templeton et al. |
| 2006/0241076 A1 | 10/2006 | Uhlmann et al. |
| 2006/0247195 A1 | 11/2006 | Ray |
| 2006/0265771 A1 | 11/2006 | Lewis et al. |
| 2006/0275747 A1 | 12/2006 | Hardy et al. |
| 2007/0037147 A1 | 2/2007 | Garcia et al. |
| 2007/0037148 A1 | 2/2007 | Fong et al. |
| 2007/0048741 A1 | 3/2007 | Getts et al. |
| 2007/0054278 A1 | 3/2007 | Cargill |
| 2007/0072175 A1 | 3/2007 | Cooper et al. |
| 2007/0087437 A1 | 4/2007 | Hu |
| 2007/0105124 A1 | 5/2007 | Getts et al. |
| 2007/0117112 A1 | 5/2007 | Diener et al. |
| 2007/0141030 A1 | 6/2007 | Yu et al. |
| 2007/0143878 A1 | 6/2007 | Bhat et al. |
| 2007/0178103 A1 | 8/2007 | Fey et al. |
| 2007/0213287 A1 | 9/2007 | Fewell et al. |
| 2007/0224635 A1 | 9/2007 | Bouquin |
| 2007/0252295 A1 | 11/2007 | Panzner et al. |
| 2007/0265220 A1 | 11/2007 | Rossi et al. |
| 2007/0280929 A1 | 12/2007 | Hoerr et al. |
| 2008/0008711 A1 | 1/2008 | Schleyer et al. |
| 2008/0020431 A1 | 1/2008 | Getts et al. |
| 2008/0025944 A1 | 1/2008 | Hoerr et al. |
| 2008/0075698 A1 | 3/2008 | Sawada et al. |
| 2008/0076174 A1 | 3/2008 | Selden et al. |
| 2008/0166414 A1 | 7/2008 | Hanes et al. |
| 2008/0171711 A1 | 7/2008 | Hoerr et al. |
| 2008/0220471 A1 | 9/2008 | Davis et al. |
| 2008/0260706 A1 | 10/2008 | Rabinovich et al. |
| 2008/0267873 A1 | 10/2008 | Hoerr et al. |
| 2008/0274463 A1 | 11/2008 | Chen et al. |
| 2008/0275468 A1 | 11/2008 | Chuang et al. |
| 2008/0286813 A1 | 11/2008 | George-Hyslop et al. |
| 2008/0293143 A1 | 11/2008 | Lin et al. |
| 2009/0042825 A1 | 2/2009 | Matar et al. |
| 2009/0042829 A1 | 2/2009 | Matar et al. |
| 2009/0048167 A1 | 2/2009 | Hillman |
| 2009/0053775 A1 | 2/2009 | Dahl et al. |
| 2009/0093433 A1 | 4/2009 | Woolf et al. |
| 2009/0144839 A1 | 6/2009 | Inana et al. |
| 2009/0208418 A1 | 8/2009 | Kohler et al. |
| 2009/0226470 A1 | 9/2009 | Mauro et al. |
| 2009/0227660 A1 | 9/2009 | Oh et al. |
| 2009/0238772 A1 | 9/2009 | Vaishnaw et al. |
| 2009/0264511 A1 | 10/2009 | de Fougerolles et al. |
| 2009/0281298 A1 | 11/2009 | Manoharan et al. |
| 2009/0286852 A1 | 11/2009 | Kariko et al. |
| 2009/0324584 A1 | 12/2009 | Hoerr et al. |
| 2010/0003337 A1 | 1/2010 | Hanes et al. |
| 2010/0004313 A1 | 1/2010 | Slobodkin et al. |
| 2010/0004315 A1 | 1/2010 | Slobodkin et al. |
| 2010/0009424 A1 | 1/2010 | Forde et al. |
| 2010/0015232 A1 | 1/2010 | Besenbacher et al. |
| 2010/0028943 A1 | 2/2010 | Thomas et al. |
| 2010/0047261 A1 | 2/2010 | Hoerr et al. |
| 2010/0086922 A1 | 4/2010 | Bryant et al. |
| 2010/0120024 A1 | 5/2010 | Cload et al. |
| 2010/0129877 A1 | 5/2010 | Sahin et al. |
| 2010/0168206 A1 | 7/2010 | Gollob et al. |
| 2010/0178271 A1 | 7/2010 | Bridger et al. |
| 2010/0189729 A1 | 7/2010 | Hoerr et al. |
| 2010/0203076 A1 | 8/2010 | Fotin-Mleczek et al. |
| 2010/0215580 A1 | 8/2010 | Hanes et al. |
| 2010/0233141 A1 | 9/2010 | Polach et al. |
| 2010/0239608 A1 | 9/2010 | Von Der Mulbe et al. |
| 2010/0260817 A1 | 10/2010 | Slobodkin et al. |
| 2010/0261231 A1 | 10/2010 | Kore et al. |
| 2010/0273220 A1 | 10/2010 | Yanik et al. |
| 2010/0285135 A1 | 11/2010 | Wendorf et al. |
| 2010/0291156 A1 | 11/2010 | Barner et al. |
| 2010/0293625 A1 | 11/2010 | Reed |
| 2010/0297750 A1 | 11/2010 | Natsume et al. |
| 2010/0305196 A1 | 12/2010 | Probst et al. |
| 2011/0020352 A1 | 1/2011 | Garcia et al. |
| 2011/0045022 A1 | 2/2011 | Tsai |
| 2011/0053829 A1 | 3/2011 | Baumhof et al. |
| 2011/0065103 A1 | 3/2011 | Sahin et al. |
| 2011/0077287 A1 | 3/2011 | Von Der Mulbe et al. |
| 2011/0091879 A1 | 4/2011 | Hillebrand et al. |
| 2011/0097716 A1 | 4/2011 | Natt et al. |
| 2011/0112040 A1 | 5/2011 | Liu et al. |
| 2011/0143397 A1 | 6/2011 | Kariko et al. |
| 2011/0143436 A1 | 6/2011 | Dahl et al. |
| 2011/0165123 A1 | 7/2011 | Hartmann et al. |
| 2011/0172126 A1 | 7/2011 | Brust |

(56) References Cited

U.S. PATENT DOCUMENTS

| | | |
|---|---|---|
| 2011/0200582 A1 | 8/2011 | Baryza et al. |
| 2011/0218231 A1 | 9/2011 | Fewell et al. |
| 2011/0244026 A1 | 10/2011 | Guild et al. |
| 2011/0245756 A1 | 10/2011 | Arora et al. |
| 2011/0247090 A1 | 10/2011 | Reed |
| 2011/0250225 A1 | 10/2011 | Fotin-Mleczek et al. |
| 2011/0269950 A1 | 11/2011 | Von Der Mulbe et al. |
| 2011/0294717 A1 | 12/2011 | Ali et al. |
| 2011/0300205 A1 | 12/2011 | Geall et al. |
| 2011/0311472 A1 | 12/2011 | Hoerr et al. |
| 2012/0009145 A1 | 1/2012 | Slobodkin et al. |
| 2012/0009221 A1 | 1/2012 | Hoerr et al. |
| 2012/0009649 A1 | 1/2012 | Dahl et al. |
| 2012/0015899 A1 | 1/2012 | Lomonossoff et al. |
| 2012/0021043 A1 | 1/2012 | Kramps et al. |
| 2012/0027813 A1 | 2/2012 | Podda et al. |
| 2012/0046346 A1 | 2/2012 | Rossi et al. |
| 2012/0053333 A1 | 3/2012 | Mauro et al. |
| 2012/0060293 A1 | 3/2012 | Stelter et al. |
| 2012/0065252 A1 | 3/2012 | Schrum et al. |
| 2012/0076836 A1 | 3/2012 | Hori et al. |
| 2012/0094906 A1 | 4/2012 | Guyon et al. |
| 2012/0095077 A1 | 4/2012 | Burrows et al. |
| 2012/0121718 A1 | 5/2012 | Lai et al. |
| 2012/0128699 A1 | 5/2012 | Kandimalla et al. |
| 2012/0129759 A1 | 5/2012 | Liu et al. |
| 2012/0171290 A1 | 7/2012 | Coursaget et al. |
| 2012/0177724 A1 | 7/2012 | Irvine et al. |
| 2012/0178702 A1 | 7/2012 | Huang |
| 2012/0189700 A1 | 7/2012 | Aguilar et al. |
| 2012/0195917 A1 | 8/2012 | Sahin et al. |
| 2012/0195936 A1 | 8/2012 | Rudolph et al. |
| 2012/0207840 A1 | 8/2012 | de los Pinos |
| 2012/0213818 A1 | 8/2012 | Hoerr et al. |
| 2012/0219573 A1 | 8/2012 | Baumhof et al. |
| 2012/0237975 A1 | 9/2012 | Schrum et al. |
| 2012/0251618 A1 | 10/2012 | Schrum et al. |
| 2012/0252117 A1 | 10/2012 | Selden et al. |
| 2012/0258046 A1 | 10/2012 | Mutzke |
| 2012/0295832 A1 | 11/2012 | Constien et al. |
| 2012/0301955 A1 | 11/2012 | Thomas et al. |
| 2012/0321719 A1 | 12/2012 | McDonnell et al. |
| 2012/0322864 A1 | 12/2012 | Rossi et al. |
| 2012/0322865 A1 | 12/2012 | Rossi et al. |
| 2013/0012426 A1 | 1/2013 | de los Pinos |
| 2013/0012450 A1 | 1/2013 | de los Pinos |
| 2013/0012566 A1 | 1/2013 | De Los Pinos |
| 2013/0017223 A1 | 1/2013 | Hope et al. |
| 2013/0017265 A1 | 1/2013 | Farokhzad et al. |
| 2013/0022538 A1 | 1/2013 | Rossi |
| 2013/0029418 A1 | 1/2013 | Angel et al. |
| 2013/0059360 A1 | 3/2013 | Bossard et al. |
| 2013/0064894 A1 | 3/2013 | Martin et al. |
| 2013/0065942 A1 | 3/2013 | Matar et al. |
| 2013/0071450 A1 | 3/2013 | Copp-Howland |
| 2013/0072709 A1 | 3/2013 | McMmanus et al. |
| 2013/0090287 A1 | 4/2013 | Alessi et al. |
| 2013/0090372 A1 | 4/2013 | Budzik et al. |
| 2013/0102034 A1 | 4/2013 | Schrum |
| 2013/0102545 A1 | 4/2013 | Gao et al. |
| 2013/0111615 A1 | 5/2013 | Kariko et al. |
| 2013/0115192 A1 | 5/2013 | Ali et al. |
| 2013/0115196 A1 | 5/2013 | Hantash et al. |
| 2013/0115247 A1 | 5/2013 | de los Pinos |
| 2013/0115272 A1 | 5/2013 | de Fougerolles et al. |
| 2013/0115273 A1 | 5/2013 | Yang et al. |
| 2013/0115274 A1 | 5/2013 | Knopov et al. |
| 2013/0115293 A1 | 5/2013 | Sabnis et al. |
| 2013/0116307 A1 | 5/2013 | Heyes et al. |
| 2013/0116408 A1 | 5/2013 | de los Pinos |
| 2013/0121954 A1 | 5/2013 | Wakefield et al. |
| 2013/0121988 A1 | 5/2013 | Hoerr et al. |
| 2013/0122104 A1 | 5/2013 | Yaworski et al. |
| 2013/0123338 A1 | 5/2013 | Heyes et al. |
| 2013/0123351 A1 | 5/2013 | Dewitt |
| 2013/0123481 A1 | 5/2013 | de Fougerolles et al. |
| 2013/0129627 A1 | 5/2013 | Delehanty et al. |
| 2013/0129726 A1 | 5/2013 | Lee et al. |
| 2013/0129785 A1 | 5/2013 | Manoharan et al. |
| 2013/0129794 A1 | 5/2013 | Kleiner et al. |
| 2013/0129830 A1 | 5/2013 | Chen et al. |
| 2013/0130348 A1 | 5/2013 | Gu et al. |
| 2013/0133483 A1 | 5/2013 | Yang et al. |
| 2013/0137644 A1 | 5/2013 | Alluis et al. |
| 2013/0138032 A1 | 5/2013 | Kim et al. |
| 2013/0142818 A1 | 6/2013 | Baumhof et al. |
| 2013/0142868 A1 | 6/2013 | Hoekman et al. |
| 2013/0142876 A1 | 6/2013 | Howard et al. |
| 2013/0149318 A1 | 6/2013 | Reynolds et al. |
| 2013/0149375 A1 | 6/2013 | Geall |
| 2013/0149783 A1 | 6/2013 | Yockman et al. |
| 2013/0150295 A1 | 6/2013 | Jaworowicz |
| 2013/0150625 A1 | 6/2013 | Budzik et al. |
| 2013/0150822 A1 | 6/2013 | Ross |
| 2013/0156721 A1 | 6/2013 | Cheng et al. |
| 2013/0156776 A1 | 6/2013 | Chang et al. |
| 2013/0156845 A1 | 6/2013 | Manoharan et al. |
| 2013/0156849 A1 | 6/2013 | de Fougerolles et al. |
| 2013/0164219 A1 | 6/2013 | Brinkmann et al. |
| 2013/0164343 A1 | 6/2013 | Hanes et al. |
| 2013/0164348 A1 | 6/2013 | Palasis et al. |
| 2013/0164400 A1 | 6/2013 | Knopov et al. |
| 2013/0165499 A1 | 6/2013 | Vaishnaw et al. |
| 2013/0165504 A1 | 6/2013 | Bancel et al. |
| 2013/0165772 A1 | 6/2013 | Traverso et al. |
| 2013/0171241 A1 | 7/2013 | Geall |
| 2013/0171646 A1 | 7/2013 | Park et al. |
| 2013/0172406 A1 | 7/2013 | Zale et al. |
| 2013/0172600 A1 | 7/2013 | Chang et al. |
| 2013/0177499 A1 | 7/2013 | Brahmbhatt et al. |
| 2013/0177523 A1 | 7/2013 | Ghandehari et al. |
| 2013/0177587 A1 | 7/2013 | Robinson et al. |
| 2013/0177611 A1 | 7/2013 | Kaplan et al. |
| 2013/0177633 A1 | 7/2013 | Schutt et al. |
| 2013/0177634 A1 | 7/2013 | Schutt et al. |
| 2013/0177635 A1 | 7/2013 | Schutt et al. |
| 2013/0177636 A1 | 7/2013 | Schutt et al. |
| 2013/0177637 A1 | 7/2013 | Schutt et al. |
| 2013/0177638 A1 | 7/2013 | Schutt et al. |
| 2013/0177639 A1 | 7/2013 | Geall et al. |
| 2013/0177640 A1 | 7/2013 | Geall et al. |
| 2013/0178541 A1 | 7/2013 | Stanton et al. |
| 2013/0183244 A1 | 7/2013 | Hanes et al. |
| 2013/0183355 A1 | 7/2013 | Jain et al. |
| 2013/0183372 A1 | 7/2013 | Schutt et al. |
| 2013/0183373 A1 | 7/2013 | Schutt et al. |
| 2013/0183375 A1 | 7/2013 | Schutt et al. |
| 2013/0184207 A1 | 7/2013 | Fares et al. |
| 2013/0184443 A1 | 7/2013 | Bentley et al. |
| 2013/0184453 A1 | 7/2013 | Davis et al. |
| 2013/0189295 A1 | 7/2013 | Arico et al. |
| 2013/0189351 A1 | 7/2013 | Geall |
| 2013/0189741 A1 | 7/2013 | Meis et al. |
| 2013/0195759 A1 | 8/2013 | Mirkin et al. |
| 2013/0195765 A1 | 8/2013 | Gho et al. |
| 2013/0195898 A1 | 8/2013 | O'Hagan et al. |
| 2013/0195967 A1 | 8/2013 | Guild et al. |
| 2013/0195968 A1 | 8/2013 | Geall et al. |
| 2013/0195969 A1 | 8/2013 | Geall et al. |
| 2013/0197068 A1 | 8/2013 | Kariko et al. |
| 2013/0202645 A1 | 8/2013 | Barner et al. |
| 2013/0202684 A1 | 8/2013 | Geall et al. |
| 2013/0203115 A1 | 8/2013 | Schrum et al. |
| 2013/0236500 A1 | 9/2013 | Zale et al. |
| 2013/0236533 A1 | 9/2013 | Von Andrian et al. |
| 2013/0236550 A1 | 9/2013 | Ausborn et al. |
| 2013/0236556 A1 | 9/2013 | Lai et al. |
| 2013/0236968 A1 | 9/2013 | Manoharan et al. |
| 2013/0243747 A1 | 9/2013 | Fima et al. |
| 2013/0243827 A1 | 9/2013 | Troiano et al. |
| 2013/0243848 A1 | 9/2013 | Lobovkina et al. |
| 2013/0243867 A1 | 9/2013 | Mohapatra et al. |
| 2013/0244972 A1 | 9/2013 | Ben-Shalom et al. |
| 2013/0245091 A1 | 9/2013 | Rozema et al. |

(56) References Cited

U.S. PATENT DOCUMENTS

| | | |
|---|---|---|
| 2013/0251679 A1 | 9/2013 | Pearlman et al. |
| 2013/0251766 A1 | 9/2013 | Zale et al. |
| 2013/0251816 A1 | 9/2013 | Zale et al. |
| 2013/0251817 A1 | 9/2013 | Zale et al. |
| 2013/0259923 A1 | 10/2013 | Bancel et al. |
| 2013/0266553 A1 | 10/2013 | Ballance et al. |
| 2013/0266617 A1 | 10/2013 | Mirosevich et al. |
| 2013/0272994 A1 | 10/2013 | Fu et al. |
| 2013/0273081 A1 | 10/2013 | Monaci et al. |
| 2013/0273117 A1 | 10/2013 | Podobinski et al. |
| 2013/0274504 A1 | 10/2013 | Colletti et al. |
| 2013/0274523 A1 | 10/2013 | Bawiec, III et al. |
| 2013/0280334 A1 | 10/2013 | Karp et al. |
| 2013/0280339 A1 | 10/2013 | Zale et al. |
| 2013/0287832 A1 | 10/2013 | O'Hagan |
| 2013/0289093 A1 | 10/2013 | Bhat et al. |
| 2013/0295183 A1 | 11/2013 | Troiano et al. |
| 2013/0295191 A1 | 11/2013 | Troiano et al. |
| 2013/0302432 A1 | 11/2013 | Zale et al. |
| 2013/0302433 A1 | 11/2013 | Troiano et al. |
| 2013/0315831 A1 | 11/2013 | Shi et al. |
| 2013/0317079 A1 | 11/2013 | Wakefield et al. |
| 2013/0323179 A1 | 12/2013 | Popov et al. |
| 2013/0323310 A1 | 12/2013 | Smyth et al. |
| 2013/0330401 A1 | 12/2013 | Payne et al. |
| 2013/0338210 A1 | 12/2013 | Manoharan et al. |
| 2013/0344158 A1 | 12/2013 | Zale et al. |
| 2014/0005379 A1 | 1/2014 | Gu |
| 2014/0017329 A1 | 1/2014 | Mousa |
| 2014/0030351 A1 | 1/2014 | Zale et al. |
| 2014/0037573 A1 | 2/2014 | Eliasof et al. |
| 2014/0037660 A1 | 2/2014 | Fotin-Mleczek et al. |
| 2014/0037714 A1 | 2/2014 | Quay et al. |
| 2014/0039032 A1 | 2/2014 | Kumboyama et al. |
| 2014/0044772 A1 | 2/2014 | MacLachlan et al. |
| 2014/0044791 A1 | 2/2014 | Basilion et al. |
| 2014/0045913 A1 | 2/2014 | Kuboyama et al. |
| 2014/0045950 A1 | 2/2014 | Lacko et al. |
| 2014/0050775 A1 | 2/2014 | Slobodkin et al. |

FOREIGN PATENT DOCUMENTS

| | | |
|---|---|---|
| CA | 2795695 | 10/2011 |
| EP | 0194809 | 3/1986 |
| EP | 0204401 | 12/1986 |
| EP | 0366400 | 10/1989 |
| EP | 0366400 | 5/1990 |
| EP | 0427073 | 5/1991 |
| EP | 0427074 | 5/1991 |
| EP | 0726319 | 8/1996 |
| EP | 0737750 | 10/1996 |
| EP | 0839912 | 5/1998 |
| EP | 0969862 | 1/2000 |
| EP | 1026253 | 8/2000 |
| EP | 1404860 | 5/2002 |
| EP | 1224943 | 7/2002 |
| EP | 1361277 | 11/2003 |
| EP | 1393745 | 3/2004 |
| EP | 1083232 | 2/2005 |
| EP | 1301614 | 11/2006 |
| EP | 1383556 | 10/2007 |
| EP | 2072618 | 6/2009 |
| EP | 1056873 | 3/2010 |
| EP | 2191840 | 8/2010 |
| EP | 2092064 | 9/2010 |
| EP | 2246422 | 11/2010 |
| EP | 1619254 | 12/2010 |
| EP | 2292771 | 3/2011 |
| EP | 2377938 | 10/2011 |
| EP | 2484770 | 8/2012 |
| EP | 1907590 | 9/2012 |
| EP | 2535419 | 12/2012 |
| EP | 2188379 | 1/2013 |
| EP | 2548960 | 1/2013 |
| EP | 2620161 | 7/2013 |
| EP | 2623121 | 7/2013 |
| EP | 2073848 | 8/2013 |
| EP | 2623121 | 8/2013 |
| WO | 8906700 | 7/1989 |
| WO | 9011092 | 10/1990 |
| WO | 9309236 | 5/1993 |
| WO | 9314778 | 8/1993 |
| WO | 9512665 | 5/1995 |
| WO | 9524485 | 9/1995 |
| WO | 9526204 | 10/1995 |
| WO | 9533835 | 12/1995 |
| WO | 9617086 | 6/1996 |
| WO | 9711085 | 3/1997 |
| WO | 9712519 | 4/1997 |
| WO | 9741210 | 11/1997 |
| WO | 9746680 | 12/1997 |
| WO | 9748370 | 12/1997 |
| WO | 9800547 | 1/1998 |
| WO | 9812207 | 3/1998 |
| WO | 9834640 | 8/1998 |
| WO | 9855495 | 12/1998 |
| WO | 99/06073 | 2/1999 |
| WO | 9914346 A2 | 3/1999 |
| WO | 9920766 | 4/1999 |
| WO | 9920774 | 4/1999 |
| WO | 9933982 | 7/1999 |
| WO | 9942618 | 8/1999 |
| WO | 9943835 | 9/1999 |
| WO | 9952503 | 10/1999 |
| WO | 9954457 | 10/1999 |
| WO | 0026226 | 5/2000 |
| WO | 0027340 | 5/2000 |
| WO | 0029561 | 5/2000 |
| WO | 0039327 | 7/2000 |
| WO | 0050586 | 8/2000 |
| WO | 0075304 | 12/2000 |
| WO | 0075356 | 12/2000 |
| WO | 0100650 | 1/2001 |
| WO | 0104313 | 1/2001 |
| WO | 0121810 | 3/2001 |
| WO | 0155306 | 8/2001 |
| WO | 0192523 | 12/2001 |
| WO | 0193902 | 12/2001 |
| WO | 0208435 | 1/2002 |
| WO | 0224873 | 3/2002 |
| WO | 0246477 | 6/2002 |
| WO | 02064799 | 8/2002 |
| WO | 02065093 | 8/2002 |
| WO | 02102839 | 12/2002 |
| WO | 03002604 | 1/2003 |
| WO | 03018798 | 3/2003 |
| WO | 03028656 | 4/2003 |
| WO | 03029401 | 4/2003 |
| WO | 03046578 | 6/2003 |
| WO | 03050258 | 6/2003 |
| WO | 03051401 | 6/2003 |
| WO | 03051923 | 6/2003 |
| WO | 03059194 | 7/2003 |
| WO | 03059381 | 7/2003 |
| WO | 03066649 | 8/2003 |
| WO | 03086280 | 10/2003 |
| WO | 03087815 | 10/2003 |
| WO | 03101401 | 12/2003 |
| WO | 2004005544 | 1/2004 |
| WO | 2004010106 | 1/2004 |
| WO | 2004037972 | 5/2004 |
| WO | 2004058159 | 7/2004 |
| WO | 2004065561 | 8/2004 |
| WO | 2004067728 | 8/2004 |
| WO | 2004085474 | 10/2004 |
| WO | 2004087868 | 10/2004 |
| WO | 2004092329 | 10/2004 |
| WO | 2005005622 A2 | 1/2005 |
| WO | 2005009346 | 2/2005 |
| WO | 2005040416 | 5/2005 |
| WO | 2005047536 | 5/2005 |
| WO | 2005098433 | 10/2005 |
| WO | 2005117557 | 12/2005 |

(56) References Cited

FOREIGN PATENT DOCUMENTS

| | | |
|---|---|---|
| WO | 2005118857 | 12/2005 |
| WO | 2006022712 | 3/2006 |
| WO | 2006044456 | 4/2006 |
| WO | 2006044503 | 4/2006 |
| WO | 2006044505 | 4/2006 |
| WO | 2006044682 | 4/2006 |
| WO | 2006058088 | 6/2006 |
| WO | 2006063249 | 6/2006 |
| WO | 2006065479 | 6/2006 |
| WO | 2006065480 | 6/2006 |
| WO | 2006071903 | 7/2006 |
| WO | 2006095259 | 9/2006 |
| WO | 2006110581 | 10/2006 |
| WO | 2006110585 | 10/2006 |
| WO | 2006110599 | 10/2006 |
| WO | 2007005645 | 1/2007 |
| WO | 2007024323 | 3/2007 |
| WO | 2007024708 | 3/2007 |
| WO | 2007024708 A2 | 3/2007 |
| WO | 2007036366 A2 | 4/2007 |
| WO | 2007062495 | 6/2007 |
| WO | 2007064952 A2 | 6/2007 |
| WO | 2007067968 | 6/2007 |
| WO | 2007100699 | 9/2007 |
| WO | 2007100789 | 9/2007 |
| WO | 2007104537 | 9/2007 |
| WO | 2008011519 | 1/2008 |
| WO | 2008014979 | 2/2008 |
| WO | 2008042973 | 4/2008 |
| WO | 2008051245 | 5/2008 |
| WO | 2008052770 A2 | 5/2008 |
| WO | 2008068631 | 6/2008 |
| WO | 2008078180 | 7/2008 |
| WO | 2008083949 A2 | 7/2008 |
| WO | 2008091799 | 7/2008 |
| WO | 2008140615 A2 | 11/2008 |
| WO | 2008144365 | 11/2008 |
| WO | 2008151058 | 12/2008 |
| WO | 2008153705 | 12/2008 |
| WO | 2008157688 | 12/2008 |
| WO | 2009006438 | 1/2009 |
| WO | 2009015071 | 1/2009 |
| WO | 2009024599 | 2/2009 |
| WO | 2009030254 | 3/2009 |
| WO | 2009030481 | 3/2009 |
| WO | 2009042971 | 4/2009 |
| WO | 2009046738 | 4/2009 |
| WO | 2009046739 | 4/2009 |
| WO | 2009046974 | 4/2009 |
| WO | 2009046975 | 4/2009 |
| WO | 2009077134 A2 | 6/2009 |
| WO | 2009095226 | 8/2009 |
| WO | 2009101407 | 8/2009 |
| WO | 2009127060 | 10/2009 |
| WO | 2009127230 A1 | 10/2009 |
| WO | WO-2009127230 A1 | 10/2009 |
| WO | 2009149253 | 12/2009 |
| WO | 2010009065 | 1/2010 |
| WO | 2010009277 | 1/2010 |
| WO | 2010027903 | 3/2010 |
| WO | 2010033906 | 3/2010 |
| WO | 2010037408 | 4/2010 |
| WO | 2010037539 | 4/2010 |
| WO | 2010042490 | 4/2010 |
| WO | 2010042877 | 4/2010 |
| WO | 2010054406 | 5/2010 |
| WO | 2010088537 | 8/2010 |
| WO | 2010088927 | 8/2010 |
| WO | 2010098861 A1 | 9/2010 |
| WO | 2010111290 A1 | 9/2010 |
| WO | WO-2010111290 A1 | 9/2010 |
| WO | 2010120266 | 10/2010 |
| WO | 2010129709 | 11/2010 |
| WO | 2010141135 | 12/2010 |
| WO | 2010144740 | 12/2010 |
| WO | 2011005799 | 1/2011 |
| WO | 2011026641 | 3/2011 |
| WO | 2011062965 | 5/2011 |
| WO | 2011068810 A1 | 6/2011 |
| WO | 2011069528 | 6/2011 |
| WO | 2011069529 | 6/2011 |
| WO | 2011069586 | 6/2011 |
| WO | 2011069587 | 6/2011 |
| WO | 2011071931 A2 | 6/2011 |
| WO | 2011071936 A2 | 6/2011 |
| WO | 2011076807 | 6/2011 |
| WO | 2011025566 | 7/2011 |
| WO | 2011088309 | 7/2011 |
| WO | 2011120053 | 9/2011 |
| WO | 2011127255 | 10/2011 |
| WO | 2011128444 | 10/2011 |
| WO | 2011130624 A2 | 10/2011 |
| WO | 2011137206 | 11/2011 |
| WO | 2011144358 | 11/2011 |
| WO | 2011161653 | 12/2011 |
| WO | 2012006369 | 1/2012 |
| WO | 2012006372 | 1/2012 |
| WO | 2012006376 | 1/2012 |
| WO | 2012006377 | 1/2012 |
| WO | 2012006378 | 1/2012 |
| WO | 2012006380 | 1/2012 |
| WO | 2012010855 | 1/2012 |
| WO | 2013006359 | 1/2012 |
| WO | 2012013326 | 2/2012 |
| WO | 2012019168 | 2/2012 |
| WO | 2012019168 A2 | 2/2012 |
| WO | 2012019630 | 2/2012 |
| WO | 2012019780 | 2/2012 |
| WO | 2012023044 | 2/2012 |
| WO | 2012024526 | 2/2012 |
| WO | 2012030683 | 3/2012 |
| WO | 2012030901 | 3/2012 |
| WO | 2012031043 | 3/2012 |
| WO | 2012031046 | 3/2012 |
| WO | 2012045075 A1 | 4/2012 |
| WO | 2012045082 A2 | 4/2012 |
| WO | 2012064429 | 5/2012 |
| WO | 2012065164 | 5/2012 |
| WO | 2012068295 | 5/2012 |
| WO | 2012068360 | 5/2012 |
| WO | 2012068470 | 5/2012 |
| WO | 2012072269 | 6/2012 |
| WO | 2012075040 | 6/2012 |
| WO | 2012088381 | 6/2012 |
| WO | 2012089225 A1 | 7/2012 |
| WO | 2012089338 A1 | 7/2012 |
| WO | 2012094304 | 7/2012 |
| WO | 2012094574 | 7/2012 |
| WO | 2012099755 | 7/2012 |
| WO | 2012099805 | 7/2012 |
| WO | 2012103985 | 8/2012 |
| WO | 2012112582 | 8/2012 |
| WO | 2012113413 | 8/2012 |
| WO | 2012113513 | 8/2012 |
| WO | 2012116714 | 9/2012 |
| WO | 2012116715 | 9/2012 |
| WO | 2012116810 | 9/2012 |
| WO | 2012116811 | 9/2012 |
| WO | 2012117377 | 9/2012 |
| WO | 2012122318 | 9/2012 |
| WO | 2012125680 | 9/2012 |
| WO | 2012125812 | 9/2012 |
| WO | 2012125987 | 9/2012 |
| WO | 2012129483 | 9/2012 |
| WO | 2012131594 | 10/2012 |
| WO | 2012135025 | 10/2012 |
| WO | 2012135805 A2 | 10/2012 |
| WO | 2012142240 | 10/2012 |
| WO | 2012143407 | 10/2012 |
| WO | 2012149246 | 11/2012 |
| WO | 2012151234 | 11/2012 |
| WO | 2012158613 | 11/2012 |
| WO | 2012158736 | 11/2012 |
| WO | 2012160177 | 11/2012 |

(56) References Cited

FOREIGN PATENT DOCUMENTS

| | | |
|---|---|---|
| WO | 2012166241 | 12/2012 |
| WO | 2012166923 | 12/2012 |
| WO | 2012168259 | 12/2012 |
| WO | 2012168491 | 12/2012 |
| WO | 2012170607 | 12/2012 |
| WO | 2012170889 A1 | 12/2012 |
| WO | 2012170930 A1 | 12/2012 |
| WO | 2012172495 | 12/2012 |
| WO | 2012172521 | 12/2012 |
| WO | 2013003475 | 1/2013 |
| WO | 2013006437 | 1/2013 |
| WO | 2013006825 | 1/2013 |
| WO | 2013006834 | 1/2013 |
| WO | 2013006837 | 1/2013 |
| WO | 2013006838 | 1/2013 |
| WO | 2013006842 | 1/2013 |
| WO | 2013009717 | 1/2013 |
| WO | 2013009736 | 1/2013 |
| WO | 2013011325 | 1/2013 |
| WO | 2013012476 | 1/2013 |
| WO | 2013016460 | 1/2013 |
| WO | 2013019669 | 2/2013 |
| WO | 2013030778 | 3/2013 |
| WO | 2013032829 | 3/2013 |
| WO | 2013033438 | 3/2013 |
| WO | 2013033563 | 3/2013 |
| WO | 2013033620 | 3/2013 |
| WO | 2013038375 | 3/2013 |
| WO | 2013039857 | 3/2013 |
| WO | 2013039861 | 3/2013 |
| WO | 2013044219 | 3/2013 |
| WO | 2013045505 | 4/2013 |
| WO | 2013049234 | 4/2013 |
| WO | 2013049247 | 4/2013 |
| WO | 2013049328 | 4/2013 |
| WO | 2013052167 | 4/2013 |
| WO | 2013052523 | 4/2013 |
| WO | 2013054307 | 4/2013 |
| WO | 2013055331 | 4/2013 |
| WO | 2013055905 | 4/2013 |
| WO | 2013055971 | 4/2013 |
| WO | 2013056132 | 4/2013 |
| WO | 2013057687 | 4/2013 |
| WO | 2013057715 | 4/2013 |
| WO | 2013059496 | 4/2013 |
| WO | 2013059509 | 4/2013 |
| WO | 2013059922 | 5/2013 |
| WO | 2013061208 | 5/2013 |
| WO | 2013062140 | 5/2013 |
| WO | 2013063468 | 5/2013 |
| WO | 2013063530 | 5/2013 |
| WO | 2013064911 | 5/2013 |
| WO | 2013066274 | 5/2013 |
| WO | 2013066427 | 5/2013 |
| WO | 2013066903 | 5/2013 |
| WO | 2013067355 | 5/2013 |
| WO | 2013067530 | 5/2013 |
| WO | 2013067537 | 5/2013 |
| WO | 2013068413 | 5/2013 |
| WO | 2013068431 | 5/2013 |
| WO | 2013068432 | 5/2013 |
| WO | 2013068847 | 5/2013 |
| WO | 2013070653 | 5/2013 |
| WO | 2013070872 | 5/2013 |
| WO | 2013071047 | 5/2013 |
| WO | 2013072392 | 5/2013 |
| WO | 2013072929 | 5/2013 |
| WO | 2013074696 | 5/2013 |
| WO | 2013075068 | 5/2013 |
| WO | 2013077907 | 5/2013 |
| WO | 2013078199 | 5/2013 |
| WO | 2013079604 | 6/2013 |
| WO | 2013082111 | 6/2013 |
| WO | 2013082418 | 6/2013 |
| WO | 2013082427 | 6/2013 |
| WO | 2013082470 | 6/2013 |
| WO | 2013082529 | 6/2013 |
| WO | 2013082590 | 6/2013 |
| WO | 2013084000 | 6/2013 |
| WO | 2013085951 | 6/2013 |
| WO | 2013086008 | 6/2013 |
| WO | 2013086322 | 6/2013 |
| WO | 2013086354 | 6/2013 |
| WO | 2013086373 | 6/2013 |
| WO | 2013086486 | 6/2013 |
| WO | 2013086502 | 6/2013 |
| WO | 2013086505 | 6/2013 |
| WO | 2013086526 | 6/2013 |
| WO | 2013087083 | 6/2013 |
| WO | 2013087791 | 6/2013 |
| WO | 2013088250 | 6/2013 |
| WO | 2013090186 | 6/2013 |
| WO | 2013090294 | 6/2013 |
| WO | 2013090601 | 6/2013 |
| WO | 2013090648 | 6/2013 |
| WO | 2013090841 | 6/2013 |
| WO | 2013090861 | 6/2013 |
| WO | 2013090897 | 6/2013 |
| WO | 2013091001 | 6/2013 |
| WO | 2013093648 | 6/2013 |
| WO | 2013096626 | 6/2013 |
| WO | 2013096709 | 6/2013 |
| WO | 2013098589 | 7/2013 |
| WO | 2013101690 | 7/2013 |
| WO | 2013103842 | 7/2013 |
| WO | 2013112778 | 8/2013 |
| WO | 2013112780 | 8/2013 |
| WO | 2013113326 | 8/2013 |
| WO | 2013113501 | 8/2013 |
| WO | 2013113502 | 8/2013 |
| WO | 2013113736 | 8/2013 |
| WO | 2013128027 | 9/2013 |
| WO | 2013130161 | 9/2013 |
| WO | 2013130535 | 9/2013 |
| WO | 2013135359 | 9/2013 |
| WO | 2013136234 | 9/2013 |
| WO | 2013138343 | 9/2013 |
| WO | 2013138346 | 9/2013 |
| WO | 2013143555 | 10/2013 |
| WO | 2013143683 | 10/2013 |
| WO | 2013143698 | 10/2013 |
| WO | 2013143699 | 10/2013 |
| WO | 2013143700 | 10/2013 |
| WO | 2013148186 | 10/2013 |
| WO | 2013149141 | 10/2013 |
| WO | 2013151650 | 10/2013 |
| WO | 2013151669 | 10/2013 |
| WO | 2013151672 | 10/2013 |
| WO | 2013151771 | 10/2013 |
| WO | 2013152351 | 10/2013 |
| WO | 2013153550 | 10/2013 |
| WO | 2013154766 | 10/2013 |
| WO | 2013154774 | 10/2013 |
| WO | 2013155487 | 10/2013 |
| WO | 2013155493 | 10/2013 |
| WO | 2013155513 | 10/2013 |
| WO | 2013158127 | 10/2013 |
| WO | 2013158141 | 10/2013 |
| WO | 2013158579 | 10/2013 |
| WO | 20130148541 | 10/2013 |
| WO | 2013166385 | 11/2013 |
| WO | 2013166498 | 11/2013 |
| WO | 2013173657 | 11/2013 |
| WO | 2013173693 | 11/2013 |
| WO | 2013174409 | 11/2013 |
| WO | 2013182683 | 12/2013 |
| WO | 2013184945 | 12/2013 |
| WO | 2013185069 | 12/2013 |
| WO | 2013188979 | 12/2013 |
| WO | 2014012994 | 1/2014 |
| WO | 2014012996 | 1/2014 |
| WO | 2014014613 | 1/2014 |
| WO | 2014015334 | 1/2014 |
| WO | 2014015422 | 1/2014 |

(56) References Cited

FOREIGN PATENT DOCUMENTS

| WO | 2014016439 | 1/2014 |
|----|------------|--------|
| WO | 2014018675 | 1/2014 |
| WO | 2014024193 | 2/2014 |
| WO | 2014025312 | 2/2014 |
| WO | 2014025795 | 2/2014 |
| WO | 2014025890 | 2/2014 |
| WO | 2014026044 | 2/2014 |
| WO | 2014026284 | 2/2014 |
| WO | 2014027006 | 2/2014 |
| WO | 2014028209 | 2/2014 |
| WO | 2014028487 | 2/2014 |
| WO | 2014028763 | 2/2014 |

OTHER PUBLICATIONS

Verma et al., "Modified oligonucleotides; synthesis and strategy for users" Ann. Res. Biochem., 67:90-134, 1998.
Warren at al., Highly Efficient Reprogramming to Pluripotericy and Directed Differentiation of Human Cell with Synthetic Modified mRNA, Cell Stem Cell, Nov. 5, 2010, vol. 7; pp. 618-630.
Petit et al, 2002. "G-CSF Induces Stem Cell Mobilization by Decreasing Bone Marrow SDF-1 and Up-Reuulating CXCR4," Nature Immunol. 3: 687-694.
Capoccia et. al. 2006. "G-CSF and AMD3100 mobilize monocytes into the blood that stimulate angiogenesis in vivo through a paracrine mechanism," Blood 108(7):2438-2445.
Verma et al., "Modified oligonucleolides; synthesis and strategy for users" Ann. Res. Biochem.. 67:99-134, 1998.
Cuburu, N. et al., Intravaginal immunization with HPV vectors induces tissue-resident CD8+ T cell responses. J Clin Invest. Dec. 3, 2012; 122(12): 4606-4620.
Gordon, S.N. et al., Targetting the vaginal mucosa with human papillomavirus pseudovirin vaccines delivering SIV DNA. J Immunol. Jan. 15, 2012; 188(2): 714-723.
Houghton, A.N. et al., Cancer antigens: immune recognition of self and altered self. J Exp Med. Jul. 1, 1994;180(1):1-4.
Hsu, F.J. et al., Vaccination of patients with B-cell lymphoma using autologous antigen-pulsed dendritic cells. Nat Med. Jan. 1996;2(1):52-8.
Hu, B., et al., Neural differentiation of human induced pluripotent stem cells follows developmental principles but with variable potency. Natl Acad Sci. Mar. 2010; 107(9): 4335-4340.
Hu, S. et al., Codon optimization, expression, and characterization of an internalizing anti-ErbB2 single-chain antibody in *Pichia pasions*. Protein Expr. Purif. May 2006;47(1):249-57. Epub Dec. 13, 2005.
Huangfu, D., et al., Induction of pluripotent stem cells by defined factors is greatly improved by small-molecule compounds. Nat Biotech. Jul. 2008; 26(7) 795-797.
Huddleston, J.A. et al., The sequence of the nucleoprotein gene of human influenza A virus, strain A/NT/60/68. Nucleic Acids Res. Feb. 11, 1982;10(3):1029-38.
Hue, K.K. et al., A polypurine sequence that acts as a 5' mRNA stabilizer in *Bacillus subtilis*. J Bacteriol. Jun. 1995;177 (12):3465-71.
Hung, C.F. et al., Ovarian cancer gene therapy using HPV-16 pseudovirion carrying the HSV-tk gene. PLoS ONE Jul. 2012; 7(7):e40983.
Inaba, K. et al., Dendritic cells pulsed with protein antigens in vitro can prime antigen-specific, MHC-restricted T cells in situ. J Exp Med. Aug. 1, 1990;172(2):631-40.
Inaba, K. et al., Direct activation of CD8+ cytotoxic T lymphocytes by dendritic cells. J Exp Med. Jul. 1, 1987;166(1):182-94.
Inaba, K. et al., Generation of large numbers of dendritic cells from mouse bone marrow cultures supplemented with granulocyte/macrophage colony-stimulating factor. J Exp Med. Dec. 1, 1992;176(6):1693-702.
Ito, M.K., ISIS 301012 gene therapy for hypercholesterolemia: sense, antisense, or nonsense? Ann Pharmacother. Oct. 2007; 41(10): 1669-78.
Ivanovska, N. et al. Immunization with a DNA chimeric molecule encoding a hemagglutinin peptide and scFv CD21-specific antiobdy fragment induces long-lasting IgM and CTL responses to influenza virus. Vaccine. Mar. 10, 2006;24(11):1830-7. Epub Nov. 2, 2005.
Iwasaki, A. et al., Enhanced CTL responses mediated by plasmid DNA immunogens encoding costimulatory molecules and cytokines. J. Immunol. May 15, 1997;158(1):4591-601.
Jady, B.E. et al., A small nucleolar guide RNA functions both in 2'-O-ribose methylation and pseudouridylation of the U5 spliceosomal RNA. EMBO J. Feb. 1, 2001;20(3):541-51.
Janeway, C. et al., Immunobiology: the immune system in health and disease. Garland Publishing, Inc, London. 1997; 13:12-13:21.
Jansen, P.L.M., Diagnosis and management of Crigler-Najjar syndrome. Eur J Pediatr. Dec. 1999;158 [Suppl 2]:S89-S94.
Janssens, S. et al., Role of Toll-like receptors in pathogen recognition. Clin Microbiol Rev. Oct. 2003;16(4):637-46.
Jemiolity, J. et al., Novel "anti-reverse" cap analogs with superior translational properties. RNA. Sep. 2003;9(9):1108-22.
Jia, F., et al., A nonviral minicircle vector for deriviing human iPS Cells. Nat Methods. Mar. 2010; 7(3): 197-199.
Jia, Z., et al., Long-term correction of hyperbilirubinemia in the Gunn Rat by repeated intravenous delivery of naked plasmid DNA into muscle. Mol Ther. Nov. 2005; 12(5): 860-866.
Jiang, J. et al., Topical application of ketoconazole stimulates hair growth in C3H/HeN mice. J Dermatol. Apr. 2005;32(4):243-7.
Jirikowski, G.F., et al., Reversal of diabetes insipidus in Brattleboro Rats: Intrahypothalamic injection of vasopressin mRNA. Science. Feb. 1992; 255(5047): 996-998.
Johndon, K.M. et al., Role of heparan sulfate in attachment to and infection of the murine female gential tract by human papillomavirus. J Virol. Mar. 2009; 83(5): 2067-2074.
Jones, P.C.T., An Alteration in Cell Morphology under the Influence of a Tumor RNA. Nature, 1964;202:1226-7.
Juliano, R.L., et al., Cell-targeting and cell-penetrating peptides for delivery of therapeutic and imaging agents. Wiley Interdisciplinary Reviews: Nanomedicine and Nanobiotechnology. May/Jun. 2009; 1(3): 324-335.
Kabanov, A V. et al., A new class of antivirals: antisense oligonucleotides combined with a hydrophobic substituent effectively inhibit influenza virus reproduction and synthesis of virus-specific proteins in MDCK cells. FEBS Lett. Jan. 1, 1990;259(2):327-30.
Kahan, F.M. et al., The role of deoxyribonucleic acid in ribonucleic acid synthesis. J Biological Chem. Dec. 1962; 287(12): 3778-3785.
Kaji, K., et al., Virus free induction of pluripotency and subsequent excision of reprogramming factors. Nature. Apr. 2009; 458(7239): 771-775.
Kalnins, A. et al., Sequence of the lacZ gene of *Escherichia coli*. EMBO J. 1983;2(4):593-7.
Kanaya, S. et al., Codon usage and tRNA genes in eukaryotes: correlation of codon usage diversity with translation efficiency and with CG-dinucleotide usage as assessed by multivariate analysis. J Mol Evol. Oct.-Nov. 2001;53(4-5):290-8.
Kandimalla, E.R. et al., Divergent synthetic nucleotide motif recognition pattern: design and development of potent immunomodulatory oligodeoxyribonucleotide agents with distinct cytokine induction profiles. Nucleic Acids Res. May 1, 2003;31(9):2393-400.
Kandimalla, E.R. et al., Immunomodulatory oligonucleotides containing a cytosine-phosphate-2'-deoxy-7-deazaguanosine motif as potent toll-like receptor 9 agonists. Proc Natl Acad Sci U S A. May 10, 2005:102(19):6925-30. Epub Apr. 28, 2005.
Karande, A.A.,et al., In vitro induction of chronic myeloid leukemia associated immune reactivity in normal human lymphocytes by xenogeneic immune RNA. Neoplasma. 1983, 30(4):403-9.
Kariko, K. et al., Incorporation of pseudouridine into mRNA yields superior nonimmunogenic vector with increased translational capacity and biological stability. Mol Ther. Nov. 2008;16(11):1833-40. Epub Sep. 16, 2008.
Kariko, K. et al., Phosphate-enhanced transfection of cationic lipid-complexed mRNA and plasmid DNA. Biochim Biophys Acta. Mar. 2, 1998;1369(2):320-34.
Kariko, K., et al., In vivo protein expression from mRNA delivered into adult rat brain. J. of Neuroscience Methods. Jan. 2001; 105(1): 77-86.

(56) References Cited

OTHER PUBLICATIONS

Kariko, K. et al., mRNA is an endogenous ligant for Toll-like receptor 3. J Biol Chem. Mar. 26, 2004;279(13):12542-50. Epub Jan. 16, 2004.
Mansour, et al., Functional Studies with Uterine RNA. PNAS, 1965, 53:764-70.
Marson, A., et al., Wnt signaling promotes reprogramming of somatic cells to pluripotency. Cell Stem Cell. Aug. 2008; 3(2): 132-135.
Martin, S.A. et al., Purification of mRNA guanylyltransferase and mRNA (guanine-7-) methyltransferase from vaccinia virions. J Biol Chem. Dec. 25, 1975;250(24):9322-9.
Martinon, F. et al., Induction of virus-specific cytotoxic T lymphocytes in vivo by liposome-entrapped mRNA. Eur J. Immunol. Jul. 1993;23(7):1719-22.
Massenet, S. et al., Pseudouridine mapping in the *Saccharomyces cerevisiae* spliceosomal U small nuclear RNAs (snRNAs) reveals that pseudouridine synthase pus1p exhibits a dual substrate specificity for U2 snRNA and tRNA. Mol Cell Biol. Mar. 1999;19(3):2142-54.
Mathers, A.R. et al., Professional antigen-presenting cells of the skin. Immunol Res. 2006;36(1-3):127-36.
Matray, T.J. et al., Synthesis and properties of RNA analogs-oligoribonucleotide N3'→P5' phosphoramidates. Nucleic Acids Res. Oct. 15, 1999;27(20):3976-85.
Maurer, N., et al., Spontaneous entrapment of polynucleotides upon electrostatic interation with ethanol-destabilized cationic liposomes. Biophys J. May 2001; 80(5): 2310-2326.
Mayfield, S.P. et al., Expression and assembly of a fully active antibody in algae. Proc Natl Acad Sci U S A. Jan. 21, 2003;100(2):438-42. Epub Jan. 8, 2003.
McCafferty, J et al., Phage antibodies: filamentous phage displaying antibody variable domains. Nature. Dec. 6, 1990;348(6301):552-4.
McCormack, A.L., et al., a-Synuclein suppression by targated small interfering RNA in the primate *Substantia nigra*. PLoS ONE. Aug. 2010; 5(8): e12122.
McCormack, M., et al., Activation of the T-cell oncogene LMO2 after gene therapy for X-linked severe combined immunodeficiency. N Engl J Med. Feb. 2004; 350: 931-922.
McDonald, J.D., et al., Characterization of mutations at the mouse phenylalanine hydroxylase locus. Genomics. 1997; 39: 402-405.
McElwee, K.J. et al., Transfer of CB8(+) cells induces localized hair loss whereas CD4(+)/CD25(−) cells promote systemic alopecia areata and CD4(+)/CD25(+) cells blockade disease onset in the C3H/HeJ mouse model. J Invest Dermatol. May 2005;124(5):947-57.
McGee, M. et al., The Quantitative determination of phenylalanine hydroxylase in rat tissues. Biochem. J. 1972; 127:669-674.
McGlynn, R. et al., Differential subcellular localization of cholesterol, gangliosides, and glycosaminoglycans in murine models of mucopolysaccharide storage disorders. J Compl Neurol. Dec. 20, 2004;480(4):415-26.
McKenzie, B.S. et al., Nucleic acid vaccines: tasks and tactics. Immunol Res. 2001;24(3):225-44.
McLean, M.J., et al., Membrane differentiation of cardiac myoblasts induced in vitro by an RNA-enriched fraction from adult heart. Exp Cell Res. Nov. 1977;110(1):1-14.
MEGAscript Kit product Manual, Ambion/Invitrogen website: http://tools.invitrogen.com/content/sfs/manuals/cms_072987.pdf, Publication Date: Oct. 27, 2009 (last accessed Mar. 17, 2013)("Ambion").
Mellits, K.H. et al., Removal of double-stranded contaminants from RNA transcripts: synthesis of adenovirus VA RNAI from a T7 vector. Nucleic Acids Res. Sep. 25, 1990;18(18):5401-6.
Meunier, L. et al., Heterogeneous populations of class II MHC+ cells in human dermal cell suspensions. Identification of a small subset responsible for potent dermal antigen-presenting cell activity with features analogous to Langerhans cells. J Immunol. Oct. 15, 1993;151(8):4067-80.

Minks, M.A. et al., Structural requirements of double-stranded RNA for the activation of 2',5'-oligo(A) polymerase and protein kinase of interferon-treated HeLa cells. J Biol Chem. Oct. 25, 1979;254(20):10180-3.
Mishra, N.C. et al., Induction by RNA of inositol independence in *Neurospora crassa*. Proc. Natl Acad. Sci. U.S.A., 1975, 72(2):642-5.
Mishra, R.K. et al., Improved leishmanicidal effect of phosphorotioate antisense oligonucleotides by LDL-mediated delivery. Biochim Biophys Acta. Nov. 7, 1995;1264(2):229-37.
Mitchell, D.A. et al., RNA transfected dendritic cells as cancer vaccines. Curr Opin Mol Ther. Apr. 2000:2(2):176-81.
Mitchell, D.A. et al., RNA-transfected dendritic cells in cancer immunotherapy. J Clin Invest. Nov. 2000;106(9):1065-9.
Mitchell, P. et al., mRNA turnover. Curr Opin Cell Biol. Jun. 2001;13(3):320-5.
Miura, K., et al., Variation in the safety of induced pluripotent stem cell lines. Nat Biotechnology. Aug. 2009; 27(8):743-745.
Morinaga, T. et al., Primary structures of human alpha-fetoprotein and its mRNA. Proc Natl Acad Sci U S A. Aug. 1983;80(15):4604-8.
Morse, M.A. et al., Generation of dendritic cells in vitro from peripheral blood mononuclear cells with granulocyte-macrophage-colony-stimulating factor, interleukin-4, and tumor necrosis factor-alpha for use in cancer immunotherapy. Ann Surg. Jul. 1997;226(1):6-16.
Mount, S.M. et al., A catalogue of splice junction sequences. Nucleic Acids Res. Jan. 22, 1982;10(2):459-72.
Muller, M.R. et al., Transfection of dendritic cells with RNA induces CD4- and CD8-mediated T cell immunity against breast carcinomas and reveals the immunodominance of presented T cell epitopes. J Immunol. Jun. 15, 2003;170(12):5892-6.
Murakawa, G.J. et al., Direct detection of HIV-1 RNA from AIDS and ARC patient samples. DNA. May 1988;7(4):287-95.
Myette, J.R. et al., Domain structure of the vaccinia virus mRNA capping enzyme. Expression in *Escherichia coli* of a subdomain possessing the RNA 5'-triphosphatase and guanylyltransferase activities and a kinetic comparison to the full-size enzyme. J Biol Chem. May 17, 1996;271(2):1936-44.
Nagata, S., et al., Molecular cloning and expression of cDNA for human granulocyte colony-stimumating factor. Nature. Jan. 30-Feb. 5, 1986; 319(6052): 415-8.
Nagata, S., et al., The chromosomal gene structure and two mRNAs for human granulocyte colony-stimulating factor. EMBO J. Mar. 1986; 5(3): 575-81.
Nagata, T. et al., Codon optimization effect on translational efficiency of DNA vaccine in mammalian cells: analysis of plasmid DNA encoding a CTL epitope derived from microorganisms. Biochem Biophys Res Commun. Aug. 2, 1999;261(2):445-51.
Nair, S. et al., Soluble proteins delivered to dendritic cells via pH-sensitive liposomes induce primary cytotoxic T lymphocyte responses in vitro. J Exp Med. Feb. 1, 1992;175(2):609-12.
Nair, S.K. et al., Antigen-presenting cells pulsed with unfractionated tumor-derived peptides are potent tumor vaccines. Eur J Immunol. Mar. 1997;27(3):589-97.
Nair, S.K. et al., Induction of cytotoxic T cell responses and tumor immunity against unrelated tumors using telomerase reverse transcriptase RNA transfected dendritic cells. Nat Med. Sep. 2000;6(9):1011-7.
Nair, S.K. et al., Induction of primary carcinoembryonic antigen (CEA)-specific cytotoxic T lymphocytes in vitro using human dendritic cells transfected with RNA. Nat Biotechnol. Apr. 1998;16(4):364-9.
Nakamura, K. et al., A model for the autosensitization autoantibody production associated with xenogeneic thymic RNA. J Immunol. Aug. 1978;121(2):702-9.
Nakamura, K. et al., Aitngen restricted hybridization between antigen primed macrophage and thymic RNA. Immunol Commun. 1981;10(4-5):367-82.
Nakamura, K. et al., Conversion of immune response patterns from high to low and low to high by an RNase-sensitive thymocyte extract. Immunology. Sep. 1980;41(1):25-35.
Nakamura, K. et al., Generation of anti-NZB red blood cell antibody-forming plasma cells from bone marrow cultures of syngeneic and allogeneic mice: functional modulation of helper T-cell subsets in autosensitization. Immunology. Mar. 1983;48(3):579-86.

(56) References Cited

OTHER PUBLICATIONS

Nakamura, K. et al., Itranuclear incorporation of thymic low molecular weight RNA by murine bone marrow immunoblasts and inhibition of plasma cell formation by a derivative of rifampicin. Microbiol Immunol. 1982;26(1):41-57.
Nakamura, K. et al., Mechanism of anti-DNA antibody formation. The functional modulation of helper T-subset plays the key role in both murine and human B-cell autosensitization. Microbiol Immunol. 1986;30(7):703-15.
Nakamura, K. et al.,The proliferation of plasma cells from mouse bone marrow in vitro. III. Primary and secondary immune responses associated with thymic RNA. Immunol Commun. 1979;8(5-6):511-29.
Nakamura, K., The proliferation of plasma cells from mouse bone marrow in vitro. II-Stimulation of IgG-producing cells by a RNase-sensitive thymocyte homogenate. Cell Immunol. Aug. 1976;25(2):163-77.
Niu, M.C., et al., Presence of liver-forming fraction in fish egg mRNAs detected by its ability to encode albumin syntehsis. Scientia Sinica. 1980, 23(4):510-6.
Niu, M.C., et al., Re-examination of the DNA-mediated transformation in goldfish. Scientia Sinica, 1983, 24(7):700-7.
Niu, M.C., The Development of Tubular heart in RNA-Treated Post-Nodal pieces of Chick Blastoderm. J Embryol. Exp. Morphol., 1973, 29:485-501.
Niu, M.C., The Effect of mRNA on Nuclear Activity in Developing Systems. 1980, 415-33.
Niu, M.C., The role of Exogenous Heart-RNA in Development of the Chick Embryo Cultivated In Vitro. J Embryol. Exp. Morphol., 1970, 64:57-64.
Niu, M.C., Thymus Ribonucleic Acid and Embryonic Differentiation. PNAS, 1958, 44:1264-1274.
Niu, M.C. et al., Transfer of information from mRNA to chromosomes by reverse transcription in early development of goldfish eggs. Cellular and Molecular Biology, 1989, 35(3):333-45.
Niu, M.C.,VII. New Approaches to the Problem of Embryonic Induction. Cellular Mechanisms, Differentiation and Growth. 1956, 155-71.
Oberhauser, B. et al., Effective incorporation of 2'-O-methyl-oligoribonucleotides into liposomes and enhanced cell association through modification with thiocholesterol. Nucleic Acids Res. Feb. 11, 1992;20(3):533-8.
Occhiogrosso, G., et al., Prolonged convection-enhanced delivery into the rat brainstem. Neurosurgery. Feb. 2003; 52(2): 388-394.
Odens, M., Prolongation of the Life Span in Rats. Journal of the American Geriatrics Soc. Oct. 1973; 11(1):450-1.
O'Doherty, U. et al., Human blood contains two subsets of dendritic cells, one immunologically mature and the other immature. Immonology. Jul. 1994:82(3):467-93.
Ofengand, J. et al., The function of pseudouridylic acid in transfer ribonucleic acid: II. Inhibition of amino acyl transfer ribonucleic acid-ribosome complex formation by ribothymidylyl-pseudouridylyl-cytidylyl-guanosine 3'-phosphate. J Biol Chem. Nov. 25, 1969; 244(22): 6241-6253.
Ohashi, H. et al., Efficient protein selection based on ribosome display system with purified components. Biochem Biophys Res Commun. Jan. 5, 2007;352(1):270-6. Epub Nov. 13, 2006.
Ohmichi, T. et al., Efficient bacterial transcription of DNA nanocircle vectors with optimized single-stranded promoters. Ohmichi T, Maki A, Kool ET. Proc Natl Acad Sci U S A. Jan. 8, 2002;99(1):54-9. Epub Dec. 18, 2001.
Okumura, K. et al., Bax mRNA therapy using cationic liposomes for human malignant melanoma. J Gene Med. 2008; 10: 910-917.
Owen, M. et al., Stromal stem cells; marrow derived osteogenic precursors. CIBA Foundation Symposium, 1988, 136:42-60.`
Ozawa, T. et al., Amplification and analysis of cDNA generated from a single cell by 5'-RACE: application to isolation of antibody heavy and light chain variable gene sequences from single B cells. Biotechniques. Apr. 2006;40(4):469-70.

Padilla, R. et al., A Y639F/H784A T7 RNA polymerase double mutant displays superior properties for synthesizing RNAs with non-canonical NTPs. Nucleic Acids Res. Dec. 15, 2002;30(24):e138.
Paglia, P. et al., Murine dendritic cells loaded in vitro with soluble protein prime cytotoxic T lymphocytes against tumor antigen in vivo. J Exp Med. Jan. 1, 1996;183(1):317-22.
Painter, H., et al., 494. Topical delivery of mRNA to the murine lung and nasal epithelium. Mol Ther. 2004; 9: S187.
Palu, G. et al., In pursuit of new developments for gene therapy of human diseases. J Biotechnol. Feb. 5, 1999:68(1):1-13.
Palucka, A.K. et al., Taming cancer by inducing immunity via dendritic cells. Immunol Rev. Dec. 2007;220:129-50.
Papapetrou, E., et al., Stoichiometric and temporal requirements of Oct4, Sox2, Klf4, and c-Myc expression for efficient human IPSC induction and differentiation. Natl. Acad. Sci USA. Aug. 2009; 106: 12759-12764.
Paradi, E. et al., Changes in the content of modified nucleotides in wheat rRNA during greening. Biologia Plantarum. Apr. 2003; 47(1):33-8.
Park, I., et al., Reprogramming of human somatic cells to pluripotency with defined factors. Nature. Jan. 2008; 451(10): 141-146.
Parker, R. et al., Recognition of the TACTAAC box during mRNA splicing in yeast involves base pairing to the U2-like snRNA. Cell. Apr. 24, 1987;49(2):229-39.
Pascolo, S. Vaccination with messenger RNA (mRNA). Handb Exp Pharmacol. 2008; 183:221-235.
Passini, M.A. et al., AAV vector-mediated correction of brain pathology in a mouse model of Niemann-Pick A disease. Mol Ther. May 2005;11(5):754-62.
Passos, G.A. et al., In vivo induction of immunological memory to human tumor extract with poly (A)-containing immune RNA. Cell Mol Biol. 1988;34(2):157-64.
Paul, S., et al., How to improve R&D productivity: the pharmaceutical industry's grand challenge. Nat Reviews Drug Discovery. Mar. 2010; 9: 203-214.
Pays, E., Characterization of double-stranded ribonucleic acid sequences present in the initial transcription products of rat liver chromatin. Biochem J. Aug. 1, 1977;165(2):235-45.
Pearson, W.R. et al., Improved tools for biological sequence comparison. Proc Natl Acad Sci U S A. Apr. 1988;85(8):2444-8.
Peculis, B. RNA processing: pocket guides to ribosomal RNA. Curr Biol. Aug. 1, 1997;7(8):R480-2.
Peng, Z.H. et al., Synthesis and application of a chain-terminating dinucleotide mRNA cap analog. Org Lett. Jan. 24, 2002;4(2):161-4.
Peoples, G.E. et al., Breast and ovarian cancer-specific cytotoxic T lymphocytes recognize the same HER2/neu-derived peptide. Proc Natl Acad Sci U S A. Jan. 17, 1995;92(2):432-6.
Perche, F., et al., Enhancement of dedritic cells transfection in vivo and of vaccination against B16F10 melanoma with mannosylated histidylated lipopolyplexes loaded with tumor antigen messenger RNA. Nanomed: Nanotech, Bio, and Med. Aug. 2011; 7(4): 445-453.
Pesole, G. et al., Structural and functional features of eukaryotic mRNA untranslated regions. Gene. Oct. 3, 2001;276(1-2):73-81.
Pesole, G. et al., UTRdb and UTRsite: specialized databases of sequences and functional elements of 5' and 3' untranslated regions of eukaryotic mRNAs. Update 2002. Nucleic Acids Res. Jan. 1, 2002;30(1):335-40.
Phillips, J. et al., Antisense RNA Amplification: A Liner Amplification Method for Analyzing the mRNA Population from single Living Cells. Methods. Dec. 1996;10(3):283-8.
Phizicky, E.M. et al., [31] Biochemical genomics approach to map activities to genes. Methods Enzymol. 2002;350:546-59.
Pollard, C., et al., Type I IFN counteracts the induction of antigen-specific immune responses by lipid-based delivery of mRNA vaccines. Mol Ther. Jan. 2013: 21(1): 251-259.
Ponsaerts, P. et al., Cancer immunotherapy using RNA-located dendritic cells. Clin Exp Immunol. Dec. 2003;134(3):378-84.
Ponsaerts, P. et al., Messenger RNA electroporation is highly efficient in mouse embryonic stem cells: successful FLPe- and Cre-mediated recombination. Gene Ther. Nov. 2004;11(21):1606-10.

(56) References Cited

OTHER PUBLICATIONS

Ponsaerts, P., et al., Highly efficient mRNA-based gene transfer in feeder-free cultured H9 human embryonic stem cells. Cloning and Stem Cells. 2004; 6(3): 211-216.
Ponsaerts, P. et al., Messenger RNA electroporation of human monocytes, followed by rapid in vitro differentiation, leads to highly stimulatory antigen-loaded mature dendritic cells. J Immunol. Aug. 15, 2002;169(4):1669-75.
Porgador, A. et al., Induction of antitumor imminity using bone marrow-generated dendritic cells. J Immunol. Apr. 15, 1996;156(8):2918-26.
Pradilla, G. et al., Prevention of vasospasm following subarachnoid hemorrhage in rabbits by anti-CD11/CD18 monoclonal antibody therapy. J Neurosurg. Jul. 2004;101(1):88-92.
Preisler, H.D. et al., Sensitization in vitro to murine myeloblastic leukemia cells by xenogeneic immune RNA. J Natl Cancer Inst. Jan. 1979;62(1):133-7.
Preiss, T. et al., Dual function of the messenger RNA cap structure in poly(A)-tall-promoted translation in yeast. Nature. Apr. 2, 1998;392(6675):516-20.
Kariko, K. et al., Suppression of RNA recognition by Toll-like receptors: the impact of nucleoside modification and the evolutionary origin of RNA. Immunity. Aug. 2005;23(2):165-75.
Kariko, K., et al., Increased erythropoiesis in mice injected with submicrogram quantities of pseudouridine-containing mRNA encoding erythropoietin. Mol Ther. May 2012; 20(5): 948-853.
Karlin, S. et al., Applications and statistics for multiple high-scoring segments in molecular sequences. Proc Natl Acad Sci U S A. Jun. 15, 1993;90(12):5873-7.
Katre, N.V. et al., Chemical modification of recombinant interleukin 2 by polyethylene glycol increases its potency in the murine Meth A sarcoma model. Proc Natl Acad Sci U S A. Mar. 1987;84(6):1487-91.
Katz, N., et al., Rapid onset of cutaneous anesthesia with EMLA cream after pretreatment with a new ultrasound-emitting device. Anesth Analg. 2004; 98: 371-376.
Kawai, T., et al., Antiviral signaling through pattern recognition receptors, J. Biochem. 2007; 141(2): 137-145.
Kawamura, T., et al., Linking the p53 tumor suppressor pathway to somatic cell reprogramming. Nature. Aug. 2009; 460(7259): 1140-1144.
Kazmierczak, K.M. et al., The phage N4 virion RNA polymerase catalytic domain is related to single-subunit RNA polymerases. EMBO J. Nov. 1, 2002;21(21):5815-23.
Keith, B., et al., HIF1a and HIF1a: sibling rivairy in hypoxic tumor growth and progression. Nat Rev Cancer. Jul. 2012; 12(1): 9-22.
Keller, E.B. et al., Intron splicing: a conserved internal signal in introns of animal pre-mRNAs. Proc Natcl Acad Sci U S A. Dec. 1984;81(23):7417-20.
Kewon, W.A., et al., [41] Methods for Introducing DNA into Mammalian Cells Methods in Enzymology. 1990, 185:527-37.
Keshishian, H., et al., Quantification of cardiovascular biomarkers in patient plasma by targeted mass spectrometry and stable isotope dilution. Mol Cell Proteomics. Oct. 2009; 8(10): 2339-2349.
Kesselheim, A.S., An empirical review of major legistation affecting drug developmement: Past experiences, effects, and unintended consequences. The Milbank Quarterly. 2011; 89(3): 450-502.
Khare, P.D. et al., Tumor growth suppression by a retroviral vector displaying scFv antibody to CEA and carrying the iNOS gene. Anticancer Res. Jul.-Aug. 2002;22(4):2443-6.
Khullar, N. et al., Comparative evaluation of the protective effect of immune spleen cells and immune RNA against *Plasmodium berghei*. Ann. Trop. Med. Parasitol., 1988, 82(6):519-26.
Kim, C.H. et al., Codon optimization for high-level expression of human erythropoietin (EPO) in mammalian cells. Gene. Oct. 15, 1997;199(1-2):293-301.
Kim, D., et al., Generation of human induced pluripotent stem cells by direct delivery of reprogramming proteins. Cell Stem Cell. Jun. 2009; 4(6): 472-476.
Kim, S.H., et al., Opsonized erythrocyte ghosts for liver-targeted delivery of antisense oligodeoxynucleotides. Biomaterials. Feb. 2009; 30(5): 959-967. Epub Nov. 22, 2008.
Kines, R.C. et al., The initial steps leading to papillomavirus infections occur on the basement membrane prior to cell surface binding. PNAS. Dec. 1, 2009; 106(48): 20458-20463.
Kinosita, K. Jr. et al., Formation and resealing of pores of controlled sizes in human erythrocyte membrane. Nature. Aug. 4, 1977;268(5619):438-41.
Kirby, K.S., A New Method for the Isolation of Ribonucleic Acids from Mammalian Tissues. J. Biochem., 1956, 64:405.
Kirshenbaum, et al., Designing polymers that mimic biomolecules. Curr Opin Struct Biol. 1999. 9:530-5.
Kirpotin, D.B., et al., Antibody targeting of long-circulating lipidic nanoparticles does not inceease tumor localization but does increase internalization in animal models. Cancer Res. 2006; 66: 6732-6740.
Kiss, T., Small nucleolar RNA-guided post-transcriptional modification of cellular RNAs. EMBO J. Jul. 16, 2001;20(14):3617-22.
Kiss, T., Small nucleolar RNAs: an abundant group of noncoding RNAs with diverse cellular functions. Cell. Apr. 19, 2002;109(2):145-8.
Kitaguchi, K. et al., Immune deficiency enhances expression of recombinant human antibody in mice after nonviral in vivo gene transfer. Int J Mol Med. oct. 2005;16(4):683-8.
Klinman, D.M. et al., DNA vaccines: safery and efficacy issues. Springer Semin Immunopathol. 1997;19(2)2:245-56.
Koch, G. and Bishop, J.M. The effect of polycations on the interaction of viral RNA with mammalian cells: Studies on the infectivity of single- and double-stranded poliovirus RNA. Virology. May 1968; 35(1): 9-17.
Koch, G., et al., Quantitative Studies on the Infectivity of ribonucleic acid from partially purified and high purified poliovirus preparations, Virology. Mar. 1960; 10(3): 329-343.
Koch, G., et al., An agar cell-suspension plaque assay for isolated viral RNA. Biochem and Biophys Res. Comm. 1966; 24(3): 304-309.
Kohler, G. et al., Continuous cultures of fused cells secreting antibody of predefined specificity. Nature. Aug. 7, 1975;256(5617):495-7.
Koide, Y. et al., DNA vaccines. Jpn J Pharmacol. Jul. 2000;83(3):167-74.
Koido, S. et al., Induction of antitumor immunity by vaccination of dendritic cells tranfected with MUC1 RNA. J. Immunol. Nov. 15, 2000;165(10):5713-9.
Kolb, A.F. et al., A virus-neutralising antibody is not cytotoxic in vitro. Mol Immunol. Feb. 2006;43(6):677-89.
Komar, A.A. et al., Synonymous codon substitutions affect ribosome traffic and protein folding during in vitro translation. FEBS Lett. Dec. 3, 1999;462(3):387-91.
Kontermann, R.E. et al., Recombinant bispecific antibodies for cancer therapy. Acta Pharmacol Sin. Jan. 2005;26(1):1-9.
Korsten, K.H. et al., The strategy of infection as a criterion for phylogenetic relationships of non-coli phages morphologically similar to phage T7. J Gen Virol. Apr. 1979;43(1):57-73.
Koski, G.K. et al., Cutting edge innate immune system discriminates between RNA containing bacterial versus eukaryotic structural features that prime for high-level IL-12 secretion by dendritic cells. J Immunol. Apr. 1, 2004;172(7):3989-93.
Kreig, P.A. et al., Functional messenger RNAs are produced by SP6 in vitro transcription of cloned cDNAs. Nucleic Acids Res. Sep. 25, 1984;12(18):7057-70.
Kreig, P.A. et al., In vitro RNA synthesis with SP6 RNA polymerase. Methods Enzymol. 1987;155:397-415.
Kreiter, S., et al., Intranodal vaccination with naked antigen-encoding RNA elicits potent prophylactic and therapeutic antitumoral immunity. Cancer Res. 2010; 70: 9031-9040.
Kreiter, S., et al., Tumor vaccination using messenger RNA: prospect of a future therapy. Curr Opinion in Immun. Jun. 23, 2011(3): 399-406.
Kudla, G. et al., High guanine and cytosine content increases mRNA levels in mammalian cells. PLoS Biol. Jun. 2006;4(6):e180. Epub May 23, 2006.
Kufe, D.W. et al., Holland-Frei cancer medicine, 6th edition. Hamilton (ON): BC Decker; 2003; Table 12-1.

(56) References Cited

OTHER PUBLICATIONS

Kugler, A. et al., Regression of human metastatic renal cell carcinoma after vaccination with tumor cell-dendritic cell hybrides. Nat Med. Mar. 2000;6(3):332-6.
Khun, A.N., et al., mRNA as a versatile tool for exogenous protein expression. Current Gene Therapy. Oct. 2012; 12(5): 347-361.
Kuhn, E., et al., Developing multiplexed assays for Troponin I and Interleukin-33 in plasma by peptide immunoaffinity enrichment and targeted mass spectrometry. Clinical Chem. 2009; 55(6): 1108-1117.
Kundu, T.K. et al., CpG islands in chromatin organization and gene expression. J Biochem. Feb. 1999;125(2):217-22.
Kusakabe, K. et al., The timing of GM-CSF expression plasmid administration influences the Th1/Th2 response induced by an HIV-1-specific DNA vaccine. J Immunol. Mar. 15, 2000;164(6):3102-11.
Kvasnica, M. et al., Platinum(II) complexed with steroidal esters of L-methonine and L-histidine: synthesis, characterization and cytotoxic activity. Bioorg Med Chem. Apr. 1, 2008;16(7):3704-13. Epub Feb. 7, 2008.
Basarkar, A. et al., Nanoparticulate systems for polynucleotide deliver. Int J Nanomedicine. 2007; 2(3): 353-360.
Bird, A.P. et al., CpG-rich islands and the function of DNA methylation. Nature. May 15-21, 1986;321(6067):209-13.
Black, D.D. et al., Similarity of the transfer factors in Novikoff ascites tumor and other amino acid-incorporating systems. Cancer Res. May 1970;30(5):1281-6.
Bloch, G. et al., Sequence-dependence of the conformational changes induced by the 5-methyl cytosine in synthetic RNA oligomers. FEBS Lett. Jul. 27, 1987;219(2):464-8.
Boczkowski, D. et al., Dendritic cells pulsed with RNA are potent antigen-presenting cells in vitro and in vivo. J Exp Med. Aug. 1, 1996;184(2):465-72.
Boczkowski, D. et al., Induction of tumor immunity and cytotoxic T lymphocyte responses using dendritic cells transfected with messenger RNA amplified from tumor cells. Cancer Res. Feb. 15, 2000;60(4):1028-34.
Bonehill, A., et al., Single-step antigen loading and activation of dendritic cells by mRNA electroporation for the purpose of therapeutic vaccination in melanoma patients. Clin Cancer Res. May 2009; 15(10): 3366-3375.
Boon, T. et al., Genes coding for tumor rejection antigens: perspectives for specific immunotherapy. Important Adv Oncol. 1994:53-69.
Bose, S. et al., Role of nucleolin in human parainfluenza virus type 3 infection of human lung epithelial cells. J Virol. Aug. 2004;78(15):8146-58.
Bouxsein, N.F., et al., Structure and gene silencing activities of monovalent and pentavalent cationic lipid vectors complexed with siRNA†. Biochem. 2007; 46(16): 4785-4792.
Brandt, B. et al., Detection of the metastatic potential of blood-borne and immunomagnetically enriched epithelial cells by quantitative erbB-2 RT-PCR. Clin Exp Metastasis. Sep. 1996;14(4):399-408.
Brieba, L.G., et al., Role of T7 RNA polymerase His784 in start site selection and initial transcription. Biochem. 2002;41: 5144-5149.
Brossart, P. et al., Her-2/neu-derived peptides are tumor-associated antigens expressed by human renal cell and colon carcinoma lines and are recognized by in vitro induced specific cytotoxic T lymphocytes. Cancer Res. Feb. 15, 1998;58(4):732-6.
Brossart, P. et al., Identification of HLA-A2-restricted T-cell epitopes derived from the MUC1 tumor antigen for broadly applicable vaccine therapies. Blood. Jun. 15, 1999;93(12):4309-17.
Brossart, P. et al., Induction of cytotoxic T-lymphocyte responses in vivo after vaccinations with peptide-pulsed dendritic cells. Blood. Nov. 1, 2000;96(9):3102-8.
Brossart, P. et al., Virus-mediated delivery of antigenic epitopes into dendritic cells as a means to induce CTL. J Immunol. Apr. 1, 1997;158(7):3270-6.
Buccoliero, R. et al., Elevation of lung surfactant phosphatidylcholine in mouse models of Sandhoff and of Niemann-Pick A disease. J Inhent Metab Dis. 2004;27(5):641-8.

Burke, B. et al., Microinjection of mRNA coding for an anti-Golgi antibody inhibits intracellular transport of a viral membrane protein. Cell. Apr. 1984;36(4):847-56.
Burks, E.A. et al. In vitro scanning saturation mutagenesis of an antibody binding pocket. Proc Natl Acad Sci U S A. Jan. 21, 1997;94(2):412-7.
Butler, E.T. et al., Bacteriophage SP6-specific RNA polymerase. I. Isolation and characterization of the enzyme. J Biol Chem. May 25, 1982;257(10):5772-8.
Cannon, G. et al., RNA based vaccines. DNA Cell Biol. Dec. 2002;21(12):953-61.
Caput, D. et al., Identification of a common nucleotide sequence in the 3'-untranslated region of mRNA molecules specifying inflammatory mediators. Proc Natl Acad Sci U S A. Mar. 1986;83(6):1670-4.
Caron, H. et al., The human transcriptome map: clustering of highly expressed genes in chromosomal domains. Science. Feb. 16, 2001;291(5507):1289-92.
Carralot, J.P. et al., Polarization of immunity induced by direct injection of naked sequence-stabilized mRNA vaccines. Cell Mol Life Sci. Sep. 2004;61(18):2418-24.
Carralot, J.P. et al., Production and characterization of amplified tumor-derived cRNA libraries to be used as vaccines against metastatic melanomas. Genet Vaccines Ther. Aug. 22, 2005;3:6.
Caudy, A.A. et al., Fragiie X-related protein and VIG associate with the RNA interference machinery. Genes Dev. Oct. 1, 2002;16(19):2491-6.
Cavaille, J. et al., Identification of brain-specific and imprinted small nucleolar RNA genes exhibiting an unusual genomic organization. Proc Natl Acad Sci U S A. Dec. 19, 2000;97(26):14311-6.
Cavaille, J. et al., Targeted ribose methylation of RNA in vivo directed by tailored antisense RNA guides. Nature. Nov. 24, 1996;383(8602):732-5.
Celluzzi, C.M. et al., Peptide-pulsed dendritic cells induce antigen-specific CTL-mediated protective tumor immunity. J Exp Med. Jan. 1, 1996;183(1):283-7.
Chan, E., et al., Live cell imaging distinguishes bona fide human iPS cells from partially reprogrammed cells. Nat Biotech. Nov. 2009; 27(11): 1033-1037.
Chappell, S.A. et al., Ribosomal tethering and clustering as mechanisms for translation initiation. Proc Natl Acad Sci U S A. Nov. 28, 2006;103(48):18077-82. Epub Nov. 16, 2006.
Charette, M. et al., Pseudouridine in RNA: what, where, how, and why. IUBMB Life. May 2000;49(5):341-51.
Chen, D., et al., Rapid discovery of potent siRNA-containing lipid nanoparticles enabled by controlled microfluidic formulation. J Am Chem Soc. 2012; 134: 6948-6951.
Chen, H., et al., TGF-beta 1 attenuates myocardial ischemia-reperfusion injury via inhibition of upregulation of MMP-1. Am J Physiol Heart Circ Physiol. May 2003; 284(5): H1612-7.
Chen, Z. et al., Enhanced protection against a lethal influenza virus challenge by immunization with both hemagglutinin- and neuraminidase-expressing DNAs. Vaccine. Feb. 26, 1999;17(7-8):653-9.
Cheng, C., et al., Multifunctional triblock copolymers for intracellular messenger RNA delivery. Biomaterials. Oct. 2012; 33(28): 6868-6876.
Cheng, W.F. et al., Enhancement of Sindbis virus self-replicating RNA vaccine potency by linkage of herpes simplex virus type 1 VP22 protein to antigen. J Virol. Mar. 2001;75(5):2368-76.
Cheng, W.F. et al., Enhancement of Sindbis virus self-replicating RNA vaccine potency by linkage of *Mycobacterium tuberculosis* heat shock protein 70 gene to an antigen gene. J Immunol. May 15, 2001;166(10):6218-26.
Cho, J.H. et al., Enhanced cellular immunity to hepatitis C virus nonstructural proteins by codelivery of granulocyte macrophage-colony stimulating factor gene in intramuscular DNA immunization. Vaccine. Mar. 5, 1999;17(9-10):1136-44.
Chui, H.M. et al., Synthesis of helix 69 of *Escherichia coli* 23S rRNA containing its natural modified nucleosides, m(3) Psi and Psi. J Org Chem. Dec. 13, 2002;67(25):6847-54.
Clawson, G.A. et al., Increased amounts of double-stranded RNA in the cytoplasm of rat liver following treatment with carcinogens. Cancer Res. Aug. 1982;42(8):3228-31.

(56) References Cited

OTHER PUBLICATIONS

Cohen, P.J. et al., Murine epidermal Langerhans cells and splenic dendritic cells present tumor-associated antigens to primed T cells. Eur J Immunol. Feb. 1994;24(2):315-9.

Collas, P. et al., Epigenetic reprogramming of nuclei using cell extracts. Stem Cell Rev. 2006;2(4):309-17.

Collas, P., Dedifferentiation of cells: new approaches. Cytotherapy. 2007;9(3):236-44.

Colot, V. et al., Eukaryotic DNA methylation as an evolutionary device. Bioessays. May 1999;21(5):402-11.

Colter, J.S., et al., Infectivity of ribonucleic acid isolated from virus-infected tissues. Virology. 1957; 4(3): 522-532.

Colter, J.S., et al. Infectivity of ribonucleic acid from Ehrlich Ascites tumour cells infected with Mengo Encephalitis. Nature. Apr. 1957; 179(4565): 859-860.

Condon, C. et al., DNA-based immunization by in viro transfection of dendritic cells. Nat Med. Oct. 1996;2(10):1122-8.

Conry, R.M. et al., A carcinoembryonic antigen polynucleotide vaccine has in viro antitumor activity. Gene Ther. Jan. 1995;2(1):59-65.

Conry, R.M. et al., Characterization of a messenger RNA polynucleotide vaccine vector. Cancer Res. Apr. 1, 1995;55(7):1397-400.

Nallagatla, S.R. et al., A brilliant disguise for self RNA: 5'-end and internal modifications of primary transcripts suppress elements of innate immunity. RNA Biol. Jul.-Sep. 2008;5(3):140-4. Epub Jul. 20, 2008.

Narayanan, A. et al., Role of the box C/D motif in localization of small nucleolar RNAs to coiled bodies and nucleoli. Mol Biol Cell. Jul. 1999;10(7):2131-47.

Naz, R.K. et al., Novel human prostate-specific cDNA: molecular cloning, expression, and immunobiology of the recombinant protein. Biochem Biophys Res Commun. Oct. 11, 2002;297(5):1075-84.

Needleman, S.B. et al., A general method applicable to the search for similarities in the amino acid sequence of two proteins. J Mol Biol. Mar. 1970;48(3):443-53.

Nestle, F.O. et al., Vaccination of melanoma patients with peptide- or tumor lysate-pulsed dendritic cells. Nat Med. Mar. 1998;4(3):328-32.

Neumann, E. et al., Fundamentals of electroporative delivery of drugs and genes. Bioelectrochem Bioenerg. Feb. 1999;48(1):3-16.

Newby, M.I. et al., Sculpting of the spliceosomal branch site recognition motif by a conserved pseudouridine. Nat Struct Biol. Dec. 2002;9(12):958-65.

Newman, A. et al., Mutations in yeast U5 snRNA alter the specificity of 5' splice-site cleavage. Cell. Apr. 5, 1991;65(1):115-23.

Newman, A.J. et al., U5 snRNA interacts with exon sequences at 5' and 3' splice sites. Cell. Feb. 21, 1992;68(4):743-54.

Newmark, J. et al., Preparation and properties of adducts of streptokinase and streptokinase-plasmin complex with poly ethylene glycol and pluronic polyol F38. J Appl Biochem. 1982; 4:185-9.

Ni, J. et al., Small nucleolar RNAs direct site-specific synthesis of pseudouridine in ribosomal RNA. Cell. May 16, 1997;89(4):565-73.

Nicholson, A.W. et al., Accurate in vitro cleavage by RNase III of phosphorothioate-substituted RNA processing signals in bacteriophage T7 early mRNA. Nucleic Acids Res. Feb. 25, 1988;16(4):1577-91.

Nielsen, D.A. et al., Preparation of capped RNA transcripts using T7 RNA polymerase. Nucleic Acids Res. Jul. 25, 1986;14(14):5936.

Nielsen, P.E., Peptide nucleic acids as therapeutic agents. Curr Opin Struct Biol. Jun. 1999;9(3):353-7.

Nikolin, V.P. et al., Resistance of Mice Exposed to Whole-Body Irradiation to Transplanted Hemopoietic Cells Modified with RNA Preparations. Bull. Exp. Biol. Med., 2000, 129:5571-4.

Niu, M.C. et al., Genetic Manipulation in Higher Organisms; III. Detection of Soya Protein in Seeds Derived from Soya mRNA-Treated Rice. Scientia Sinica. 1980, 23:119-23.

Niu, M.C. et al., Ribonucleic acid-induced changes in mammalian cells. Proc Natl Acad Sci U S A., Oct. 15; 1981;47:1689-700.

Matsuda, A. et al., Nucleosides. 120. Synthesis of 2'-Deoxy-?-isocytidine and 2'-Deoxy-1-methyl-?-uridine from ?-Uridine^1. J Org Chem. 1981; 46:3603-3609.

Matsuda, A. et al., Synthesis of 3-Methylpseudouridine and 2'-Deoxy-3-Methyl-pseudouridine. Carbohydr Res. Mar. 1, 1982: 100: 297-302.

Bhattacharya, B.K. et al., A practical synthesis of N1-Methyl-2'-deoxy-?-uridine (?-Thymidine) and its incorporation into G-rich triple helix forming oligonucleotides. Nucleosides & Nucleotides. 1995; 14(6): 1269-1287.

Desaulniers, J.P. et al., Synthesis of 15N-enriched pseudouridine derivatives. Org. Lett. Oct. 30, 2003; 5(22): 4093-4096.

Jachertz, D. et al., Treatment of P815 mastocyloma in DBA/2 mice with RNA. J Immunogen. 1974; 1: 355-362.

McGary, E.C. et al., Post-transcriptional regulation of erythropoietin mRNA stability by erythropoietin mRNA-binding protein. J Biologic Chem. Mar. 28, 1997; 272(13): 8628-8634.

Hornung, V. et al., 5'-triphosphate RNA is the ligand for RIG-I. Science. Nov. 10, 2006: 314(5801): 994-997.

Davis, D.R. Stabilization of RNA stacking by pseudouridine. Nucleic Acids Res. 1995; 23(24): 5020-5026.

Monobe, M. et al., Beta-pseudouridine, a beer component, reduces radiation-induced chromosome aberations in human lymphocytes. Mutat Res. Jul. 8, 2003; 538(1-2): 93-99.

Hanessian, S. et al., A highly stereocontrolled and efficient synthesis of alpha- and beta-pseudouridines. Tetrahedron Letters. 2003; 44: 8321-8323.

Shi, Y. et al., Identification and characterization of pancreatic eukaryotic initiation factor 2 alpha-subunit kinase. PEK, involved in translational control. Mol Cell Biol. Dec. 1998; 18(12): 7499-7509.

Nguyen, A. et al., Quantitative assessment of the use of modified nucleoside triphosphates in expression profiling: differential effects on signal intensities and impacts on expression ratios. BMC Biotechnol. Jul. 31, 2002; 2:14.

Carrington, J.C. et al., Cap-independent enhancement of translation by a plant polyvirus 5' nontranslated region. J Virol. Apr. 1990; 64(4): 1590-1597.

Gallie, D. R. The 5'-leader of tobacco mosaic virus promotes translation through enhanced recruitment of eIF4F. Nuc Acids Red. 2002; 30(15): 3401-3411.

Decatur, W. A. et al., RNA-guided nucleotide modification of ribosomal and other RNAs. J Biologic Chem. Jan. 10, 2003; 278(2): 695-698.

Badis, G. et al., A snoRNA that guides the two most conserved pseudouridine modifications within rRNA confers a growth advantage in yeast. RNA. Jul. 2003; 9(7): 771-779.

Nitin, N. et al., Peptide-linked molecular beacons for efficient delivery and rapid mRNA detection in living cells. Nuc Acids Res. 2004; 32(6): e58.

Cho, E.J. et al., mRNA capping enzyme is recruited to the transcription complex by phosphorylation of the RNA polymerase II carboxy-terminal domain. Genes Dev. Dec. 15, 1997; 11(24): 3319-3326.

Santi, D.V. Mechanistic studies of RNA modifying enzymes. RNA pseudouridine synthase and m5Cytosine methyl transferase. Nucleic Acids Symp Ser. 2000; 44: 147-148.

Strobel, I. et al., Human dendritic cells transfected with either RNA or DNA encoding influenza matrix protein M1 differ in their ability to stimulate cytotoxic T lymphocytes. Gene Ther. Dec. 2000; 7(23): 2028-2035.

Takahashi, T.T. et al., mRNA display: ligand discovery, interaction analysis and beyond. Trends in Biochem Sci. Mar. 2003; 28(3): 159-165.

Niu, M.C. et al., The Developmental Potentiality of the Liver-RNA-Treated Posterior Primitive Streak in the Chick Embryo. Biol. Bull. 1968; 135:200-7.

Niu, M.C. et al., The Entrance of Exogenous RNA into the Mouse Ascites Cell. Proc. Soc. Exp. Biol. Med., 1968, 128(2):560-5.

Niu, M.C., RNA-Induced Biosynthesis of Specific Enzymes. PNAS, 1962, 48:1964-9.

Niu, M.C., Antagonistic Action of Exogenous Histone and RNA in Mouse Ascites Cells. Proc. Soc. Exp. Biol. Med., 1972, 140:256-62.

(56) References Cited

OTHER PUBLICATIONS

Niu, M.C., Causal Analysis of Embryonic Differentiation: I. Responsiveness of Presumptive Ecioderm as a Regulating Factor in RNA Function. Exp. Cell Res., 1971, 64:57-64.

Niu, M.C., Causal Analysis of Embryonic Differentiation: II. Dual Function of Exogenous RNA in differentiation of Presumptive Ectoderm. Exp. Cell Res., 1971, 64:65-76.

Niu, M.C., Current Evidence Concerning Chemical Inducers. Evolution of Nervous Control from Primitive Organisms. 1959, 7-30.

Niu, M.C., Functional Potentiality of Ribonucleic Acid. Acta. Unio. Int. Contra. Cancrum. third meeting Philadelphia, 1964, 20:995-6.

Niu, M.C., Genetic manipulation in higher organisms: I Goldfish ova as materials of operation, mRNA mediated alteration of the liver specific isozymes. Scientia Sinica, 1977, 20(6):803-8.

Niu, M.C., Glucose-6-Phosphate: Re-examination of the RNA-Induced Activity in Mouse Ascites Tumor Cells. Science. 1965, 148:513-6.

Niu, M.C., Mode of Action of the Exogenous Ribonucleic Acid in Cell Function. Natl Cancer Inst. Monogr. 1964, 13:167-77.

Niu, M.C., et al., Poly(A)-attached RNA as activator in embryonic differentiation. Proc. Soc Exp Biol Med. Oct. 1974;147(1):318-22.

Elbashir, S.M. et al., Duplexes of 21-nucleotide RNAs mediate RNA interference in cultured mammalian cells. Nature. May 24, 2001;411(6836):494-8.

Ellem, K.A.O., and Colter, J.S. The isolation of three variants of mengo virus differing in plaque morphology and hemagglutinating characteristics. Virology. Nov. 1961; 15(3): 340-347.

Ellem, K.A.O., and Colter, J.S. The interaction of infectious ribonucleic acid with mammalian cell line: I. Relationship between the osmotic pressure of the medium and the production of infectious centers. Virology. Jun. 1960; 11(2): 434-443.

Ellem, K.A.O. and Colter, J.S. The interaction of infectious ribonucleic acids with a mammalian cell line: II. Kinetics of the formation of infectious centers. Virology. Dec. 1960; 12(4): 511-520.

Ellem, K.A.O. and Colter, J.S. The interaction of infectious ribonucleic acids with mammalian cells: III. Comparison of infection and RNA uptake in the HeLa cell-polio RNA and L cell-mengo RNA systems. Virology. Oct. 1961; 15(2): 113-126.

Epicentre Forum. Tools and Techniques for Genomics and RNA Research. 2006; 13(2): 1-8.

Esposito, S., Effect on Leukaemic Cells of Ribonucleic Acid Extracted from Calf's Spleen. Nature. Sep. 1964; 203: 1078-1079.

Esvelt, K., et al., A system for the continous directed evolution of biomolecules. Nature. Apr. 2011; 427(7344): 499-503.

Fahy, E. et al., Self-sustained sequence replication (3SR): an isothermal transcription-based amplification system alternative to PCR. PCR Methods Appl. Aug. 1991;1(1):25-33.

Faissner, A. et al., Analysis of polypeptides of the tree shrew (*Tupaia*) herpesvirus by gel electrophoresis. J Gen Virol. Jan. 1982;58 Pt 1:139-48.

Fan, X.C., et al., Overexpression of HuR, a nuclear-cytoplasmic shuttling protein, increases the in vivo stability of ARE-containing mRNAs. Embo J. 1998; 17(12): 3448-3460.

Fandrich, F. et al., Preimplantation-stage stem cells induce long term allogeneic graft acceptance without supplementary host conditioning. Nat Med. Feb. 2002;8(2):171-8.

Fang, S.H. et al., Functional measurement of hepatitis C virus core-specific CD8(+) T-cell responses in the livers or peripheral blood of patients by using autologous peripheral blood mononuclear cells as targets or stimulators. J Clin Microbiol. Nov. 2001;39(11):3895-901.

Fearnley, D.B. et al., Monitoring human blood dendritic cell numbers in normal individuals and in stem cell transplantation. Blood. Jan. 15, 1999;93(2):728-36.

Felgner, P.L., et al., Lipofection: a highly efficient, lipid-mediated DNA-transfection procedure. Proc Natl Acad Sci U S A. Nov. 1987;84(21):7413-7.

Felgner, P.L. Particulate systems and polymers for in vitro and in vivo delivery of polynucleotides. Adv. Drug Delivery Rev. 1990; 5(3): 163-187.

Fisch, P. et al., Generation of antigen-presenting cells for soluble protein antigens ex vivo from peripheral blood CD34+ hematopoietic progenitor cells in cancer patients. Eur J Immunol. Mar. 1996;26(3):595-600.

Fisher, K.J. and Wilson, J.M. The transmembrane domain if diphtheria toxin improves molecular conjugate gene transfer. Biochem. J. Jan. 1997; 321(1): 49-58.

Fishman, M. et al., In vitro transfer of macrophate RNA to lymph node cells. Nature. May 11, 1963;198:549-51.

Fisk, B. et al., Identification of an immunodominant peptide of HER-2/neu protooncogene recognized by ovarian tumor-specific cytotoxic T lymphocyle lines. J Exp Med. Jun. 1, 1995;181(6):2109-17.

Frank, B. et al., Interanimal "memory" transfer: results from brain and liver homogenates. Science. Jul. 24, 1970;169 (3943):399-402.

Franklin, R.M., Purification and properties of the replicative intermediate of the RNA bacteriophage R17. Proc Natl Acad Sci U S A. Jun. 1966;55(6):1504-11.

Frey, M.R. et al., RNA-mediated interaction of Cajal bodies and U2 snRNA genes. J Cell Biol. Aug. 6, 2001;154(3):499-509.

Fukuda, I. et al., In vitro evolution of single-chain antibodies using mRNA display. Nucleic Acids Res. 2006;34(19):e127. Epub Sep. 29, 2006.

Fusaki, N., et al., Efficient induction of transgene-free human pluyripotent stem cells using a vector based on Sendai virus, an RNA virus that does not integrate into the host genome. Proc Jpn Acad Ser B Phys Biol Sci. 2009; 85(8): 348-362.

Fynan, E.F. et al., DNA vaccines: protective immunizations by parenteral, mucosal, and gene-gun inoculations. Proc Natl Acad Sci U S A. Dec. 15, 1993;90(24):11478-82.

Gall, J.G. et al., A role for Cajal bodies in assembly of the nuclear transcription machinery. FEBS Lett. Jun. 8, 2001;498(2-3):164-7.

Gall, J.G. The centennial of the Cajal body. Nat Rev Mol Cell Biol. Dec. 2003;4(12):975-80.

Gallie, D.R. A tale of two termini: a functional interaction between the termini of an mRNA is a prerequisite for efficient translation initiation. Gene. Aug. 17, 1998;216(1):1-11.

Gallie, D.R. The cap and poly(A) tail function synergistically to regulate mRNA translational efficiency. Genes Dev. Nov. 1991;5(11):2108-16.

Ganot, P. et al., Site-specific pseudouridine formation in preribosomal RNA is guided by small nucleolar RNAs. Cell. May 30, 1997;89(5):799-809.

Gao, M. et al., A novel mRNA-decapping activity in HeLa cytoplasmic extracts is regulated by AU-rich elements. EMBO J. Mar. 1, 2001;20(5):1134-43.

Gao, X. et al., Nonviral gene delivery, what we know and what is next. AAPS J. Mar. 23, 2007;9(1):E92-104.

Garbe, C. et al., [Epidemiology of malignant melanoma in West Germany in an international comparison]. Onkologie. Dec. 1989;12(6):253-62.

Gardiner-Garden, M. et al., CpG islands in vertebrate genomes. J Mol Biol. Jul. 20, 1987;196(2):261-82.

Gasche, C. et al., Sequential treatment of anemia in ulcerative colitis with intravenous iron and erythropoietin. Digestion. 1999;60(3):262-7.

GenBank NP_000651.3. Transforming growth factor beta-1 precursor [*Homo sapiens*]. Nov. 13, 2001; online.

Gerbi, S.A. et al., All small nuclear RNAs (snRNAs) of the [U4/U6,U5] Tri-snRNP localize to nucleoli; Identification of the nucleolar localization element of U6 snRNA. Mol Biol Cell. Sep. 2002;13(9):3123-37.

Gershon, P.D., (A)-tail of two polymerase structures. Nat Struct Biol. Oct. 2000;7(10):819-21.

Gierer, A and Schramm, G. Infectivity of ribonucleic acid from tobacco mosaic virus. Nature. Apr. 1956; 177(4511):702-703.

Gilboa, E. et al., Cancer immunotherapy with mRNA-transfected dendritic cells. Immunol Rev. Jun. 2004;199:251-63.

Giljohann, D.A., et al., Gene regulation with polyvalent siRNA-nanoparticle conjugates. J Am Chem Soc. Feb. 2009;131(6): 2072-2073.

Gilkeson, G.S. et al., Induction of cross-reactive anti-dsDNA antibodies in preautoimmune NZB/NZW mice by immunization with bacterial DNA. J Clin Invest. Mar. 1995;95(3):1398-402.

(56) References Cited

OTHER PUBLICATIONS

Ginsberg, S.D. et al., Expression profile of transcripts in Alzheimer's disease tangle-bearing CA1 neurons. Ann Neurol. Jul. 2000;48(1):77-87.
Ginsberg, S.D. et al., Predominance of neuronal mRNAs in individual Alzheimer's disease senile plaques. Ann Neurol. Feb. 1999;45(2):174-81.
Goldberg, I.H. et al., The incorporation of 5-ribosyluracil triphosphate into RNA in nuclear extracts of mammalian cells. Biochemical Biophyasical Research Communications. 1961; 6(5): 394-398.
Goldberg, I.H. et al., Comparative utilization of pseudouridine triphosphate and uridine triphosphate by ribonucleic acid polymerase. J Biological Chem. May 1963; 238(5): 1793-1800.
Grabbe, S. et al., Dendritic cells as initiators of tumor immune responses: a possible strategy for tumor immunotherapy? Immunol Today. Mar. 1995;16(3):117-21.
Grabbe, S. et al., Tumor angiten presentation by epidermal antigen-presenting cells in the mouse: modulation by granulocyte-macrophage colony-stimulating factor, tumor necrosis factor alpha, and utraviolet radiation. J Leukoc Biol. Aug. 1992;52(2):209-17.
Felgner, P.L. Cationic lipid/polynucleotide condensates for in vitro and in vivo polynucleotide delivery—the cytofectins. J. of Liposome Research. 1993; 3(1): 3-16.
Grabbe, S. et al., Tumor antigen presentation by murine epidermal cells. J Immunol. May 15, 1991;146(10):3656-61.
Graf, M. et al., Codon-optimized genes that enable increased heterologous expression in mammalian cells and elicit efficient immune responses in mice after vaccination of naked DNA. Methods Mol Med. 2004;94:197-210.
Graham, F.L., et al., A new technique for the assay of infectivity of human adenovirus 5 DNA. Virology. Apr. 1973;52(2):456-87.
Gram, G.J. et al., Immunological analysis of a *Lactococcus lactis*-based DNA vaccine expressing HIV gp120. Genet Vaccines Ther. Jan. 29, 2007;5:3.
Granstein, R.D. et al., Induction of anti-tumor immunity with epidermal cells pulsed with tumor-derived RNA or intradermal administration of RNA. J Invest Dermatol. Apr. 2000;114(4):632-6.
Greenblatt, M.S. et al., Mutations in the p53 tumor suppressor gene; clues to cancer etiology and molecular pathogenesis. Cancer Res. Sep. 15, 1994;54(18):4856-78.
Grentzmann, G. et al., A dual-luciferase reporter system for studying recording signals. RNA. Apr. 1998;4(4):479-86.
Grosjean, H., Modification and editing of RNA: historical overview and important facts to remember. Fine-tuning of RNA functions by modification and editing. Topics Curr Gen. Jan. 2005; 12: 1-22.
Gross, G. et al., Heterologous expression as a tool for gene identification and analysis. J Biol Chem. Jul. 31, 1995;41(2):91-110.
Grudzien, E. et al., Novel cap analogs for in vitro synthesis of mRNAs with high transiational efficiency. RNA. Sep. 2004;10(9):1479-87.
Grudzien-Nogalska, E. et al., Phosphorothioate cap analogs stabilize mRNA and increase translational efficiency in mammalian cells. RNA. Oct. 2007;13(10):1745-55. Epub Aug. 24, 2007.
Gryaznov, S.M., Oligonucleotide N3'→P5' phosphoramidates as potential therapeutic agents. Biochim Biophys Acta. Dec. 10, 1999;1489(1):131-40.
Guhaniyogi, J. et al., Regulation of mRNA stability in mammalian cells. Gene. Mar. 7, 2001;265(1-2):11-23.
Guo, L. et al., Structure and function of a cap-independent translation element that functions in either the 3' or the 5' untranslated region. RNA. Dec. 2000;6(12):1808-20.
Haas, J. et al., Codon usage limitation in the expression of HIV-1 envelope glycoprotein. Curr Biol. Mar. 1, 1996;6(3):315-24.
Hakelien, A.M. et al., Novel approaches to transdifferentiation. Cloning Stem Cells. 2002;4(4):379-87.
Hakelien, A.M., Reprogramming fibroblasts to express T-cell functions using cell extracts. Nat Biotechnol. May 2002;20(5):460-6.

Hambraeus, G. et al., A 5' stem-loop and ribosome binding but not translation are important for the stability of *Bacillus subtilis* aprE leader mRNA. Microbiology. Jun. 2002;148(Pt 6):1795-803.
Hancock, J.F., Reticulocyte lysate assay for in vitro translation and posttranslational modification of Ras proteins. Methods Enzymol. 1995;255:60-5.
Hannon, G.J. et al., Trans splicing of nematode pre-messenger RNA in vitro. Cell. Jun. 29, 1990;61(7):1247-55.
Harel, J., Action of polyribonucleotides, extracted by the phenol method, on the growth of mouse tumor cells. C.R. Hebd Seances Acad. Sci., 1962, 254:4390-2.
Harris, J. et al., An improved RNA amplification procedure results in increased yield of autologus RNA transfected dendritic cell-based vaccine. Biochim Biophys Acta. Jun. 20, 2005;1724(1-2):127-36. Epub Apr. 7, 2005.
Hausmann, R. Bacteriophage T7 genetics. Curr Top Microbiol Immunol. 1976:75:77-110.
Hays, E.F. et al., Induction of mouse leukaemia with purified nucleic acid preparations. Nature. Dec. 21, 1957;180(4599):1419-20.
He, K. et al., Synthesis and Separation of Diastereomers of Ribonucleoside 5'-(alpha-P-Borano)triphosphates. J Org Chem. Aug. 21, 1998;63(17):5769-5773.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Hedman, M, et al., Safety and feasibility of catheter-based local intracoronary vascular endothelial growth factor gene transfer in the prevention of postangioplasty and in-stent restenosis and in the treatment of chronic myocardial ischemia: phase II results of the Kuopio Angiogenesis Trial (KAT). Circulation. Jun. 3, 2003; 107(21): 2677-83. Epub May 12, 2003.
Heidenreich, O. et al., Chemically modified RNA: approaches and applications. FASEB J. Jan. 1993;7(1):90-6.
Heidenreich, O. et al., High activity and stability of hammerhead ribozymes containing 2'-modified pyrimidine nucleosides and phosphorothioates. J Biol Chem. Jan. 21, 1994;269(3):2131-8.
Heil, F. et al., Species-specific recognition of single-stranded RNA via toll-like receptor 7 and 8. Science. Mar. 5, 2004;303(5663):1526-9. Epub Feb. 19, 2004.
Heilman, K.L. et al., Internal 6-methyladenine residues increase the in vitro translation efficiency of dihydrofolate reductase messenger RNA. Int J Biochem Cell Biol. Jul. 1996; 28(7): 823-829.
Heiser, A. et al., Autologous dendritic cells transfected with prostate-specific antigen RNA stimulate CTL responses against metastatic prostate tumors. J Clin Invest. Feb. 2002;109(3):409-17.
Heiser, A. et al., Human dendritic cells transfected with renal tumor RNA stimulate polyclonal T-cell responses against antigens expressed by primary and metastatic tumors. Cancer Res. Apr. 15, 2001;61(8):3388-93.
Heiser, A. et al., Human dendritic cells transfected with RNA encoding prostate-specific antigen stimulate prostate-specific CTL responses in vitro. J Immunol. May 15, 2000;164(10):5508-14.
Heiser, A. et al., Induction of polyclonal prostate cancer-specific CTL using dendritic cells transfected with amplified tumor RNA. J Immunol. Mar. 1, 2001;166(5):2953-60.
Helbock, H.J. et al., N2-methyl-8-oxoguanine: a tRNA urinary metabolite—role of xanthine oxidase. Free Radic Biol Med. 1996;20(3):475-81.
Hemmi, H. et al., A Toll-like receptor recognized bacterial DNA. Nature. Dec. 7, 2000;408(6813):740-5.
Herweijer, H,. et al., Gene therapy progress and prospects: hydrodynamic gene delivery. Gene Ther. Jan. 2007;14(2):99-107. Epub Nov. 30, 2006.
Hess, M. et al., The effects of nucleic acids on pituitary ACTH content. Endocrinology. Mar. 1961;68:548-52.
Higman, M.A. et al., The mRNA (guanine-7-)methyltransferase domain of the vaccinia virus mRNA capping enzyme. Expression in *Escherichia coli* and structural and kinetic comparision to the intact capping enzyme. J Biol Chem. May 27, 1994;269(21):14974-81.
Higman, M.A. et al., The vaccina virus mRNA (guanine-N7-)-methyltransferase requires both subunits of the mRNA capping enzyme for activity. J Biol Chem. Aug. 15, 1992;267(23):16430-7.

(56) References Cited

OTHER PUBLICATIONS

Hilleren, P. et al., Mechanisms of mRNA surveillance in eukaryotes. Annu Rev Genet. 1999;33:229-60.

Hillman, N.W. et al., Chick Cephalogenesis. I. The Effect of RNA on Early Cephalic Development. PNAS, 1963, 50:486-93.

Ho, CS., et al., Electrospray ionisation mass spectrometry: Principles and clinical applications. Clin Biochem Rev. Feb. 2003; 24: 3-12.

Hoath, S.B. et al., The organization of human epidermis: functional epidermal units and phi proportionality. J Invest Dermatol. Dec. 2003;121(6):1440-6.

Hoerr, I. et al., In vivo application of RNA leads to induction of specific cytotoxic T lymphocytes and antibodies. Eur J Immunol. Jan. 2000;30(1):1-7.

Hoerr, I. et al., Stabilized Messenger RNA (RNActiveTM) as a Tool for Innovative Gene Delivery. Tissue Engineering. Apr. 2007; 13(4): 865-925.

Holcik, M. et al., Four highly stable eukaryotic mRNAs assemble 3' untranslated region RNA-protein complexes sharing cis and trans components. oc Natl Acad Sci U S A. Mar. 18, 1997;94(6):2410-4.

Holmes, D. et al., Cell positioning and sorting using dielectrophoresis. Eur Cell Mater. 2002; 4(2):120-2.

Holtkamp, S. et al., Modification of antigen-encoding RNA increases stability, translational efficacy, and T-cell stimulatory capacity of dendritic cells. Blood. Dec. 15, 2006;108(13):4009-17.

Kwissa, M. et al., Cytokine-facilitated priming of CD8+ T cell responses by DNA vaccination. J Mol Med (Berl). Feb. 2003;81(2):91-101. Epub Nov. 22, 2002.

Kwoh, D.Y. et al., Transcription-based amplification system and detection of amplified human immunodeficiency virus type 1 with a bead-based sandwich hybridization format. Proc Natl Acad Sci U S A. Feb. 1989;86(4):1173-7.

Lacour, F. et al., Transplantable malignant tumors in mice induced by preparations containing ribonucleic acid extracted from human and mouse tumors. J. Natl Cancer Inst., 1960, 24(2):301-27.

Lai, C.J. et al., Patterning of the neural ectoderm of *Xenopus laevis* by the amino-terminal product of hedgehog autoproteolytic cleavage. Development. Aug. 1995;121(8):2349-60.

Lai, S.K., et al., Rapid transport of large polymeric nanoparticles in fresh undiluted human mucus. PNAS. Jan. 30, 2007;104(5): 1482-1487.

Lai, S.K., et al., Mucus-penetrating nanoparticles for drug and gene delivery to mucosal tissues. Adv Drug Deliv Rev. Feb. 27, 2009; 61(2): 158-171.

Langer, T.S., et al., Transient nucleolar localization of U6 small nuclear RNA in *Xenopus laevis* oocytes. Mol Biol Cell. Jul. 2000;11(7):2419-28.

Langer, R., New methods of drug delivery. Science. Sep. 28, 1990;249(4976):1527-33.

Langford, C.J. et al., Evidence for an intron-contained sequence required for the splicing of yeast RNA polymerase II transcripts. Cell. Jun. 1983;33(2):519-27.

Larregina, A.T. et al., Changing paradigms in cutaneous immunology: adapting with dendritic cells. J Invest Dermatol. Jan. 2005;124(1):1-12.

Latarjet, R., Production of multiple cancers in mice having received nucleic acid extract from isologous & homologous leukemic tissues. C.R. Hebd Seances Acad. Sci., 1958, 246(5):853-5.

Lathe, R., Synthetic oligonucleotide probes deduced from amino acid sequence data: Theoretical and practical considerations. J Mol Biol. May 5, 1985;183(1):1-12.

Leader B., et al., Protein therapeutics: a summary and pharmacological classification. Nat Rev Drug Discov. Jan. 2008; 7(1): 21-39.

Lee, G. et al., Modeling pathogenesis and treatment of familial dysautonomia using patient-specific iPSCs. Nature. Sep. 17, 2009;461(7262):402-6. Epub Aug. 19, 2009.

Lee, J. et al., Molecular basis for the immunostimulatory activity of guanine nucleoside analogs: activation of Toll-like receptor 7. Proc Natl Acad Sci U S A. May 27, 2003;100(11):6646-51. Epub May 8, 2003.

Lee, J. T., et al., An arginine to glutamine mutation in residue 109 of human ornithine transcarbamylase completely abolishes enzymatic activity in Cos1 cells. J. Clin. Invest. Dec. 1989; 84: 1762-1766.

Lehto, T., et al., Cell-penetrating peptides for the delivery of nucleic acids. Expert Opin. Drug Deliv. Jul. 2012; 9(7): 823-836.

Leitner, W.W. et al., DNA and RNA-based vaccines: principles, progress and prospects. Vaccine. Dec. 10, 1999;18(9-10):765-77.

Lenz, A. et al., Human and murine dermis contain dendritic cells. Isolation by means of a novel method and phenotypical and functional characterization. J Clin Invest. Dec. 1993;92(6):2587-96.

Lerner, M.R. et al., Are snRNPs involved in splicing? Nature. Jan. 10, 1980;283(5743):220-4.

Lesaffre, B. et al., Direct non-cell autonomous Pax6 activity regulates eye development in the zebrafish. Neural Dev. Jan. 17, 2007;2:2.

Lewandowski, L.J. et al., Separation of the infectious ribonucleic acid of potato spindle tuber virus from double-stranded ribonucleic acid of plant tissue extracts. J Virol. Nov. 1971;8(5):809-12.

Lewis, David, Dynamic Polyconjugates (DPC) Technology: An elegant solution to the siRNA delivery problem. Arrowhead Research Corp (NASDAQ: ARWR). Nov. 2011.

Lewis, J.D. et al., The influence of 5' and 3' end structures on pre-mRNA metabolism. J Cell Sci Suppl. 1995;19:13-9.

Lewis, J.K., et al., Matrix-assisted laser desorption/ionization mass spectrometry in peptide and protein analysis. Enc of Anal Chem. 2000; R.A. Meyers (Ed.) 5880-5894.

Li, L. et al., Preparation and gene delivery of alkaline amino acids-based cationic liposomes. Arch Pharm Res. Jul. 2008;31(7):924-31. Epub Aug. 14, 2008.

Li, L. et al., Overcoming obstacles to develop effective and safe siRNA therapeutics. Expert Opin Biol Ther. May 2009;9(5): 609-19.

Li, X. et al., Generation of destabilized green flourescent protein as a transcription reporter. J Biol Chem. Dec. 25, 1998;273(52):34970-5.

Lian, T. et al., Trends and developments in liposome drug delivery systems. J Pharm Sci. Jun. 2001;90(6):667-80.

Liang, X.H. et al., The spliced leader-associated RNA is a trypanosome-specific sn(o) RNA that has the potential to guide pseudouridine formation on the SL RNA. RNA. Feb. 2002;8(2):237-46.

Licatalosi, D.D. et al., Splicing regulation in neurologic disease. Neuron. Oct. 5, 2006;52(1):93-101.

Linehan, D.C. et al., Tumor-specific and HLA-A2 restricted cytolysis by tumor-associated lymphocytes in human metastatic breast cancer. J Immunol. Nov. 1, 1995;155(9):4486-91.

Lobenberg, R. et al., Improved body distribution of 14C-labelled AZT bound to nanoparticles in rats determined by radioimmunography. J Drug Target. 1998;5(3):171-9.

Loging, W.T. et al., Identifying potential tumor markers and antigens by database mining and rapid expression screening. Genome Res. Sep. 2000;10(9):1393-402.

Lopez, M.F., et al., Selected reaction monitoring-mass spectrometric immunoassay responsive to parathyroid hormone and related variants. Clinical Chem. 2010; 56(2): 281-290.

Lopez-Berestein, G. et al., Treatment of systemic fungal infections with liposomal amphotericin B. Arch Intern Med. Nov. 1989;149(11):2533-6.

Lorenzi, J.C., et al., Intranasal vaccination with messenger RNA as a new approach in gene therapy: Use against tuberculosis. BMC Biotechnocol. Oct. 2010; 10(77): 1-11.

Lowe, T.M. et al., A computational screen for methylation guide snoRNAs in yeast. Science. Feb. 19, 1999;283(5405):1168-71.

Lowry, W.E., et al., Generation of human induced pluripotent stem cells from dermal fibroblasts. Proc Natl Acad Sci USA. Feb. 2008; 105(8): 2883-2888.

Lukkonen, B.G. et al., A conditional U5 snRNA mutation affecting pre-mRNA splicing and nuclear pre-mRNA retention identifies SSD1/SRK1 as a general splicing mutant suppressor. Nucleic Acids Res. Sep. 1, 1999;27 (17):3455-65.

Lund, P.E., et al., Pseudovirions as vehicles for the delivery of siRNA. Pharm Res. Mar. 2010; 27(3): 400-420. Epub Dec. 9, 2009.

Luo, D. et al., Synthetic DNA delivery systems. Nat Biotechnol. Jan. 2000;18(1):33-7.

Ma, B. et al., HPV pseudovirions as DNA delivery vehicles. Ther Deliv. Apr. 2011;2(4): 427-430.

(56) References Cited

OTHER PUBLICATIONS

Ma, X. et al., Pseudouridylation (Psi) of U2 snRNA in *S. cerevisiae* is catalyzed by an RNA-independent mechanism. EMBO J. Apr. 15, 2003;22(8):1889-97.
Mackie, G.A., Vectors for the synthesis of specific RNAs in vitro. Biotechnology. 1988;10:253-67.
Maden, B.E.H. et al., Classical and novel approaches to the detection and localization of the numerous modified nucleotides in eukaryotic ribosomal RNA. Biochime. 1995;77(1-2):22-9.
Magee, W.E. et al., Marked stimulation of lymphocyte-mediated attack on tumor cells by target-directed liposomes containing immune RNA. Cancer Res., 1978, 38(4):1173-6.
Malone, R.W. et al., Cationic liposome-mediated RNA transfection. Proc Natl Acad Sci U S A. Aug. 1989;86(16):6077-81.
Mannick, J.A. et al., Transformation of Nonimmune Lymph Node Cells to a State of Transplantation Immunity by RNA. A Preliminary Report, Ann. Surg., 1962, 156:356-66.
Mansour, S.L. et al., Disruption of the proto-oncogene int-2 in mouse embryo-derived stem-cells: a general strategy for targeting mutations to non-selectable genes. Nature, 1988, 336:348-52.
US 2002/0198163, 12/2002, Felgner et al. (withdrawn).
Abuchowki, A. et al., Immunosuppressive properties and circulating life of *Achromobacter glutaminase*-asparaginase covalently attached to polythylene glycol in man. Cancer Treat Rep. Nov.-Dec. 1981;65(11-12):1077-81.
Abuchowski, A. et al., Reduction of plasma urate levels in the cockerel with polyethylene glycol-uricase. J Pharmacol Exp Ther. Nov. 1981;219(2):352-4.
Aduri, R., et al., AMBER force field parameters for the naturally occuring modified nucleosides in RNA. J Chem Theory Comput. 2007; 3: 1464-1475.
Agaisse, H. et al., STAB-SD: a Shine-Dalgarno sequence in the 5' untranslated region is a determinant of mRNA stability. Mol Microbiol. May 1996;20(3):633-43.
Aissani, B. et al., CpG islands, genes and isochores in the genomes of vertebrates. Gene. Oct. 15, 1991;106(2):185-95.
Akashi, H., Gene expression and molecular evolution. Curr Opin Genet Dev. Dec. 2001;11(6):660-666.
Aksenova, N.N. et al., Influence of ribonucleic acids from the liver on implantation and growth of transplantable tumours. Nature. Nov. 3, 1962;196:443-4.
Alberts, et al., Miolecular Biology of the Cell, 3rd ed. Garland Publishing, Inc. New York, NY. 1994, pp. 369-369.
Aleku, M., et al., Atu027, a liposomal small interfering RNA formulation targeting protein kinase N3, inhibits cancer progression. Cancer Res. 2008; 68: 9788-9798.
Anderson, B.R., et al., Nucleoside modifications in RNA limit activation of 2'-5'-oligoadenylate synthetase and increase resistance to cleavage by Rnase L. Nucleic Acids Res. 2011: 1-10.
Anderson, D.M. et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.
Andrews-Pfannkoch, C. et al., Hydroxyapatite-mediated separation of double-stranded DNA, single-stranded DNA, and RNA genomes from natural viral assemblages. pl Environ Microbiol. Aug. 2010;76(15):5039-45. Epub Jun. 11, 2010.
Andries, O., et al., Comparison of the gene transfer efficiency of mRNA/GL67 and pDNA/GL67 complexes in respiratory cells. Mol Pharmaceutics. 2012; 9: 2136-2145.
Anichini, A. et al., Cytotixic T cells directed to tumor antigens not expressed on normal melanocytes dominate HLA-A2.1-restricted immune repertoire to melanoma. J Immunol. Jan. 1, 1996;156(1):208-17.
Aota, S. et al., Diversity in G + C content at the third position of codons in vertebrate genes and its cause. Nucleic Acids Res. Aug. 26, 1986;14(16):6345-55.
Apostolopoulos, V. et al., Cellular mucins: targets for immunotherapy. Crit Rev Immunol. 1994;14(3-4):293-309.

Archer, S.J., Induction of a T-cell specific antigen on bone marrow lymphocytes with thymus RNA. Immunology Jan. 1978;34(1):123-9.
Ashley, D.M. et al., Bone marrow-generated dendritic cells pulsed with tumor extracts or tumor RNA induce antitumor immunity against central nevrous system tumors. J Exp Med. Oct. 6, 1997;186(7):1177-82.
Ast, G., How did alternative splicing evolve? Nat Rev Genet. Oct. 2004;5(10):773-82.
Aurup, H. et al., Translation of 2'-modified mRNA in vitro and in vivo. Nucleic Acids Res. Nov. 25, 1994;22(23):4963-8.
Austyn, J.M. et al., New insights into the mobilization and phagocytic activity of dendritic cells. J Exp MNed. Apr. 1, 1996;183(4):1287-92.
Babich, F.R. et al., Cross-species transfer of learning: effect of ribonuclec acid from hamsters on rat behavior. Proc Natl Acad Sci U S A. Nov. 1965;54(5):1299-302.
Bachellerie, J.P. et al., Antisense snoRNAs: a family of nucleolar RNAs with long complementarities to rRNA. Trends Biochem Sci. Jul. 1995;20(7):261-4.
Bag, J., Recovery of normal protein synthesis in heat-shocked chicken myotubes by liposome-mediated transfer of mRNAs. Can. J. Biochem. Cell Biol. 1985: 63(3): 231-235.
Bagnall, et al., Rat strain difference on performance in the Morris water maze. Animal Technology. 1999. 50(2):69-77.
Baker, D.L., et al., RNA-guided RNA modification: functional organization of the archaeal H/ACA RNP. Genes Dev. May 15, 2005;19(10):1238-48. Epub May 3, 2005.
Bakker, J.M. et al, Therapeutic antibody gene transfer: an active approach to passive immunity. Mol Ther. Sep. 2004;10(3):411-6.
Balakin, A.G. et al., The RNA world of the nucleolus: two major families of small RNAs defined by different box elements with related functions. Cell. Sep. 6, 1996:86(5):823-34.
Bandbon Balenga, N.A. et al., Bicistronic expression plasmid encoding allergen and anti-IgE single chain variable fragment antibody as a novel DNA vaccine for allergy therapy and prevention. Med Hypotheses. 2006;67(1):71-4. Epub Mar. 2, 2006.
Banerjee, A.K., 5'-terminal cap structure in eucaryotic messenger ribonucleic acids. Microbiol Rev. Jun. 1980;44(2):175-205.
Barber, R., The chromatographic separation of ribonucleic acids. Biochim Biophys Acta. Feb. 21, 1966;114(2):422-4.
Bargmann, C.I. et al., The neu oncogene encodes an epidermal growth factor receptor-related protein. Nature. Jan. 16-22, 1986;319(6050):226-30.
Barlow, P.G., et al., The human cathelicidin LL-37 preferentially promotes apoptosis of infected airway epithelium. Am J Respir Cell Mol Biol. Dec. 2010; 43(6): 692-702.
Basha, G. et al., Influence of cationic lipid composition on gene silencing properties of lipid nanoparticle formulations of siRNA in antigen-presenting cells. Mol Ther. Dec. 2011; 19(12): 2186-2200.
Bechler, K., Influence of capping and polydenylation on mRNA expression and on antisense RNA mediated inhibition of gene expression. Biochem Biophys Res Commun. Dec. 8, 1997;241(1):193-9.
Baljanski, et al., Iron stimulated RNA-dependent DNA polymerase activity from goldfish eggs. Cell Mol Biol. 1988;34(1):17-25.
Belliveau, N.M., et al., Microfluidic synthesis of highly potent limit-size lipid nanoparticles for in viro delivery of siRNA. Mol Ther Nucleic Acids. Aug. 2012; 1(8): e37.
Bernardi, G. et al., The vertebrate genome: isochores and evolution. Mol Biol Evol. Jan. 1993;10(1):186-204.
Bernhard, H. et al., Generation of immunostimulatory dendritic cells from human CD34+ hematopoietic progenitor cells of the bone marrow and peripheral blood. Cancer Res. Mar. 1, 1995;55(5):1099-104.
Bernstein, E. et al., Role for a bidentate ribonuclease in the initiation step of RNA interference. Nature Jan. 18, 2001;409(6818):363-6.
Bernstein, P. et al., Poly(A), poly(A) binding protein and the regulation of mRNA stability. Trends Biochem Sci. Sep. 1989;14(9():373-7.
Bertolini, M.C., et al., Fractionation of immune RNA isolated from the spleens of mice infected with *Trypanosoma cruz*. J Infect Dis. Jun. 1981;143(6):827-31.
Bertolini, In vitro effect of 18S immune RNA on macrophage resistance to *Trypanosoma cruzi*. Cell Mol Biol. 1986;32(2):167-71.

(56) References Cited

OTHER PUBLICATIONS

Bertolini, The protective effect of the 4-5S immune RNA against *Trypanosoma cruzi* infection in mice. Trop Med Parasitol. Sep. 1985;36(3):131-4.

Bertrand, E. et al., Assembly and traffic of small nuclear RNPs. Prog Mol Subcell Biol. 2004;35:79-97.

Bettinger, T. et al., Peptide-mediated RNA delivery: a novel approach for enhanced transfection of primary and post-mitotic cells. Nucleic Acids Res. Sep. 15, 2001;29(18):3882-91.

Bevan, M.J. et al., Antigen presentation to cytototix T lymphocytes in vivo. J Exp Med. Sep. 1, 1995;182(3):639-41.

Bevilacqua, A. et al., Post-transcriptional regulation of gene expression by degradation of messenger RNAS. J Cell Physiol. Jun. 2003;195(3):356-72.

Bieler, K. et al., Plasmids for Therapy and Vaccination. Wiley-VCH GmbH. Weinheim, Feb. 2001.

Binder, R. et al., Evidence that the pathway of transferrin receptor mRNA degradation involves an endonucleolytic cleavage within the 3' UTR and does not involve poly(A) tail shortening. EMBO J. Apr. 15, 1994;13(8):1969-80.

Conry, R.M. et al., Immune response to a carcionoembryonic antigen polynucleotide vaccine. Cancer Res. Mar. 1, 1994;54(5):1164-8.

Copreni, E. et al., Lentivirus-mediated gene transfer to the respiratory epithelium: a promising approach to gene therepy of cystic fibrosis. Gene Ther. Oct. 2004;11 Suppl 1:S67-75.

Cortes, J.J. et al., Mutations in the conserved loop of human U5 snRNA generate use of novel cryptic 5' splice sites in vivo. EMBO J. Dec. 15, 1993;12(13):5181-9.

Coughlin, C.M. et al., Targeting adult and pediatric cancers via cell-based vaccines and the prospect of activated B lymphocytes as a novel modality. Cancer Biol Ther. Sep.-Oct. 2003;2(5):466-70.

Cox, G.J. et al., Bovine herpesvirus 1: immune responses in mice and cattle injected with plasmid DNA. J Virol. Sep. 1993;67(9):5664-7.

Craig, J.M. et al., The distribution of CpG islands in mammalian chromosomes. Nat Genet. Jul. 1994;7(3):376-82.

Cramer, P. et al., Functional association between promoter structure and transcript alternative splicing. Proc Natl Acad Sci U S A. Oct. 14, 1997;94(21):11456-60.

Cree, B. et al., Tolerability and effects of rituxamab (anti CD20 antibody) in neuromyelitis optica (NMO) and rapidly worsening multiple sclerosis (MS). Neurology. 2004; 62(S5):A492.

Culver, K.W. et al., Gene Therapy. A Handbook for Physicians. Mary Ann Lieber, Inc. New York. 1994; 63-77.

Cunningham, S. et al., AAV2/8-mediated correction of OTC deficiency is robust in adult but not neonatal Spf^ash Mice. Mol Ther. Aug. 2009; 17(8): 1340-1346.

Daguer, J.P. et al., Increasing the stability of sacB transcript improves levansucrase production in *Bacilius subtilis*. Lett Appl Microbiol. 2005;41(2):221-6.

Dai, M.S. et al., Introduction of human erythropoietin receptor complementary DNA by retrovirus-mediated gene transfer into murine embryonic stem cells enhances erythropoiesis in developing embryoid bodieds. Biol Blood Marrow Transplant. 2000;6(4):395-407.

Davidson, E.H., An Analysis of Niu Menchang's Research on Transformation by RNA. Biotechnology in China, 1989, 92-102.

Davis, H.L. et al., DNA-based immunization induces continuous secretion of hepatitis B surface antigen and high levels of circulating antibody. Hum Mol Genet. Nov. 1993;2(11):1847-51.

De Carvalho, S. et al., Biologic properties of human leukemic and tumoral RNA. IV. Leukemia and neoplasms induced in mice with human leukemic RNA carried in tissue culture. J Lab Clin Med. May 1960;55:706-14.

De Carvalho, S. et al., Comparative effects of liver and tumour ribonucleic acids on the normal liver and the Novikoff hepatoma cells of the rat. Nature. Mar. 11, 1961;189:815-7.

De Carvalho, S. et al., Differences in information content of ribonucleic acids from malignant tissues and homologous organs as expressed by their biological activities. Exp Mol Pathol. Apr. 1962;1:96-103.

De Carvalho, S., Angiokines, angiogenesis and angiolymphoproliferative syndromes (ALPS). Angiology. Apr. 1983;34(4):231-43.

De Carvalho, S., Biologic properties of human leukemic and tumoral RNA, III. The effect of different media on the cytopathogenicitv in tissue culture. J Lab Clin Med. May 1960;55:694-705.

De Carvalho, S., Cancer 1974: an analytical vademecum of oncologic relevance. Oncology. 1973;28(4):289-98.

De Carvalho, S., Effect of RNA from normal human bone marrow on leukaemic marrow in vivo. Nature. Mar. 16, 1963;197:1077-80.

De Carvalho, S., Epigenetic transformation by RNA from human neoplastic cells. Oncology. 1973;27(1):3-29.

De Carvalho, S., In vitro angiogenic activity of RNA from leukemic lymphocytes. Angiology. Jul. 1978;29(7):497-505.

De Carvalho, S., Natural history of cogenital leukemia. An experiment of nature revealing unexplored features of fetal-material isoimmunity, longest recorded survival following use of leukemostatic maternal isoantibody. Oncology. 1973;27(1):52-63.

De Lucca, F.L., et al., Effect of the calcium phosphate-mediated RNA uptake on the transfer of cellular immunity of a synthetic peptide of HIV-1 to human lymphocytes by exogenous RNA. Mol Cell Biochem. Dec. 2001;228(1-2):9-14.

DeLafontaine, P. et al., Regulation of vascular smooth muscle cell insulin-like growth factor I receptors by phosphorothioate oligonucleotides. Effects on cell growth and evidence that sense targeting at the ATG site increases receptor expression. J Biol Chem. Jun. 16, 1995;270(24):14383-8.

Deres, K. et al., In vivo priming of virus-specific cytotoxic T lymphocytes with synthetic lipopeptide vaccine. Nature. Nov. 30, 1989;342(6249):561-4.

Deshayes, S. et al., Cell-penetrating peptides: tools for intracellular delivery of therapeutics. Cell Mol Life Sci. Aug. 2005;62(16):1839-49.

Desrosiers, R. et al., Identification of methylated nucleosides in messenger RNA from Novikoff hepatoma cells. Proc Natl Acad Sci U S A. Oct. 1974;71(10):3971-5.

Diebold, S.S. et al., Innate antiviral responses by means of TLR7-mediated recognition of single-stranded RNA. Science. Mar. 5, 2004;303(5663):1529-31. Epub Feb. 19, 2004.

Dimari, J.F. et al., Initiation of mRNA decay in *Bacillus subtilis*. Mol Bicrobiol. Mar. 1993;7(5):705-17.

Ding, Z., et al., State-of-the-art 2003 on PKU gene therapy. Mol Genet Metab. Jan. 2004;81(1):3-8.

Dingman, W. et al., Molecular theories of memory. Science. Apr. 3, 1964;144(3614):26-9.

Disbrow, G.L. et al., Codon optimization of the HPV-16 E5 gene enhances protein expression. Virology. Jun 20, 2003;311(1):105-14.

Dong, Y. et al., Poly(d.l-lactide-co-glycolide)/montmorillonite nanoparticles for oral delivery of anticancer drugs. Biomaterials. Oct. 2005;26(30):6068-76.

Donnelly, J. et al., Technical and regulatory hurdles for DNA vaccines. Int J Parasitol. May 2003;33(5-6):457-67.

Dubes, G.R. and Klingler, E.A. Jr. Facilitation of infection of monkey cells with poliovirus "ribonucleic acid." Science. Jan. 1961; 133(3446): 99-100.

Dunham, S.P. et al., The application of nucleic acid vaccines in veterinary medicine. Res Vet Sci. Aug. 2002;73(1):9-16.

Dunn, J.J. et al., Different template specificities of phage T3 and T7 RNA polymerases. Nat New Biol. Mar. 17, 1971;230(11):94-6.

Duret, L. et al., Expression pattern and surprisingly, gene length shape codon usage in *Caenorhabditis, Drosophila*, and *Arabidopsis*. Proc Natl Acad Sci U S A. Apr. 13, 1999;96(8):4482-7.

Duret, L., Evolution of synonymous codon usage in metazonas. Curr Opin Genet Dev. Dec. 2002;12(6):640-9.

Earl, R.A., et al., A chemical synthesis of the nucleoside 1-Methylpseudouridine. A facile chemical synthesis of 1-methylpseudouridine has been accomplished by direct methylation of pseudouridine. J Heterocylic Chem. Jun. 1977;14:699-700.

Easton, L.E. et al., Rapid, nondenaturing RNA purification using weak anion-exchange fast performance liquid chromatography. RNA. Mar. 2010;16(3):647-53. Epub Jan. 25, 2010.

Eberwine, J. et al., Analysis of gene expression in single live neurons. Proc Natl Acad Sci U S A. Apr. 1, 1992;89(7):3010-4.

(56) References Cited

OTHER PUBLICATIONS

Edelstein, M. L. et al., Gene therapy clinical trials worldwide 1989-2004—an overview. J Gene Med. Jun. 2004;6(6):597-602.
Edery, I. et al., An efficient strategy to isolate full-length cDNAs based on an mRNA cap retention procedure (CAPture). Mol Cell Biol. 1995; 15(6): 3363-3371.
Edmonds, M., Polyadenylate polymerases. Methods Enzymol. 1990:181:161-70.
Egeter, O. et al., Eradication of disseminated lymphomas with CpG-DNA activated T helper type 1 cells from nontransgenic mice. Cancer Res. Mar. 15, 2000;60(6):1515-20.
El Ouahabi, A., et al., Double long-chain amidine liposome-mediated self replicating RNA transfection. FEBS Letters. Feb. 1996; 380(1-2): 108-112.
Elango, N., et al., Optimized transfection of mRNA transcribed from a d(A/T)100 tall-containing vector. Biochem Biophys Res Commun. 2005; 330: 958-966.
Probst, J., et al., Spontaneous cellular uptake to exogenous messenger RNA in vivo is nucleic acid-specific, saturable and ion dependent. Gene Therapy. 2007; 14: 1175-1180.
Puga, A., et al., Diference between functional and structural integrity of messenger RNA. Proc Natl Acad Sci U S A. Jul. 1973;70(7):2171-5.
Pulford, B., et al., Liposome-siRNA-peptide complexes cross the blood-brain barrier and significantly decrease $PrP^AC$ on neuronal cells and $PrP^ARES$ in infected cell cultures. PLoS ONE. 2010; 5(6): e11085.
Purchio, A.F. et al., [24] Methods for molecular cloning in eukaryotic cells. Methods Enzymol. 1979; 68:357-75.
Query, C.C. et al., Branch nucleophile selection in pre-mRNA splicing; evidence for the bulged duplex model. Genes Dev. Mar. 1, 1994;8(85):587-97.
Rabinovich, P.M., et al., Synthetic messenger RNA as a tool for gene therapy. Hum. Gen Ther. Oct. 17, 2006; 1027-1035.
Rabinovich, P.M., et al., Chemeric receptor mRNA transfection as a tool to generate Antineoplastic Lymphocytes. Hum. Gene Ther. Jan. 2009; 20: 51-61.
Raff, M., Adult stem cell plasticity: fact or artifact? Annu Rev Cell Biol. 2003;19:1-22.
Rajagopalan, L.E. et al., Turnover and translation of in vitro synthesized messenger RNAs in transfected, normal cells. J Biol Chem. Aug. 16, 1996;271(33):19871-6.
Ramazeilles, C. et al., Antisense phoaphorothioate oligonucleotides: selective killing of the intracellular parasite *Leishmania amazonensis*. Proc Natl Acad Sci U S A. Aug. 16, 1994;91(17):7859-63.
Rammensee, H.G. et al., Peptides naturally presented by MHC class I molecules. Annu Rev Immunol. 1993;11:213-44.
Rascati, R.J. et al., Characterization of Fv-1 gene-produce-mediated resistance transfer. Intervirology. 1981;15(2):87-96.
Ratajczak, J. et al., Embryonic stem cell-derived microvesicles reprogram hematopoletic progenitors: evidence for horizontal transfer of mRNA and protein delivery. Leukemia. May 2006;20(5):847-86.
Ratajczak, J. et al., Membrane-derived microvesicles: important and underappreciated mediators of cell-to-cell communication. Leukemia. Sep. 2006;20(9):1487-95. Epub Jul. 20, 2006.
Read, M.L., et al., A versatile reducible polycation-based system for efficient delivery of a broad range of nucleic acids. Nucleic Acids Res. 2005; 33(9): e86.
Reddy, A. et al., The effect of labour and placental separation on the shedding of syncytiotrophoblast microparticles, cell-free DNA and mRNA in normal pregnancy and pre-eclampsia. Placenta. Nov. 2008;29(11):942-9. Epub Oct. 1, 2008.
Reed, R. et al., Intron sequences involved in lariat formation during pre-mRNA splicing. Cell. May 1985;41(1):95-105.
Regnier, P. et al., Degradation of mRNA in bacteria; emergence of ubiquitous features. Bioessays. Mar. 2000;22(3):235-44.
Rejman, J., et al., mRNA transfection of cervical carcinoma and mesenchymal stem cells mediated by cationic carriers. J Controlled Rel. Nov. 2010; 147(3): 385-391.
Renkvist, N. et al., A listing of human tumor antigens recognized by T cells. Cancer Immunol Immunother. Mar. 2001;50(1);3-15.
Reyes-Sandoval, A. et al., DNA Vaccines. Curr Mol Med. May 2001;1(2):217-43.
Raynolds, B.A. et al., Generation of neurons and astrocytes from isolated cells of the adult mammalian central nervous system. Science. Mar. 27, 1992;255(5052):1707-10.
Ruhnke, M. et al., Long-term culture and differentiation of rat embryonic stem cell-like cells into neuronal, glial, endothelial, and hepatic lineages. Stem Cells. 2003;21(4):428-36.
Richter, J.D., Cytoplasmic polyadenylation in development and beyond. Microbiol Mol Biol Rev. Jun. 1999;63(2):446-56.
Roberts, J.N. et al., Genital transmission of HPV in a mouse model is potentiated by nonoxynol-9 and inhibited by carrageenan. Nat Med. Jul. 2007; 13(7): 857-861.
Robbins, P.F. et al., Human tumor antigens recognized by T cells. Curr Opin Immunol. Oct. 1996;8(5):628-36.
Robinson, F. et al., Expression of human nPTB is limited by extreme suboptimal codon content. PLoS One, Mar. 12, 2008;3(3):e1801.
Robinson, H.L. et al., Protection against a lethal influenza virus challenge by immunization with a heamagglutinin-expressing plasmid DNA Vaccine. 1993;11(9):957-60.
Robles, A.I. et al., Reduced skin tumor development in cyclin D1-dificient mice highlights the oncogenic ras pathway in vivo. Genes Dev. Aug. 15, 1998;12(16):2469-74.
Rock, K.L. et al., A new foreign policy: MHC class I molecules monitor the outside world. Immunol Today. Mar. 1996;17(3):131-7.
Rodriguez, P.L., et al., Minimal "self" peptides that inhibit phagocytic clearance and enhance delivery of nanoparticles. Science. Feb. 22, 2013; 339(6122): 971-975.
Rohloff, C.M., et al., DUROS® Technology delivers peptides and proteins at consistent rate continuously for 3 to 12 months. J Diabetes Sci Technol. May 2008; 2(3): 461-467.
Romani, N. et al., Generation of mature dendritic cells from human blood. An improved method with special regard to clinical applicability. J Immunol Methods. Sep. 27, 1996;196(2):137-51.
Romani, N. et al., Presentation of exogenous protein antigens by dendritic cells to T cell clones. Intact protein is presented best by immature. epidermal Langerhans cells. J Exp Med. Mar. 1, 1989;189(3):1169-78.
Rosa, A., et al., Synthetic mRNAs: Powerful tools for reprogramming and differentiation of human cells. Cell Stem Cell. Nov. 2010; 7: 549-550.
Rosenberg, S.A. et al., Cancer immunotherapy: moving beyond current vaccines. Nat Med. Sep. 2004;10(9):909-15.
Ross, B.S. et al., Synthesis and incorporation of 2'-O-methyl-pseudouridine into oligonucleotides. Nucleosides and Nucleotides. 1997; 16(7/9):1547-9.
Ross, J. Control of messenger RNA stability in higher eukaryotes. Trends Genet. May 1996;12(5):171-5.
Rossi, Derrick, Open letter Entitled "Change to mRNA Reprogramming Protocol" Publication Date: Aug. 13, 2011 ("Rossi")(available at Addgene website: http://www.addgene.org/static/data/83/87/3686c0f2-c9a2-11e0-b8a9-003048dd8500.pdf, last retrieved Mar. 17, 2013).
Ryser, M., et al., S1P1 overexpression stimulates S1P-dependent chemotaxis of human CD34+ hematopoietic progenitor cells but strongly inhibits SDF-1/CXCR4-dependent migration and in vivo homing. Mol Immunology. 2008, 46: 166-171.
Saenz-Badillos, J. et al., RNA as a tumor vaccine: a review of the literature. Exp Dermatol. Jun. 2001;10(3):143-54.
Saison-Behmoaras, T. et al., Short modified antisense oligonucleotides directed against Ha-ras point mutation induce selective cleavage of the mRNA and inhibit T24 cells proliferation. EMBO J. May 1991;10(5):1111-8.
Saito, K. et al., Cell participation in immune response by immune ribonucleic acid. I. The role of T lymphocytes in immune response by immune RNA against T-depedent antigens. Immunology. Dec. 1980;41(4):937-45.
Saito, R., et al., Distribution of liposomes into brain and rat brain tumor models by convetion-enhanced delivery monitored with magnetic resonance imaging. Cancer Res. Apr. 2004; 64: 2572-2579.

(56) References Cited

OTHER PUBLICATIONS

Sakuma, S. et al., Mucaodhesion of polystyrene nanoparticles having surface hydrophilic polymeric chains in the gastrointestinal tract. Int J Pharm. Jan. 25, 1999;177(2):161-72.
Sallusto, F. et al., Dendritic cells use macropinocytosis and the mannose receptor to concentrate macromolecules in the major histocompatibility complex class II compartment: downregulation by cytokines and bacterial products. J Exp Med. Aug. 1, 1995;182(2):389-400.
Sallusto, F. et al., Efficient presentation of soluble antigen by cultured human dendritic cells is maintained by granulocyte/macrophage colony-stimulating factor plus interleukin 4 and downregulated by tumor necrosis factor alpha. J Exp Med. Apr. 1, 1994;179(4):1109-18.
Samarsky, D.A. et al., The snoRNA box C/D motif directs nucleolar targeting and also couples snoRNA synthesis and localization. EMBO J. Jul. 1, 1998;17(13):3747-57.
Santini, S.M. et al., Type I interferon as a powerful adjuvant for monocyte-derived dendritic cell development and activity in vitro and in Hu-PBL-SCID mice. J Exp Med. May 15, 2000;191(10):1777-88.
Sanyal, S. et al., Effects of RNA on the developmental potentiality of the posterior primitive streak of the chick blastoderm. Proc Natl Acad Sci U S A. Apr. 1966;55(4):743-50.
Trollet et al., Delivery of DNA into muscle for treating systemic diseases: advantages and challenges. Methods Mol. Biol. 2008., 423: 199-214.
Lorenzi, J.C., et al., Protein expression from exogenous mRNA: Uptake by receptor-mediated endocytosis and trafficking via the lysosomal pathway. RNA Biology, vol. 8, No. 4, Jul. 1, 2011, pp. 252-258.
Kassim et al., Gene Therapy in A humanized Mouse Model of Familial Hypercholesterolemia Leads to a Marked Regression of Atherosclerosis, PLOS ONE, Oct. 2010, vol. 5, Issue 10, pp. e13424.
Supplementary Data from Zhang et al., (J. Biol. Chem 282(25) 18602-12, 2007.
Bell et al., Predisposition to Cancer Caused by Genetic and Functional Defects of Mammalian Atad5, PLOS Genetics, Aug. 2011, vol. 7, Issue 8, e1002245 pp. 1-15.
Gupta et al., Project Report Condon Optimization, 2003, pp. 1-13.
Whiteside, George, The Orgins and the future of microfluidics, Nature, vol. 442, Jul. 27, 2006 pp. 368-373.
Pridgen, et al.; Transepithelial Transport of Fc-Targeted Nanoparticles by the Neonatal Fc Receptor for Oral Delivery, Sci Translation Med., vol. 5, Issue 213, Nov. 27, 2013, pp. 1-8.
Nguyen, M. et al., Injectable Biodegradable Hydrogels, Macromolecular Bioscience, 2010,10, 563-579.
Morton, S. Scalable Manufacture of Built-to-Order Nanomedicine: Spray-Assisted Layer-by-Layer Functionalization of Print Nanoparticles, Advanced Materials, 2013, 25, 4708-4712.
Cu, Y. et al., Enhanced Delivery and Potency of Self-Amplifying mRNA Caccines by Electroporation in Situ, Vaccines, 2013, 1, 367-383.
Chang, C. et al., Non-ionic amphiphilic biodegradable PEG-PLGA-PEG copolymer enhances gene delivery efficiency in rat skeletal muscle; Science Direct, Journal of Controlled Release 118 (2007) 245-253.
Stroock, A. et al., Chaotic Mixer for Microchannels, Science, vol. 295, Jan. 25, 2002, pp. 1-6.
Zangi, L. et al., Modified mRNA directs the fate of heart progenitor cells and indices vasuclar regeneration after myocardial infarction, Nature Biology, Advanced Online Publication, May 10, 2013, pp. 1-9.
Valencia, P. et al., Microfluidic Platform for Combinatorial Synthesis and Optimization of Targeted Nanoparticles for Cancer Therapy, ACS Nano. Dec. 23, 2013; 7(12):10671-80.
Chen, Y., Self-assembled rosette nanotubes encapsulate and slowly release dexamethasone, International Journal of Nanomedicine, 2011:6 pp. 1035-1044.
Mitragotri, S.; Devices for Overcoming Biological Barriers: The use of physical forces to disrupt the barriers, Advance Drug Delivery Reviews, 65 (2013)100-103.
Wang, X; Re-evaluating the Roles of Proposed Modulators of Mammalian Target of Rapamycin Complex 1 (mTORCI) Signaling,The Journal of Biological Chemistry, Nov. 7, 2008, vol. 283, No. 45, pp. 30482-30492.
Dreyer Hans C., Leucine-enriched essential amino acid and carbohydrate ingestion following resistance exercise ehances mTOR signaling and protein synthesis in human muscle, AM J. Physiol Endocrinol Metab,; 294; E392-E400,2008.
Laiatsa, Aikaterini, Amphiphilic poly (I-amino acids)—New materials for drug delivery. Journal of Controlled Release, 161 (2012) 523-536.
Stelic Institute & Co., Contract Research Services Specialized in NASH-HCC, Ver.2012.11, 2012, 99.1-10.
Limberis, M et al., Intranasal Antibody Gene Transfer in Mice and Ferrets Elicits Broad Protection Against Pandemic Influenza, Science Transl Med vol. 5, Issue 187, 99, 1-8.
Wei, et al., Induction of Broadly Neutralizing H1N1 Influenza Antibodies by Vaccination, Science vol. 329, (2010) pp. 1060-1064.
Palese, P., Making Better Influenza Virus Vaccines?, Emerging Infectious Diseases, vol. 12, No. 1, Jan. 2006, pp. 61-65.
Kwong, P et al., Broadly Neutralizing Antibodies and the Search for an HIV-1 Vaccine: The End of the Beginning, Nature Reviews, Immunology, vol. 13, Sep. 2013, pp. 693-701.
DeMarco, et al., A Non-VH1-69 Hetetrosubtypic Neutrilizing Human Minoclonal Antibody Protects Mice Against H1N1 and H5N1 Viruses, PLOS One, Apr. 2012, vol. 7, Issue 4, pp. 1-9.
Anderson, et al., The Bridge, National Academy of Engineering of the National Academies, Fall 2006, vol. 36., Nov. 3, pp. 1-55.
Hillery et al., Effects of altering dosing on cationic liposomemediated gene transfer to the respiratory epithelium. Gene Therapy (1999) 6, 1313-1316.
Tripathy, Sandeep et al., Long-term expression of erythopoietin in the systemic circulation of mice after intramuscular injection of a plasmid DNA vector, Proc. Natl. Acad. Sci. USA 93, 1996, pp. 10670-10880.
Yarovoi, Helen, et al., Factor VIII ectopically expressed in platelets: efficacy in hemophilia A treatment, Blood Journal, Dec. 1, 2003, olume 102, No. 12, pp. 4005-4013.
Kenneth Stanley, Design of Randomized Controlled Trials, Circulation, 2007; 115: pp. 1164-1169.
Chen XL., et al., Expression of human factor IX in retrovirus-transfected human umbilical cord tissue derived mesenchymal stem cells, PubMed, Feb. 2009; 17 (1): 184-87.
Cowling (Jan. 15, 2010, online Dec. 23, 2009, "Regulation of mRNA cap methylation," Biochemical Journal, 425 (Pt 2): 295-302.
Kozak, Marilyn, Regulation of translation via mRNA structure in prokaryotes and eukaryotes, Gene 361 (2005), pp. 13-37.
Fuke, Hiroyuki et al., Role of poly (A) tail as an identity element of mRna nuclear export, Nucleic Acids Research, 2008, vol. 36 No. 3, pp. 1037-1049.
Tracy, M., "Progress in the Development of LNP Delivery for siRNA Advancing LNPs to the Clinic," International Liposome Research Days Meeting, Vancouver, Canada. Aug. 2010, pp. 1-52.
Epicentre Forum. Mels et al.,Tools and Techniques for Genomics and RNA Research. 2007; 14(1); 1-24.
Anderson, B.R., et al., Incorporation of pseudouridine into mRNA enhances translation by diminishing PKR activation, Nucleic Acids Res. vol. 38, No. 17, Sep. 1, 2010, pp. 5884-5892.
Kariko, K. et al , Generating the optimal mRNA for therapy: HPLC purification eliminates immune activation and improves translation of nucleoside-modified, protien-encoding mRNA. Nucleic Acids Res. vol. 39, No. 21, Nov. 1, 2011 pp. e142-1, XP002696190.
Love et al., Lipid-like materials for low-dose, in vivo genes silencing, PNAS vol. 107 No. 5, pp. 1864-1869, Feb. 2, 2010.
Mockey et al., mRNA-based cancer vaccine: prevention of B16 melanoma progression and metastasis by systemic injection of MART1 mRNA histidylated lipopolyplexes, Cancer Gene Therapy, 2001, 14, pp. 802-814.
Kwon et al. Molecular Basis for LDL receptor recognition by PCSK9. PNAS. 2008 105(6), 1820-1825.

(56) References Cited

OTHER PUBLICATIONS

Bates et al., Detection of Familial Hypercholesterolaemia: A Major Treatment Gap in Preventative Cardiology, Heart, Lung and Circulation 2008;17:411-413.
Garber et al.; A sensitive and convenient method for lipoprotein profile analysis of individual mouse plasma samples. Journal of Lipid Research. 2000. 14: 1020-1026.
Goldstein et al., History of Discovery: The LDL Receptor, Arterioscler Thromb Vasc Biol. Apr. 2009 ; 29(4): 431-438.
Hovingh et al., Diagnosis and treatment of familial hypercholesterolaemia, European Heart Journal (2013) 34, 962-971.
Kobayashi et al., Roles of the WHHL Rabbit in Translational Research on Hypercholesterolemia and Cardiovascular Diseases, Journal of Biomedicine and Biotechnology, vol. 2011, Article ID 406473, pp. 1-10.
Lambert et al., Thernatic Review Series: New Lipid and Lipoprotein Targets for the Treatment of Cardiometabolic Diseases The PCSK9 decade, Journal of Lipid Research vol. 53, 2012 pp. 2515-2524.
Lipari et al., Furin-cleaved Proprotein Convertase Subtilisin/Kexin Type 9 (PCSK9) is Active and Modulates Low Density Lopoprotein Receptor and Serum Cholesterol Levels. J Biol Chem. 2012, 287(52); 43482-43491.
Surdo et al., Mechanistic implications for LDLreceptor degradation from the PCSK9/LDLR structure at neutral pH, European Molecular Biology Organization, vol. 12 | No. 12 | 2011, pp. 1300-1130.
McNutt et al., Antagonism of Secreted PCSK9 Increases Low Density Lipoprotein Receptor Expression in HepG2 Cells. J Biol Chem. 2009. 284(16): 10561-10570.
Rader et al., Monogenic hypercholesterolemia: new insights in pathogenesis and treatment, J. Clin. Invest. 111:1795-1803 (2003).
Stein et al., Effect of a Monoclonal Antibody of PCSK9 on LDL Cholesterol, N Engl J Med 2012;366:1108-18.
Watts et al., Familial hypercholesterolemia: a missed opportunity in preventive medicine, Nature Clinical Practice, Cardiovascular Medicine, Aug. 2007 , vol. 4, No. 8, pp. 404-405.
Zhang et al., Binding of Proprotein Convertase Subtilisin/Kexin Type 9 to Epidermal Growth Factor-like Repeat A of Low Density Lipoprotein Receptor Decreases Receptor Recycling and Increases Degradation. The Journal of Biological Chemistry, vol. 282, No. 25, pp. 18602-18612, Jun. 22, 2007.
Penheiter et al., Type II Transforming Growth Factor-β Receptor Recyclins is Dependent upon the Clathrin Adaptor Protein Dab2, Molecular Biology of the Cell, vol. 21, 4009-4019, Nov. 15, 2010.
Song et al., A putative role of micro RNA in regulation of cholesterol 7α-hydroxylase expression in human hepatocytes, Nature Blotechnol. 2005, 23:709-717.
Beigneux et al., Human CYP7A1 deficiency: progress and enigmas; The Journal of Clinica Investigation; Jul. 2002, vol. 110, No. 1, pp. 29-31.
Pullinger et al., Human cholesterol 7α-hydroxylase (CYP7A1) deficiency has a hypercholesterolemic phenotype, J. Clin Invest. 110:109-117 (2002).
Akinc et al., Targeted Delivery of RNAi Therapeutics With Endogenous and Exogenous Ligand-Based Mechanisms, Mol The. 2009 17:872-879.
Yamamoto et al., Current prospects for mRNA gene delivery, European Journal of Pharmaceutics and Biopharmaceutics 71 (2009) 484-489.
Vilee, D.B., Ribonucleic acid; control of steroid synthesis in endocrine tissue. Science. Nov. 3, 1967;158(3801):652-3.
Villaret, D.B. et al., Identification of genes overexpressed in head and neck squamous cell carcinoma using a combination of complementary DNA subtraction and microarray analysis. Laryngoscope. Mar. 2000;110(3 Pt 1):374-81.
Virovic, L. et al., Novel delivery methods for treatment of viral hepatitis: an update. Exppert Opin Drug Deliv. Jul. 2005;2(4):707-17.
Viza, D. et al., Human lymphoblastoid cells in culture replicate immune information carried by xenogeneic RNA. Differentiation. 1978;11(3):181-4.

Wagner, E. Polymers for siRNA delivery: Inspired by viruses to be targeted, dynamic, and precise. Acc Chem Res. 2012; 45(7): 1005-1013.
Wahle, E. Poly(A) tail length control is caused by termination of processive synthesis. J Biol Chem. Feb. 10, 1995; 270(6): 2800-2808.
Wang, B. et al., Gene inoculation generates immune responses against human immunodeficiency virus type 1. Proc Natl Acad Sci U S A. May 1, 1993;90(9):4156-60.
Wang, B. et al., Immunization by direct DNA inoculatuion induces rejection of tumor cell challenge. Hum Gene Ther. Apr. 1995;6(4):407-18.
Wang, B.S. et al., Fractionation of immune RNA capable of transferring tumor-specific cellular cytotoxicity. Cell Immunol. May 1978;37(2):358-68.
Wang, S.P. et al., Phylogeny of mRNA capping enzymes. Proc Natl Acad Sci U S A. Sep. 2, 1997;94(18):9573-8.
Wang, Y., et al., Systemic delivery of modified mRNA enoxiing herpes simplex virus 1 thymidine kinase for targeted cancer gene theraopy. Mol Therapy. 2012; 11: 1-10.
Warren, L. et al. Highly efficient reprogramming to pluripotency and directed differentiation of human cells with synthetic modified mRNA. Cell Stem Cell. Nov. 5, 2010;7(5):618-30.
Warren, T.I. et al., Uses of granulocyte-macrophage colony-stimulating factor in vaccine development. Curr Opin Hematol. May 2000;7(3):168-73.
Watanabe, T. et al., Induction of wild-type p53 activity in human cancer cells by ribozymes that repair mutant p53 transcripts. Proc Natl Acad Sci U S A. Jul. 18, 2000;97(15):8490-4.
Weaver, J.C., Electroporation theory. Concepts and mechanisms. Methods Mol Biol. 1995;55:3-28.
Weber, J. et al., Granulocyte-macrophage-colony-stimulating factor added to a multipeptide vaccine for resected Stage II melanoma. Cancer. Jan. 1, 2003;97(1):186-200.
Weide, B. et al., Results of the first phase I/II clinical vaccination trial with direct injection of mRNA. J Immunother. Feb.-Mar. 2008;31(2):180-8.
Weide, B., et al., Direct injection of protamine-protected mRNA: Results of a phase 1/2 vaccination trial in metastatic melanoma patients. J. of Immunotherapy. Jun. 2009; 32(5): 498-507.
Nakamura, O. et al., Abstract: The Role of Immune RNA in the Immunotherapy of Malignant Brain Tumor. 1982, 34(2);333-9.
Weisberger, A.S., Induction of altered globin synthesis in human immature erythrocytes incubated with ribonucleoprotein. Proc Natl Acad Sci USA. Jan. 1962; 48(1): 68-80.
Weiss, S.B. et al., Pseudouridine Formation: Evidence for RNA as an Intermediate. Science. Jul. 23, 1965: 149(3682): 429-431.
Weissman, D. et al., Dendritic cells express and use multiple HIV coreceptors. Adv Exp Med Biol. 1997;417:401-6.
Weissman, D. et al., HIV GAG mRNA transfection of dendritic cell (DC) delivers encoded antigen to MHC class I and II molecules, causes DC maturation, and induced a potent human in vitro primary immune response. J Immunol. Oct. 15, 2000;165(8):4710-7.
Wels, W., et al., Construction, bacterial expresion and characterization of a bifunctional single-chain antibody-phosphate fusion protein targeted to the human erbb-2 receptor. Biotechnology (NY). Oct. 1992; 10(10): 1128-1132.
Wickens, M. et al., A PUF family portrait: 3'UTR regulation as a way of life. Trends Genet. Mar. 2002;18(3):150-7.
Wiehe, J.M. et al., mRNA-mediated gene delivery into human progenitor cells promotes highly efficient protein expression. J Cell Mol Med. May-Jun. 2007;11(3):521-30.
Wilkie, G.S. et al., Regulation of mRNA translation by 5'- and 3'-UTR-binding factors. Trends Biochem Sci. Apr. 2003;28(4):182-8.
Wilusz, C.J. et al., Bringing the role of mRNA decay in the control of gene expression into focus. Trends Genet. Oct. 2004;20(10):491-7.
Wilusz, J. et al., A B4 kd nuclear protein binds to RNA segments that include the AAUAAA polyadenylation motif. Cell. Jan. 29, 1988;52(2):221-8.
Winnicka, B, et al., CD13 is dispensable for normal hematopoiesis and myeloid cell functions in the mouse. J Leukoc Biol. Aug. 2010: 88(2); 347-359. Epub Apr. 29, 2010.

(56) References Cited

OTHER PUBLICATIONS

Wolff, J.A. et al., Direct gene transfer into mouse muscle in vivo. Science. Mar. 23, 1990;247(4949 Pt 1):1465-8.

Woltjen, K. et al., piggyBac transposition reprograms fibroblasts to induced pluripotent stem cells. Nature. Apr. 2009 (458): 10.1038-07863.

Woodberry, T. et al., Immunogenicity of a human immunodeficiency virus (HIV) polytope vaccine containing multiple HLA A2 HIG CD8(+) cytotoxic T-cell epitopes. J Virol. Jul. 1999;73(7):5320-5.

Wu, J. et al., Mammalian pre-mRNA branch site selection by U2 snRNP involves base pairing. Genes Dev. Oct. 1989;3(10):1553-61.

Wu, L. et al., Fusion protein vectors to increase protein production and evaluate the immunogenicity of genetic vaccines. Mol Ther. Sep. 2000;2(3):288-97.

Wu, X.C. et al., Engineering a *Bacillus subtilis* expression-secretion system with a strain deficient in six extracellular proteases. J Bacteriol. Aug. 1991;173(16):4952-8.

Wurm, F. et al., Suppression of melanoma development and regression of melanoma in xiphophorine fish after treatment with immune RNA. Cancer Res. Sep. 1981;41(9 Pt 1):3377-83.

Wyatt, J.R. et al., Site-specific cross-linking of mammalian U5 snRNP to the 5' splice site before the first step of pre-mRNA splicing. Genes Dev. Dec. 1992;6(12B):2542-53.

Xu, C. et al., Feeder-free growth of undifferentiated human embryonic stem cells. Nat Biotechnol. Oct. 2001;19(10):971-4.

Xu, J. et al., Identification of differentially expressed genes in human prostate cancer using subtraction and microarray. Cancer Res. Mar. 15, 2000;60(6):1677-82.

Yamamoto, A., et al., Current prospects for mRNA gene delivery. Eur J Pharm Biopharm. Mar. 2009; 71(3): 484-489.

Yamashita, A. et al., Concerted action of poly(A) nucleases and decapping enzyme in mammalian mRNA turnover. Nat Struct Mol Biol. Dec. 2005;12(12):1054-63. Epub Nov. 13, 2005.

Yang, S.F. et al., Albumin synthesis in mouse uterus in response to liver mRNA. Proc Natl Acad Sci U S A. May 1977;74(5):1894-8.

Ye, X., et al., Prolonged metabolic correction in adult ornithine transcarbamylase-deficient mice with adenoviral vectors. Biological Chem. Feb. 1996; 271(7): 3639-3646.

Yi, Y., et al., Current advances in retroviral gene therapy. Current Gene Ther. 2011; 11: 218-228.

Ying, H. et al., Cancer therapy using a self-replicating RNA vaccine. Nat Med. Jul. 1999;5(7):823-7.

Yisraeli, J.K. et al., [4] Synthesis of long, capped transcripts in vitro by SP6 and T7 RNA Polymerases. Methods in Enzymology, vol. 180. 1989; 180, 42-50.

Yokoe, H. et al., Spatial dynamics of GFP-tagged proteins investigated by local fluorescence enhancement. Nat Biotechnol. Oct. 1996;14(10):1252-6.

Yoshida, Y. et al., Hypoxia enhances the generation of induced pluripotent stem cells. Cell Stem Cells 5, Sep. 2009; 5: 237-241.

You, Z. et al., A retrogen strategy for presentation of an intracellular tumor antigen as an exogenous antigen by dendritic cells induces potent antitumor T helper and CTL responses. Cancer Res. Jan. 1, 2001;61(1):197-205.

Studier, F.W. et al., Use of bacteriophage T7 RNA polymerase to direct selective high-level expression of cloned genes. J Mol Biol. May 5, 1986;189(1):113-30.

Studier, F.W. et al., [6] Use of T7 RNA polymerase to direct expression of cloned genes. Methods Enzymol. 1990;185-60-89.

Su, Z. et al., Enhanced induction of telomerase-specific CD4(+) T Cells using dendritic cells transfected with RNA encoding a chimeric gene product. Cancer Res. Sep. 1, 2002;62(17):5041-8.

Su, Z. et al., Immunological and clinical responses in metastatic renal cancer ptaients vaccinated with tumor RNA-transfected dendritic cells. Cancer Res. May 1, 2003;63(9):2127-33.

Suda, T. et al., Hydrodynamic gene delivery: its principles and applications. Mol Ther. Dec. 2007;15(12):2063-9. Epub Oct. 2, 2007.

Sullenger, B.A. et al., Emerging clinical applications of RNA. Nature. Jul. 11, 2002;418(6894):252-8.

Svinarchuk, F.P. et al., Inhibition of HIV proliferation in MT-4 cells by antisense oligonucleotide conjugated to lipophilic groups. Biochimie. 1993;75(1-2):49-54.

Takahashi, K., et al., Induction of pluripotent stem cells from mouse embryonic and adult fibroblast cultures by defined factors. Cell. Aug. 2006; 126(4): 663-76.

Takahashi, K., et al., Induction of pluripotent stem cells from adult human fibroblasts by defined factors. Cell. Nov. 2007; 131(5): 861-72.

Tam, C., et al., Cytokeratins mediate epithelial innate defense through their antimicrobial properties. J Clin Invest. Oct. 1, 2012; 122(10): 3665-3677.

Tanaka, M. et al., Inhibiton of heart transplant injury and graft coronary artery disease after prolonged organ ischemia by selective protein kinase C regulators. J Thorac Cardiovasc Surg. May 2005;129(6):1160-7.

Tanguay, R.L. et al., Translational efficiency is regulated by the length of the 3' untranslated region. Mol Cell Biol. Jan. 1996;16(1):146-56.

Taranger, C.K. et al., Induction of dedifferentiation, genomewide transcriptional programming, and epigenetic reprogramming by extracts of carcinoma and embryonic stem cells. Mol Biol Cell. Dec. 2005;16(12):5719-35.

Tavernier, G., et al., mRNA as gene therapeutic: How to control protein expression. J. of Controlled Release. Mar. 2011; 150(3): 238-247.

Tazi, J. et al., Alternative chromatin structure at CpG islands. Cell. Mar. 23, 1990;60(6):909-20.

Teufel, R. et al., Human peripheral blood mononuclear cells transfected with messenger RNA stimulate antigen-specific cytotoxic T-lymphocytes in vitro. Cell Mol Life Sci. Aug. 2005;62(15);1755-62.

Thompson, M. et al., Nucleolar clustering of dispersed tRNA genes. Science. Nov. 21, 2003;302(5649):1399-401.

Thurner, B. et al., Vaccination with mage-3A1 peptide-pulsed mature, monocyte-derived dendritic cells expands specific cytotoxic T cells and induces regression of some metastates in advanced stage IV melanoma. J Exp Med. Dec. 6, 1999;190(11):1669-78.

Tourriere, H. et al., mRNA degradation machines in eukaryotic cells. Biochimie. Aug. 2002;84(8):821-37.

Towle, H.C. et al., Purification and characterization of bacteriophage gh-l-induced deoxyribonucleic acid-dependent ribonucleic acid polymerase from *Pseudomonas putida*. J Biol Chem. Mar. 10, 1975;250(5):1723-33.

Treat, J. et al., In Liposomes in the Therapy of Infectious Disease and Cancer, Lopez-Berestein and Fidler (eds.), Liss, New York, 1989. 353-65.

Trinchieri, G. et al., Cooperation of Toll-like receptor signals in innate immune defence. Nat Rev Immunol. Mar. 2007;7(3):179-90.

Trojan, A. et al., Immune reactivity against a novel HLA-A3-restricted influenza virus peptide identified by predictive algorithms and interferon-gamma quantitative PCR. J Immunother. Jan.-Feb. 2003;26(1):41-6.

Tsuchiya, M, et al., Isolation and characterization of the cDNA for murine granulocyte colony-stimumating factor. Proc Natl Acad Sci USA. Oct. 1986; 83(20): 7633-7637.

Tung, T.C. et al., Organ formation caused by nucleic acid from different class.—Urodele DNA mediated balancer formation in goldfish. Sci Sin. Jan.-Feb. 1977;20(1):56-8.

Tung, T.C. et al., The effect of carp EGG-mRNA on the transformation of goldfish tail. Sci Sin. Jan.-Feb. 1977;20(1):59-63.

Tung, T.C. et al., Transmission of the nucleic acid-induced character, caudal fin, to the offspring in goldfish. Sci Sin. Mar.-Apr. 1975;18(2):223-31.

Tuting, T. et al., Gene-based strategies for the immunotherapy of cancer. J Mol Med (Berl). Jul. 1997;75(7):478-91.

Tycowski, K.T. et al., A small nucleolar RNA requirement for site-specific ribose methylation of rRNA in *Xenopus*. Proc Natl Acad Sci U S A. Dec. 10, 1996;93(25):14480-5.

Undenfriend, S., et al., The enzymatic conversion of phenylalanine to tyrosine. J. Biol. Chem. 1952; 194: 503-511.

(56) References Cited

OTHER PUBLICATIONS

Ueda, T. et al., Phosphorothioate-containing RNAs show mRNA activity in the prokaryotic translation systems in vitro. Nucleic Acids Res. Feb. 11, 1991;19(3):547-52.
Ulmer, J.B. et al., Heterologous protection against influenza by injection of DNA encoding a viral protein. Science. Mar. 19, 1993;259(5102):1745-9.
Ulmer, J.B., An update on the state of the art of DNA vaccines. Curr Opin Drug Discov Devel. Mar. 4, 2001(2);192-7.
Utikal, J., et al., Immortalization eliminates a roadblock during cellular reprogramming into iPS cells. Nature. Aug. 2009; 460: 1145-1148.
Uzgun, S., et al., PEGylation improves nanoparticle formation and transfection efficiency of messenger RNA. Pharm Res. Sep. 2011; 28(9): 2223-2232.
Uzri, D., et al., Nucleotide sequences and modifications that determine RIG-I/RNA binding and signaling activities. J. Virol. May 2009; 83 (9): 4174-4184.
Vaheri, A. and Pagano, J.S. Infectious poliovirus RNA: a sensitive method of assay. Virology. Nov. 1965; 27(3): 434-436.
Valcarcel, J. et al., The protein Sex-lethal antagonizes the splicing factor U2AF to regulate alternative splicing of transformer pre-mRNA. Nature. Mar. 11; 1993;362(6416):171-5.
Van Den Bosch, G.A., et al., Simultaneous activation of viral Antigen-specific Memory CD4+ and CD8+ T-cells using mRNA-eletroporated CD40-activated autologus B-cells. J Immunother. Sep./Oct. 2006; 29, 512-23.
Van Gelder, R.N. et al., Amplified RNA synthesized from limited quantities of heterogeneous cDNA. Proc Natl Acad Sci U S A. Mar. 1990;87(5):1663-7.
Van Tendeloo, V.F. et al., Highly efficient gene delivery by mRNA electroporation in human hematopoietic cells: superiority to lipofection and passive pulsing of mRNA and to electroporation of plasmid cDNA for tumor antigen loading of dendritic cells. Blood. Jul. 1, 2001;98(1):49-56.
Van Tendeloo, V.F., et al., mRNA-based gene transfer as a tool for gene and cell therapy. Curr Opin Mol Therapeitucs. 2007; 9(5): 423-431.
Vaquero, C. et al., Transient expression of a tumor-specific single-chain fragment and a chimeric antibody in tobacco leaves. Proc Natl Acad Sci U S A,. Sep. 28, 1999;96(20):1128-33.
Varambally, S. et al., Genomic loss of microRNA-101 leads to overexpression of histone methyltransferase EZH2 in cancer. Science. Dec. 12, 2008;322(5908):1695-9. Epub Nov. 13, 2008.
Vassilev, V.B. et al., Microparticle-mediated RNA immunization against bovine viral diarrhea virus. Vaccine. Feb. 28, 2001;19(15-16):2012-9.
Veres, G., et al., The molecular basis of the sparse fur mouse mutation. Science. Jul. 1987;237(4813):415-7.
Verheggen, C. et al., Box C/D small nucleolar RNA trafficking involves small nucleolar RNP proteins, nucleolar factors and a novel nuclear domain. EMBO J. Oct. 1, 2001;20(19):5480-90.
Verheggen, C. et al., Mammalian and yeast U3 snoRNPs are matured in specific and related nuclear compartments. EMBO J. Jun. 3, 2002;21(11):2736-45.
Verma, I.M. et al., Gene therapy: promises, problems and prospects. Nature. Sep. 18, 1997;389(6648):239-42.
Verma, I.M. et al., Gene therapy: twenty-first century medicine. Annu Rev Biochem. 2005;74:711-38.
Yu, J. et al., Structural and functional analysis of an mRNP complex that mediates the high stability of human beta-globin mRNA. Mol Cell Biol. Sep. 2001;21(17):5879-88.
Yu, J. et al., Induced pluripotent stem cell lines derived from human somatic cells. Science. Dec. 21, 2007; 318(5856): 1917-1920.
Yu, J. et al., Human induced pluripotent stem cells of vector and transgene sequences. Science. May 8, 2009; 324(5938): 797-801.
Yu, Y.T. et al., Modifications of U2 snRNA are required for snRNP assembly and pre-mRNA splicing. EMBO J. Oct. 1, 1998;17(19):5783-95.

Zebarjadian, Y. et al., Point mutations in yeast CBF5 can abolish in vivo pseudouridylation of rRNA. Mol Cell Biol. Nov. 1999;19(11):7461-72.
Zeitlin, S. et al., In vivo splicing products of the rabbit beta-globin pre-mRNA. Cell. Dec. 1984;39(3 Pt 2):589-602.
Zelcer, A. et al., The detection and characterization of viral-related double-stranded RNAs in tobacco mosaic virus-infected plants. Virology. Sep. 1981;113(2);417-27.
Zeytin, H.E. et al., Construction and characterization of DNA vaccines encoding the single-chain variable fragment of the anti-idiotype antibody 1A7 mimicking the tumor-associated antigen disialoganglioside GD2. Cancer Gene Ther. Nov. 2000;7(11):1426-36.
Zhang, X. et al., Advances in dendritic cell-based vaccine of cancer. Cancer Biother Radiopharm. Dec. 2002;17(6):601-19.
Zhang, Y., et al., In vivo gene delivery by nonviral vectors: overcoming hurdles? Mol. Therapy. Jul. 2012; 20(7): 1298-1304.
Zhao, X. et al., Pseudouridines in and near the branch site recognition region of U2 snRNA are required for snRNP biogenesis and pre-mRNA splicing in *Xenopus oocytes*. RNA. Apr. 2004;10(4):681-90.
Zhigaltsev, I.V., et al., Bottom-Up design and synthesis of limit size lipid nanoparticle systems with aqueous and triglyceride cores using millisecond microfluidic mixing. Langmuir. Feb. 21, 2012; 28(7): 3633-3640.
Zhou, W.Z. et al., RNA melanoma vaccine: induction of antitumor immunity by human glycoprotein 100 mRNA immunization. Hum Gene Ther. Nov. 1, 1999;10(16):2719-24.
Zhou, H., et al., Generation of induced pluripotent stem cells using recombinant proteins. Cell Stem Cell. May 4, 2009(5):381-4.
Zhou, J., et al., Short Communicatiobn Bilirubin Glucuronidation Revisited: Proper assay conditions to estimate enzyme kinetics with recombinant UGT1A1. Drug metabolism and Disp. 2010; 38(11): 1907-1911.
Zhuang, Y. et al., A compensatory base change in human U2 snRNA can suppress a branch site mutation. Genes Dev. Oct. 1989;3(10):1545-52.
Zimmermann, E. et al., Electrolyte- and pH-stabilities of aqueous solid lipid nanoparticle (SLN™) dispersions in artificial gastrointestinal media. Eur J Pharm Biopharm. Sep. 2001;52(2):203-10.
Zitvogel, L. et al., Therapy of murine tumors with tumor peptide-pulsed dendritic cells: dependence on T cells, B7 costimulation, and T helper cell 1-associated cytokines. J Exp Med. Jan. 1, 1996;183(1);87-97.
Zohra, F.T., et al., Drastic effect of nanoapatite particles on liposome-mediated mRNA delivery to mammalian cells. Analytical Biochem. Oct. 2005; 345(1): 164-166.
Zohra, F.T., et al., Effective delivery with enhanced translational activity synergistically accelerates mRNA-based transfection. Biochem Biophys Res Comm. Jun. 2007; 358(1): 373-378.
Zonta, S. et al., Uretero-neocystostomy in a swine model of kidney transplantation: a new technique. J Surg Res. Apr. 2005;124(2):250-5.
Zorio, D.A. et al., Both subunits of U2AF recognize the 3' splice site in *Caenorhabditis elegans* . Nature. Dec. 16, 1999;402(6763):835-8.
Chang, N. et al., Genome editing with RNA-guided Cas9 nuclease in Zebrafish embryos. Cell Res. Apr. 23, 2013(4):465-472.
Cong, L. et al., Multiplex genome engineering using CRISPR/Cas systems. Science. Feb. 15, 2013; 339(6121): 819-823.
Jinek, M. et al., A programmable dual-RNA-guided DNA endonuclease in adaptive bacterial immunity. Science. Aug. 17, 2012; 337(6096): 816-821.
Jinek, M. et al., RNA-programmed genome editing in human cells. Elife. 2013;2:e00471.
Maehr, R. et al., Generation of pluripotent stem cells from patients with type 1 diabetes. Proc Natl Acad Sci USA. Sep. 15, 2009; 106(37): 15768-15773.
Mali, P. et al., RNA-guided human genome engineering via Cas9. Science. Feb. 15, 2013; 339(6121): 823-826.
Qi, L.S. et al., Repurposing CRISPR as an RNA-guided platform for sequence-specific control of gene expression. Cell. Feb. 28, 2013: 152(5): 1173-1183.

(56) References Cited

OTHER PUBLICATIONS

Shen, B. et al., Generation of gene-modified mice via Cas9/RNA-mediated gene targeting. Cell Res. Apr. 2, 2013; 1-4.
Yi, P. et al., Betatrophin: A hormone that control pancreatic beta cell proliferation. Cell. May 9, 2013, 153: 1-12.
Graf, T and Enver T. Forcing cells to change lineages. Nature. Dec. 3, 2009; 462(7273): 587-594.
Ieda, M. et al., Direct reprogramming of fibroblasts into functional cardiomyocytes by defined factors. Cell. Aug. 6, 2010; 142(3); 375-386.
Huangfu, D. et al., Induction of pluripotent stem cells from primary human fibroblasts with only Oct4 and Sox2. Nat Biotechnol. Nov. 2008; 26(11): 1269-1275.
Dong, X.Y. et al., Identification of genes differentially expressed in human hepatocellular carcinoma by a modified suppression subtractive hybridization method. Int J Cancer. Nov. 1, 2004; 112(2): 239-248.
Okita, K. et al., Generation of mouse induced pluripotent stem cells without viral vectors. Science. 2008; 322; 949-953.
Stadtfeld, M. et al., Induced pluripotent stem cells generated without viral integration. Science. Nov. 7, 2008; 322 (5903): 945-949.
Aoi, T. et al., Generation of pluripotent stem cells from adult mouse liver and stomach cells. Science. Aug. 1, 2008; 321 (6889): 699-702.
Feng, R. et al., PU.1 and C/EBPalpha/beta convert fibroblasts into macrophage-like cells. Proc Natl Acad Sci USA. Apr. 22, 2008; 105(16): 6057-6062.
Szabo, E. et al., Direct conversion of human fibroblasts to multilineage blood progenitors Nature. Nov. 25, 2010; 468(7323): 521-526.
Gonzalez, F. et al., Generation of mouse-induced pluripotent stem cells by transient expression of a single nonviral polycistronic vector. Proc Natl Acad Sci USA. Jun. 2, 2009; 106(22): 8918-8922.
Aasen, T. et al., Efficient and rapid generation of induced pluripotent stem cells from human keratinocytes. Nat Biotechnol. Nov. 2008: 26(11): 1276-1284.
Ebert, A.D. et al., Induced pluripotent stem cells from a spinal muscular atrophy patient. Nature. Jan. 15, 2009; 457 (7227): 277-280.
Vierbuchen, T. et al., Direct conversion of fibroblasts to functional neurons by defined factors. Nature. Feb. 25, 2010; 463(7284): 1035-1041.
Racila, D. et al., Transient expresion of OCT4 is sufficient to allow human keratinocytes to change their differentiation pathway. Gene Ther. Mar. 2011; 18(3): 294-303.
Nakagawa, M. et al., Generation of induced pluripotent stem cells without Myc from mouse and human fibroblasts. Nat Biotechnol. Jan. 2008: 26(1); 101-106. Epub Nov. 30, 2007.
Haft, D.H. et al., A guild of 45 CRISPR-associated (Cas) protein families and multiple CRISPR/Cas subtypes exist in prokaryotic genomes. PLoS Comput Biol. Nov. 2005; 1(6): e60. Epub Nov. 11, 2005.
Brown, C.E., et al., Poly(A) Tail Lengeth Control in *Saccharomyces cerevisiae* Occurs by Message-Specific Deadenylation. Molecular and Cellular Biology. Nov. 1998 p. 6548-6559.
Saponara, A.G. et al., The isolation from ribonucleic acid of substituted uridines containing alpha-aminobutyrate moieties derived from methionine. Biochem Biophys Acta. Apr. 27, 1974;349(1):61-77.
Satoh, M. et al., X-linked immunodeficient mice spotaneously produce lupus-related anti-RNA helicase A autoantibodies, but are resistant to pristane-induced lupus. Int Immunol. Sep. 2003;15(9):1117-24.
Sattthaporn, S. et al., Dendritic cells (II): Role and therapeutic implications in cancer. J R Coll Surg Edinb. Jun. 2001;46(3):159-67.
SAtz, M I. et al., Mechanism of immune transfer by RNA extracts. Immune RNA induces the synthesis of idiotype-bearing antigen receptors in noncommitted cells. Mol Cell Biochem. Dec. 16, 1980;33(3):105-13.
Scheel, B. et al., Immunostimulating capacities of stabilized RNA molecules. Eur J Immunol. Feb. 2004;34(2):537-47.
Schirrmacher, V. et al., Intra-pinna anti-tumor vaccination with self-replicating infectious RNA or with DNA encoding a model tumor antigen and a cytokine. Gene Ther. Jul. 2000;7(13):1137-47
Schmidt, W.M. et al., CapSelect: a highly sensitive method for 5' CAP-dependent enrichment of full-length cDNA in PCR-mediated analysis of mRNAs. Nucleic Acids Res. Nov. 1, 1999;27(21):e31.
Schmitt, W.E. et al., In vitro induction of a bladder cancer-specific T-cell response by mRNA-transfected dendritic cells. J Cancer Res Clin Oncol. 2001;127(3):203-6.
Scholte, B.J. et al., Animal models of cystic fibrosis. J Cyst Fibros. Aug. 2004;3 Suppl 2:183-90.
Schott, J.W., et al., Viral and non-viral approaches for transient delivery of mRNA and proteins. Current Gene Ther. 2011; 11(5): 382-398.
Schuler, G. et al., Murine epidermal Langerhans cells mature into potent immunostimulatory dendritic cells in vitro. J Exp Med. Mar. 1, 1985;161(3):526-46.
Schuler-Thurner, B. et al., Mage-3 and influenza-matrix peptide-specific cytotoxic T cells are inducible in terminal stage HLA-A2.1+ melanoma patients by mature monocyte-derived dendritic cells. J Immunol. Sep. 15, 2000;165(6):3492-6.
Segura, J., et al., Monitoring gene therapy by extranal imaging of mRNA: Pilot study on murine erythropoietin. Ther Drug Monit. Oct. 2007; 29(5): 612-8.
Semple, S.C., et al., Efficient encapsulation of antisense oligonucleotides in lipid vesicles using ionizable aminolipids: formation of novel small multilamellar vesicle structures. Biochim Biophys Acta. Feb. 9, 2001; 1510(1-2): 152-166.
Semple, S.C., et al., Rational design of cationic lipids for siRNA delivery. Nat Biotechnol. Feb. 2010; 28(2): 172-176.
Serrate, S. et al., Transfer of cellular immunity in vivo with immune RNA in an allogeneic murine model. Clin Immunol Immunopathol. Jan. 1982;22(1):75-82.
Sharp, J.S. et al., Effect of translational signals on mRNA decay in *Bacillus subtilis*. J Bacteriol. Sep. 2003;185(18)5372-9.
Sharp, P.M. et al., DNA sequence evolution: the sounds of silence. Philos Trans R Soc Lond B Biol Sci. Sep. 29, 1995;349(1329):241-7.
Shea, R.G. et al., Synthesis, hybridization properties and antiviral activity of lipid-oligodeoxynucleotide conjugates. Nucleic Acids Res. Jul. 11, 1990;18(13):3777-83.
Shi, Y., et al., A combined chemical and genetic approach for the generation of induced pluripotent stem cells. Cell Stem Cell. Jun. 2008; 2: 525-528.
Shingo, T. et al., Erythropoietin regulates the in vitro and in vivo production of neuronal progenitors by mammalian forebrain neural stem cells. J Neurosci. Dec. 15, 2001;21(24):9733-43.
Shuman, S. et al., Purification and characterization of a GTP-pyrophosphate exchange activity from vaccinia virions. Association of the GTP-pyrophosphate exchange activity with vaccinia mRNA guanylyltransferase. RNA (guanine-7-) methyltransferase complex (capping enzyme). J Biol Chem. Dec. 10, 1980;256(23):1588-98.
Shuman, S., Structure, mechanism, and evolutuion of the mRNA capping apparatus. Prog Nucleic Acid Res Mol Biol. 2001;66:1-40.
Siena, S. et al., Expansion of Immunostimulatory Dendritic Cells from Peripheral Blood of Patients with Cancer. Oncologist. 1997;2(1);65-69.
Simonaro, C.M. et al., Joint and bone disease in mucopolysaccharidoses VI and VII: identification of new therapeutic targets and biomarkers using animal models. Pediatr Res. May 2005;57(5 Pt 1):701-7. Epub Mar. 3, 2005.
Slapikoff, S. et al., Mechanism of ribonucleic acid polymerase action. Effect of nearest neighbors on competition between uridine triphosphate and uridine triphosphate analogs for incorporation into ribonucleic acid. Biochemistry. Dec. 1967; 6(12): 3654-3658.
Sleeman, J. et al., Dynamic interactions between splicing snRNPs, coiled bodies and nucleoli revealed using snRNP protein fusions to the green fluorescent protein. Exp Cell Res. Sep. 15, 1998;243(2):290-304.
Smith, C.M. et al., Sno storm in the nucleolus: new roles for myriad small RNPs Cell. May 30, 1997;89(5):669-72.
Smith, J.P., et al., Drug retention and distribution after intratumoral chemotherapy with fluorouracil/epinephrine injectable gel in human pancreatic cancer xenografts. Cancer Chemother Pharmacol. 1999; 44: 267-274.

(56) References Cited

OTHER PUBLICATIONS

Smith, K.P. et al., Interactions of U2 gene loci and their nuclear transcripts with Cajal (coiled) bodies: evidence for PreU2 within Cajal bodies. Mol Biol Cell. Sep. 2000;11(9):2987-98.
Smith, W.S. et al., RNA modified uridines: VI: conformations of 3-[3-(S)-Amino-3-Carboxyprolyl]Uridine (acp3U) from tRNA and 1-Methyl-3-[3-(S)-Amino-3-Carboxypropyl]Pseudouridine (m1acp3?) from rRNA. Nucleosides and Nucleotides. 1992; 11(10):1683-94.
Smits, E., et al., RNA-based gene transfer for adult stem cells and T cells. Leukemia. 2004; 18: 1898-1902.
Smull, C.E. and Ludwig, E.H. Enhancement of the plaque-forming capacity of poliovirus ribonucleic acid with basic proteins. Journal of Bacteriology. 1962; 84(5): 1035-1040.
Sohn, R.L., et al., In-vivo particler mediated delivery of mRNA to mammalian tissues: ballistic and biological effects. Wound Rep and Regen. Jul.-Aug. 2001; 287-296.
Soll, D. Enzymatic modification of transfer RNA. Science. Jul. 23, 1971; 173(3994): 293-299.
Sontheimer, E.J. et al., The U5 and U6 small nuclear RNAs as active site components of the spliceosome. Science. Dec. 24, 1993;262(5142):1989-96.
Sousa, R. et al., T7 RNA polymerase. Prog Nucleic Acid Res Mol Biol. 2003;73:1-41.
Sousa, R., Use of T7 RNA polymerase and its mutants for incorporation of nucleoside analogs into RNA. Methods Enzymol. 2000;317:65-174.
Spooner, R.A. et al., DNA vaccination for cancer treatment. Gene Ther. May 1995;2(3):173-80.
Sproat, B.S., Chemistry and applications of oligonucleotide analogues. J Biotechnol. Jul. 31, 1995;41(2-3):221-38.
Staley, J.P. et al., Mechanical devices of the spliceosome: motors, clocks, springs, and things. Cell. Feb. 6, 1998;92(3):315-26.
Stanek, D. et al., Detection of snRNP assembly intermediates in Cajal bodies by fluorescence resonance energy transfer. J Cell Biol. Sep. 27, 2004;166(7):1015-25.
Steege, D.A., Emerging features of mRNA decay in bacteria. RNA. Aug. 2000;6(8):1079-90.
Steinman, R.M. et al., Dendritic cells: antigen presentation, accessory function and clinical relevance. Adv Exp Med Biol. 1993;329:1-9.
Steinman, R.M., The dendritic cell system and its role in immunogenicity. Annu Rev Immunl. 1991;9:271-96.
Stepinski, J. et al., Synthesis and properties of mRNAs containing the novel "anti-reverse" cap analogs 7-methyl(3'-O-methyl)GpppG and 7-methyl (3'deoxy)GpppG. RNA Oct. 2001;7(10):1486-95.
Sterner, D.E. et al., Acetylation of histones and transcription-related factors. Microbiol Mol Biol Rev. Jun. 2000;64(2):435-59.
Stiles, D.K., et al., Widespread suppresion of huntingtin with convection-enhanced delivery of siRNA. Experimental Neurology. Jan. 2012; 233(1): 463-471.
Stinchcomb, D.T. et al., Isolation and characterisation of a yeast chromosomal replicator. Nature. Nov. 1, 1979;282(5734):39-43.
Strong, V.T. et al., Incorporation of beta-globin untranslated regions into a Sindbis virus vector for augmentation of heterologous mRNA expression. Gene Ther. Jun. 1997;4(6):624-7.
Mignone, F. et al., Untranslated regions of mRNAs. Genome Biol. 2002;3(3):REVIEWS0004. Epub Feb. 28, 2002. pp. 1-10.
Yu, P.W. et al., Sustained correction of B-cell development and function in a murine model of X-linked agammaglobulinemia (XLA) using retroviral-mediated gene transfer. Sep. 1, 2004;104(5):1281-90. Epub May 13, 2004.
Yu, Y.T. et al., Internal modification of U2 small nuclear (sn)RNA occurs in nucleoli of *Xenopus oocytes*. J Cell Biol. Mar. 19, 2001;152(6):1279-88.
Gao, G., et al., Erythropoietin gene therapy leads to autoimmune anemia in macaques. 2004 103: 3300-3302.

Liu, C., et al., Peptidoglycan Recognition Proteins. A Novel Family of Four Human Innate Immunity Pattern Recognition Molecules. The Journal of Biological Chemistry. vol. 276, No. 37, Issue of Sep. 14, pp. 686-34694, 2001.
Lu, X., Peptidoglycan Recognition Proteins are a New Class of Human Bactericidal Proteins. The Journal of Biological Chemistry. Mar. 3, 2006, vol. 281, No. 9, pp. 5895-5907.
Ngai, P.H.K., et al., Agrocybin, an antifungal peptide from the edible mushroom. Department of Biochemistry, The Chinese University of Hong Kong. Peptides 26 (2005) 191-196.
Endo, F., et al., A Nonsense Mutation in the 4-Hydroxyphenylpyruvic Acid Dioxygenase Gene (Hpd) Causes Skipping of the Constitutive Exon and Hypertyrosinemia in Mouse Strain III. Genomics 25, 164-169 (1995).
Ren, W., et al. Molecular clong and characterization of 4-hydroxyphenylpyruvate dioxygenase gene from *Lactuca sativa*. Journal of Patent Physiology 168 (2011 pp. 1076-1083).
Neve, S., et al. Tissue distribution, intracellular localization and proteolytic processing of rat 4-hydorxyphenylpyruvate dioxygenase. Cell Biology International 27 (2003) pp. 611-624.
Ruetschu, U., et al. Human 4-Hydroxyphenylpyruvate Dioxygenase Gene (HPD). Genomics 44, pp. 292-299 (1997).
Seabury, C.M., et al., Analysis of sequence variability and protein domain architectures for bovine peptidoglycan recognition protein 1 and Toll-like receptors 2 and 6. Genomics 92 (2008) pp. 235-245.
Sumathipala, N. et al., Involvement of *Manduca sexta* peptidoglycan recognition protein-1 in the recognition of bacteria and activation of prophenoloxidase system. Insect Biochemistry and Molecular Biology 40 (2010) 487-495.
Wei, X. et al., Molecular cloning and MRNA expression of two peptidoglycan recognition protein (PGRP genes from mollusk *Solen grandis*. Fish & Shellfish Immunology 32 (2012) 178-185.
Anonymous: "Messenger RNA". Internet: Wikipedia. Jun. 19, 2013, XP002699196, Retrieved from the Internet: URL: http://en.wikipedia.org/wiki/Messenger RNA.
Grosjean, H., DNA and RNA Modification Enzymes Structure, Mechanisms, Functions and Evolution. Molecular Biology Intelligence Unit. Estimated Publication Date: May 2009. pp. 1-2.
Grosjean, H., Nucleic Acids are not Boring Long Polymers of Only Four Types of Nucleotides: A Guided Tour. Chapter 1. Landes Bioscience. 2009. pp. 1-18.
Grosjean, H., et al. How Nucleic Acids Cope with High Temperature. Physiology and Biochemistry of Extremophiles. 2007. Chapter 4, pp. 39-58.
Grosjean, H., Modification and editing of RNA: historical overview and important facts to remember. pp. 1-22.
Hunt, D.M., et al., The L Protein of Vesicular Stomatitis Cirus Modulates the Response of the Polyadenylic Acid Polymerase to S-Adenosylhomocysteine. J. gen. Virol. (1988), 69, 2555-2561.
Grosjean, H., et al. Fine-Tuning of RNA Functions by Modification and Editing. Topics in Current Genetics, vol. 12, 2005, XXIV, p. 442.
Bouloy, M., et al., Both the 7-methyl and the 2'-O-methyl groups in the cap of mRNA strongly influence its ability to act as primer for influenza virus RNA transcription. Proc. Natl. Acad. Sci. USA, vol. 77, No. 7, pp. 3952-3956, Jul. 1980.
Fernandez, I., et al. Unusual base pairing during the decoding of a stop codon by the ribosome. Doi: 10.1038/nature12302.
Edelheit, S. et al., Transcriptome-Wide Mapping of 5-methylcytidine RNA Modifications in Bacteria, Archaea, and Yeast Reveals m5C within Archaeal mRNAs. PLOS Genetics, Jun. 2013, vol. 9, Issue 6, pp. 1-14.
Cun, Dongmei, et al., Preparation and characterization of poly(DL-lactide-co-glycolide) nanoparticles for siRNA delivery. International Journal of Pharmaceutics 390 (2010) 70-75.
Oster, C.G., et al., Comparative study of DNA encapsulation into PLGA microparticles using modified double emulsion methos and spray drying techniques. Journal of Microencapsulation, May 2005; 22(3): 235-244.
GenBank: *Homo sapiens* 15 kDA selenoprotein (SEP 15), transcript variant 1, mRNA, NCBI Reference sequence: NM_004261.3, pp. 1-4.
Thomson A. James., et al. Isolation of a primate embryonic stem cell line. vol. 92, pp. 7844-7848, Aug. 1995. Proc. Natl. Acad. Sci. USA.

(56) References Cited

OTHER PUBLICATIONS

Tahiliani., et al.Conversion of 5-Methylcytosine to 5-Hydroxymethylcytosine in Mammalian DNA by MLL Partner TET1 Science 323, 930 (2009);www.sciencemag.org.

The Human Embryonic Stem Cell and the Human Embryonic Germ Cell. NIH Stem Cells: Scientific Progress and Future Research Directions, Department of Health and Human Services, Chapter 3, Jun. 2001.

The Stem Cell. NIH Stem Cells: Scientific Progress and Future Research Directions, Department of Health and Human Services, Chapter 1, Jun. 2001.

Morgan, D. Hugh, et al. Molecular Basis of Cell and Developmental Biology:Activation-induced Cytidine Dreaminase Deaminates 5-Methylcytosine in DNA and is Expressed in Pluripotent Tissues: Implications for Epigenetic Reprogramming. J. Biol. Chem. 2004, 279:52353-52360 published online Sep. 24, 2004.

Moore, J.E., et al., The Corneal Epithelial Stem Cell. vol. 21, No. 5/6, 2002. Mary Ann Liebert, Inc. pp. 443-451.

Koh, Peng Kian, et.al. Tet1 and Tet2 Regulate 5-Hydroxymethylcytosine Production and Cell Lineage Specification in Mouse Embryonic Stem Cells. 200-213, Feb. 4, 2011 2011 Elsevier Inc.

Kariko, Katalin, et.al. Naturally occurring nucleoside modifications suppress the immunostimulatory activity of RNA: Implication for therapeutic RNA development. Current Opinion in Drug Discovery & Development 2007 10(5): 523-532 The Thomson Corporation ISSN 1367-6733.

Ito, Shinsuke, et.al. Role of Tet proteins in 5mC to 5hmC conversion, ES-cell self-renewal and inner cell mass specification. vol. 466|Aug. 26, 2010| Macmillan Publishers Limited. pp. 1129-1133.

Freudenberg, M. Johannes, et.al. Acute depletion of Tet1-dependent 5-hydroxymethylcytosine levels impairs LIF/Stat3 signaling and results in loss of embryonic stem cell identity. Published online Dec. 30, 2011. 3364-3377 Nucleic Acids Research, 2012, vol. 40, No. 8.Published by Oxford University Press 2011.

Ficz, Gabriella, et al. Dynamic regulation of 5-hydroxymethylcytosine in mouse ES cells and during differentiation. NATURE | vol. 473 | May 19, 2011. pp. 398-401. Macmillian Publishers.

Blelloch, Robert, et al. Generation of Induced Pluripotent Stem Cells in the Absence of Drug Selection. Sep. 13, 2007. pp. 245-247.

Verma, Sandeep et.al. Modified Oligonucleotides: Synthesis and Strategy for Users. Biochem. 1998. 67:99-134. 1998 by Annual Reviews.

Leung W. David. The Structure and Functions of Human Lysophosphatidic Acid Acyltransferases. Frontiers in Bioscience 6. pp. 944-953, Aug. 1, 2001.

Lu, Biao, et al. Cloning and characterization of murine 1-acyl-sn-glycerol 3-phosphate acyltransferases and their regulation by PPAR in murine heart. Biochem J. (2005) 385, 469-477 (printed in Great Britain).

West, James, et.al. Cloning and Expression of Two Human Lysophosphatidic Acid Acyltransferase cDNAs That Enhahce Cytokine-Induced Signialing Responses in Cells. DNA and Cell Biology vol. 16, No. 6, 1997. Mary Ann Liebert, Inc. pp. 691-791.

Bionaz, Massimo, et.al. ACSL1, AGPAT6, FABP3, LPIN1, and SLC27A6 are the Most Abundant Isoforms in Bovine Mammary Tissue and Their Expression is affected by Stage of Lactation. The Journal of Nutrition, 2008. pp. 1019-2024.

\* cited by examiner

ENGINEERED NUCLEIC ACIDS AND METHODS OF USE THEREOF

CLAIM OF PRIORITY

This application claims priority to U.S. Ser. No. 61/401,052, filed on Aug. 6, 2010, the contents of which are incorporated herein by reference.

BACKGROUND OF THE INVENTION

Naturally occurring RNAs are synthesized from four basic ribonucleotides: ATP, CTP, UTP and GTP, but may contain post-transcriptionally modified nucleotides. Further, approximately one hundred different nucleoside modifications have been identified in RNA (Rozenski, J, Crain, P, and McCloskey, J. (1999). The RNA Modification Database: 1999 update. Nucl Acids Res 27: 196-197). The role of nucleoside modifications on the immuno-stimulatory potential and on the translation efficiency of RNA, however, is unclear.

There is a need in the art for biological modalities to address the modulation of intracellular translation of nucleic acids.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described herein. The materials, methods, and examples are illustrative only and not intended to be limiting. Other features of the disclosure are apparent from the following detailed description and the claims.

SUMMARY OF THE INVENTION

Provided herein are modified nucleic acids encoding melanocyte-stimulating hormone (MSH), insulin, and granulocyte colony-stimulating factor (G-CSF), precursors thereof or partially or fully processed forms of these proteins or these precursors. In certain embodiments, the modified nucleic acids comprise mRNA. In particular embodiments, the modified mRNA (mRNA) is derived from cDNA. In certain embodiments, the mRNA comprises at least two nucleoside modifications. In certain embodiments, these nucleoside modifications are 5-methylcytosin and pseudouridine.

Further, provided herein are formulations comprising the modified nucleic acids described herein. In certain embodiments, the formulations further comprise a pharmaceutically acceptable carrier. In certain embodiments, the carrier is formulated for systemic or local administration. In certain embodiments, the administration is oral or topical. In certain embodiments, the compositions comprise naked modified nucleic acids. In other embodiments, the modified nucleic acids are complexed or encapsulated.

Provided herein are methods of treating a subject having or being suspected of having a disease, the methods comprising administering to a subject in need of such treatment a formulation described herein in an amount sufficient to treat the disease. In specific embodiments, the disease is associated with one or more cellular and/or molecular changes affecting, for example, the level, activity, and/or localization of precursors of melanocyte-stimulating hormone (MSH), insulin, and granulocyte colony-stimulating factor (G-CSF), or a partially or fully processed form of these precursors. In certain embodiments, the methods of treating a subject having or being suspected of having a disease comprise administering to the subject in need of such treatment a formulation comprising a modified nucleic acid described herein in an amount sufficient to modulate one or more activities associated with MSH, G-CSF or insulin to treat the disease.

Provided herein are pharmaceutical formulations comprising: (i) an effective amount of a synthetic messenger ribonucleic acid (mRNA) encoding a granulocyte colony-stimulating factor (G-CSF) polypeptide; and (ii) a pharmaceutically acceptable carrier, wherein i) the mRNA comprises pseudouridine, 5'methyl-cytidine or a combination thereof, or ii) wherein the mRNA does not comprise a substantial amount of a nucleotide or nucleotides selected from the group consisting of uridine, cytidine, and a combination of uridine and cytidine, and wherein the formulation is suitable for repeated intravenous administration to a mammalian subject in need thereof. In certain embodiments, the G-CSF polypeptide comprises: (a) the amino acid sequence of SEQ ID NOs: 13 or 14; (b) an amino acid sequence at least 95% identical to SEQ ID NOs: 13 or 14; (c) a fragment of SEQ ID NOs: 13 or 14; (d) the amino acid sequence encoded by the nucleic acid of SEQ ID NO: 2 or SEQ ID NO: 17; or (e) the amino acid sequence encoded by a nucleic acid at least 95% identical to SEQ ID NO: 2 or SEQ ID NO: 17. In some embodiments, the pharmaceutical formulation provided herein further comprise a lipid-based transfection reagent. In some embodiments, the synthetic messenger ribonucleic acid (mRNA) encoding a granulocyte colony-stimulating factor (G-CSF) polypeptide lacks at least one destabilizing element.

Provided herein are kits comprising a pharmaceutical formulation described herein and AMD3100 (1,1'-[1,4-phenylene-bis(methylene)]-bis-1,4,8,11-tetraazacyclotetradecane), in one or more containers, and instructions for use thereof.

Further provided herein are pharmaceutical formulations consisting essentially of: (i) an effective amount of a synthetic messenger ribonucleic acid (mRNA) encoding a granulocyte colony-stimulating factor (G-CSF) polypeptide; (ii) a cell penetration agent; and (iii) a pharmaceutically acceptable carrier, wherein i) the mRNA comprises pseudouridine, 5'methyl-cytidine or a combination thereof, or ii) wherein the mRNA does not comprise a substantial amount of a nucleotide or nucleotides selected from the group consisting of uridine, cytidine, and a combination of uridine and cytidine, and wherein the formulation is suitable for repeated intravenous administration to a mammalian subject in need thereof.

Further provided herein are methods to obtain progenitor and/or stem cells from a mammalian subject, comprising the steps of: (a) administering to the subject a composition comprising a synthetic messenger ribonucleic acid (mRNA) encoding a granulocyte colony-stimulating factor (G-CSF) polypeptide in an amount effective to mobilize the progenitor and/or stem cells into the peripheral blood of the subject; followed by (b) harvesting the progenitor and/or stem cells. In certain embodiments, methods are provided wherein the mRNA or a pharmaceutically acceptable salt thereof is administered to the subject in the dosage range of about 1.0 µg/kg-100 mg/kg of body weight. In some embodiments, methods are provided wherein the subject is human. In certain embodiments, compositions are administered to the subject by an intravenous route. In some embodiments, the methods provided herein further comprise the step of administering an effective amount of AMD3100 (1,1'-[1,4-phenylene-bis(methylene)]-bis-1,4,8,11-tetraazacyclotetradecane) to the subject after administering the composition. In some embodiments, the composition is administered at least twice but fewer than ten times prior to administering the AMD3100. In some embodiments, methods are provided, wherein the composition further comprises a synthetic messenger ribonucleic acid (mRNA) encoding i) a macrophage inflammatory protein (MIP) polypeptide or ii) an antibody that prevents EGF binding by EGFR.

Further provided herein are improved regimens for mobilizing hematopoietic stem and progenitor cells in a mammalian subject in need thereof, the regimen comprising an amount of a synthetic messenger ribonucleic acid (mRNA) encoding a G-CSF polypeptide effective to enhance mobilization of hematopoietic stem cells and progenitor cells (HSPC), and an effective amount of AMD3100 (1,1'-[1,4-phenylene-bis(methylene)]-bis-1,4,8,11-tetraazacyclotetradecane).

Further provided herein are pharmaceutical formulations comprising: (i) an effective amount of a synthetic messenger ribonucleic acid (mRNA) encoding an insulin polypeptide; and (ii) a pharmaceutically acceptable carrier, wherein i) the mRNA comprises pseudouridine, 5'methyl-cytidine or a combination thereof, or ii) wherein the mRNA does not comprise a substantial amount of a nucleotide or nucleotides selected from the group consisting of uridine, cytidine, and a combination of uridine and cytidine, and wherein the formulation is suitable for repeated intravenous administration or intramuscular administration to a mammalian subject in need thereof. In certain embodiments, pharmaceutical formulations comprising synthetic messenger ribonucleic acid (mRNA) encoding an insulin polypeptide are provided, wherein the insulin polypeptide comprises: (a) the amino acid sequence of SEQ ID NOs: 15 or 16; (b) an amino acid sequence at least 95% identical to SEQ ID NOs: 15 or 16; (c) a fragment of SEQ ID NOs: 15 or 16; (d) the amino acid sequence encoded by the nucleic acid of SEQ ID NOs: 3 or 4, or SEQ ID NO: 21 or 23; or (e) the amino acid sequence encoded by a nucleic acid at least 95% identical to SEQ ID NOs: 3 or 4, or SEQ ID NO: 21 or 23. In certain embodiments, the pharmaceutical formulations further comprise a lipid-based transfection reagent.

Further provided herein are methods of regulating carbohydrate and lipid metabolism in a mammalian subject in need thereof, comprising the step of: (a) administering to the subject a composition comprising a synthetic messenger ribonucleic acid (mRNA) encoding an insulin polypeptide in an amount effective to regulate carbohydrate and lipid metabolism in the subject.

Provided herein are isolated nucleic acids comprising a translatable region and at least two different nucleoside modifications, wherein the nucleic acid exhibits reduced degradation in a cell into which the nucleic acid is introduced, relative to a corresponding unmodified nucleic acid. In certain embodiments, the nucleic acids comprise RNA, DNA, TNA, GNA or a hybrid thereof. In certain embodiments, the nucleic acids comprise messenger RNA (mRNA). In certain embodiments the mRNA does not substantially induce an innate immune response of a cell into which the mRNA is introduced. In certain embodiments, the mRNA comprises at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In certain embodiments, the mRNA comprises at least one nucleoside selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In other embodiments, the mRNA comprises at least one nucleoside selected from the group consisting of 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl)adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine. In yet other embodiments, the mRNA comprises at least one nucleoside selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleic acids provided herein comprise a 5'untranslated region (UTR) and/or a 3'UTR, wherein each of the two different nucleoside modifications are independently present in the 5'UTR and/or 3'UTR. In some embodiments, nucleic acids are provided herein, wherein at least one of the two different nucleoside modifications are present in the translatable region. In some embodiments, nucleic acids are provided herein are capable of binding to at least one polypeptide that prevents or reduces an innate immune response of a cell into which the nucleic acid is introduced.

Further provided herein are isolated polypeptides produced by translation of the mRNAs described herein.

Further provided herein are isolated complexes comprising a conjugate of a protein and a nucleic acid, comprising (i) a mRNA comprising a translatable region and at least two different nucleoside modifications; and (ii) one or more polypeptides bound to the mRNA in an amount effective to prevent or reduce an innate immune response of a cell into which the complex is introduced.

Further provided herein are isolated mRNAs comprising (i) a translatable region, (ii) at least two different nucleoside modifications, and (iii) a degradation domain.

Further provided herein are isolated mRNAs comprising i) a translatable region and ii) at least two different nucleoside modifications, wherein the translatable region encodes a polypeptide variant having an altered activity relative to a reference polypeptide. In certain embodiments, isolated mRNAs are provided, wherein the altered activity comprises an increased activity or wherein the altered activity comprises a decreased activity.

Further provided herein are non-enzymatically synthesized mRNAs comprising at least one nucleoside modification, optionally comprising a translatable region. In certain embodiments, the non-enzymatically synthesized mRNAs comprise at least two different nucleoside modifications. In certain embodiments, the non-enzymatically synthesized mRNAs are substantially not translatable. In certain embodiments, the non-enzymatically synthesized mRNAs are provided in an amount effective as a vaccine when administered to a mammalian subject.

Further provided herein are isolated nucleic acids comprising (i) a translatable region, (ii) at least one nucleoside modification, and (iii) at least one intronic nucleotide sequence capable of being excised from the nucleic acid.

Further provided herein are libraries comprising a plurality of polynucleotides, wherein the polynucleotides individually comprise: (i) a first nucleic acid sequence encoding a polypeptide; (ii) at least one nucleoside modification. In certain embodiments, libraries are provided, wherein the polypeptide comprises an antibody or functional portion thereof. In certain embodiments, libraries are provided, wherein the polynucleotides comprise mRNA. In certain embodiments, libraries are provided, wherein the at least one nucleoside modification is selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

Further provided herein are methods for treating or preventing a symptom of cystic fibrosis in a mammalian subject, comprising contacting a cell of the subject with the nucleic acid of claim 1, wherein the translatable region encodes a Cystic Fibrosis Transmembrane Conductance Regulator (CFTR) polypeptide, under conditions such that an effective amount of the CTFR polypeptide is present in the cell, thereby treating or preventing a symptom of cystic fibrosis in the subject. In certain embodiments, the cell is an epithelial cell, an endothelial cell, or a mesothelial cell. In certain embodiments, the nucleic acid comprises an RNA molecule formulated for administration by inhalation.

Further provided herein are methods for inducing an alteration in cell fate in a mammalian cell, comprising the steps of: (a) providing a precursor cell; and (b) contacting the precursor cell with an effective dose of a cell fate inductive polypeptide encoded by the nucleic acids described herein, under conditions such that an alteration in cell fate is induced.

Further provided herein are methods for enhancing protein product yield in a cell culture process, comprising the steps of: (a) providing a cell culture comprising a plurality of host cells; (b) contacting the cell culture with a composition comprising a nucleic acid comprising a translatable region and at least one nucleoside modification, wherein the nucleic acid exhibits increased protein production efficiency in a cell culture into which the nucleic acid is introduced, relative to a corresponding unmodified nucleic acid. In certain embodiments, methods are provided, wherein the increased protein production efficiency comprises increased cell transfection. In certain embodiments, the increased protein production efficiency comprises increased protein translation from the nucleic acid. In certain embodiments, the increased protein production efficiency comprises decreased nucleic acid degradation. In certain embodiments, the increased protein production efficiency comprises reduced innate immune response of the host cell. In certain embodiments, methods are provided, wherein the cell culture comprises a fed-batch mammalian cell culture process.

Further provided herein are methods for optimizing expression of an engineered protein in a target cell, comprising the steps of: (a) providing a plurality of target cell types; (b) independently contacting with each of the plurality of target cell types an isolated nucleic acid comprising a translatable region encoding an engineered polypeptide and at least one nucleoside modification; and (c) detecting the presence and/or level of the engineered polypeptide in the plurality of target cell types, thereby optimizing expression of an engineered polypeptide in a target cell. In certain embodiments, the engineered polypeptide comprises a post-translational modification. In certain embodiments, the engineered polypeptide comprises a tertiary structure. In certain embodiments, methods are provided, wherein the target cell comprises a mammalian cell line.

Further provided herein are methods for inducing in vivo translation of a recombinant polypeptide in a mammalian subject in need thereof, comprising the step of administering to the subject an effective amount of a composition comprising a nucleic acid comprising: (i) a translatable region encoding the recombinant polypeptide; and (ii) at least one nucleoside modification, under conditions such that the nucleic acid is localized into a cell of the subject and the recombinant polypeptide is capable of being translated in the cell from the nucleic acid. In certain embodiments, the composition comprises mRNA. In certain embodiments, methods are provided, wherein the recombinant polypeptide comprises a functional activity substantially absent in the cell in which the recombinant polypeptide is translated. In certain embodiments, the recombinant polypeptide comprises a polypeptide substantially absent in the cell in the absence of the composition. In certain embodiments, the recombinant polypeptide comprises a polypeptide that antagonizes the activity of an endogenous protein present in, on the surface of, or secreted from the cell. In certain embodiments, the recombinant polypeptide comprises a polypeptide that antagonizes the activity of a biological moiety present in, on the surface of, or secreted from the cell. In certain embodiments, the biological moiety comprises a lipid, a lipoprotein, a nucleic acid, a carbohydrate, or a small molecule toxin. In certain embodiments, the recombinant polypeptide is capable of being secreted from the cell. In certain embodiments, the recombinant polypeptide is capable of being translocated to the plasma membrane of the cell. In certain embodiments, methods are provided, wherein the composition is formulated for administration intramuscularly, transarterially, intraperitoneally, intravenously, intranasally, subcutaneously, endoscopically, transdermally, or intrathecally. In certain embodiments, methods are provided, wherein the composition is formulated for extended release. In certain embodiments, the recombinant polypeptide is capable of being translocated to the plasma membrane of the cell.

Further provided herein are methods for inducing translation of a recombinant polypeptide in a cell population, comprising the step of contacting the cell population with an effective amount of a composition comprising a nucleic acid comprising: (i) a translatable region encoding the recombinant polypeptide; and (ii) at least one nucleoside modification, under conditions such that the nucleic acid is localized into one or more cells of the cell population and the recombinant polypeptide is translated in the cell from the nucleic acid. In certain embodiments, methods are provided, wherein the composition comprises mRNA. In certain embodiments, the composition comprises a cell penetrating compound. In certain embodiments, methods are provided, wherein the step of contacting the cell with the composition is repeated one or more times. In certain embodiments, the step of contacting the cell with the composition is repeated a sufficient number of times such that a predetermined efficiency of protein translation in the cell population.

Further provided herein are methods of reducing the innate immune response of a cell to an exogenous nucleic acid, comprising the steps of: (a) contacting the cell with a first composition comprising a first dose of a first exogenous nucleic acid comprising a translatable region and at least one nucleoside modification; (b) determining the level of the innate immune response of the cell to the first exogenous nucleic acid; (c) contacting the cell with a second composition comprising either: (i) a second dose of the first exogenous nucleic acid, wherein the second dose contains a lesser amount of the first exogenous nucleic acid as compared to the first dose; or (ii) a first dose of a second exogenous nucleic acid, thereby reducing the innate immune response of the cell. In certain embodiments, methods are provided, wherein the step of contacting the cell with the first composition and/or the second composition is repeated one or more times. In certain embodiments, a predetermined efficiency of protein translation in the cell is achieved.

Further provided herein are methods for silencing gene expression in a cell, comprising the step of contacting the cell with a nucleic acid comprising: (i) a translatable region encoding a polypeptide capable of directing sequence-specific histone H3 methylation, under conditions such that the polypeptide is translated and reduces gene transcription of a target gene; and (ii) and at least one nucleoside modification. In certain embodiments, the cell is present in a mammalian subject. In certain embodiments, the target gene is a mutated Janus Kinase-2 family member and the mammalian subject suffers from a myeloproliferative disease.

Further provided herein are methods of reducing cellular differentiation in a target cell population, comprising the step of contacting the target cell population comprising a precursor cell with a composition comprising an effective amount of a nucleic acid comprising a translatable region encoding a polypeptide and at least one modified nucleoside, under conditions such that the polypeptide is translated and reduces the differentiation of the precursor cell. In certain embodiments, the target cell population comprises injured tissue. In certain embodiments, the target cell population comprises tissue affected by a surgical procedure. In certain embodiments, the precursor cell is selected from the group consisting of a stromal precursor cell, a neural precursor cell, and a mesenchymal precursor cell.

Further provided herein are isolated nucleic acids comprising a noncoding region and at least one nucleoside modification that reduces an innate immune response of a cell into which the nucleic acid is introduced, wherein the nucleic acid sequesters one or more translational machinery components. In certain embodiments, the isolated nucleic acids comprising a noncoding region and at least one nucleoside modification described herein are provided in an amount effective to reduce protein expression in the cell. In certain embodiments, the translational machinery component is a ribosomal protein or a transfer RNA (tRNA). In certain embodiments, the nucleic acid comprises a small nucleolar RNA (sno-RNA), micro RNA (miRNA), small interfering RNA (siRNA) or Piwi-interacting RNA (piRNA).

Further provided herein are isolated nucleic acids comprising (i) a first translatable region, (ii) at least one nucleoside modification, and (iii) an internal ribosome entry site (IRES). In certain embodiments, the IRES is obtained from a picornavirus, a pest virus, a polio virus, an encephalomyocarditis virus, a foot-and-mouth disease virus, a hepatitis C virus, a classical swine fever virus, a murine leukemia virus, a simian immune deficiency virus or a cricket paralysis virus. In certain embodiments, the isolated nucleic acids further comprise a second translatable region. In certain embodiments, the isolated nucleic acids further comprise a Kozak sequence.

Further provided herein are methods of antagonizing a biological pathway in a cell, comprising the step of contacting the cell with an effective amount of a composition comprising a nucleic acid comprising: (i) a translatable region encoding a recombinant polypeptide; and (ii) at least one nucleoside modification, under conditions such that the nucleic acid is localized into the cell and the recombinant polypeptide is capable of being translated in the cell from the nucleic acid, wherein the recombinant polypeptide inhibits the activity of a polypeptide functional in the biological pathway. In certain embodiments, methods are provided, wherein the biological pathway is defective in an autoimmune or inflammatory disorder selected from the group consisting of multiple sclerosis, rheumatoid arthritis, psoriasis, lupus erythematosus, ankylosing spondylitis and Crohn's disease.

Further provided herein are methods of agonizing a biological pathway in a cell, comprising the step of contacting the cell with an effective amount of a composition comprising a nucleic acid comprising: (i) a translatable region encoding a recombinant polypeptide; and (ii) at least one nucleoside modification, under conditions such that the nucleic acid is localized into the cell and the recombinant polypeptide is capable of being translated in the cell from the nucleic acid, wherein the recombinant polypeptide induces the activity of a polypeptide functional in the biological pathway. In certain embodiments, the agonized biological pathway modulates cell fate determination. In certain embodiments, the biological pathway is reversibly agonized.

Further provided herein are methods for enhancing nucleic acid delivery into a cell population, comprising the steps of: (a) providing a cell culture comprising a plurality of host cells; (b) contacting the cell population with a composition comprising an enhanced nucleic acid comprising a translatable region and at least one nucleoside modification, wherein the enhanced nucleic acid exhibits enhanced retention in the cell population, relative to a corresponding unmodified nucleic acid. In certain embodiments, methods are provided, wherein the retention of the enhanced nucleic acid is at least about 50% greater than the retention of the unmodified nucleic acid. In some embodiments, the retention of the enhanced nucleic acid is at least about 100% greater than the retention of the unmodified nucleic acid. In other embodiments, the retention of the enhanced nucleic acid is at least about 200% greater than the retention of the unmodified nucleic acid. In certain embodiments, methods are provided, wherein the step of contacting the cell with the composition is repeated one or more times.

Further provided herein are methods of nucleic acid co-delivery into a cell population, comprising the steps of: (a) providing a cell culture comprising a plurality of host cells; (b) contacting the cell population with a composition comprising: (i) a first enhanced nucleic acid comprising a translatable region and at least one nucleoside modification; and (ii) a first unmodified nucleic acid, wherein the composition does not substantially induce an innate immune response of the cell population.

Further provided herein are methods of nucleic acid delivery into a cell population, comprising the steps of: (a) providing a cell culture comprising a plurality of host cells; (b) contacting the cell population with a first composition comprising: (i) a first enhanced nucleic acid comprising a translatable region and at least one nucleoside modification; and (ii) a first unmodified nucleic acid, wherein the composition does not substantially induce an innate immune response of the cell population; and (c) contacting the cell population with a second composition comprising a first unmodified nucleic acid.

Patients who have had chemotherapy and/or radiation therapy may require infusions of progenitor and/or stem cells to restore their immune system. To obtain the stem cells, they need to be mobilized or moved into the peripheral blood. A fast and durable recovery of a patient's immune system is usually achieved if a sufficient number of stem cells is available for transplantation. Stem cell transplantation can be either allogenic (cells are transplanted from a healthy donor, e.g. a sibling), or autologous (cells are collected from the patient and reinfused after chemotherapy). Following chemotherapy, the stored stem cells can be transplanted into the patient, through an intravenous infusion. Patients may be given antibiotics and/or blood transfusions to prevent infection while their immune systems are recovering. Once in the bloodstream the stem cells migrate back into the bone marrow. Over a period of one to five weeks, these stem cells can increase in number and develop into various types of cells including neutrophils. Current strategies of mobilizing bone marrow progenitor and/or stem cells into the blood stream employ G-CSF, e.g. as described in U.S. Pat. No. 5,582,823. Agents that may further increase circulating white blood cells and progenitor cells and that can be used in combination with G-CSF include AMD3100, granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor (SCF), thrombopoietin, flt3, myelopoietin, anti-VLA-4 antibody, anti-VCAM-1 and growth related oncogene (GRO). PCT publication No. WO/2008/019371; Dale D et al. Am. J. of Hematol. 57:7-15 (1998); Rosenfeld C et al. Bone Marrow Transplantation 17:179-183 (1997); Pruijt J et al. Cur. Op. in Hematol. 6:152-158 (1999); Broxmeyer H et al. Exp. Hematol. 23:335-340 (1995); Broxmeyer H et al. Blood Cells, Molecules and Diseases 24: 14-30 (1998); Glaspy J et al. Cancer Chemother. Pharmacol. 38(suppl):S53-S57 (1996); Vadhan-Raj S et al. Ann. Intern. Med. 126:673-681 (1997); King A et al. Blood 97:1534-1542 (2001); Glaspy J et al. Blood 90:2939-2951 (1997); and Papayannopoulou T et al. PNAS 92:9647-9651 (1995). AMD3100 (1,1[1,4-phenylene-bis(methylene)]-bis-1,4,8,11-tetraazacyclotetradecane) has been shown to mobilize progenitor/stem cells to permit their harvest (PCT publication No. WO 03/011277) and to elevate white blood cell count (WO 00/458140).

Provided herein are improved regimens for mobilizing hematopoietic stem and progenitor cells in a mammalian subject in need thereof, the regimen comprising an amount of a modified mRNA (mRNA) encoding a G-CSF polypeptide effective to enhance mobilization of hematopoietic stem cells and progenitor cells (HSPC), and an effective amount of AMD3100.

Further provided herein are methods to obtain progenitor and/or stem cells from a mammalian subject, comprising the steps of: (a) administering to the subject a composition comprising a modified mRNA encoding G-CSF polypeptide in an amount effective to mobilize the progenitor and/or stem cells into the peripheral blood of the subject; (b) administering an effective amount of AMD3100 to the subject after administering the composition; followed by (c) harvesting the progenitor and/or stem cells. In some embodiments, the composition is administered at least twice but fewer than ten times prior to administering the AMD3100.

Further provided herein are kits comprising a pharmaceutical formulation comprising a modified mRNA encoding G-CSF polypeptide and AMD3100 in one or more containers, and instructions for use thereof.

DETAILED DESCRIPTION OF THE INVENTION

Figure 1A:
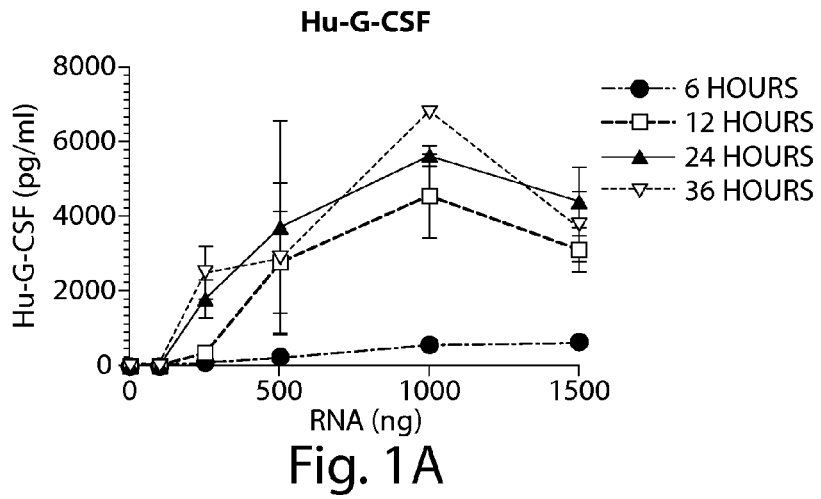
FIG. 1 depicts graphs showing human G-CSF (FIG. 1A), α-MSH (FIG. 1B) and mouse insulin (FIG. 1C) secretion into the media (μg/ml) measured by ELISA following transfection of human keratinocytes with various amounts of modified mRNA.
Figure 1B:
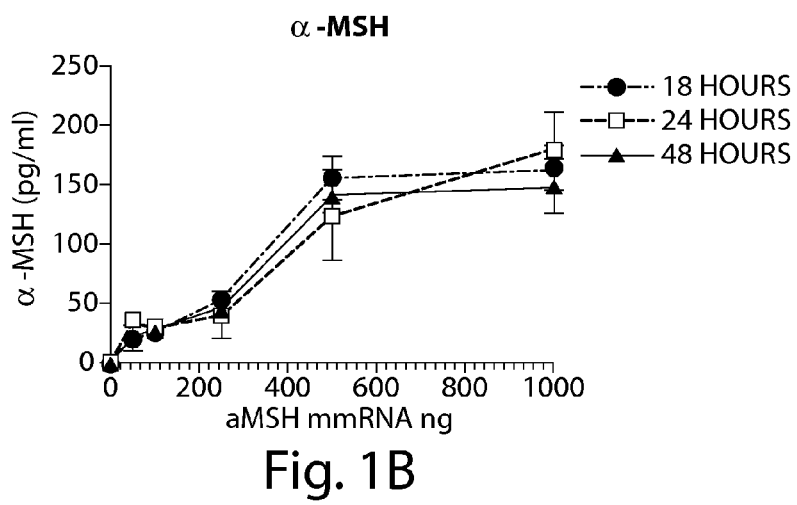

In general, exogenous nucleic acids, particularly viral nucleic acids, introduced into cells induce an innate immune response, resulting in interferon (IFN) production and cell death. However, it is of great interest for therapeutics, diagnostics, reagents and for biological assays to deliver a nucleic acid, e.g., a ribonucleic acid (RNA) inside a cell, either in vivo or ex vivo, such as to cause intracellular translation of the nucleic acid and production of the encoded protein. Of particular importance is the delivery and function of a non-integrative nucleic acid, as nucleic acids characterized by integration into a target cell are generally imprecise in their expression levels, deleteriously transferable to progeny and neighbor cells, and suffer from the substantial risk of mutation. Provided herein in part are nucleic acids encoding useful polypeptides capable of modulating a cell's function and/or activity, and methods of making and using these nucleic acids and polypeptides. As described herein, these nucleic acids are capable of reducing the innate immune activity of a population of cells into which they are introduced, thus increasing the efficiency of protein production in that cell population. Further, one or more additional advantageous activities and/or properties of the nucleic acids and proteins of the invention are described.

Provided herein are modified nucleic acids encoding the precursors of melanocyte-stimulating hormone (MSH), insulin, and granulocyte colony-stimulating factor (G-CSF), or partially or fully processed forms of these precursors. In certain embodiments, the modified nucleic acids comprise mRNA. In particular embodiments, the modified mRNA (mRNA) is derived from cDNA. In certain embodiments, the mRNA comprises at least two nucleoside modifications. In certain embodiments, these nucleoside modifications are 5-methylcytosin and pseudouridine. In some embodiments, around 25%, around 50%, around 75%, or up to and including 100% of cytosine and uridine nucleotides of the modified nucleic acid are modified nucleotides. In certain embodiments, the mRNA comprises a 5' cap structure and a 3' poly-A tail. In specific embodiments, the 5' cap structure is a Cap 1 structure. In specific embodiments, the poly-A tail comprises at least 10, 20, 30, 40, 50, 60, 70, 80, 90, 100, 110, 120, 130, 140, or 150 nucleotides.

Further, provided herein are compositions comprising the modified nucleic acids described herein. In certain embodiments, the compositions further comprise a pharmaceutically acceptable carrier. In certain embodiments, the carrier is formulated for systemic or local administration. In certain embodiments, the administration is oral or topical. In certain embodiments, the compositions comprise naked modified nucleic acids. In other embodiments, the modified nucleic acids are complexed or encapsulated. For example, the modified nucleic acids may be complexed in liposomal form or may be encapsulated in a nanoparticle. In certain embodiments, the modified nucleic acids, the complex or the nanoparticle further comprise one or more targeting moieties. These moieties can be used to target delivery in vivo to certain organs, tissues or cells.

Provided herein are methods of treating a subject having or being suspected of having a disease, the methods comprising administering to a subject in need of such treatment a composition described herein in an amount sufficient to treat the disease. In specific embodiments, the disease is associated with one or more cellular and/or molecular changes affecting, for example, the level, activity, and/or localization of precursors of melanocyte-stimulating hormone (MSH), insulin, and granulocyte colony-stimulating factor (G-CSF), or a partially or fully processed form of these precursors. Cellular and/or molecular changes may affect transcription, translation, post-translational modification, processing, folding, intra- and/or extracellular trafficking, intra- and/or extracellular stability/turnover, and/or signaling of one or more molecules associated with MSH, G-CSF or insulin activity. In certain embodiments, activities associated with MSH, G-CSF or insulin are compromised, e.g. 90%, 80%, 70%, 60%, 50%, 40%, 30%, 20%, 10%, 5% or less of wild-type activity. For signaling molecules, such as hormones, whether they are autocrine or paracrine, the one or more defects resulting in reduced activity may be exhibited by the cell in which MSH, G-CSF or insulin are generated and/or may be exhibited by the cell on which MSH, G-CSF or insulin act. In certain embodiments, the methods of treating a subject having or being suspected of having a disease comprise administering to the subject in need of such treatment a composition comprising a modified nucleic acid described herein in an amount sufficient to modulate one or more activities associated with MSH, G-CSF or insulin to treat the disease.

A major drawback of many current treatments for diseases described herein is the necessity to produce MSH, insulin, and G-CSF as polypeptides. Polypeptides are ordinarily expressed in and isolated from mammalian or bacterial cultures. Bacterial cultures and many cancer-derived cell culture systems do not faithfully recapitulate post-translational modifications, such as e.g. glycosylation (G-CSF) and amidation (MSH) and protein precursors may not be fully processed. In some instances, the lack of posttranslational modification and processing influences the activity of the final protein product, its localization and/or its target specificity. For example, pro-opiomelanocortin (POMC) if not fully processed may give rise to adrenocorticotropic hormone (ACTH) which is MC2R-specific, while MC1R has the highest affinity to α-MSH, which is identical to the first 13 amino acids at the amino terminal of ACTH. Precursors and final cleavage products can have different physiological effects. In type 2 diabetes, an elevated proinsulin-to-insulin ratio in blood circulation has been detected, likely as a consequence of compromised proteolytic processing of insulin precursor. For production of recombinant proteins, the polypeptide product that is effective for a particular treatment must usually be predetermined because the proteins if administered do not undergo any additional processing. Any modification that is vital for activity must also be present on the recombinant protein because they will not be added by the host when the recombinant proteins are administered. Recombinant protein production and purification is expensive and labor intensive. Protein expression host systems may harbor pathogens (e.g. viruses) that may contaminate the purified product. Proteins and particularly protein modifications are inherently unstable and require specific storage conditions and generally have a short shelf life. To be efficacious, recombinant proteins must be further modified, particularly by pegylation to avoid rapid degradation in vivo. For example, Filgrastim was readily degraded in vivo and made repeated daily injections necessary during the course of chemotherapy. Only site-specific pegylation at the N-terminus of G-CSF (PEG-Filgrastim, U.S. Pat. Nos. 5,824,784 and 7,090,835) made the product stable enough to be given at less frequent intervals. Still, site-specific pegylation remains difficult because it can lead to loss of activity, loss of target specificity and/or protein aggregation. Veronese et al. Bioconjugate Chem. 18:1824-1830 (2007).

The modified mRNA molecules described herein do not share these problems. In comparison to recombinant proteins, they exhibit increased stability for shipping, handling and storage, are easy to mass produce, and when translated from the modified mRNA, the polypeptide can undergo an array of cell- and/or tissue-specific posttranslational processing, folding and modification.

Melanocyte-Stimulating Hormones (MSH).

The melanocyte-stimulating hormones (MSH) are peptide hormones primarily produced by cells in the intermediate lobe of the pituitary gland. MSH belongs to a group called the melanocortins. This group includes and adrenocorticotropic hormone (ACTH), α-MSH, β-MSH and γ-MSH. These peptides are all cleavage products of a large precursor peptide called pro-opiomelanocortin (POMC). α-MSH is identical to the first 13 amino acids at the amino terminal of ACTH. Proteolytic cleavage has been identified in several cell types such as melanocytes, keratinocytes, epithelial cells, B cells, natural killer cells and subsets of T cells. MSH is an agonist of and exerts its biological function through five different melanocortin-receptors (MCRs). MCRs are G-protein coupled receptors with seven-transmembrane domains that signal by activating adenylate cyclase resulting in an increase of intracellular cAMP. α-MSH is largely non-selective, although MC1R has the highest affinity to α-MSH, while ACTH is MC2R-specific and γ-MSH is MC3R specific. MCRs are inhibited by antagonists agouti signaling peptide and agouti-related peptide.

The amino acid sequences of melanocyte-stimulating hormones are set forth below:

α-MSH:
(SEQ ID NO: 10)
Ser-Tyr-Ser-Met-Glu-His-Phe-Arg-Trp-Gly-Lys-Pro-Val

β-MSH (human):
(SEQ ID NO: 11)
Ala-Glu-Lys-Lys-Asp-Glu-Gly-Pro-Tyr-Arg-Met-Glu-His-Phe-Arg-Trp-Gly-Ser- Pro-Pro-Lys-Asp γ-MSH:
(SEQ ID NO: 12)
Tyr-Val-Met-Gly-His-Phe-Arg-Trp-Asp-Arg-Phe-Gly Synthetic analogs of α-MSH have been developed for human use, e.g. afamelanotide (melanotan-1, SCENESSE® or CUV1647) (Clinuvel Pharmaceuticals, Australia) and bremelanotide (PT-141) (Palatin Technologies, NJ).

Conditions affecting cortisol levels (e.g. Cushing's syndrome and primary Addison's) influence ACTH production from POMC and can also increase MSH levels which can cause hyper-pigmentation. Subjects who do not tan well may express variant MCRs that are refractory to MSH in the blood. Subjects with red hair have a predominance of red phaeomelanin in hair and skin and/or a reduced ability to produce black eumelanin Eumelanin is photoprotective whereas phaeomelanin can generate free radicals in response to UV radiation and may contribute to UV-induced skin damage, which is one reason why red haired subjects fail to tan and are at risk from UV-radiation. In mammals the relative proportions of phaeomelanin and eumelanin are regulated by MSH via MC1R. A variant MC1R is present in over 80% of subjects with red hair and/or fair skin who tan poorly which can be found in only 4% of subjects who show a good tanning response. Valverde P et al. Nat. Genet. 11:328-30 (1995). Certain mutations in the MC1R gene are strongly associated with increased melanoma incidence by sensitizing melanocytes to the cytotoxic effects of UV irradiation. Abdel-Malek Z A et al. Photochem Photobiol 84:501-508 (2008). The MC1R coding sequence is highly polymorphic and certain allelic variants are associated with pigmentation phenotypes and risk factors for melanoma and non-melanoma skin cancer development. Wong T H et al. Peptides 26: 1965-1971 (2005), Sturm R A Melanoma Res 12: 405-416 (2002). Sánchez-Laorden B L et al. J Biol Chem 282: 3241-3251 (2007). Four alleles have a strong association with the red hair/fair skin phenotype: D84E, R151c, R160W, and D294H. V60L, V92M, and R163Q are weakly associated. Loss of function alleles, such as R151c, R160W, R142H, and D294H, which modulate α-MSH binding and/or adenylyl cyclase activation, lead to increased sensitivity to UV radiation and an increased risk for developing skin cancer, e.g. melanoma. Makova K et al. Peptides 26: 1901-1908 (2005), Sturm R A et al. Gene 277: 49-62 (2001), Scott M C et al. J Cell Sci 115: 2349-2355 (2002). UV irradiation is thought to up-regulate α-MSH/MC1R signaling resulting in increased pigmentation of the skin and enhanced levels of cytotoxic $CD8^+$ T cell surveillance to protect against skin cancer development. Loss-of-function mutations in the MC1R gene might prevent the induction of tumor protection.

α-MSH is responsible for tanning in humans and α-MSH polypeptide analogs are being investigated for photo-protection in subjects with various indications, such as erythropoietic protoporphyria (EPP), polymorphous light eruption (PLE), actinic keratosis (solar keratosis) and squamous cell carcinoma. MSH agonist effects are thought to be mediated by MC1R. α-MSH is responsible for pigmentation by stimulating the production and release of melanin in melanocytes of the skin and hair. When ultraviolet light contacts keratinocytes, p53 is activated which in turn activates transcription of the POMC gene. POMC protein cleavage produces α-MSH which is secreted from the cells and stimulates melanocytes in a paracrine manner to synthesize melanin. The melanin is secreted by the melanocytes and taken up by the skin cells. ACTH is secreted into the blood and may help reduce skin inflammation by stimulating the release of glucocorticoids from the adrenal cortex.

α-MSH plays a role in MHC class I-restricted cytotoxicity. Treatment of skin cancer with α-MSH might ameliorate disease or improve anti-tumoral immune responses. It was recently demonstrated that MC1R is expressed in murine and human $CD8^+$ T cells and that α-MSH/MC1R-mediated signaling induces up-regulation of the expression of cytotoxic genes and enhances the cytolytic activity in tumor-specific $CD8^+$ T cells. Loser K et al. PLoS ONE 5(2): e8958. α-MSH has an inhibitory effect on melanoma proliferation and metastasis formation and its anti-inflammatory properties may also affect melanoma progression. Lunec J et al. Melanoma Res 2: 5-12 (1992), Gehlsen K R et al. Pigment Cell Res 5: 219-223 (1992), Eves P et al. Br J Cancer 89: 2004-2015 (2003).

Provided herein are methods of treating a subject having a skin cancer, the methods comprising administering to a subject in need of such treatment a composition comprising a modified nucleic acid encoding a MSH precursor or a partially or fully processed form thereof in an amount sufficient to treat the skin cancer. In certain embodiments, the skin cancer is a melanoma or a squamous cell carcinoma. In certain embodiments, the treatment is local. In certain embodiments, the treatment is topical. In certain embodiments, cells, e.g. dendritic cells, autologously derived from the recipient subject are stimulated ex vivo using a modified nucleic acid encoding a MSH precursor or a partially or fully processed form. These cells may be re-administered to the subject having the skin cancer to treat the condition.

Provided herein are methods of preventing the development of skin cancer or reducing the likelihood that a subject develops skin cancer. The methods comprise administering to a subject in need of such prevention a composition comprising a modified nucleic acid encoding a MSH precursor or a partially or fully processed form thereof in an amount sufficient to prevent the development of skin cancer or to reduce the likelihood that a subject develops skin cancer. In certain embodiments, the subject in need of prevention is a subject exposed to sun light. In certain embodiments, the skin cancer is a melanoma or a squamous cell carcinoma. In certain embodiments, the administration is local. In certain embodiments, the administration is topical. For example, a composition comprising a modified nucleic acid encoding a MSH precursor or a partially or fully processed form thereof may comprise suntan lotion. In certain embodiments, the composition is applied as a prophylactic, before exposure to light, e.g. sun light.

Provided herein are methods of preventing the development of a condition associated with photo-sensitivity or reducing the likelihood that a subject develops the condition and/or displays one or more symptoms of the condition. The methods comprise administering to a subject in need of such prevention a composition comprising a modified nucleic acid encoding a MSH precursor or a partially or fully processed form thereof in an amount sufficient to prevent the development of a condition associated with photo-sensitivity or reducing the likelihood that the subject develops the condition and/or displays one or more symptoms of the condition. In certain embodiments, the condition associated with photo-sensitivity is erythropoietic protoporphyria (EPP), polymorphous light eruption (PLE), or actinic keratosis (solar keratosis). In certain embodiments, the administration is local. In certain embodiments, the administration is topical. For example, a composition comprising a modified nucleic acid encoding a MSH precursor or a partially or fully processed form thereof may comprise suntan lotion. In certain embodiments, the composition is applied as a prophylactic, before exposure to a light source, e.g. an interior or exterior light source. In specific embodiments, the exterior light source is the sun.

Provided herein are methods of increasing or accelerating the process of tanning in a subject. The methods comprise administering to a subject wishing to increase or accelerate the process of tanning a composition comprising a modified nucleic acid encoding a MSH precursor or a partially or fully processed form thereof in an amount sufficient to increase or accelerate the process of tanning. In certain embodiments, the treatment is local. In certain embodiments, the treatment is topical. For example, a composition comprising a modified nucleic acid encoding a MSH precursor or a partially or fully processed form thereof may comprise a lotion for use as a cosmetic.

In certain embodiments, the subject exhibits wild-type MSH/MCR signaling. In other embodiments, the subject exhibits impaired MSH/MCR signaling. The impairment may be reduced signaling. For example, impaired signaling may be caused by reduced intra- or extracellular levels of MSH or a lack of MSH. Impaired signaling may be caused by dysfunctional MC receptor, e.g. as a result of a mutation in a gene encoding an MCR. MSH/MCR signaling may be impaired by at least 5%, 10%, 20%, 30%, 40%, 50%, 60%, 70%, 80%, 90%, 95%, or 99% compared to wild-type MSH/MCR signaling. The resulting impairment may lead to a reduction in melanin production, a change in the relative proportions of phaeomelanin and eumelanin toward phaeomelanin, a reduction in inflammatory responses, a reduction in general immune surveillance and/or a reduction specifically in surveillance by cytotoxic $CD8^+$ T cell. In some embodiments, compositions comprising a modified nucleic acid encoding a MSH precursor or a partially or fully processed form thereof are administered to modulate MSH/MCR signaling. In certain embodiments, impaired MSH/MCR signaling and/or MSH activity is partially or fully restored compared to wildtype. In certain embodiments, impaired MSH/MCR signaling and/or MSH activity is restored to 5%, 10%, 20%, 30%, 40%, 50%, 60%, 70%, 80%, 90%, 95%, 99% or 100% of wild-type MSH/MCR signaling and/or MSH activity. In other embodiments, restored MSH/MCR signaling and/or MSH activity exceeds that of wildtype activity by 5%, 10%, 20%, 30%, 40%, 50%, 60%, 70%, 80%, 90%, 95%, 100%, 200%, 300%, 400%, 500%, 600%, 700%, 800%, 900%, or 1000%. In certain embodiments, MSH/MCR signaling and/or MSH activity is not impaired in a subject, and compositions comprising a modified nucleic acid encoding a MSH precursor or a partially or fully processed form thereof are administered to increase MSH/MCR signaling above wildtype levels. In some embodiments, MSH/MCR signaling and/or MSH activity exceeds that of wildtype activity by 5%, 10%, 20%, 30%, 40%, 50%, 60%, 70%, 80%, 90%, 95%, 100%, 200%, 300%, 400%, 500%, 600%, 700%, 800%, 900%, or 1000%. In certain embodiments, increased MSH/MCR signaling and/or MSH activity may lead to increased melanin production, increased accumulation of eumelanin, an increased inflammatory, an increased immune response and/or an increase in surveillance by (and/or number of) cytotoxic $CD8^+$ T cell.

MSH signaling in the brain has been shown to affect sexual arousal and appetite. MC1R, MC3R and MC4R are widely expressed in the brain, and are also thought to be responsible for effects on mood and cognition.

α-MSH analogs (e.g. melanotan II) are being investigated for their aphrodisiac effects. Enhanced libido and penile erections were noted in male test subject and enhanced arousal in female test subjects. These effects are thought to be mediated by actions in the hypothalamus on neurons that express MSH receptors MC3R and MC4R.

Provided herein are methods of treating a subject suffering from impotence, the methods comprising administering to a subject in need of such treatment a composition comprising a modified nucleic acid encoding a MSH precursor or a partially or fully processed form thereof in an amount sufficient to treat impotence. In certain embodiments, the treatment is targeted to the hypothalamus. In other embodiments, the treatment is systemic. In certain embodiments, penile erections are restored partially or fully.

Provided herein are methods of enhancing libido, penile erections and/or sexual arousal in a subject, the methods comprising administering to a subject in need of such enhancement a composition comprising a modified nucleic acid encoding a MSH precursor or a partially or fully processed form thereof in an amount sufficient to provide the enhancement. In some embodiments, the treatment is systemic. In certain embodiments, the treatment is targeted to the hypothalamus. In certain embodiments, the subject is a male. In other embodiments, the subject is a female.

α-MSH is found in the brain where it is thought to act to suppress appetite. Some cases of extreme obesity have been traced to mutations in the brain receptor for α-MSH. Defects in MCR4 may cause autosomal dominant obesity, accounting for an estimated 5-6% of all cases of early-onset obesity. Farooqi I S et al. N Engl J Med 348:1085-95 (2003), Branson R et al. N Engl J Med 348:1096-103 (2003), Vaisse C et al. J Clin Invest 106:253-62 (2000). Several different monogenic causes of childhood obesity have been identified of which binding of α-MSH to MC4R appears critical. MC4R is expressed in the hypothalamus. Stimulation of MC4R by α-MSH binding triggers the activation of anorexigenic signals, which, are thought to reduce food intake by creating the perception of satiety. Children with MC4R-related obesity are largely unable to experience a sense of satiety. In vitro studies have shown that certain obesity-linked MC4R mutations render the receptor dys- or non-functional thus preventing the activation of anorexigenic signals in response to α-MSH binding. Lubrano-Berthelier C et al. Hum Mol Genet. 12:145-53 (2003); Yeo G S et al. Hum Mol Genet. 12:561-74 (2003), Nijenhuis W A J Biol Chem 278:22939-45 (2003). MC4R-associated early onset obesity symptoms include binge eating behavior, severe hyperinsulinemia, an increase in bone minerals, a higher linear growth velocity, and an earlier than normal onset of puberty. Early onset obesity first occurs in children under ten years of age. Subjects who are heterozygous for mutations in the mc4r gene exhibit a less severe phenotype than subjects who are homozygous for mc4r gene mutations. In heterozygotes, expression of the obesity phenotype appears to be due to haploinsufficiency and insufficient levels of wildtype MC4R protein are expressed from the normal gene copy. Penetrance of the mutation varies within and between families and not all heterozygous individuals carrying an obesity-associated MC4R mutation are obese. Within families, female carriers of obesity-linked MC4R mutations are often more severely affected than males with the same mutation. Hinney A et al. J Clin Endocrinol Metab 88:4258-67 (2003). A majority of subjects with MC4R-associated obesity are heterozygous carriers. Therapy for MC4R-associated obesity may be targeted to increase stimulation of the remaining wildtype MC4R protein to compensate for the loss-of-function in the mutated receptor. Mutations within POMC genes are also associated with early-onset obesity. Patients have been identified carrying heterozygous mutations in exon 3 (G7013T, C7133delta) which interfere with appropriate synthesis of ACTH and α-MSH, or carrying homozygous mutations in exon 2 (C3804A) which abolishes POMC translation. Krude H et al. Nat Genet. 19:155-7 (1998).

Medical and behavioral interventions, such as lifestyle modifications, pharmacotherapy and bariatric surgery, as treatment for obesity in childhood remain scarce and largely ineffective. Lifestyle modifications, e.g. changes to dietary and exercise habits, are effective in less than 5% of obese subjects. Pharmacotherapy is not routinely proposed as a treatment for childhood obesity and the long-term safety and efficacy of anti-obesity drugs (e.g. sibutramine (Meridia®) and orlistat (Xenical®)) have not been determined in children or adolescents. Invasive bariatric surgery to combat morbid obesity in children is not universally accepted as a tool for subjects in childhood or adolescence. Choquet et al. Genome Medicine 2010 2:36.

Provided herein, are methods of treating a subject having early onset obesity, the methods comprising administering to a subject in need of such treatment a composition comprising a modified nucleic acid encoding a MSH precursor or a partially or fully processed form thereof in an amount sufficient to treat early onset obesity. In certain embodiments, the subject is a child or an adolescent. In specific embodiments, the child or an adolescent is female. In certain embodiments, the treatment is systemic. In certain embodiments, the treatment is targeted to the hypothalamus.

Further provided herein, are methods of preventing the development of early onset obesity in a subject suspected of developing early onset obesity, the methods comprising administering to a subject in need of such treatment a composition comprising a modified nucleic acid encoding a MSH precursor or a partially or fully processed form thereof in an amount sufficient to prevent the development of early onset obesity. In certain embodiments, the subject is a child or an adolescent. In specific embodiments, the child or an adolescent is female. In certain embodiments, the treatment is systemic. In certain embodiments, the treatment is targeted to the hypothalamus.

Further provided herein, are methods of delaying the onset of early onset obesity in a subject suspected of developing early onset obesity, the methods comprising administering to a subject in need of such treatment a composition comprising a modified nucleic acid encoding a MSH precursor or a partially or fully processed form thereof in an amount sufficient to delay the onset of early onset obesity. In certain embodiments, the subject is a child or an adolescent. In specific embodiments, the child or an adolescent is female. In certain embodiments, the treatment is systemic. In certain embodiments, the treatment is targeted to the hypothalamus. In certain embodiments, the subject suspected of developing early onset obesity was genetically tested for the presence of one or more mutations in the mc4r gene(s) and/or pomc gene(s). In certain embodiments, testing comprises DNA sequencing of one or more regions of the subject's mc4r gene(s) and/or pomc gene(s). In certain embodiments, DNA is obtained from leukocytes derived from a sample of the subject's blood.

α-MSH exhibits immunomodulatory effects in vivo. Mouse model have shown that systemic as well as epicutaneous application of α-MSH suppressed the sensitization and elicitation phase of contact allergy and induced a hapten-specific tolerance. Grabbe S et al. J Immunol 156:473-478 (1996). Systemic administration of α-MSH inhibits the development of experimentally induced inflammatory bowel disease (IBD, colitis), experimental autoimmune encephalomyelitis and allergic airway inflammation in mice as well as experimentally induced arthritis and experimental uveitis in rats. Rajora N et al Peptides 18: 381-385 (1997), Lipton J M et al. Ann N Y Acad Sci 741: 137-148 (1994), Han D et al. Gene Ther 14: 383-395 (2007), Raap U et al. J Immunol 171: 353-359 (2003) Nishida T et al. Int Immunopharmacol 4: 1059-1066 (2004).

Provided herein, are methods of providing immunomodulatory effects to a subject having an inflammatory disease, the methods comprising administering to a subject in need of such immunomodulation a composition comprising a modified nucleic acid encoding a MSH precursor or a partially or fully processed form thereof in an amount sufficient to provide an immunomodulatory effect. In certain embodiments, the immunomodulatory effect suppressed the sensitization and/or elicitation phase of contact allergy. In certain embodiments, the immunomodulatory effect inhibits the development of, delays the onset of, or reduces the severity of an inflammatory disease or condition. In certain embodiments, the inflammatory disease or condition is inflammatory bowel disease (IBD, e.g. colitis), autoimmune encephalomyelitis, allergic airway inflammation, arthritis or uveitis. In some embodiments, administration is systemic or epicutaneous. In some embodiments, administration is oral, topical, or pulmonary.

Mucin hypersecretion is a clinical feature of several respiratory diseases such as asthma, cystic fibrosis, nasal allergy, rhinitis, and sinusitis. α-MSH may be used to decrease mucin overproduction initiated by NF-κB activation, because it inhibits NF-κB activation induced by pro-inflammatory cytokines such as TNF-α. α-MSH may be used to alleviate the symptoms of these diseases. Lee S N Am J Respir Cell Mol Biol 44:716-724 (2011).

Provided herein, are methods of modulating NF-κB activation, the methods comprising administering to a subject in need of such modulation a composition comprising a modified nucleic acid encoding a MSH precursor or a partially or fully processed form thereof in an amount sufficient to modulate NF-κB activation. In certain embodiments, modulating NF-κB activation is inhibiting NF-κB activation. In certain embodiments, NF-κB activation is associated with mucine hypersecretion.

Further provided herein, are methods of treating a subject having a disease or condition associated with mucin hypersecretion, the methods comprising administering to a subject in need of such treatment a composition comprising a modified nucleic acid encoding a MSH precursor or a partially or fully processed form thereof in an amount sufficient to treat disease or condition associated with mucin hypersecretion. In some embodiments, mucin hypersecretion is associated with a respiratory disease. In some embodiments, the respiratory disease is asthma, cystic fibrosis, nasal allergy, rhinitis, or sinusitis. In some embodiments, administration is systemic. In certain embodiments, the administered composition is targeted to the lung. In some embodiments, administration is pulmonary.

Hyperactivation of melanotrophs in the pituitary gland and increased levels of plasma α-MSH have been detected in an animal model of chronic stress. Chronic fatigue syndrome (CFS) is associated with chronic stress and CFS patients with a disease duration of less than 5 years have significantly higher levels of α-MSH in their peripheral blood than healthy controls. Shishioh-Ikejima et al BMC Neurology 10:73 (2010).

Insulin.

Insulin is produced in the pancreas by β-cells of the islets of Langerhans and released upon increase of the blood glucose level. Insulin signaling modulates cellular glucose uptake and storage (as glycogen) in the liver, muscle, and fat tissue by regulating membrane glucose transporters. In β-cells proinsulin is synthesized as a single chain, a 110 amino acid pro-precursor that contains a 24 amino acid signal sequence and an 86 amino acid proinsulin. Insulin is synthesized from the proinsulin precursor molecule by the action of proteolytic enzymes, prohormone convertases PC1 and PC2 and exoprotease carboxypeptidase E. Following removal of the signal peptide, the proinsulin peptide undergoes further proteolysis to generate mature insulin, a 51 amino acid (molecular weight: 5,808 Da) disulfide-linked dimer that consists of a 30 amino acid B chain (amino acid 25-54) bound to a 21 amino acid A chain (amino acid 90-110). The 34 amino acid intervening peptide (amino acid 55-89) that connects the B and A chains and allows for the correct formation of the intra-chain disulphide bonds is referred to as the C-peptide. Human proinsulin shares 84% and 80% amino acid sequence identity with rat and bovine proinsulin, respectively. Most of the sequence variation between species occurs in the region of the C-peptide.

Low insulin levels or lack of insulin are associated with type 2 and type 1 diabetes mellitus, respectively. These conditions are associated with an increased risk for microvascular complications such as retinopathy, nephropathy, and peripheral neuropathy. Patients with type 1 diabetes depend on external insulin (commonly injected subcutaneously) because they lack the insulin hormone. Patients with type 2 diabetes are often insulin resistant. Over 40% of patients with Type 2 diabetes require insulin as part of their diabetes management plan. In type 2 diabetes, an elevated proinsulin-to-insulin ratio in blood circulation has been detected, likely as a consequence of compromised proteolytic processing of insulin precursor. Proinsulin stimulates amylin secretion by β-cells and amyloid formation in pancreatic islets. Insulin has been shown to be produced inside the brain and reduced levels of these proteins are linked to Alzheimer's disease. De la Monte S M et al. J. Alzheimers Dis. 7: 45-61 (2005), Steen E et al J. Alzheimers Dis. 7: 63-80 (2005). Insulin in the brain enhances learning and memory. Benedict C et al. Psychoneuroendocrinology 29: 1326-34 (2004).

Neonatal diabetes (ND), developing within the first few weeks or months of life, is a very rare condition with an incidence of 1 in 300,000 to 500,000 live births. ND can be a potentially devastating metabolic disorder characterized by mild to severe hyperglycemia with low levels of circulating insulin. Disease presentation can be transient, transient neonatal diabetes (TND) or permanent, permanent neonatal diabetes (PND). Over 50% of TND cases are associated with abnormalities of an imprinted region on chromosome 6q24, whereas mutations in the two subunits Kir6.2 and SUR1) of the ATP-sensitive $K^+$ channel of pancreatic β-cell s are a common cause of both TND and PND. Few cases of PND are associated with mutations in the genes encoding glucokinase (GCK) and insulin promoter factor-1 (IPF-1), and rare mutations in PTF1A, FOXP3, GLIS3, TCF2, and EIF2AK3. Spontaneous mutations are common in ND, with 80% of the mutations in KCNJ11 (encoding Kir6.2) occurring de novo. Missense mutations in insulin and its precursors, preproinsulin and proinsulin, affecting insulin structure and biosynthesis are also a cause of ND. Støy J et al. PNAS 104:15040-15044 (2007), Polak M et al. Diabetes 57: 1115-1119 (2008), Colombo C et al. J Clin Invest. 118:2148-2156 (2008), Nishi, M et al J Diabetes Invest 2: 92-100. (2011). Mutations are either inherited in an autosomal dominant manner or occur de novo. The mutations are in critical regions of the preproinsulin molecule and are predicted to prevent normal folding and progression of proinsulin in the insulin secretory pathway. The abnormally folded proinsulin molecule may induce the unfolded protein response and undergo degradation in the endoplasmic reticulum, leading to severe endoplasmic reticulum stress and potentially β cell death by apoptosis. Akita and Munich mouse models that have dominant-acting missense mutations in the Ins2 gene show loss of β cell function and mass and one of the human missense mutations is identical to that in the Akita mouse model. The human missense mutations generate polypeptides that display unpaired reactive cysteine residues and are very likely to act in a dominant manner analogous to the Akita and/or Munich mouse Ins2 mutations to disrupt insulin biosynthesis and induce endoplasmic reticulum (ER) stress.

Provided herein, are methods of treating a subject having neonatal diabetes, the methods comprising administering to a subject in need of such treatment a composition comprising a modified nucleic acid encoding an insulin precursor or a partially or fully processed form thereof in an amount sufficient to treat neonatal diabetes.

Further provided herein, are methods of preventing the development of neonatal diabetes, or delaying the onset of neonatal diabetes in a subject suspected of developing neonatal diabetes, the methods comprising administering to a subject in need of such treatment a composition comprising a modified nucleic acid encoding an insulin precursor or a partially or fully processed form thereof in an amount sufficient to prevent the development of neonatal diabetes, or to delay the onset of neonatal diabetes. In certain embodiments, the subject is an infant. In some embodiments, the infant is less than one month old, less than two months old, less than three months old, less than four months old, less than five months old, or less than one year old.

In certain embodiments, the subject suspected of developing early onset obesity was genetically tested for the presence of one or more mutations in the insulin gene. In certain embodiments, testing comprises DNA sequencing of one or more regions of the subject's insulin gene.

Granulocyte Colony-Stimulating Factor (G-CSF).

Granulocyte colony-stimulating factor (G-CSF, GCSF, CSF 3) is a cytokine growth factor produced primarily by monocytes and macrophages (and neutrophils, fibroblasts, endothelial cells, and bone marrow stromal cells) upon activation by endotoxin, TNF-α, IFN-γ (and IL-1, IL-17 and GM-CSF) to stimulate the bone marrow (hematopoietic progenitors of neutrophil/granulocyte lineage) to produce granulocytes and stem cells for release into the blood. G-CSF also stimulates the survival, proliferation, differentiation, and function of neutrophil precursors and mature neutrophils via Janus kinase (JAK)/signal transducer and activator of transcription (STAT), Ras/mitogen-activated protein kinase (MAPK) and phosphatidylinositol 3-kinase (PI3K)/protein kinase B (Akt) signal transduction pathways. G-CSF can target endothelial cells to stimulate proliferation and migration. G-CSF has two forms, a 174- and 180-amino-acid-long protein. The 174-amino acid polypeptide is more abundant in vivo and shows higher biological activity. In unstimulated cells G-CSF mRNA is unstable and it is thought that the presence of a G-CSF factor stem-loop destabilizing element enhances the rate of shortening of the poly(A) tail. Putland R A et al. Mol Cell Biol 22: 1664-1673 (2002).

The amino acid sequence of G-CSF (long form including signal peptide) is set forth in (SEQ ID No: 13):

are two commercially-available forms of rhG-CSF (recombinant human G-CSF). Filgrastim is a non-glycosylated 175 amino acid polypeptide (identical to human G-CSF except for the addition of an N-terminal methionine that is necessary for expression in *E coli*). and has a molecular weight of 18,800 Da. G-CSF isolated from a human cell is glycosylated.

The amino acid sequence of G-CSF (175 amino acid form, Filgrastim) is set forth in (SEQ ID No: 14):

```
                                                    (SEQ ID No: 14)
MTPLGPASSLPQSFLLKCLEQVRKIQGDGAALQEKLCATYKLCHPEELVLLG

HSLGIPWAPLSSCPSQALQLAGCLSQLHSGLFLYQGLLQALEGISPELGPTLDTLQLDVA

DFATTIWQQMEELGMAPALQPTQGAMPAFASAFQRRAGGVLVASHLQSFLEVSYRVLR

HLAQP
```

Another form of recombinant human G-CSF, called lenograstim (Granocyte®), is synthesized in Chinese Hamster Ovary (CHO) cells. As this is a mammalian cell expression system, lenograstim is indistinguishable from the 174-amino acid natural human G-CSF. Recombinant G-CSF has been used in humans for over ten years and is generally well tolerated.

G-CSF stimulates the production of white blood cells (WBC). The G-CSF-receptor (CD114, G-CSFR) is present on precursor cells in the bone marrow (of neutrophilic granulocyte lineage) and initiates proliferation and differentiation into mature granulocytes in response to stimulation by G-CSF. In addition, G-CSF can enhance the survival and activate the immunological functions of mature neutrophils. G-CSF is also a potent inducer of hematopoietic stem cells (HSCs) mobilization from the bone marrow into the bloodstream. Recombinant G-CSF is used to increase the number of hematopoietic stem cells (HSC) in the blood of a donor before collection by leukapheresis for use in hematopoietic stem cell transplantation. It may also be given to the recipient, to compensate for conditioning regimens. Recipients may be given chemotherapy or irradiation to aid the eradication of the patient's disease prior to the infusion of HSC and/or to suppress immune reactions. Recombinant forms of G-CSF are used in cancer patients to accelerate recovery from neutropenia (low white blood cell count) after chemotherapy, allowing higher-intensity treatment regimens. Chemotherapy can cause myelosuppression and unacceptably low levels of white blood cells, making patients prone to infections and sepsis. Complications associated with a low white blood cell count are the most common causes of dose reductions or delays in chemotherapy. Link et al. Cancer 92:1354-1367 (2001), Lyman et al. J Clin Oncol. 21:4524-4531 (2003),

```
                                            (SEQ ID No: 13)
MAGPATQSPMKLMALQLLLWHSALWTVQEATPLGPASSLPQSFLLKCLEQV

RKIQGDGAALQEKLVSECATYKLCHPEELVLLGHSLGIPWAPLSSCPSQALQLAGCLSQL

HSGLFLYQGLLQALEGISPELGPTLDTLQLDVADFATTIWQQMEELGMAPALQPTQGAM

PAFASAFQRRAGGVLVASHLQSFLEVSYRVLRHLAQP
```

The 174-amino acid form of G-CSF has been used in recombinant from for the development of pharmaceutical products. Recombinant human G-CSF is synthesized in *E. coli*. Filgrastim (Neupogen®, Nivestim®, Ratiograstim®, Zarzio®) and PEG-filgrastim (a pegylated form, Neulasta®)

Lyman et al. Am J. Med. 112:406-411 (2002). Filgrastim (Neupogen®) was approved in 1991 by the U.S. FDA for the treatment of patients suffering from chemotherapy-induced neutropenia. In 1993, lenograstim (Granocyte®) was approved in Europe.

Provided herein, are methods of increasing the number of hematopoietic stem cells (HSC) in the blood, the method comprising administering to a HSC donor subject a composition comprising a modified nucleic acid encoding a G-CSF precursor or a partially or fully processed form thereof in an amount sufficient to increasing the number of HSCs. In certain embodiments, the HSCs derived from the donor subject are used for allogenic HSC transplantation into a recipient subject. In certain embodiments, the blood of the donor subject is collected by leukapheresis. In some embodiments, an increase in the number of HSCs is determined by analysis of the blood of the donor subject.

Provided herein, are methods of to accelerate recovery from neutropenia, the method comprising administering to a subject in need of such recovery a composition comprising a modified nucleic acid encoding a G-CSF precursor or a partially or fully processed form thereof in an amount sufficient to accelerate recovery from neutropenia. In certain embodiments, the subject in need of recovery is a cancer patient. In certain embodiments, the cancer patient has undergone a conditioning regimen. In some embodiments, the conditioning regiment comprises chemotherapy or irradiation.

Provided herein, are methods to prevent infection and/or sepsis in a subject at risk of developing infection and/or sepsis, the method comprising administering to a subject in need of such prevention a composition comprising a modified nucleic acid encoding a G-CSF precursor or a partially or fully processed form thereof in an amount sufficient to prevent infection and/or sepsis. In certain embodiments, the subject at risk of developing infection and/or sepsis is a cancer patient. In certain embodiments, the cancer patient has undergone a conditioning regimen. In some embodiments, the conditioning regiment comprises chemotherapy or irradiation.

Further provided herein, are methods to treat infection and/or sepsis in a subject, the method comprising administering to a subject in need of such treatment a composition comprising a modified nucleic acid encoding a G-CSF precursor or a partially or fully processed form thereof in an amount sufficient to treat an infection and/or sepsis. In certain embodiments, the subject in need of treatment is a cancer patient. In certain embodiments, the cancer patient has undergone a conditioning regimen. In some embodiments, the conditioning regiment comprises chemotherapy or irradiation.

Further provided herein, are methods to prevent a dose reduction and/or delay in chemotherapy and/or irradiation therapy during the treatment of a cancer patient, the method comprising administering to a subject in need of such prevention a composition comprising a modified nucleic acid encoding a G-CSF precursor or a partially or fully processed form thereof in an amount sufficient to prevent a dose reduction and/or delay in chemotherapy and/or irradiation therapy during the treatment. In certain embodiments, the cancer patient exhibits neutropenia. In certain embodiments, the cancer patient is at risk to develop an infection and/or sepsis.

Neutropenia is also considered a major factor in delayed wound healing. Wound healing proceeds through three phases: an inflammatory phase, a proliferative phase, and a remodeling phase. During the inflammatory phase a moist environment is generated in which granulocytes cleanse and free the wound from cellular debris, foreign bodies, and bacteria, aided by macrophages that stimulate endothelial cell and fibroblast migration. The migration event initiates angiogenesis and fibroplasias. During the proliferative phase, fibroblasts appear that facilitate wound contraction and restructuring of the extracellular matrix. The wound is supplied with nutrients and oxygen and catabolites are removed. The remodeling phase begins 20-30 days after injury and may continue for 12-24 months thereafter. It involves collagen degradation and synthesis of new repair matrix components. Fibroblasts transform into myofibroblasts that provide the contractile capacity necessary to reduce scarring. If a wound does not heal within 2-4 weeks it can become chronic. Delayed wound healing represents a major clinical problem for patients receiving radiotherapy, chemotherapy, steroids, and/or ultraviolet radiation. Further, patients with microvascular disorders, such as diabetes, can suffer from delayed wound healing. In these patients, neutropenia and neutrophil dysfunction can lead to severe or chronic bacterial infections. Poor wound healing remains a difficult clinical problem.

G-CSF has been proved to be efficient in treating neutropenia in a number of clinical settings. G-CSF stimulates the production of polymorphonuclear neutrophils (PMN) and also enhances PMN function. G-CSF may enhance PMN function by a number of different ways, e.g. by (i) enhancing CD11b and FcγRi expression; (ii) enhancing PMN adhesion; (iii) phagocytosis; (iv) degranulation; and (v) chemokinesis. G-CSF may also modulate peripheral mature PMN activation and/or regulate PMN chemokine responsiveness. Anderlini P et al. Blood 88: 2819-2825 (1996), Betsuyacu T et al. J Clin Invest 103: 825-832 (1999), Hakanson L et al. Br J Haematol 98: 603-611 (1997), Gericke G H et al. J Leukocyte Biol 57: 455-61 (1995), Hoglund M et al. Eur J Haematol 58: 195-202 (1997), Xu S et al. Br J Haematol 93: 558-68 (1996), Yong K L Br J Haematol 94: 40-7 (1996), Metcalf D et al. Blood 88: 3755-3764 (1996). Favorable effects of subcutaneous application of recombinant G-CSF have been reported, including reduction of bacterial translocation due to burn wound sepsis and acceleration of wound healing in neutropenic patient using recombinant human G-CSF (hG-CSF). Yalcin O et al. Surg Today 27: 154-158 (1997), Harada T et al Burns 24: 120-122 (1998), Cody D T et al. Head Neck 21: 172-175 (1999). G-CSF has also been shown to improve incisional wound healing in animal models of third degree burns. Eroglu E et al. Tohoku J Exp Med 204:11-16 (2004). Plasmid DNA encoding hG-CSF gene was successfully delivered into surgical wound sites, resulting in G-CSF expression. Both local and systemic gene delivery with either plasmid DNA alone (naked DNA) or with cationic liposome DNA complexes specifically to sites of wounded skin was performed. Meuli M et al. J Invest Dermatology 116, 131-135 (2001).

Provided herein, are methods to accelerate wound healing, the method comprising administering to a subject exhibiting delayed wound healing a composition comprising a modified nucleic acid encoding a G-CSF precursor or a partially or fully processed form thereof in an amount sufficient to accelerate wound healing. In certain embodiments, the subject exhibits neutropenia. In certain embodiments, the subject exhibits neutrophil dysfunction. In certain embodiments, the subject exhibits severe or chronic bacterial infections. In certain embodiments, the subject has received or is receiving a therapy. In certain embodiments, the therapy is radiotherapy, chemotherapy, steroids, or ultraviolet radiation. In certain embodiments, the patient suffers from a microvascular disorder. In some embodiments, the microvascular disorder is diabetes. In some embodiments, the wound is an ulcer. In a specific embodiment, the wound is a diabetic foot ulcer. In certain embodiments, the subject has one or more burn wounds. In certain embodiments, the administration is local or systemic. In certain embodiments, the administration is subcutaneous. In certain embodiments, the administration is topical.

G-CSF can also act on neuronal cells as a neurotrophic factor in the central nervous system (CNS). The G-CSFreceptor is expressed by neurons in the brain and spinal cord. G-CSF has been shown to decrease infectious episodes and acute inflammatory response in patients with a variety of brain pathologies, including brain tumors, acute traumatic brain injury, and cerebral hemorrhage. Shyu W C Circulation 110:1847-1854 (2004), Schneider A et al. J Clin Invest 115: 2083-2098 (2005), Kawada H et al. Circulation 113:701-710 (2006). Recombinant G-CSF is currently under investigation for cerebral ischemia (stroke) in a clinical phase IIb (AXIS 2: AX200 for the Treatment of Ischemic Stroke, NCT00927836 Sygnis Bioscience, Germany). As a neuroprotectant G-CSF is considered to be more effective in the early phase of cerebral ischemia and during reperfusion. G-CSF was found to be neuroprotective in experimental models of thromboembolic stroke (thromboembolic occlusion (TE) of the middle cerebral artery in male Wistar rats) when given early after TE. Kollmar R Exp & Transl Stroke Med 2:9 (2010). G-CSF's neuroprotective and regenerative properties are likely a result of a combination of anti-apoptotic activity on neurons, stimulation of neurogenesis, enhancement of vessel formation, mobilization of bone marrow derived cells and systemic anti-inflammatory effects. G-CSF receptor and G-CSF itself are expressed in alpha motoneurons. G-CSF has been shown to protect motoneurons from apoptosis, and to improve outcome in a SOD1(G93A) transgenic mouse model for the motorneuron disease amyotrophic lateral sclerosis (ALS, Lou Gehrig's disease), which affects 5 out of 100,000 people worldwide. Henriques et al. BMC Neuroscience 11:25 (2010).

G-CSF has also been proposed as a candidate for the treatment of Alzheimer's disease (AD). Tsai K J et al. J Exp Med. 204:1273-80 (2007). AD affects more than 12 million patients worldwide. AD brains develop neurofibrillary tangles and senile plaques. β-Amyloid (Aβ) is the major extracellular component of the senile plaques. Mattson, M P Nature 430:631-639 (2004), Blennow K et al. Lancet 368: 387-403 (2006). Clinical treatments for AD are largely symptomatic and none are capable of stopping the progression of AD. Acetylcholinesterase inhibitors improve cognitive ability and psychotropic drugs modify patient behaviors. Treatments that focus on delaying the onset of symptoms and slowing the rate of disease progression include (i) tacrine (Cognex®), the first FDA-approved drug for AD therapy; (ii) memantine (Namenda®), an N-methyl-D-aspartate antagonist; and (iii) antioxidants such as vitamin E. Other AD therapies include anti-amyloid immunotherapy, amyloid vaccination, and the use of secretase inhibitors that prevent the formation of Aβ and neurofibrillary tangles. However, these therapies all cause side effects and clinical problems. Francis P T et al. Trends Pharmacol Sci. 26:104-111 (2005), Schenk D Nat. Rev. Neurosci. 3:824-828 (2002), Citron M Nat. Rev. Neurosci. 5:677-685 (2004). Animal studies employing Aβ aggregate-induced AD mouse models suggest that G-CSF treatment has potential applications in AD. G-CSF induced stem cell release from the bone marrow, stimulated neurogenesis surrounding the Aβ plaques in mouse brains, and improved the neurological function of AD mice, judged by the enhanced levels of acetylcholine in the brains of Tg2576 mice. Tsai K J et al. J Exp Med. 204:1273-80 (2007).

Provided herein, are methods of treating a subject exhibiting acute brain pathology, the methods comprising administering to a subject in need of such treatment a composition comprising a modified nucleic acid encoding a G-CSF precursor or a partially or fully processed form thereof in an amount sufficient to treat the acute brain pathology. In certain embodiments, the acute brain pathology is acute traumatic brain injury, cerebral hemorrhage or cerebral ischemia (stroke). In certain embodiments, the modified nucleic acid encoding a G-CSF precursor or a partially or fully processed form thereof is administered immediately after or shortly after the subject exhibits an acute brain pathology. In certain embodiments, the modified nucleic acid encoding a G-CSF precursor or a partially or fully processed form thereof is administered directly into the brain. In other embodiments, administration is systemic.

Provided herein, are methods of treating a subject having a neurodegenerative disease, the methods comprising administering to a subject in need of such treatment a composition comprising a modified nucleic acid encoding a G-CSF precursor or a partially or fully processed form thereof in an amount sufficient to treat the neurodegenerative disease.

Further provided herein, are methods of preventing the development of a neurodegenerative disease, or delaying the onset of a neurodegenerative disease in a subject suspected of developing neurodegenerative disease, the methods comprising administering to a subject in need of such prevention a composition comprising a modified nucleic acid encoding a G-CSF precursor or a partially or fully processed form thereof in an amount sufficient to prevent the development of the neurodegenerative disease, or to delay the onset of the neurodegenerative disease. In certain embodiments, the subject is an adult over 40, 50, 60, or 70 year of age. In certain embodiments, the neurodegenerative disease is a motorneuron disease. In specific embodiments, the motorneuron disease is amyotrophic lateral sclerosis (ALS, Lou Gehrig's disease). In other embodiments, the disease is Alzheimer's disease (AD). In certain embodiments, the modified nucleic acid encoding a G-CSF precursor or a partially or fully processed form thereof is administered directly into the brain. In other embodiments, administration is systemic.

G-CSF has been shown to improve cardiac function after myocardial infarction (MI) by mobilizing bone marrow cells and/or by protecting cardiomyocytes from apoptotic cell death. G-CSF has also been tested for its role in collateral artery growth (arteriogenesis) in a murine MI model. G-CSF administration after MI stimulates arteriogenesis, attenuates ischemic cardiomyopathy and results in a significant improvement of post-MI survival. Deindl E et al. FASEB J 20:956-958 (2006).

Provided herein, are methods of treating a subject having myocardial infarction (MI), the methods comprising administering to a subject in need of such treatment a composition comprising a modified nucleic acid encoding a G-CSF precursor or a partially or fully processed form thereof in an amount sufficient to treat MI.

Provided herein, are methods of improving cardiac function in a subject having myocardial infarction (MI), the methods comprising administering to a subject in need of such improvement a composition comprising a modified nucleic acid encoding a G-CSF precursor or a partially or fully processed form thereof in an amount sufficient to improve cardiac function.

Provided herein, are methods of protecting cardiomyocytes from apoptotic cell death in a subject having myocardial infarction (MI), the methods comprising administering to a subject in need of such improvement a composition comprising a modified nucleic acid encoding a G-CSF precursor or a partially or fully processed form thereof in an amount sufficient to protect cardiomyocytes from apoptotic cell death.

Provided herein, are methods of promoting collateral artery growth (arteriogenesis) in a subject having myocardial infarction (MI), the methods comprising administering to a subject in need of such improvement a composition comprising a modified nucleic acid encoding a G-CSF precursor or a partially or fully processed form thereof in an amount sufficient to promote collateral artery growth (arteriogenesis). In certain embodiments, the modified nucleic acid encoding a G-CSF precursor or a partially or fully processed form thereof is administered directly into myocardium. In other embodiments, administration is systemic.

G-CSF also exerts anti-inflammatory and pro-Th2 effects. G-CSF, when administered at the onset of clinical signs, provided durable protection from experimental autoimmune encephalomyelitis (EAE), a murine model (SJL/J mice) for multiple sclerosis that is driven by Th1-oriented auto-aggressive cells. G-CSF reduces the T cell infiltration and autoimmune inflammation within the CNS. G-CSF-treated mice displayed limited demyelination, reduced recruitment of T cells to the CNS, very discrete autoimmune inflammation, and low levels of CNS mRNA levels of cytokines and chemokines G-CSF also limited the production of TNF-α, a cytokine associated with early CNS infiltration and neurological deficit. Zavala F et al. J Immunol 168: 2011-2019 (2002). Treatment with G-CSF has also been shown to protect mice from the development of spontaneous systemic lupus, another autoimmune disease. Zavala, F et al. J Immunol 163: 5125 (1999).

Provided herein, are methods of treating a subject having an autoimmune disease, the methods comprising administering to a subject in need of such treatment a composition comprising a modified nucleic acid encoding a G-CSF precursor or a partially or fully processed form thereof in an amount sufficient to treat the autoimmune disease. In certain embodiments, the autoimmune disease is multiple sclerosis (MS) or systemic lupus.

Modified Nucleic Acids.

This invention provides nucleic acids, including RNAs such as mRNAs that contain one or more modified nucleosides (termed "modified nucleic acids"), which have useful properties including the lack of a substantial induction of the innate immune response of a cell into which the mRNA is introduced. Because these modified nucleic acids enhance the efficiency of protein production, intracellular retention of nucleic acids, and viability of contacted cells, as well as possess reduced immunogenicity, these nucleic acids having these properties are termed "enhanced nucleic acids" herein.

The term "nucleic acid," in its broadest sense, includes any compound and/or substance that is or can be incorporated into an oligonucleotide chain. Exemplary nucleic acids for use in accordance with the present invention include, but are not limited to, one or more of DNA, RNA, hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc., described in detail herein.

Provided are modified nucleic acids containing a translatable region and one, two, or more than two different nucleoside modifications. In some embodiments, the modified nucleic acid exhibits reduced degradation in a cell into which the nucleic acid is introduced, relative to a corresponding unmodified nucleic acid. Exemplary nucleic acids include ribonucleic acids (RNAs), deoxyribonucleic acids (DNAs), threose nucleic acids (TNAs), glycol nucleic acids (GNAs), peptide nucleic acids (PNAs), locked nucleic acids (LNAs) or a hybrid thereof. In preferred embodiments, the modified nucleic acid includes messenger RNAs (mRNAs). As described herein, the nucleic acids of the invention do not substantially induce an innate immune response of a cell into which the mRNA is introduced.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl)adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In certain embodiments it is desirable to intracellularly degrade a modified nucleic acid introduced into the cell, for example if precise timing of protein production is desired. Thus, the invention provides a modified nucleic acid containing a degradation domain, which is capable of being acted on in a directed manner within a cell.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

Other components of nucleic acid are optional, and are beneficial in some embodiments. For example, a 5' untranslated region (UTR) and/or a 3'UTR are provided, wherein either or both may independently contain one or more different nucleoside modifications. In such embodiments, nucleoside modifications may also be present in the translatable region. Also provided are nucleic acids containing a Kozak sequence.

Additionally, provided are nucleic acids containing one or more intronic nucleotide sequences capable of being excised from the nucleic acid.

Further, provided are nucleic acids containing an internal ribosome entry site (IRES). An IRES may act as the sole ribosome binding site, or may serve as one of multiple ribosome binding sites of an mRNA. An mRNA containing more than one functional ribosome binding site may encode several peptides or polypeptides that are translated independently by the ribosomes ("multicistronic mRNA"). When nucleic acids are provided with an IRES, further optionally provided is a second translatable region. Examples of IRES sequences that can be used according to the invention include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

Prevention or Reduction of Innate Cellular Immune Response Activation Using Modified Nucleic Acids.

The term "innate immune response" includes a cellular response to exogenous single stranded nucleic acids, generally of viral or bacterial origin, which involves the induction of cytokine expression and release, particularly the interferons, and cell death. Protein synthesis is also reduced during the innate cellular immune response. While it is advantageous to eliminate the innate immune response in a cell, the invention provides modified mRNAs that substantially reduce the immune response, including interferon signaling, without entirely eliminating such a response. In some embodiments, the immune response is reduced by 10%, 20%, 30%, 40%, 50%, 60%, 70%, 80%, 90%, 95%, 99%, 99.9%, or greater than 99.9% as compared to the immune response induced by a corresponding unmodified nucleic acid. Such a reduction can be measured by expression or activity level of Type 1 interferons or the expression of interferon-regulated genes such as the toll-like receptors (e.g., TLR7 and TLR8). Reduction of innate immune response can also be measured by decreased cell death following one or more administrations of modified RNAs to a cell population; e.g., cell death is 10%, 25%, 50%, 75%, 85%, 90%, 95%, or over 95% less than the cell death frequency observed with a corresponding unmodified nucleic acid. Moreover, cell death may affect fewer than 50%, 40%, 30%, 20%, 10%, 5%, 1%, 0.1%, 0.01% or fewer than 0.01% of cells contacted with the modified nucleic acids.

The invention provides for the repeated introduction (e.g., transfection) of modified nucleic acids into a target cell population, e.g., in vitro, ex vivo, or in vivo. The step of contacting the cell population may be repeated one or more times (such as two, three, four, five or more than five times). In some embodiments, the step of contacting the cell population with the modified nucleic acids is repeated a number of times sufficient such that a predetermined efficiency of protein translation in the cell population is achieved. Given the reduced cytotoxicity of the target cell population provided by the nucleic acid modifications, such repeated transfections are achievable in a diverse array of cell types.

Polypeptide Variants.

Provided are nucleic acids that encode variant polypeptides, which have a certain identity with a reference polypeptide sequence. The term "identity" as known in the art, refers to a relationship between the sequences of two or more peptides, as determined by comparing the sequences. In the art, "identity" also means the degree of sequence relatedness between peptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the polypeptide variant has the same or a similar activity as the reference polypeptide. Alternatively, the variant has an altered activity (e.g., increased or decreased) relative to a reference polypeptide. Generally, variants of a particular polynucleotide or polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular reference polynucleotide or polypeptide as determined by sequence alignment programs and parameters described herein and known to those skilled in the art.

As recognized by those skilled in the art, protein fragments, functional protein domains, and homologous proteins are also considered to be within the scope of this invention. For example, provided herein is any protein fragment of a reference protein (meaning a polypeptide sequence at least one amino acid residue shorter than a reference polypeptide sequence but otherwise identical) 5, 10, 15, 20, 25, 30, 35, 40, 45, 50, 55, 60, 70, 80, 90, 100 or greater than 100 amino acids in length In another example, any protein that includes a stretch of about 20, about 30, about 40, about 50, or about 100 amino acids which are about 40%, about 50%, about 60%, about 70%, about 80%, about 90%, about 95%, about 98%, or about 100% identical to any of the sequences described herein can be utilized in accordance with the invention. In certain embodiments, a protein sequence to be utilized in accordance with the invention includes 2, 3, 4, 5, 6, 7, 8, 9, 10, or more mutations as shown in any of the sequences provided or referenced herein.

Polypeptide Libraries.

Also provided are polynucleotide libraries containing nucleoside modifications, wherein the polynucleotides individually contain a first nucleic acid sequence encoding a polypeptide, such as an antibody, protein binding partner, scaffold protein, and other polypeptides known in the art. Preferably, the polynucleotides are mRNA in a form suitable for direct introduction into a target cell host, which in turn synthesizes the encoded polypeptide.

In certain embodiments, multiple variants of a protein, each with different amino acid modification(s), are produced and tested to determine the best variant in terms of pharmacokinetics, stability, biocompatibility, and/or biological activity, or a biophysical property such as expression level. Such a library may contain 10, $10^2$, $10^3$, $10^4$, $10^5$, $10^6$, $10^7$, $10^8$, $10^9$, or over $10^9$ possible variants (including substitutions, deletions of one or more residues, and insertion of one or more residues).

Polypeptide-Nucleic Acid Complexes.

Proper protein translation involves the physical aggregation of a number of polypeptides and nucleic acids associated with the mRNA. Provided by the invention are complexes containing conjugates of protein and nucleic acids, containing a translatable mRNA having one or more nucleoside modifications (e.g., at least two different nucleoside modifications) and one or more polypeptides bound to the mRNA. Generally, the proteins are provided in an amount effective to prevent or reduce an innate immune response of a cell into which the complex is introduced.

Targeting Moieties. In embodiments of the invention, modified nucleic acids are provided to express a protein-binding partner or a receptor on the surface of the cell, which functions to target the cell to a specific tissue space or to interact with a specific moiety, either in vivo or in vitro. Suitable protein-binding partners include antibodies and functional fragments thereof, scaffold proteins, or peptides. Additionally, modified nucleic acids can be employed to direct the synthesis and extracellular localization of lipids, carbohydrates, or other biological moieties.

Untranslatable Modified Nucleic Acids; Vaccines.

As described herein, provided are mRNAs having sequences that are substantially not translatable. Such mRNA is effective as a vaccine when administered to a mammalian subject.

Also provided are modified nucleic acids that contain one or more noncoding regions. Such modified nucleic acids are generally not translated, but are capable of binding to and sequestering one or more translational machinery component such as a ribosomal protein or a transfer RNA (tRNA), thereby effectively reducing protein expression in the cell. The modified nucleic acid may contain a small nucleolar RNA (sno-RNA), micro RNA (miRNA), small interfering RNA (siRNA) or Piwi-interacting RNA (piRNA).

Additionally, certain modified nucleosides, or combinations thereof, when introduced into modified nucleic acids activate the innate immune response. Such activating modified nucleic acids, e.g., modified RNAs, are useful as adjuvants when combined with polypeptide or other vaccines. In certain embodiments, the activated modified mRNAs contain a translatable region which encodes for a polypeptide sequence useful as a vaccine, thus providing the ability to be a self-adjuvant.

Modified Nucleic Acid Synthesis.

Nucleic acids for use in accordance with the invention may be prepared according to any available technique including, but not limited to chemical synthesis, enzymatic synthesis, which is generally termed in vitro transcription, enzymatic or chemical cleavage of a longer precursor, etc. Methods of synthesizing RNAs are known in the art (see, e.g., Gait, M. J. (ed.) *Oligonucleotide synthesis: a practical approach*, Oxford (Oxfordshire), Washington, D.C.: IRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005; both of which are incorporated herein by reference).

Modified nucleic acids need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially decreased. A modification may also be a 5' or 3' terminal modification. The nucleic acids may contain at a minimum one and at maximum 100% modified nucleotides, or any intervening percentage, such as at least 50% modified nucleotides, at least 80% modified nucleotides, or at least 90% modified nucleotides.

Generally, the length of a modified mRNA of the present invention is greater than 30 nucleotides in length. In another embodiment, the RNA molecule is greater than 35, 40, 45, 50, 60, 75, 100, 125, 150, 175, 200, 250, 300, 350, 400, 450, 500, 600, 700, 800, 900, 1000, 1100, 1200, 1300, 1400, 1500, 1800, 2000, 3000, 4000, or 5000 nucleotides, or greater than 5000 nucleotides.

Uses of Modified Nucleic Acids.

Therapeutic Agents.

Provided are compositions, methods, kits, and reagents for treatment or prevention of disease or conditions in humans and other mammals. The active therapeutic agents of the invention include modified nucleic acids, cells containing modified nucleic acids or polypeptides translated from the modified nucleic acids, polypeptides translated from modified nucleic acids, and cells contacted with cells containing modified nucleic acids or polypeptides translated from the modified nucleic acids.

Provided are methods of inducing translation of a recombinant polypeptide in a cell population using the modified nucleic acids described herein. Such translation can be in vivo, ex vivo, in culture, or in vitro. The cell population is contacted with an effective amount of a composition containing a nucleic acid that has at least one nucleoside modification, and a translatable region encoding the recombinant polypeptide. The population is contacted under conditions such that the nucleic acid is localized into one or more cells of the cell population and the recombinant polypeptide is translated in the cell from the nucleic acid.

An effective amount of the composition is provided based, at least in part, on the target tissue, target cell type, means of administration, physical characteristics of the nucleic acid (e.g., size, and extent of modified nucleosides), and other determinants. In general, an effective amount of the composition provides efficient protein production in the cell, preferably more efficient than a composition containing a corresponding unmodified nucleic acid. Increased efficiency may be demonstrated by increased cell transfection (i.e., the percentage of cells transfected with the nucleic acid), increased protein translation from the nucleic acid, decreased nucleic acid degradation (as demonstrated, e.g., by increased duration of protein translation from a modified nucleic acid), or reduced innate immune response of the host cell.

Aspects of the invention are directed to methods of inducing in vivo translation of a recombinant polypeptide in a mammalian subject in need thereof. Therein, an effective amount of a composition containing a nucleic acid that has at least one nucleoside modification and a translatable region encoding the recombinant polypeptide is administered to the subject using the delivery methods described herein. The nucleic acid is provided in an amount and under other conditions such that the nucleic acid is localized into a cell of the subject and the recombinant polypeptide is translated in the cell from the nucleic acid. The cell in which the nucleic acid is localized, or the tissue in which the cell is present, may be targeted with one or more than one rounds of nucleic acid administration.

Other aspects of the invention relate to transplantation of cells containing modified nucleic acids to a mammalian subject. Administration of cells to mammalian subjects is known to those of ordinary skill in the art, such as local implantation (e.g., topical or subcutaneous administration), organ delivery or systemic injection (e.g., intravenous injection or inhalation), as is the formulation of cells in pharmaceutically acceptable carrier. Compositions containing modified nucleic acids are formulated for administration intramuscularly, transarterially, intraocularly, vaginally, rectally, intraperitoneally, intravenously, intranasally, subcutaneously, endoscopically, transdermally, or intrathecally. In some embodiments, the composition is formulated for extended release.

Topical Delivery Applied to the Skin.

The skin is an ideal target site for nucleic acid delivery. It is readily accessible, and gene expression may be restricted not only to the skin, potentially avoiding nonspecific toxicity, but also to specific layers and cell types within the skin. The site of cutaneous expression of the delivered nucleic acid will depend on the route of nucleic acid delivery. Three routes are commonly considered to deliver nucleic acids to the skin: (i) topical application (e.g. for local/regional treatment); (ii) intradermal injection (e.g. for local/regional treatment); and (iii) systemic delivery (e.g. for treatment of dermatologic diseases that affect both cutaneous and extracutaneous regions). Nucleic acids can be delivered to the skin by several different approaches. Most have been shown to work for DNA, such as, topical application of non-cationic liposome—DNA complex, cationic liposome—DNA complex, particle-mediated (gene gun), puncture-mediated gene transfections, and viral delivery approaches. After gene delivery, gene products have been detected in a number of skin cell types, including but not limited to basal keratinocytes, sebaceous gland cells, dermal fibroblasts and dermal macrophages.

Wound Management.

For wound treatment, e.g. of wounds exhibiting delayed healing, comprising administration of modified nucleic acids encoding for a G-CSF precursor or a partially or fully processed form thereof, wound management may further comprise steps carried out either prior to, concurrent with or post administration of the modified nucleic acids. For example, steps may involve cleaning and preparing the wound bed to facilitate wound healing and obtain closure of the wound. Several strategies may be used in order to promote wound healing and achieve wound closure including, but not limited to: (i) debridement, optionally repeated, sharp debridement (surgical removal of dead or infected tissue from a wound), optionally including chemical debriding agents, such as enzymes, to remove necrotic tissue; (ii) wound dressings to provide the wound with a moist, warm environment and to promote tissue repair and healing. Examples of materials that are used in formulating wound dressings include: hydrogels (e.g., Aquasorb®; Duoderm®), hydrocolloids (e.g., Aquacel®; Comfeel®), foams (e.g., LYOfoam®; Spyrosorb®), and alginates (e.g., AlgiSite®; Curasorb®); (iii) additional growth factors to stimulate cell division and proliferation and to promote wound healing e.g. becaplermin (Regranex Gel®), a human recombinant platelet-derived growth factor that is approved by the FDA for the treatment of neuropathic foot ulcers; (iv) soft-tissue wound coverage, a skin graft may be necessary to obtain coverage of clean, non-healing wounds. Examples of skin grafts that may be used for soft-tissue coverage include: autologous skin grafts, cadaveric skin graft, bioengineered skin substitutes (e.g., Apligraf®; Dermagraft®).

In certain embodiments, wound dressing formulations comprising hydrogels (e.g., Aquasorb®; Duoderm®), hydrocolloids (e.g., Aquacel®; Comfeel®), foams (e.g., LYOfoam®; Spyrosorb®), and/or alginates (e.g., AlgiSite®; Curasorb®) are provided further comprising modified nucleic acids encoding for a G-CSF precursor or a partially or fully processed form described herein.

In certain embodiments, skin grafts comprising autologous skin grafts, cadaveric skin graft, or bioengineered skin substitutes (e.g., Apligraf®; Dermagraft®) are provided further comprising modified nucleic acids encoding for a G-CSF precursor or a partially or fully processed form described herein.

The modified nucleic acids encoding for a G-CSF precursor or a partially or fully processed form described herein may be intermixed with the wound dressing formulations and/or skin grafts or may be applied separately, e.g. by soaking or spraying.

The subject to whom the therapeutic agent is administered suffers from or is at risk of developing a disease, disorder, or deleterious condition. Provided are methods of identifying, diagnosing, and classifying subjects on these bases, which may include clinical diagnosis, biomarker levels, genome-wide association studies (GWAS), and other methods known in the art.

In certain embodiments, nucleic acids encoding G-CSF are administered to subjects in need of G-CSF administration. Subjects in need of G-CSF administration may, for example, have low levels white blood cells, e.g. a neutropenic patient, G-CSF may be administered in healthy donors to boost the white blood cell count, or G-CSF may be administered to stimulate or mobilize hematopoietic stem cells ((HSC) in a subject for any reason. To assess, for example, whether a subject is in need of G-CSF administration and/or to assess the activity of administered G-CSF in vivo, whole blood of a subject may be analyzed using a complete blood count (CBC). A CBC test may comprise one or more of the following:
  a. White blood cell (WBC) count: A count of the actual number of white blood cells per volume of blood.
  b. White blood cell differential: A count of the types of white blood cells present in the blood: neutrophils, lymphocytes, monocytes, eosinophils, and basophils.
  c. Red blood cell (RBC) count: A count of the actual number of red blood cells per volume of blood.
  d. Hemoglobin level: A measure of the amount of oxygen-carrying protein in the blood.
  e. Hematocrit level: A measures of the percentage of red blood cells in a given volume of whole blood.
  f. P latelet count: A count of the number of platelets in a given volume of blood.
  g. Mean platelet volume (MPV): A measurement of the average size of platelets. Newly produced platelets are larger and an increased MPV occurs when increased numbers of platelets are being produced in the bone marrow.
  h. Mean corpuscular volume (MCV): A measurement of the average size of RBCs (e.g. RBCs are larger than normal (macrocytic) or RBCs are smaller than normal (microcytic)).
  i. Mean corpuscular hemoglobin (MCH): A calculation of the average amount of oxygen-carrying hemoglobin inside a red blood cell.
  j. Mean corpuscular hemoglobin concentration (MCHC): A calculation of the average concentration of hemoglobin inside a red cell (e.g. decreased MCHC values (hypochromia) or increased MCHC values (hyperchromia)).
  k. Red cell distribution width (RDW): A calculation of the variation in the size of RBCs (e.g. amount of variation (anisocytosis) in RBC size and/or variation in shape (poikilocytosis) may cause an increase in the RDW).

In certain embodiments, the administered modified nucleic acid directs production of one or more recombinant polypeptides that provide a functional activity which is substantially absent in the cell in which the recombinant polypeptide is translated. For example, the missing functional activity may be enzymatic, structural, or gene regulatory in nature. In related embodiments, the administered modified nucleic acid directs production of one or more recombinant polypeptides that increases (e.g., synergistically) a functional activity which is present but substantially deficient in the cell in which the recombinant polypeptide is translated.

In other embodiments, the administered modified nucleic acid directs production of one or more recombinant polypeptides that replace a polypeptide (or multiple polypeptides) that is substantially absent in the cell in which the recombinant polypeptide is translated. Such absence may be due to genetic mutation of the encoding gene or regulatory pathway thereof. In some embodiments, the recombinant polypeptide increases the level of an endogenous protein in the cell to a desirable level; such an increase may bring the level of the endogenous protein from a subnormal level to a normal level, or from a normal level to a super-normal level.

Alternatively, the recombinant polypeptide functions to antagonize the activity of an endogenous protein present in, on the surface of, or secreted from the cell. Usually, the activity of the endogenous protein is deleterious to the subject, for example, do to mutation of the endogenous protein resulting in altered activity or localization. Additionally, the recombinant polypeptide antagonizes, directly or indirectly, the activity of a biological moiety present in, on the surface of, or secreted from the cell. Examples of antagonized biological moieties include lipids (e.g., cholesterol), a lipoprotein (e.g., low density lipoprotein), a nucleic acid, a carbohydrate, a protein toxin such as shiga and tetanus toxins, or a small molecule toxin such as botulinum, cholera, and diphtheria toxins. Additionally, the antagonized biological molecule may be an endogenous protein that exhibits an undesirable activity, such as a cytotoxic or cytostatic activity.

The recombinant proteins described herein are engineered for localization within the cell, potentially within a specific compartment such as the nucleus, or are engineered for secretion from the cell or translocation to the plasma membrane of the cell.

Targeting Moieties.

In embodiments of the invention, modified nucleic acids are provided to express a protein-binding partner or a receptor on the surface of the cell, which functions to target the cell to a specific tissue space or to interact with a specific moiety, either in vivo or in vitro. Suitable protein-binding partners include antibodies and functional fragments thereof, scaffold proteins, or peptides. Additionally, modified nucleic acids can be employed to direct the synthesis and extracellular localization of lipids, carbohydrates, or other biological moieties.

As described herein, a useful feature of the modified nucleic acids of the invention is the capacity to reduce the innate immune response of a cell to an exogenous nucleic acid. Provided are methods for performing the titration, reduction or elimination of the immune response in a cell or a population of cells. In some embodiments, the cell is contacted with a first composition that contains a first dose of a first exogenous nucleic acid including a translatable region and at least one nucleoside modification, and the level of the innate immune response of the cell to the first exogenous nucleic acid is determined. Subsequently, the cell is contacted with a second composition, which includes a second dose of the first exogenous nucleic acid, the second dose containing a lesser amount of the first exogenous nucleic acid as compared to the first dose. Alternatively, the cell is contacted with a first dose of a second exogenous nucleic acid. The second exogenous nucleic acid may contain one or more modified nucleosides, which may be the same or different from the first exogenous nucleic acid or, alternatively, the second exogenous nucleic acid may not contain modified nucleosides. The steps of contacting the cell with the first composition and/or the second composition may be repeated one or more times. Additionally, efficiency of protein production (e.g., protein translation) in the cell is optionally determined, and the cell may be re-transfected with the first and/or second composition repeatedly until a target protein production efficiency is achieved.

Therapeutics for Diseases and Conditions.

Provided are methods for treating or preventing a symptom of diseases characterized by missing or aberrant protein activity, by replacing the missing protein activity or overcoming the aberrant protein activity. Because of the rapid initiation of protein production following introduction of modified mRNAs, as compared to viral DNA vectors, the compounds of the present invention are particularly advantageous in treating acute diseases such as sepsis, stroke, and myocardial infarction. Moreover, the lack of transcriptional regulation of the modified mRNAs of the invention is advantageous in that accurate titration of protein production is achievable.

In some embodiments, modified mRNAs and their encoded polypeptides in accordance with the present invention may be used for therapeutic purposes. In some embodiments, modified mRNAs and their encoded polypeptides in accordance with the present invention may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

Diseases characterized by dysfunctional or aberrant protein activity include cystic fibrosis, sickle cell anemia, epidermolysis bullosa, amyotrophic lateral sclerosis, and glucose-6-phosphate dehydrogenase deficiency. The present invention provides a method for treating such conditions or diseases in a subject by introducing nucleic acid or cell-based therapeutics containing the modified nucleic acids provided herein, wherein the modified nucleic acids encode for a protein that antagonizes or otherwise overcomes the aberrant protein activity present in the cell of the subject.

Specific examples of a dysfunctional protein are the missense mutation variants of the cystic fibrosis transmembrane conductance regulator (CFTR) gene, which produce a dysfunctional protein variant of CFTR protein, which causes cystic fibrosis.

Diseases characterized by missing (or substantially diminished such that proper protein function does not occur) protein activity include cystic fibrosis, Niemann-Pick type C, β thalassemia major, Duchenne muscular dystrophy, Hurler Syndrome, Hunter Syndrome, and Hemophilia A. Such proteins may not be present, or are essentially non-functional. The present invention provides a method for treating such conditions or diseases in a subject by introducing nucleic acid or cell-based therapeutics containing the modified nucleic acids provided herein, wherein the modified nucleic acids encode for a protein that replaces the protein activity missing from the target cells of the subject. Specific examples of a dysfunctional protein are the nonsense mutation variants of the cystic fibrosis transmembrane conductance regulator (CFTR) gene, which produce a nonfunctional protein variant of CFTR protein, which causes cystic fibrosis.

Thus, provided are methods of treating cystic fibrosis in a mammalian subject by contacting a cell of the subject with a modified nucleic acid having a translatable region that encodes a functional CFTR polypeptide, under conditions such that an effective amount of the CTFR polypeptide is present in the cell. Preferred target cells are epithelial, endothelial and mesothelial cells, such as the lung, and methods of administration are determined in view of the target tissue; i.e., for lung delivery, the RNA molecules are formulated for administration by inhalation.

In another embodiment, the present invention provides a method for treating hyperlipidemia in a subject, by introducing into a cell population of the subject with a modified mRNA molecule encoding Sortilin, a protein recently characterized by genomic studies, thereby ameliorating the hyperlipidemia in a subject. The SORT1 gene encodes a trans-Golgi network (TGN) transmembrane protein called Sortilin. Genetic studies have shown that one of five individuals has a single nucleotide polymorphism, rs12740374, in the 1p13 locus of the SORT1 gene that predisposes them to having low levels of low-density lipoprotein (LDL) and very-low-density lipoprotein (VLDL). Each copy of the minor allele, present in about 30% of people, alters LDL cholesterol by 8 mg/dL, while two copies of the minor allele, present in about 5% of the population, lowers LDL cholesterol 16 mg/dL. Carriers of the minor allele have also been shown to have a 40% decreased risk of myocardial infarction. Functional in vivo studies in mice describes that overexpression of SORT1 in mouse liver tissue led to significantly lower LDL-cholesterol levels, as much as 80% lower, and that silencing SORT1 increased LDL cholesterol approximately 200% (Musunuru K et al. From noncoding variant to phenotype via SORT1 at the 1p13 cholesterol locus. *Nature* 2010; 466: 714-721).

Modulation of Cell Fate.

Provided are methods of inducing an alteration in cell fate in a target mammalian cell. The target mammalian cell may be a precursor cell and the alteration may involve driving differentiation into a lineage, or blocking such differentiation. Alternatively, the target mammalian cell may be a differentiated cell, and the cell fate alteration includes driving de-differentiation into a pluripotent precursor cell, or blocking such de-differentiation, such as the dedifferentiation of cancer cells into cancer stem cells. In situations where a change in cell fate is desired, effective amounts of mRNAs encoding a cell fate inductive polypeptide is introduced into a target cell under conditions such that an alteration in cell fate is induced. In some embodiments, the modified mRNAs are useful to reprogram a subpopulation of cells from a first phenotype to a second phenotype. Such a reprogramming may be temporary or permanent. Optionally, the reprogramming induces a target cell to adopt an intermediate phenotype.

Additionally, the methods of the present invention are particularly useful to generate induced pluripotent stem cells (iPS cells) because of the high efficiency of transfection, the ability to re-transfect cells, and the tenability of the amount of recombinant polypeptides produced in the target cells. Further, the use of iPS cells generated using the methods described herein is expected to have a reduced incidence of teratoma formation.

Also provided are methods of reducing cellular differentiation in a target cell population. For example, a target cell population containing one or more precursor cell types is contacted with a composition having an effective amount of a modified mRNA encoding a polypeptide, under conditions such that the polypeptide is translated and reduces the differentiation of the precursor cell. In non-limiting embodiments, the target cell population contains injured tissue in a mammalian subject or tissue affected by a surgical procedure. The precursor cell is, e.g., a stromal precursor cell, a neural precursor cell, or a mesenchymal precursor cell.

In a specific embodiment, provided are modified nucleic acids that encode one or more differentiation factors Gata4, Mef2c and Tbx4. These mRNA-generated factors are introduced into fibroblasts and drive the reprogramming into cardiomyocytes. Such a reprogramming can be performed in vivo, by contacting an mRNA-containing patch or other material to damaged cardiac tissue to facilitate cardiac regeneration. Such a process promotes cardiomyocyte genesis as opposed to fibrosis.

Targeting of Pathogenic Organisms; Purification of Biological Materials.

Provided herein are methods for targeting pathogenic microorganisms, such as bacteria, yeast, protozoa, helminthes and the like, using modified mRNAs that encode cytostatic or cytotoxic polypeptides. Preferably the mRNA introduced into the target pathogenic organism contains modified nucleosides or other nucleic acid sequence modifications that the mRNA is translated exclusively, or preferentially, in the target pathogenic organism, to reduce possible off-target effects of the therapeutic. Such methods are useful for removing pathogenic organisms from biological material, including blood, semen, eggs, and transplant materials including embryos, tissues, and organs.

Targeting of Diseased Cells.

Provided herein are methods for targeting pathogenic or diseased cells, particularly cancer cells, using modified mRNAs that encode cytostatic or cytotoxic polypeptides. Preferably the mRNA introduced into the target pathogenic cell contains modified nucleosides or other nucleic acid sequence modifications that the mRNA is translated exclusively, or preferentially, in the target pathogenic cell, to reduce possible off-target effects of the therapeutic. Alternatively, the invention provides targeting moieties that are capable of targeting the modified mRNAs to preferentially bind to and enter the target pathogenic cell.

Methods of Protein Production.

The methods provided herein are useful for enhancing protein product yield in a cell culture process. In a cell culture containing a plurality of host cells, introduction of the modified mRNAs described herein results in increased protein production efficiency relative to a corresponding unmodified nucleic acid. Such increased protein production efficiency can be demonstrated, e.g., by showing increased cell transfection, increased protein translation from the nucleic acid, decreased nucleic acid degradation, and/or reduced innate immune response of the host cell. Protein production can be measured by ELISA, and protein activity can be measured by various functional assays known in the art. The protein production may be generated in a continuous or a fed-batch mammalian process.

Additionally, it is useful to optimize the expression of a specific polypeptide in a cell line or collection of cell lines of potential interest, particularly an engineered protein such as a protein variant of a reference protein having a known activity. In one embodiment, provided is a method of optimizing expression of an engineered protein in a target cell, by providing a plurality of target cell types, and independently contacting with each of the plurality of target cell types a modified mRNA encoding an engineered polypeptide. Additionally, culture conditions may be altered to increase protein production efficiency. Subsequently, the presence and/or level of the engineered polypeptide in the plurality of target cell types is detected and/or quantitated, allowing for the optimization of an engineered polypeptide's expression by selection of an efficient target cell and cell culture conditions relating thereto. Such methods are particularly useful when the engineered polypeptide contains one or more post-translational modifications or has substantial tertiary structure, situations which often complicate efficient protein production.

Methods of Gene Silencing.

The modified mRNAs described herein are useful to silence (i.e., prevent or substantially reduce) expression of one or more target genes in a cell population. A modified mRNA encoding a polypeptide capable of directing sequence-specific histone H3 methylation is introduced into the cells in the population under conditions such that the polypeptide is translated and reduces gene transcription of a target gene via histone H3 methylation and subsequent heterochromatin formation. In some embodiments, the silencing mechanism is performed on a cell population present in a mammalian subject. By way of non-limiting example, a useful target gene is a mutated Janus Kinase-2 family member, wherein the mammalian subject expresses the mutant target gene suffers from a myeloproliferative disease resulting from aberrant kinase activity.

Co-administration of modified mRNAs and siRNAs are also provided herein. As demonstrated in yeast, sequence-specific trans silencing is an effective mechanism for altering cell function. Fission yeast require two RNAi complexes for siRNA-mediated heterochromatin assembly: the RNA-induced transcriptional silencing (BITS) complex and the RNA-directed RNA polymerase complex (RDRC) (Motamedi et al. Cell 2004, 119, 789-802). In fission yeast, the BITS complex contains the siRNA binding Argonaute family protein Agol, a chromodomain protein Chp1, and Tas3. The fission yeast RDRC complex is composed of an RNA-dependent RNA Polymerase Rdp1, a putative RNA helicase Hrr1, and a polyA polymerase family protein Cid12. These two complexes require the Dicer ribonuclease and Clr4 histone H3 methyltransferase for activity. Together, Agol binds siRNA molecules generated through Dicer-mediated cleavage of Rdp1 co-transcriptionally generated dsRNA transcripts and allows for the sequence-specific direct association of Chp1, Tas3, Hrr1, and Clr4 to regions of DNA destined for methylation and histone modification and subsequent compaction into transcriptionally silenced heterochromatin. While this mechanism functions in cis- with centromeric regions of DNA, sequence-specific trans silencing is possible through co-transfection with double-stranded siRNAs for specific regions of DNA and concomitant RNAi-directed silencing of the siRNA ribonuclease Eri1 (Buhler et al. Cell 2006, 125, 873-886).

Modulation of Biological Pathways.

The rapid translation of modified mRNAs introduced into cells provides a desirable mechanism of modulating target biological pathways. Such modulation includes antagonism or agonism of a given pathway. In one embodiment, a method is provided for antagonizing a biological pathway in a cell by contacting the cell with an effective amount of a composition comprising a modified nucleic acid encoding a recombinant polypeptide, under conditions such that the nucleic acid is localized into the cell and the recombinant polypeptide is capable of being translated in the cell from the nucleic acid, wherein the recombinant polypeptide inhibits the activity of a polypeptide functional in the biological pathway. Exemplary biological pathways are those defective in an autoimmune or inflammatory disorder such as multiple sclerosis, rheumatoid arthritis, psoriasis, lupus erythematosus, ankylosing spondylitis colitis, or Crohn's disease; in particular, antagonism of the IL-12 and IL-23 signaling pathways are of particular utility. (See Kikly K, Liu L, Na S, Sedgwick J D (2006) Curr. Opin. Immunol. 18 (6): 670-5). Further, provided are modified nucleic acids encoding an antagonist for chemokine receptors; chemokine receptors CXCR-4 and CCR-5 are required for, e.g., HIV entry into host cells (Arenzana-Seisdedos F et al. (1996) Nature 383:400).

Alternatively, provided are methods of agonizing a biological pathway in a cell by contacting the cell with an effective amount of a modified nucleic acid encoding a recombinant polypeptide under conditions such that the nucleic acid is localized into the cell and the recombinant polypeptide is capable of being translated in the cell from the nucleic acid, and the recombinant polypeptide induces the activity of a polypeptide functional in the biological pathway. Exemplary agonized biological pathways include pathways that modulate cell fate determination. Such agonization is reversible or, alternatively, irreversible.

Methods of Cellular Nucleic Acid Delivery.

Methods of the present invention enhance nucleic acid delivery into a cell population, in vivo, ex vivo, or in culture. For example, a cell culture containing a plurality of host cells (e.g., eukaryotic cells such as yeast or mammalian cells) is contacted with a composition that contains an enhanced nucleic acid having at least one nucleoside modification and, optionally, a translatable region. The composition also generally contains a transfection reagent or other compound that increases the efficiency of enhanced nucleic acid uptake into the host cells. The enhanced nucleic acid exhibits enhanced retention in the cell population, relative to a corresponding unmodified nucleic acid. The retention of the enhanced nucleic acid is greater than the retention of the unmodified nucleic acid. In some embodiments, it is at least about 50%, 75%, 90%, 95%, 100%, 150%, 200% or more than 200% greater than the retention of the unmodified nucleic acid. Such retention advantage may be achieved by one round of transfection with the enhanced nucleic acid, or may be obtained following repeated rounds of transfection.

In some embodiments, the enhanced nucleic acid is delivered to a target cell population with one or more additional nucleic acids. Such delivery may be at the same time, or the enhanced nucleic acid is delivered prior to delivery of the one or more additional nucleic acids. The additional one or more nucleic acids may be modified nucleic acids or unmodified nucleic acids. It is understood that the initial presence of the enhanced nucleic acids does not substantially induce an innate immune response of the cell population and, moreover, that the innate immune response will not be activated by the later presence of the unmodified nucleic acids. In this regard, the enhanced nucleic acid may not itself contain a translatable region, if the protein desired to be present in the target cell population is translated from the unmodified nucleic acids.

Pharmaceutical Compositions

The present invention provides enhanced nucleic acids, and complexes containing enhanced nucleic acids associated with other deliverable moieties. Thus, the present invention provides pharmaceutical compositions comprising one or more enhanced nucleic acids, or one or more such complexes, and one or more pharmaceutically acceptable excipients. Pharmaceutical compositions may optionally comprise one or more additional therapeutically active substances. In some embodiments, compositions are administered to humans. For the purposes of the present disclosure, the phrase "active ingredient" generally refers to an enhanced nucleic acid to be delivered as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween®20], polyoxyethylene sorbitan [Tween®60], polyoxyethylene sorbitan monooleate [Tween®80], sorbitan monopalmitate [Span®40], sorbitan monostearate [Span®60], sorbitan tristearate [Span®65], glyceryl monooleate, sorbitan monooleate [Span®80]), polyoxyethylene esters (e.g. polyoxyethylene monostearate [Myrj®45], polyoxyethylene hydrogenated castor oil, polyethoxylated castor oil, polyoxymethylene stearate, and Solutol®), sucrose fatty acid esters, polyethylene glycol fatty acid esters (e.g. Cremophor®), polyoxyethylene ethers, (e.g. polyoxyethylene lauryl ether [Brij®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic®F 68, Poloxamer®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate)(Veegum®, and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall®115, Germaben®II, Neolone™, Kathon™, and/or Euxyl®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient. Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are suitably in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* 21$^{st}$ ed., Lippincott Williams & Wilkins, 2005 (incorporated herein by reference).

The present invention provides methods comprising administering modified mRNAs and their encoded proteins or complexes in accordance with the invention to a subject in need thereof. Nucleic acids, proteins or complexes, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Kits.

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

DEFINITIONS

Therapeutic Agent: The term "therapeutic agent" refers to any agent that, when administered to a subject, has a therapeutic, diagnostic, and/or prophylactic effect and/or elicits a desired biological and/or pharmacological effect.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, where a nucleic acid is biologically active, a portion of that nucleic acid that shares at least one biological activity of the whole nucleic acid is typically referred to as a "biologically active" portion.

Conserved: As used herein, the term "conserved" refers to nucleotides or amino acid residues of a polynucleotide sequence or amino acid sequence, respectively, that are those that occur unaltered in the same position of two or more related sequences being compared. Nucleotides or amino acids that are relatively conserved are those that are conserved amongst more related sequences than nucleotides or amino acids appearing elsewhere in the sequences. In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Functional: As used herein, a "functional" biological molecule is a biological molecule in a form in which it exhibits a property and/or activity by which it is characterized.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% similar. The term "homologous" necessarily refers to a comparison between at least two sequences (nucleotides sequences or amino acid sequences). In accordance with the invention, two nucleotide sequences are considered to be homologous if the polypeptides they encode are at least about 50% identical, at least about 60% identical, at least about 70% identical, at least about 80% identical, or at least about 90% identical for at least one stretch of at least about 20 amino acids. In some embodiments, homologous nucleotide sequences are characterized by the ability to encode a stretch of at least 4-5 uniquely specified amino acids. Both the identity and the approximate spacing of these amino acids relative to one another must be considered for nucleotide sequences to be considered homologous. For nucleotide sequences less than 60 nucleotides in length, homology is determined by the ability to encode a stretch of at least 4-5 uniquely specified amino acids. In accordance with the invention, two protein sequences are considered to be homologous if the proteins are at least about 50% identical, at least about 60% identical, at least about 70% identical, at least about 80% identical, or at least about 90% identical for at least one stretch of at least about 20 amino acids.

Identity: As used herein, the term "identity" refers to the overall relatedness between polymeric molecules, e.g., between nucleic acid molecules (e.g. DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Atschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe).

Isolated: As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Similarity: As used herein, the term "similarity" refers to the overall relatedness between polymeric molecules, e.g. between nucleic acid molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Treating: As used herein, the term "treating" refers to partially or completely alleviating, ameliorating, improving, relieving, delaying onset of, inhibiting progression of, reducing severity of, and/or reducing incidence of one or more symptoms or features of a particular disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to the protein or agent prior to being modified.

EQUIVALENTS AND SCOPE

Those skilled in the art will recognize, or be able to ascertain using no more than routine experimentation, many equivalents to the specific embodiments, described herein. The scope of the present invention is not intended to be limited to the above Description, but rather is as set forth in the appended claims.

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

Modified mRNAs (mRNAs) according to the invention were made using standard laboratory methods and materials. The open reading frame (ORF) of the gene of interest is flanked by a 5' untranslated region (UTR) containing a strong Kozak translational initiation signal and an alpha-globin 3' UTR terminating with an oligo(dT) sequence for templated addition of a polyA tail. The mRNAs were modified with pseudouridine ($\psi$) and 5-methyl-cytidine (5meC) to reduce the cellular innate immune response. Kariko K et al. Immunity 23:165-75 (2005), Kariko K et al. Mol Ther 16:1833-40 (2008), Anderson B R et al. NAR (2010).

The cloning, gene synthesis and vector sequencing was performed by DNA2.0 Inc. (Menlo Park, Calif.). Vector sequences and insert sequences are set forth in SEQ ID NOs: 5-8. The ORFs were restriction digested using XbaI or HindIII and used for cDNA synthesis using tailed-PCR. This tailed-PCR cDNA product was used as the template for the modified mRNA synthesis reaction using 25 mM each modified nucleotide mix (modified U/C was manufactured by TriLink Biotech, San Diego, Calif., unmodified A/G was purchased from Epicenter Biotechnologies, Madison, Wis.) and CellScript MegaScript™ (Epicenter Biotechnologies, Madison, Wis.) complete mRNA synthesis kit. The in vitro transcription reaction was run for 3-4 hours at 37° C. PCR reaction used HiFi PCR 2× Master Mix™ (Kapa Biosystems, Woburn, Mass.). The In vitro transcribed mRNA product was run on an agarose gel and visualized. mRNA was purified with Ambion/Applied Biosystems (Austin, Tex.) MEGA-Clear RNA™ purification kit. PCR used PureLink™ PCR purification kit (Invitrogen, Carlsbad, Calif.) or PCR cleanup kit (Qiagen, Valencia, Calif.). The product was quantified on Nanodrop™ UV Absorbance (ThermoFisher, Waltham, Mass.). Quality, UV absorbance quality and visualization of the product was performed on an 1.2% agarose gel. The product was resuspended in TE buffer.

When transfected into mammalian cells, the modified mRNAs may have a stability of between 12-18 hours.

For animal experiments, the IV delivery solution was 150 mM NaCl, 2 mM $CaCl_2$, 2 mM Na+-phosphate, and 0.5 mM EDTA, pH 6.5 and 10 µl lipofectamine (RNAiMax™, Invitrogen, Carlsbad, Calif.).

Example 1

The nucleic acid sequence for the precursor of human granulocyte colony stimulating factor (G-CSF) is set forth in SEQ ID NO. 1:

(SEQ ID No. 1)
agcttttggaccctcgtacagaagctaatacgactcactatagggaaataagagagaaaagaagagtaagaagaaatataagagccaccat ggccggtcccgcgacccaaagcccatgaaacttatggccctgcagttgctgctttggcactcggccctctggacagtccaagaagcgact cctctcggacctgcctcatcgttgccgcagtcattccttttgaagtgtctggagcaggtgcgaaagattcagggcgatggagccgcactcca agagaagctctgcgcgacatacaaactttgccatcccgaggagctcgtactgctcgggcacagcttggggattccctgggctcctctctcgt cctgtccgtcgcaggctttgcagttggcagggtgcctttcccagctccactccggtttgttcttgtatcagggactgctgcaagcccttgaggg aatctcgccagaattgggcccgacgctggacacgttgcagctcgacgtggcggatttcgcaacaaccatctggcagcagatggaggaact ggggatggcacccgcgctgcagcccacgcaggggcaatgccggcctttgcgtccgcgtttcagcgcagggcgggtggagtcctcgta gcgagccaccttcaatcatttttggaagtctcgtaccgggtgctgagacatcttgcgcagccgtgaagcgctgccttctgcggggcttgcctt ctggccatgccttcttctctcccttgcacctgtacctcttggtctttgaataaagcctgagtaggaaggcggccgctcgagcatgcatctaga gggcccaattcgccctattcgaagtcg The nucleic acid sequence for G-CSF mRNA is set forth in SEQ ID NO. 17:

(SEQ ID No. 17)
agcuuuuggacccucguacagaagcuaauacgacucacuauagggaaauaagagagaaaagaagaguaagaagaaauauaaga gccaccauggccgguccgcgacccaaagcccaugaaacuuauggcccugcaguugcugcuuuggcacucggcccucuggac aguccaagaagcgacuccucucggaccugccucaucguugccgcagucauuccuuuugaagugucuggagcaggugcgaaag auucagggcgauggagccgcacuccaagagaagcucugcgcgacauacaaacuuugccaucccgaggagcucguacugcucgg gcacagcuuggggauucccugggcccucucucgcccuguccgucgcaggcuuugcaguuggcagggugccuuucccagcu ccacuccgguuuguucuuguaucagggacugcugcaagcccuugagggaaucucgccagaauugggcccgacgcuggacacg uugcagcucgacguggcggauuucgcaacaaccaucuggcagcagauggaggaacuggggauggcacccgcgcugcagccca cgcaggggcaaugccggccuuugcguccgcguuucagcgcagggcggguggaguccucguagcgagccaccuucaaucauu uuuggaagucucguaccggguggcugagacaucuugcgcagccgugaagcgcugccuucugcggggcuugccuucuggccau gccuucuucucucccuugcaccuguaccucuuggucuuugaauaaagccugaguaggaaggcggccgcucgagcaugcauc uagagggcccaauucgcccuauucgaagucg The nucleic acid sequence for an exemplary G-CSF modified mRNA (mRNA) is set forth in SEQ ID NO. 18:

(SEQ ID No. 18)
ag5meCψψψψgga5meC5meC5meCψ5meCgψa5meCagaag5meCψaaψa5meCga5meC5meCa5 meCψaψagggaaaψaagagagaaaagaagagψaagaagaaaψaψaagag5meC5meCa5meC5meCaψgg5meC

5meCggψ5meC5meC5meCg5meCga5meC5meC5meCaaag5meC5meC5meC5meCaψgaaa5meC

ψψaψgg5meC5meC5meCψ5meCagψψg5meCψg5meCψψψψgg5meCa5meCψ5meCgg5meC5me

C5meCψ5meCψgga5meCagψ5meC5meCaagaag5meCga5meCψ5meC5meCψ5meCψ5meCgga5 meC5meCψg5meC5meCψ5meCaψ5meCgψψg5meC5meCg5meCagψ5meCaψψ5meC5meCψψψ

ψgaagψgψ5meCψggag5meCaggψg5meCgaaagaψψ5meCagggg5meCgaψggag5meC5meCg5meCa

5meCψ5meC5meCaagagaag5meCψ5meCψg5meCg5meCga5meCaψa5meCaaa5meCψψψg5me

C5meCaψ5meC5meC5meCgaggag5meC5meCgψa5meCψg5meCψ5meCggg5meCa5meCag5 meCψψggggaψψ5meC5meC5meCψggg5meCψ5meC5meCψ5meCψ5meCgψ5meC5meC

ψgψ5meC5meCgψ5meCg5meCagg5meCψψψg5meCagψψgg5meCagggψg5meC5meCψψψ5me

C5meC5meCagψ5meCψ5meC5meCa5meC5meC5meCggψψψgψψ5meCψψgψaψ5meCaggga5m eCψg5meCψg5meCaag5meC5meC5meCψψgagggaaψ5meCψ5meCg5meC5meCagaaψψggg5me -continued

```
C5meC5meCga5meCg5meCψgga5meCa5meCgψψg5meCag5meCψ5meCga5meCgψgg5meCgg aψψψ5meCg5meCaa5meCaa5meC5meCaψ5meCψgg5meCag5meCagaψggaggaa5meCψggggaψ gg5meCa5meC5meC5meCg5meCg5meCψg5meCag5meC5meC5meCa5meCg5meCagggggg5me

Caaψg5meC5meCgg5meC5meCψψψg5meCgψ5meC5meCg5meCgψψψ5meCag5meCg5meCag gg5meCgggψggagψ5meC5meCψ5meCgψag5meCgag5meC5meCa5meC5meCψψ5meCaaψ5me Caψψψψψggaagψ5meCψ5meCgψa5meC5meCgggψg5meCψgaga5meCaψ5meCψψg5meCg5me Cag5meC5meCgψgaag5meCg5meCψg5meC5meCψψ5meCψg5meCgggg5meCψψg5meC5meC ψψ5meCψgg5meC5meCaψg5meC5meC5meCψψ5meCψψ5meCψ5meCψ5meC5meC5meCψψg 5meCa5meC5meCψgψa5meC5meCψ5meCψψggψ5meCψψψgaaψaaag5meC5meCψgagψaggaag g5meCgg5meC5meCg5meCψ5meCgag5meCaψg5meCaψ5meCψagaggg5meC5meC5meCaaψψ

5meCg5meC5meC5meCψaψψ5meCgaagψ5meCg
```

FIG. 1*a* shows an Enzyme-linked immunosorbent assay (ELISA) for Human Granulocyte-Colony Stimulating Factor (G-CSF) of in vitro transfected Human Keratinocyte cells. Keratinocytes were grown in EpiLife medium with Supplement S7 from Invitrogen until they reached a confluence of 50-70%. Cells were transfected with 0, 100, 250, 500, 1000, and 1500 ng mRNA complexed with RNAiMAX from Invitrogen. The RNA:RNAiMAX complex was formed by first incubating the RNA with Supplement-free EpiLife media in a 5× volumetric dilution for 10 minutes at room temperature. In a second vial, RNAiMAX reagent was incubated with Supplement-free EpiLife Media in a 10× volumetric dilution for 10 minutes at room temperature. The RNA vial was then mixed with the RNAiMAX vial and incubated for 20-30 at room temperature before being added to the cells in a drop-wise fashion. Secreted huG-CSF concentration in the culture medium was measured at 6, 12, 24, and 36 hours post-transfection for each of the 6 concentrations. Secretion of Human Granulocyte-Colony Stimulating Factor (G-CSF) from transfected human keratinocytes was quantified using an ELISA kit from Invitrogen following the manufacturers recommended instructions. HuG-CSF shows a dose response, with 1000 ng mRNA showing the best response. Also, production peaked between 24 and 36 hours after transfection. These data show that huG-CSF mRNA (SEQ ID NO: 1) is capable of being translated in Human Keratinocyte cells and that huG-CSF is transported out of the cells and released into the extracellular environment.

FIG. 2 shows human keratinocytes transfected with 0 or 1.5 μg G-CSF mRNA. Cells were grown in EpiLife Media with Supplement S7 from Invitrogen according to standard protocols in 24-well collagen-coated plates. Cells were fixed with 4% paraformaldehyde in PBS and permeabilized with 0.1% Triton X-100 in PBS for 5-10 minutes at room temperature. Cells were then washed 3× with room temperature PBS. G-CSF protein staining was performed using G-CSF mouse monoclonal antibody 5D7 (ab9818, abcam, Cambridge, Mass.) and goat polyclonal secondary antibody to mouse IgG conjugated to DyLight®594 (ab97017, abcam) according to the manufacturer's recommended dilutions. Nuclear DNA staining was performed with DAPI dye from Invitrogen. The cellular actin cytoskeleton was stained using AlexaFluor488-conjugated phalloidin from Invitrogen. G-CSF protein is translated and localized to the cytoplasm upon G-CSF mRNA transfection. The pictures were taken 36 hours after transfection.

Mice (C57 BL/6NTac males approx. 8 weeks old, group housed) were intravenously (IV) injected in the tail vein (Dosing regimen: once daily on days 0, 2, and 4) with human G-CSF mRNA (SEQ ID No. 1) and complete blood cell count with full differential following mRNA injection was measured. Group size: N=5 for each treatment group and time of bleeding.

Experimental Design:

| mmRNA hpreG-CSF IV Tail vein | Unmodified mRNA hpreG-CSF IV Tail vein | Control Scramble IV Tail vein | Control Vehicle IV Tail vein | Number of animals |
|---|---|---|---|---|
| 1 day (n = 5) | 1 day (n = 5) | 1 day (n = 5) | 1 day (n = 5) | 20 (squad A) |
| 5 days (n = 5) | 5 days (n = 5) | 5 days (n = 5) | 5 days (n = 5) | 20 (squad B) |
| 8 days (n = 5) | 8 days (n = 5) | 8 days (n = 5) | 8 days (n = 5) | squad A |
| 14 days (n = 5) | 14 days (n = 5) | 14 days (n = 5) | 14 days (n = 5) | squad B |
| 20 days (n = 5) | 20 days (n = 5) | 20 days (n = 5) | 20 days (n = 5) | Squad A |
| Total Mice | | | | 40 |

Treatment Groups:

mRNA hpreG-CSF unmodified hpreG-CSF

Control: non-specific RNA (total yeast RNA)

Control: vehicle

Diet: Regular chow diet: Pico Rodent Chow (5053)

Assay:

Whole blood for hematological analysis was collected, and the following cells were counted: Total white blood cells, neutrophils, lymphocytes, monocytes/macrophages, eosinophils, basophils, red blood cells, platelets. Body weights were measured during blood collection.

Results:

FIG. 4 shows the results for in vivo activity of huG-CSF mRNA on total blood counts and granulocytes. Row 1 shows the total white blood cell (WBC) count. huG-CSF mRNA alone elevated the total WBC count on day 5 after administration by IV. In contrast, non-modified hu-G-CSF, vehicle alone, non-specific mRNA (scramble: total yeast RNA) did not alter WBC counts. G-CSF is known to stimulate the proliferation, differentiation and mobilization of myeloid progenitor cells including terminally differentiated granulocyte populations of neutrophil, eosinophils, monocytes, and basophils. G-CSF does not stimulate lymphoid or erythrocyte cell types including lymphocytes, red blood cells or platelets. Row 2 shows the neutrophil count. G-CSF is known to particularly stimulate neutrophil proliferation, mobilization and progenitor differentiation. Again, only huG-CSF mRNA, but not vehicle alone, non-specific mRNA (scramble: total yeast RNA) or non-modified huG-CSF mRNA elevated neutrophils 4-fold above vehicle control on day 5 after administration by IV. Additional granulocyte cell types in Rows 3 and 5 show slight elevation of monocytes and basophils at days 5 and 8 for animals treated with huG-CSF mRNA, while Row 4 shows significant upregulation of the granulocyte lineage eosinophils on day 5.

Figures 1, 5:
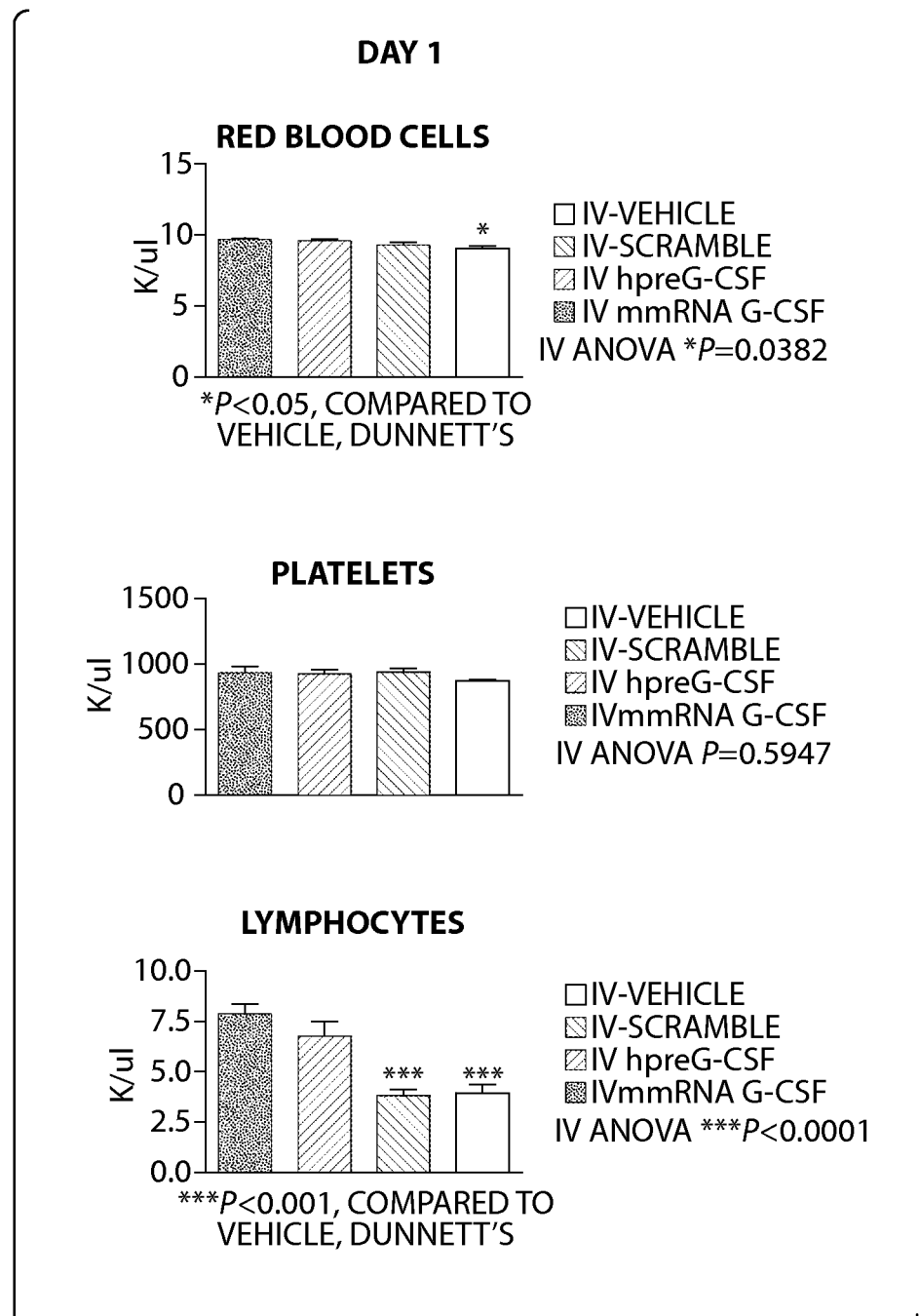
FIG. 5 depicts bar graphs of erythrocyte and lymphocyte lineage cell types of a mouse following intravenous injection of modified huG-CSF mRNA (FIGS. 5-1, 5-2, and 5-3).
Figures 2, 5:
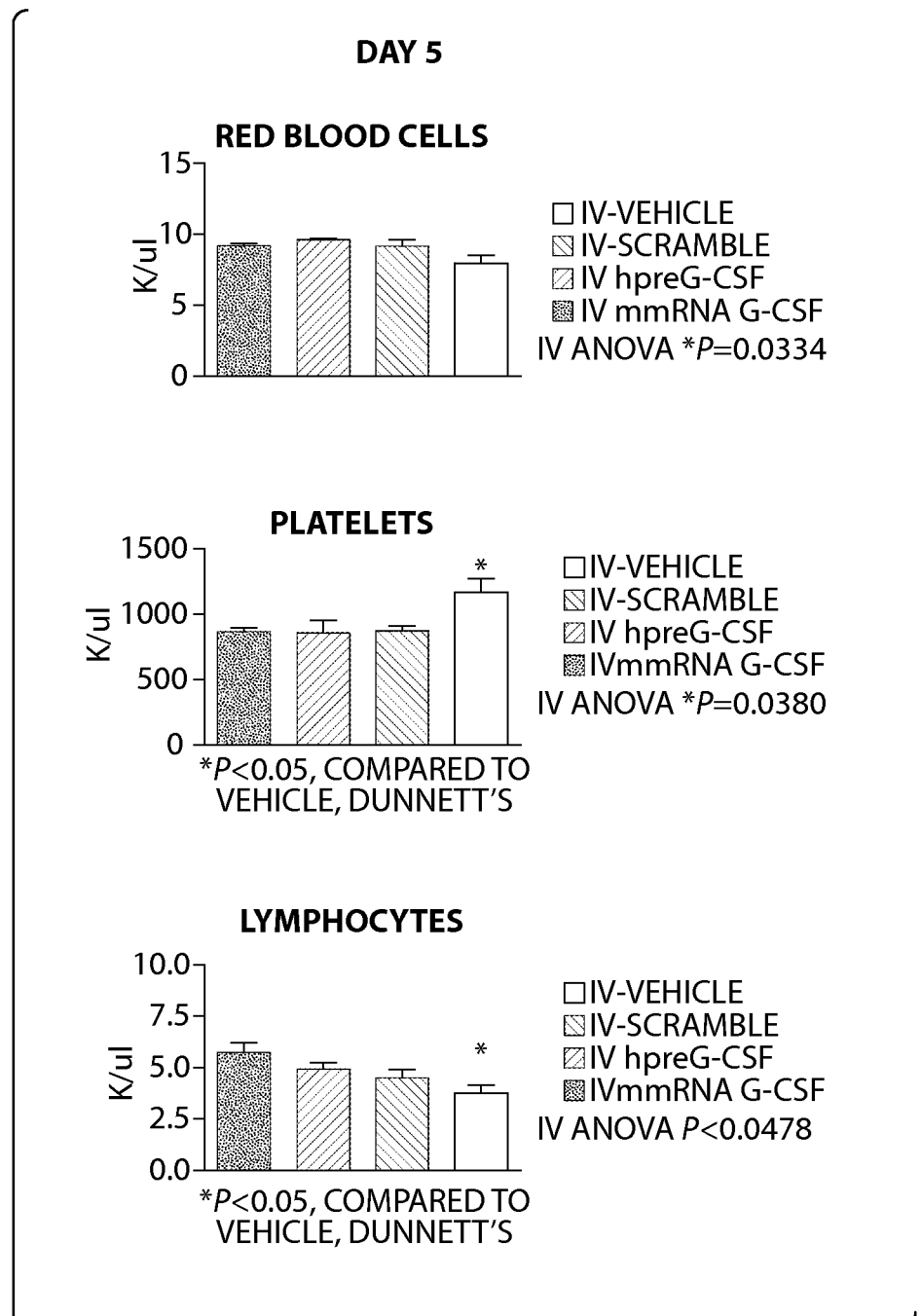
Figures 3, 5:
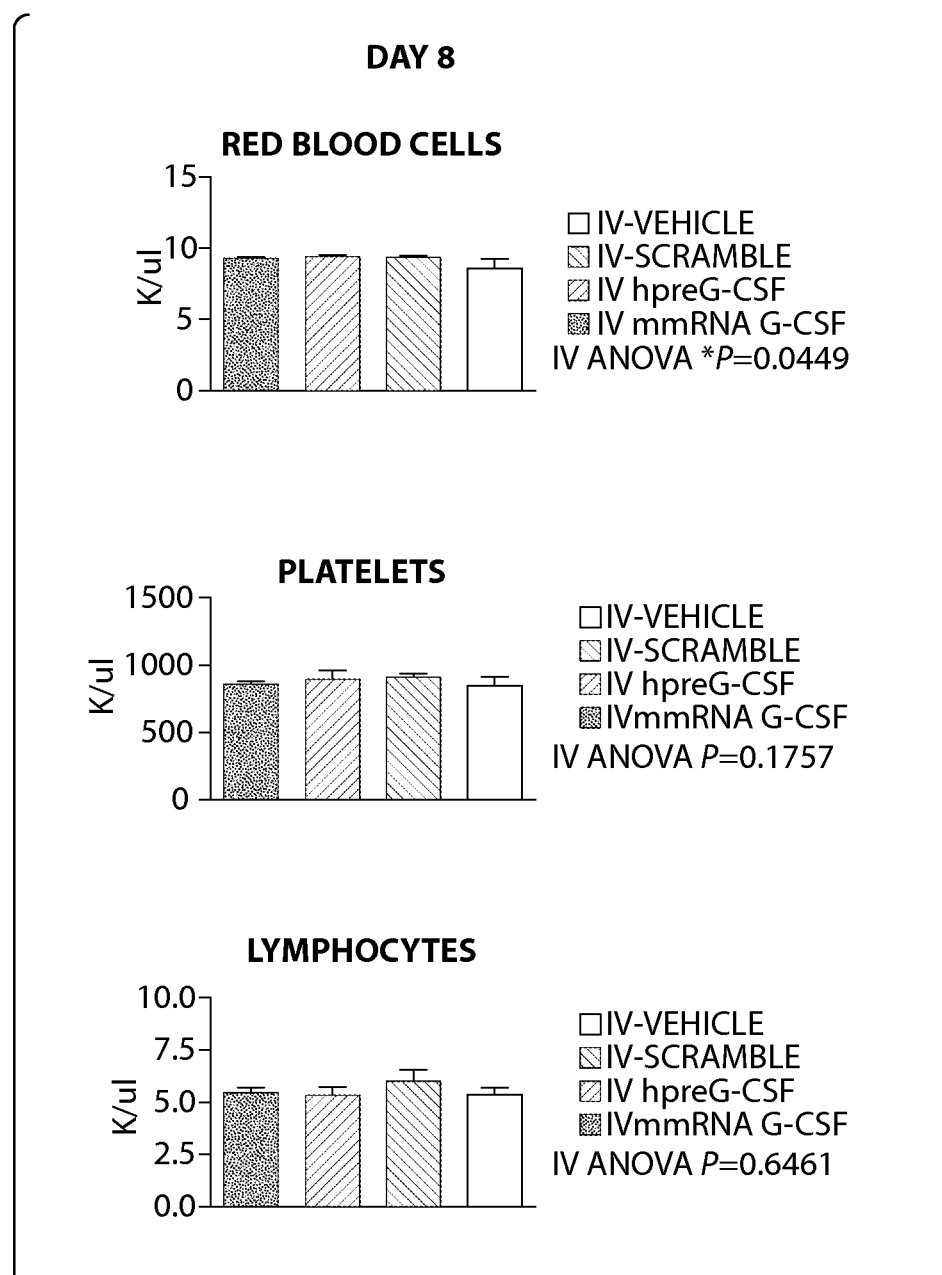

FIG. 5 shows the results for in vivo activity of huG-CSF mRNA on erythrocyte and lymphocyte cell types. Row 1 shows that the red blood cell (RBC) count stays relative stable, which is expected. Row 2 shows platelet count. Row 3 shows the lymphocyte count, which remains stable across all treatment groups as expected. Together, these data shows that huG-CSF mRNA is translated in mouse cells in vivo, correctly processed and released. The G-CSF precursor form contains a signal peptide that must be cleaved for the protein to be secreted. G-CSF contains the human signal peptide not that of the mouse. It appears that the human signal peptide was correctly processed and led huG-CSF to be released from the transfected cells resulting the pronounced physiological response. huG-CSF peptide made from mRNA was active in vivo. huG-CSF elevated total WBC count and stimulated each granulocyte cell type (neutrophil, monocytes, eosinophils, basophils) but not non-granulocyte populations.

Example 2

The effects of modified mRNA encoding G-CSF on stimulating polymorphonuclear neutrophil (PMN) and modulating PMN functions are tested using G-CSFR-deficient mice according to Betsuyacu T et al. J Clin Invest 103: 825-832 (1999). G-CSFR-deficient mice (C57BL/6×129 SvJ) are generated as described in Liu F et al. Immunity 5:491-501 (1996). The mice carry a homozygous null mutation in the granulocyte colony-stimulating factor receptor (G-CSFR) gene. G-CSFR-deficient mice show decreased numbers of normal circulating neutrophils, hematopoietic progenitors are decreased in the bone marrow, and the expansion and terminal differentiation of these progenitors into granulocytes is impaired. Neutrophils isolated from G-CSFR-deficient mice are prone to apoptosis. Six- to 10-week-old wild-type and G-CSFR-deficient mice may be used for studies. PMNs can be purified from bone marrow of mice using a discontinuous Percol gradient, e.g. to reach 40%-60% purity.

Example 3

The effects of modified mRNA encoding G-CSF are tested using C57BL/6 mice with homozygous inactivation of the G-CSF gene (G-CSF−/−) according to Lieschke G J et al. Blood 84:1737 (1994). Mice are analyzed between 2 and 3 months of age. To induce an acute neutrophil inflammatory response, mice are injected intraperitoneal (IP) with a preparation comprising casein containing bacteria, e.g. 2 mL of an 0.2% (wt/vol) solution of casein in mouse tonicity phosphate-buffered saline (MTPBS), using either calcium caseinate, casein C5890 (Sigma Chemical Co, St Louis, Mo.), casein 44016, casein C3400, casein hydrolysate L41, casein sodium 2330. In other experiments, peritoneal inflammatory responses are induced by the IP injection of 2 mL of 0.3% sodium thioglycollate (wt/vol in distilled water) according to Metcalf D et al. Blood 88: 3755-3764 (1996). White blood cell counts are performed under anesthesia on orbital plexus blood before and, on the opposite eye, 3 hours after the IP injections. At 3 hours after injection, blood is collected from the axilla during anesthesia-induced killing. The abdominal cavity is then injected with 2 mL MTPBS and massaged to ensure adequate mixing of the cell population with the harvesting fluid. The peritoneal cavity cells are then collected. The marrow cells are collected from one femur using 2 mL of medium. The marrow plug is converted to a dispersed cell suspension. Total marrow cell counts are calculated. The spleen is weighed and converted to a dispersed cell suspension. Mice are injected with modified mRNA, recombinant G-CSF (rhG-CSF) vehicle control and unspecific mRNA control. For recombinant G-CSF 2.5 pg (in 0.2 mL of 0.9% saline containing 5% bovine calf serum) is injected subcutaneously twice daily for 5 days. A 2.5-day period is then allowed to elapse before the mice are injected IP with MTPBS or casein. Control mice are injected twice daily with 0.2 mL MTPBS containing 5% FCS (vehicle control).

Example 4

Delivery of modified mRNA encoding G-CSF is tested in female ICR mice (e.g. two months old). For skin injection, to mimic a surgical wound, mice are anesthetized, their backs shaved and disinfected with 70% ethanol, and then a 1 cm long, full thickness surgical incision is made at individual sites on the dorsum of the back of each animal. Immediately thereafter, various concentrations of modified mRNA either uncomplexed (naked) or complexed (e.g. liposome) are injected into the wound edges of each of the wound sites on each animal. Wounds are closed using a metal clip. For intravenous injection (e.g. tail vein), mice each receive various concentrations of modified mRNA either uncomplexed (naked) or complexed. The mice are killed and skin samples as well as liver, spleen, heart, lungs, and lymph nodes were harvested at 0 (control), 1, 3, 6, and 24 h and 1, 2, 5, and 8 wk after injection, according to Meuli M et al. J Invest Dermatology 116, 131-135 (2001).

Example 5

The effects of modified mRNA encoding G-CSF on cerebral ischemia are tested using adult male Sprague-Dawley rats (weight, 250 to 300 g). One day after induction of cerebral ischemia, rats are injected subcutaneously with modified mRNA encoding G-CSF or recombinant human G-CSF (50 µg/kg per day; Amgen Biologicals) once daily for 5 days. Control animals are subjected to cerebral ischemia and injected with saline, according to Shyu W C Circulation 110: 1847-1854 (2004). Under anesthesia, ligations of the right middle cerebral artery (MCA) and bilateral common carotid arteries (CCAs) are performed to induce cerebral infarction. Bilateral CCAs are clamped with nontraumatic arterial clips. With the use of a surgical microscope, the right MCA is ligated with a 10-0 nylon suture. Cortical blood flow is measured continuously with a laser-Doppler flowmeter (PF-5010, Periflux system, Perimed AB) in anesthetized animals. After 90 minutes of ischemia, the suture on the MCA and arterial clips on CCAs are removed to allow reperfusion. During recovery from the anesthesia, body temperature is maintained at 37° C. with a heat lamp. Bromodeoxyuridine (BrdU) pulse labeling is performed to observe the time course of proliferative cells in the brain after cerebral ischemia. G-CSF-treated rats and control rats are injected intraperitoneally with BrdU (50 mg/kg) every 4 hours for 12 hours before they are killed. Rats are killed at 7 days, 14 days, and 28 days after cerebral ischemia. A cumulative labeling method is used to examine the population of proliferative cells during 14 days of cerebral ischemia. Rats G-CSF-treated rats and control rats receive daily injections of BrdU (50 mg/kg IP) for 14 consecutive days, starting the day after MCA ligation. These rats are euthanized 14 days after the last injection. Behavioral assessments are performed 5 days before cerebral ischemia and 1, 7, 14, and 28 days subsequent to MCA ligation. The tests measure (1) body asymmetry and (2) locomotor activity. The baseline-tested scores are recorded to normalize those taken after cerebral ischemia. (1) The elevated body swing test is used to assess body asymmetry after MCA ligation and is evaluated quantitatively. (2) For locomotor activity, rats are subjected to OPTO-VARIMAX (Columbus Instruments) activity monitoring for about 2 hours for behavioral recording. Motor activity is counted as the number of beams broken by rat movement in the chamber. Two parameters of vertical movement are calculated: (1) vertical activity and (2) vertical time. MRI is performed in an imaging system (General Electric) at 3.0 T. Under anesthesia, the 6 to 8 coronal image slices are each 2 mm thick without any gaps. T2-weighted imaging (T2WI) pulse sequences are obtained with the use of a spin-echo technique (repetition time, 4000 ms; echo time, 105 ms) and are captured sequentially for each animal at 1, 7, and 28 days after cerebral ischemia. To measure the infarction area in the right cortex, the non-infarcted area in the right cortex is subtracted from the total cortical area of the left hemisphere. The brains of experimental rats are fixed by transcardial perfusion with saline, followed by perfusion and immersion in 4% paraformaldehyde, followed by BrdU immunostaining Quantification of BrdU-immunoreactive cells is performed on paraffin-embedded tissue sections and is counted digitally. Shyu W C Circulation 110:1847-1854 (2004).

Example 6

The effects of modified mRNA encoding G-CSF on thromboembolic cerebral ischemia (TE) are tested using a rat model of TE of male Wistar rats according to Kollmar R Exp & Transl Stroke Med 2:9 (2010). Intravenous administration of modified mRNA encoding G-CSF follows TE after 60 minutes or 180 minutes. TE is induced by exposing the right common carotid (CCA), internal carotid (ICA), and external carotid artery (ECA) and further dissection to identify the origin of the pterygopalatine artery (PPA). The ECA and the PPA are permanently ligated while the CCA is only temporarily clipped for embolization. A PE 50 catheter is inserted into the ECA proximal to its ligation and 12 red blood clots (each 0.35 mm in diameter and 3 mm in length) are injected at the origin of the right middle cerebral artery (MCA). All animals are subjected to MRI monitoring including perfusion weighted imaging (PWI), diffusion weighted imaging (DWI), T2, and T2* at 0.5, 2.5, 4, and 24 hours after TE followed by silver-infarct staining (SIS). All surviving animal are tested for neurological outcome: no apparent deficit, contralateral forelimb flexion; decreased grip of contralateral forelimb grip while tail pulled; spontaneous movement in all directions, contralateral circling only if pulled by tail; spontaneous contralateral circling.

Example 7

The effects of modified mRNA encoding G-CSF on Alzheimer's disease is tested in an AD mouse model according to Tsai K J et al. J Exp Med. 204:1273-80 (2007). The acute Aβ-induced model is generated according to Stephan A et al. J. Neurosci. 21:5703-5714 (2001) and Yan J J et al. Br. J. Pharmacol. 133:89-96 (2001) using 8-wk-old C57BL/6 male mice. The Aβ aggregate is prepared from a solution of 10 mM of soluble Aβ$_{(1-42)}$ (Sigma-Aldrich) in 0.01 M PBS, pH 7.4. The solution is incubated at 37° C. for 3 days to form the aggregated Aβ and stored at −70° C. Animals are intraperitoneally anesthetized injected with aggregated Aβ bilaterally into the dorsal hippocampus. The animals are subjected to stereotaxic surgery with the incisor bar set at the following coordinates: 2 mm posterior to the bregma, 2.1 mm bilateral to the midline, and 1.8 mm ventral to the skull surface. The volume of injection is 1 µl of aggregated Aβ or 1 µl PBS, and 7 days are allowed for AD symptoms to develop in the mice. For the chronic AD model, Tg2576 mice are purchased from Taconic (Hudson, N.Y.). For the acute AD model, 7 days after injection of the aggregated Aβ, mice are subcutaneously injected with various concentrations of modified mRNA encoding G-CSF and as a control with either 50 µg/kg of recombinant human G-CSF (Amgen Biologicals) or carrier (PBS) once daily for 5 consecutive days. Tg2576 mice are treated similarly. Behavioral measurements are conducted, using e.g. the Morris water maze learning task for spatial learning. Acetycholin levels are measured in the mouse brains. The mice are killed, and their brains are quickly removed and frozen on dry ice. The brains are homogenized on ice and subjected to the ACh assay, e.g. the Amplex Red Acetylcholine/Acetylcholinesterase Assay Kit (Invitrogen), according to the manufacturer's instructions. Quantifications of the Aβ levels and Aβ plaque burden are carried out measuring the levels of soluble and insoluble Aβ were quantified according to the procedures of Kawarabayashi T et al. J. Neurosci. 21:372-381 (2001) and Janus C et al. Nature. 408: 979-982 (2000).

Example 8

The effects of modified mRNA encoding G-CSF on improved cardiac function after myocardial infarction (MI) its anti-apoptotic effects on cardiomyocytes, as well as its role in collateral artery growth (arteriogenesis), can be tested using a model of MI according to Deindl E et al. FASEB J 20:956-958 (2006). MI is induced in male C57BL/6 mice 8-12 wk of age by surgical occlusion of the left anterior descending artery (LAD) through a left anterolateral approach. Mice are anesthetized by intraperitoneal (ip) injection of a mixture of 100 mg/kg ketamine and 5 mg/kg Xylazine, intubated, and artificially ventilated by a mouse ventilator with 200 strokes/min and 200 µl/stroke. Mice are treated with various concentrations of modified mRNA encoding G-CSF and as a control with recombinant G-CSF (100 µg/kg/day, subcutaneous s.c., Amgen Biologicals) directly after MI for 5 consecutive days. Additional controls are sham-operated animals and not operated animals receiving saline. All animals receive bromodeoxyuridine (BrdU; 50 µg/kg/day for 5 consecutive days). BrdU and cytokine treatment is started 30 min after ligation of the LAD. Peripheral blood is harvested from each mouse by aspirating the carotid artery. To define the number of leukocytes, heparinized blood samples are analyzed using a hematological cell analyzer. Mononuclear cells are separated by density-gradient centrifugation, purified, and resuspended in PBS containing 1% BSA. Cells are stained with various markers and are analyzed using FACS. Hearts are excised, fixed, cut transversally into 2 mm thick slices, processed, and embedded in paraffin by standard methods; 4 µm thick sections are cut and mounted on positively charged glass slides. Standard histological procedures (hematoxylin/eosin and Masson trichrome) and immunostaining (see below) are performed. Infarct size is determined as area of infarction (AI) correlated to the area of the left ventricle (including LV-septum). Wall thickness is also measured. Pressure-volume relationships in vivo are analyzed on surviving mice.

Example 9

The effects of modified mRNA encoding G-CSF on autoimmune disease is tested using an EAE mouse model according to Zavala F et al. J Immunol 168: 2011-2019 (2002). EAE is induced in female SJL/J mice (8-10 wk of age) immunized by s.c. injection at two sites at the tail base on day 0, and boosted on day 7 in the flanks, with 400 μg guinea pig MBP (Sigma, St. Louis, Mo.) emulsified in CFA containing 50 μg heat-inactivated *Mycobacterium tuberculosis* H37Ra (Sigma), in a volume of 50 μl/site. The disease develops with an acute phase characterized by loss of weight and progressive ascending clinical paralysis, followed by periods of remission with weight recovery, and subsequent relapses or chronic disease. Clinical symptoms are scored, e.g. no symptoms, flaccid tail, impairment of righting reflex or abnormal gait, severe hind limb weakness, complete hind limb paralysis, or paraplegia, moribund. Various concentrations of modified mRNA encoding G-CSF are administered. As a control recombinant human G-CSF (Amgen, Thousand Oaks, Calif.) is injected s.c. at 200 μg/kg/day. The excipient consists of 5% dextrose in sterile H$_2$O. The disease is followed histologically and immunohistochemically. TNF-α concentration in serum is measured, cytokine and chemokine levels and the T cell autoreactive response is assessed.

Example 10

The effects of modified mRNA encoding G-CSF on autoimmune disease is tested using an MRL-$^{lpr/lpr}$ mouse model, a genetic model of the human autoimmune disease systemic lupus erythematosus. Six-week-old female MRL-lpr/lpr mice are maintained under specific pathogen-free conditions. Modified mRNA encoding G-CSF or recombinant human G-CSF (Amgen, Thousand Oaks, Calif.) is injected s.c. every 6 wk for five consecutive days, starting at 9 wk of age. Mice at this age have no albuminuria, they have detectable anti-nucleosome but no anti-dsDNA antibodies, which is typical of the onset of the autoantibody response in young lupus mice. As controls, two doses of recombinant G-CSF are used: 10 μg/kg and 200 μg/kg, while the other control group receives the carrier solution (5% dextrose in sterile H$_2$O), according to Zavala, F et al. J Immunol 163:5125 (1999). Renal disease is evaluated by the development of albuminuria and histological modifications of the kidney. Albuminuria was measured colorimetrically using commercially available sticks, with albumin concentrations over 1 mg/ml considered positive. Kidney histology is performed on mice killed at 20 wk of age. The kidneys are removed, fixed in 3.6% paraformaldehyde in PBS, and included in paraffin. Sections of 5 μm are stained with hematoxylin-eosin and analyzed for glomerulonephritis. Evaluation of the Ig deposits in the glomeruli is performed on frozen kidneys frozen. Spleen and bone marrow cells are analyzed by FACS. Cytokine production by splenocytes and cytokine concentrations in serum are measured.

Example 11

The nucleic acid sequence for ACTH1-17 resulting in human alpha-melanocyte stimulating hormone (α-MSH) is set forth in SEQ ID NO. 2:

```
                                                                (SEQ ID No. 2)
aagcttttggaccctcgtacagaagctaatacgactcactatagggaaataagagagaaaagaagagtaagaagaaatataagagccacc atgcctagatcatgttgttcacgatcgggagcgttgttgctggcactcttgctccaagcctcgatggaagtgcggggatggtgccttgagagc tcccagtgccaggacctcacaacggagtcgaaccttctggaatgcatccgcgcgtgtaaaccgagggaaggtaaaaggtcctacagcatg gagcacttcagatgggggaagcccgtcgggaagaagcggtgaagcgctgccttctgcggggcttgccttctggccatgcccttcttctctc ccttgcacctgtacctcttggtctttgaataaagcctgagtaggaaggcggccgctcgagcatgcatctagag
```

The nucleic acid sequence for α-MSH mRNA is set forth in SEQ ID NO. 19:

```
                                                                (SEQ ID No. 19)
aagcuuuuggacccucguacagaagcuaauacgacucacuauagggaaauaagagagaaaagaagaguaagaagaaauauaag agccaccaugccuagaucauguuguucacgaucgggagcguuguucggcacucuugcuccaagccucgauggaagugcgg ggauggugccuugagagcucccagugccaggaccucacaacggagucgaaccuucuggaaugcauccgcgcguguaaaccga gggaagguaaaagguccuacagcauggagcacuucagaugggggaagcccgucgggaagaagcggugaagcgcugccuucug cggggcuugccuucuggccaugcccuucuucucucccuugcaccuguaccucuuggucuuugaauaaagccugaguaggaag gcggccgcucgagcaugcaucuagag
```

The nucleic acid sequence for an exemplary α-MSH modified mRNA (mRNA) is set forth in SEQ ID NO. 20:

```
                                                                (SEQ ID No. 20)
aag5meCψψψψψgga5meC5meC5meCψ5meCgψa5meCagaag5meCψaaψa5meCga5meCψ5meCa5 meCψaψaggggaaaψaagagagaaaagaagagψaagaagaaaψaψaagag5meC5meCa5meC5meCaψg5meC5
```

-continued meCψagaψ5meCaψgψψgψψ5meCa5meCgaψ5meCgggag5meCgψψgψψg5meCψgg5meCa5meC

ψ5meCψψg5meCψ5meC5meCaag5meC5meCψ5meCgaψggaagψg5meCggggaψggψg5meC5me

Cψψgagag5meCψ5meC5meC5meCagψg5meC5meCagga5meC5meCψ5meCa5meCaa5meCgga gψ5meCgaa5meC5meCψψ5meCψggaaψg5meCaψ5meC5meCg5meCg5meCgψgψaaa5meC5me Cgagggaaggψaaaaggψ5meC5meCψa5meCag5meCaψggag5meCa5meCψψ5meCagaψgggggaag5 meC5meC5meCgψ5meCgggaagaag5meCggψgaag5meCg5meCψg5meC5meCψψ5meCψg5meC gggg5meCψψg5meC5meCψψ5meCψgg5meC5meCaψg5meC5meC5meCψψ5meCψψ5meCψ5m eCψ5meC5meC5meCψψg5meCa5meC5meCψgψa5meC5meCψ5meCψψggψ5meCψψψgaaψaaa g5meC5meCψgagψaggaagg5meCgg5meC5meCg5meCψ5meCgag5meCaψg5meCaψ5meCψaga g The amino acid sequence of ACTH1-17 is set forth in SEQ ID No. 9: SYSMEHFRWGKPVGKKR. The C-terminal end contains amino acids necessary for amidation of αMSH (GKK). Melanocyte-stimulating hormone (αMSH) is a 13 amino acid peptide derived from pro-opiomelanocortin (POMC), a pro-hormone that is post-translationally processed. POMC contains a signal peptide (amino acid residues 1-26) and a sorting peptide (amino acid residues 27-52) that direct POMC to the lumen of the endoplasmic reticulum (ER) where it is processed by hormone convertases (PC1 and PC2). Native αMSH is produced via cleavage of ACTH1-17 to ACTH1-13, followed by amidation of the carboxyl terminus (the signal for amidation is located at amino acids 14-16 of ACTH (Gly, Lys, Lys)) and acetylation of the amino terminus. The release of αMSH from the cell occurs in response to certain stimuli with some constitutive secretion activity. Yin P et al. Gene Therapy 10: 348-355 (2003).

FIG. 1*b* shows an Enzyme-linked immunosorbent assay (ELISA) for Human alpha-Melanocyte Stimulating Hormone (α-MSH) of in vitro transfected Human Melanocyte cells. Melanocytes were grown in Medium 254 with supplement MHGS-2 from Invitrogen until they reached a confluence of 50-70%. Cells were transfected with 0, 50, 100, 250, 500, or 1000 ng mRNA complexed with RNAiMAX from Invitrogen. The RNA:RNAiMAX complex was formed by first incubating the RNA with Supplement-free Medium 254 media in a 5× volumetric dilution for 10 minutes at room temperature. In a second vial, RNAiMAX reagent was incubated with Supplement-free Medium 254 Media in a 10× volumetric dilution for 10 minutes at room temperature. The RNA vial was then mixed with the RNAiMAX vial and incubated for 20-30 at room temperature before being added to the cells in a drop-wise fashion. Secreted α-MSH concentration in the culture medium was measured at 18, 24, and 48 hours post-transfection for each of the 6 concentrations. Secretion of α-MSH from transfected human melanocytes was quantified using an ELISA kit from *Phoenix* Pharmaceuticals following the manufacturers recommended instructions. α-MSH shows a dose response, with 1000 ng mRNA showing the best response. Also, production peaked at 48 hours after transfection. These data show that α-MSH mRNA (SEQ ID NO: 2) is capable of being translated in Human Melanocytes cells and that α-MSH is transported out of the cells and released into the extracellular environment.

Mice (DBA/2 males approx. 8 weeks old (20 total mice), group housed) are topically treated (Dosing regimen: 3×/day for 3 days) with αMSH mRNA (SEQ ID NO. 2) at 50 m/dose to stimulate melanin production. Group Size: N=5 for each treatment group.

Experimental Design:

| Study compound mmRNA α-MSH | Control: Unmodified mRNA α-MSH | Control Scramble | Control Vehicle | Total Mice |
|---|---|---|---|---|
| Shave and topical dosing, n = 5 | Shave and topical dosing, n = 5 | Shave and topical dosing, n = 5 | Shave and topical dosing, n = 5 | 20 |

Treatment Groups:

mRNA α-MSH

Unmodified mRNA α-MSH

Control: non-specific RNA (total yeast RNA)

Control: Vehicle

Diet: Regular chow diet: Pico Rodent Chow (5053).

Assay:

A patch of skin is shaved in the mid lumbar region and the compounds are applied to the skin For 10 days, every 12 hours, the shaved patch is photographed (20 total photographs). The beginning and ending body weights are measured.

Example 12

The nucleic acid sequence of mouse proinsulin is set forth in SEQ ID NO. 3:

(SEQ ID No. 3)

agcttttggaccctcgtacagaagctaatacgactcactatagggaaataagagagaaaagaagagtaagaagaaatataagagccaccat ggcgctctggtgaggtttctgcctttgttggccttgctgttcctctgggagtcccaccccacacaggcgtttgtgaagcagcacttgtgcgggt cgcatctggtggaggcactttatctcgtctgcggcgagcgaggattcttctacaccccgatgagcagacgcgaagtggaagatccgcaagt cgcgcagctcgaacttgggggtggtcccggagccggagacttgcaaactctcgctctcgaggtagcgcagcagaaacggggtatcgtag -continued

```
accagtgttgcacgtcgatctgttcactttatcaacttgagaactactgtaattgaagcgctgccttctgcggggcttgccttctggccatgccct
tcttctctcccttgcacctgtacctcttggtctttgaataaagcctgagtaggaaggcggccgctcgagcatgcatctagagggcccaattcgc
cctattcg
```

The nucleic acid sequence of human proinsulin is set forth in SEQ ID NO. 4:

(SEQ ID No. 4)
```
agcttttggaccctcgtacagaagctaatacgactcactatagggaaataagagagaaaagaagagtaagaagaaatataagagccaccat
ggctctctggatgcggcttcttccactgctcgccctcttggcgttgtggggacccgaccctgcagcagcgtttgtgaatcagcacctctgcgg
gtcccatctggtcgaagcccttacctgtgtgtggcgagcgcgggttcttctacacgcccaagacaaggcgcgaggcggaggatctccaa
gtagggcaggtggaattgggaggggggaccgggagccggttcactccagcccctggcgttggaggggtcgctgcagaaaagaggtattg
tcgaacagtgttgcactagcatctgctcgctgtatcaacttgagaactattgtaactgaagcgctgccttctgcggggcttgccttctggccatg
cccttcttctctcccttgcacctgtacctcttggtctttgaataaagcctgagtaggaaggcggccgctcgagcatgcatctagagggcccaat
tcgccctattcgaag
```

The nucleic acid sequence of mouse proinsulin mRNA is set forth in SEQ ID NO. 21:

(SEQ ID No. 21)
```
agcuuuuggacccucguacagaagcuaauacgacucacuauagggaaauaagagagaaaagaagaguaagaagaaauauaaga
gccaccauggcgcucuggugagguuucugccuuuguuggccuugcuguuccucugggaguccacccccacacaggcguuug
ugaagcagcacuugugcgggucgcaucgguggaggcacuuuaucucgucugcggcgagcgaggauucuucuacaccccgau
gagcagacgcgaaguggaagauccgcaagucgcgcagcucgaacuuggggguggucccggagccggagacuugcaaacucuc
gcucucgagguagcgcagcagaaacggggguaucguagaccagucguugcacgucgaucuguucacuuuaucaacuugagaacu
acuguaauugaagcgcugccuucugcggggcuugccuucuggccaugcccuucuucucucccuugcaccuguaccucuuggu
cuuugaauaaagccugaguaggaaggcggccgcucgagcaugcaucuagagggcccaauucgcccuauucg
```

The nucleic acid sequence of mouse proinsulin exemplary modified mRNA (mRNA) is set forth in SEQ ID NO. 22:

(SEQ ID No. 22)
```
ag5meCψψψψgga5meC5meC5meCψ5meCgψa5meCagaag5meCψaaψa5meCga5meCψ5meCa5
meCψaψagggaaaψaagagagaaaagaagagψaagaagaaaψaψaagag5meC5meCa5meC5meCaψgg5meC
g5meCψ5meCψggψgagg ψψψψ5meCψg5meC5meCψψψψgψψψgg5meC5meCψψg5meCψgψψψ5meC
5meCψ5meCψgggagψ5meC5meC5meCa5meC5meC5meC5meCa5meCa5meCagg5meCgψψψψg
ψgaag5meCag5meCa5meCψψgψ5meCgggψ5meCg5meCaψ5meCψggψggagg5meCa5meCψψψψ
aψ5meCψ5meCgψ5meCψg5meCgg5meCgag5meCgaggaψψ5meCψψ5meCψa5meCa5meC5me
C5meC5meCgaψgag5meCaga5meCg5meCgaagψggaagaψ5meCg5meCaagψ5meCg5meCg
5meCag5meCψ5meCgaa5meCψψψggggggψggψ5meC5meCggag5meC5meCggaga5meCψψg
5meCaaa5meCψ5meCψ5meCg5meC5meCψ5meCgaggψag5meCg5meCag5meCagaaa5meCgg
ggψaψ5meCgψaga5meC5meCagψgψψψ5meCa5meCgψ5meCgaψ5meCψgψψ5meCa5meCψψψa
ψ5meCaa5meCψψψgagaa5meCψa5meCψgψaaψψgaag5meCg5meC5meCg5meC5meCψψ5meCψg5m
eCgggg5meCψψg5meC5meCψψ5meCψgg5meC5meCaψg5meC5meC5meCψψ5meCψψ5meCψ
```

-continued

5meCψ5meC5meC5meCψψg5meCa5meC5meCψgψa5meC5meCψ5meCψψggψ5meCψψψgaaψ aaag5meC5meCψgagψaggaagg5meCgg5meC5meCg5meCψ5meCgag5meCaψg5meCaψ5meCψ agaggg5meC5meC5meCaaψψ5meCg5meC5meC5meCψaψψ5meCg

The nucleic acid sequence of human proinsulin mRNA is set forth in SEQ ID NO. 23:

(SEQ ID No. 23)
agcuuuuggacccucguacagaagcuaauacgacucacuauagggaaauaagagagaaaagaagaguaagaagaaauauaaga gccaccauggcucucuggaugcggcuucuuccacugcucgcccucuuggcguuguggggacccgacccugcagcagcguuug ugaaucagcaccucugcggguccccaucuggucgaagcccuuuaccuugugugugggcgagcgcggguucuucuacacgcccaa gacaaggcgcgaggcggaggaucuccaaguagggcagguggaauugggaggggggaccgggagccgguucacuccagcccug gcguuggaggggucgcucgcagaaaagagguaauugucgaacagguguugcacuagcaucugcucgcuguaucaacuugagaacu auuguaacugaagcgcugccuucugcggggcuugccuucuggccaugcccuucuucucucccuugcaccuguaccucuuggu cuuugaauaaagccugaguaggaaggcggccgcucgagcaugcaucuagagggcccaauucgcccuauucgaag The nucleic acid sequence of an exemplary human proinsulin modified mRNA (mRNA) is set forth in SEQ ID NO. 24:

(SEQ ID No. 24)
ag5meCψψψψgga5meC5meC5meCψ5meCgψa5meCagaag5meCψaaψa5meCga5meCψ5meCa5 meCψaψagggaaaψaagagagaaaagaagagψaagaagaaaψaψaagag5meC5meCa5meC5meCaψgg5meC

ψ5meCψ5meCψggaψg5meCgg5meCψψ5meCψψ5meC5meCa5meCψg5meCψ5meCg5meC5me

C5meCψ5meCψψgg5meCgψψgψψggggga5meC5meC5meCga5meC5meC5meCψg5meCag5meCa g5meCgψψψgψψgaaψ5meCag5meCa5meC5meCψ5meCψg5meCgggψ5meC5meC5meCaψ5meC ψggψ5meCgaag5meC5meC5meCψψψa5meC5meCψψgψgψgψgg5meCgag5meCg5meCgggψψ5 meCψψ5meCψa5meCa5meCg5meC5meC5meCaaga5meCaagg5meCg5meCgagg5meCggaggaψ

5meCψ5meC5meCaagψaggg5meCaggψggaaψψgggaggggga5meC5meCgggag5meC5meCggψψ5 meCa5meCψ5meC5meCag5meC5meC5meC5meCψgg5meCgψψggaggggψ5meCg5meCψg5me

Cagaaaagaggψaψψgψ5meCgaa5meCagψgψψg5meCa5meCψag5meCaψ5meCψg5meCψ5meCg5 meCψgψaψ5meCaa5meCψψgagaa5meCψaψψgψaa5meCψgaag5meCg5meCψg5meC5meCψψ5 meCψg5meCggg5meCψψg5meC5meCψψ5meCψgg5meC5meCaψg5meC5meC5meCψψ5meC

ψψ5meCψ5meCψ5meC5meCψψg5meCa5meC5meCψgψa5meC5meCψ5meCψψggψ5me

Cψψψgaaψaaag5meC5meCψgagψaggaagg5meCgg5meC5meCg5meCψ5meCgag5meCaψg5me

Caψ5meCψagaggg5meC5meC5meCaaψψ5meCg5meC5meC5meCψaψψ5meCgaag

The proinsulin contains a signal peptide that must be cleaved for the protein to be secreted. The amino acid sequence of mouse insulin is set forth in SEQ ID NO: 15:

(SEQ ID NO: 15)
MALWMRFLPLLALLFLWESHPTQAFVKQHLCGSHLVEALYLVCGERGFFY

TPMSRREVEDPQVAQLELGGGPGAGDLQTLALEVAQQKRGIVDQCCTSIC

SLYQLENYCN

The amino acid sequence of human insulin is set forth in SEQ ID NO: 16:

(SEQ ID NO: 16)
MALWMRLLPLLALLALWGPDPAAAFVNQHLCGSHLVEALYLVCGERGFFY

TPKTRREAEDLQVGQVELGGGPGAGSLQPLALEGSLQKRGIVEQCCTSIC

SLYQLENYCN

Figure 1C:
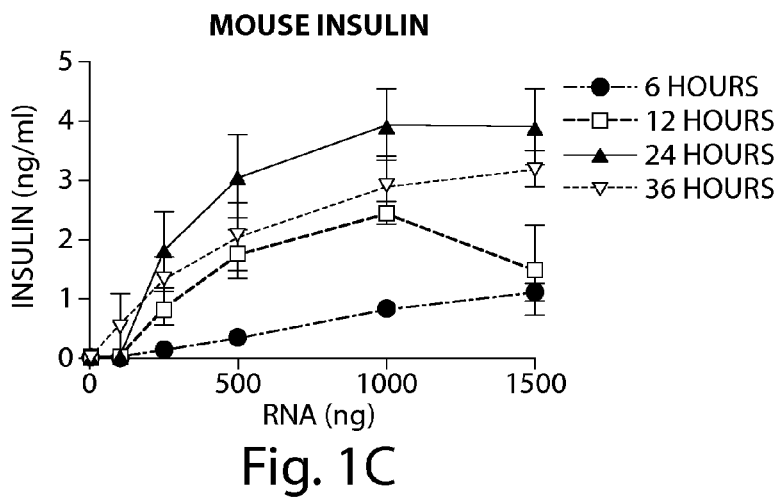
Figure 2:
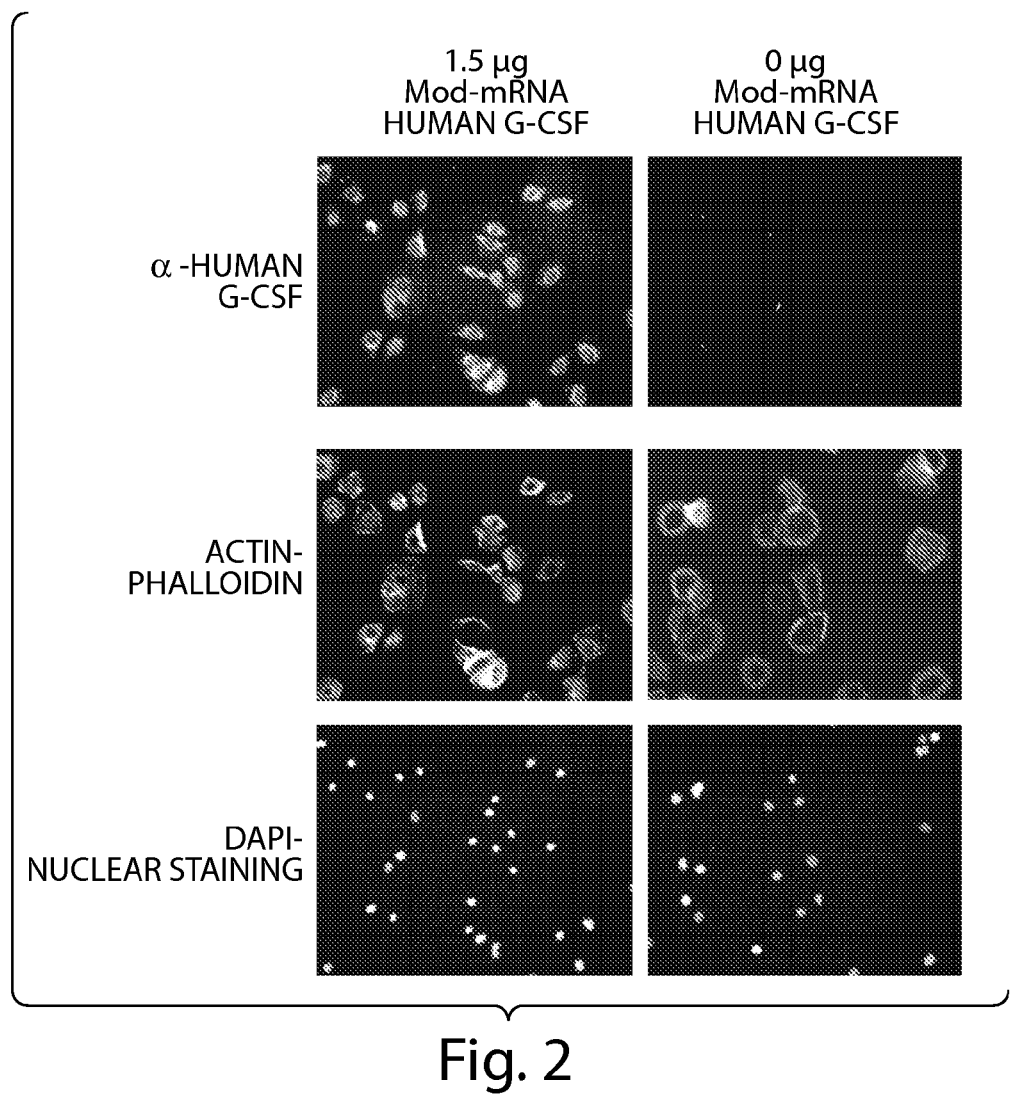
FIG. 2 depicts a photograph showing human G-CSF expression in human cells following transfection with modified mRNA as measured by immunofluorescence.

FIG. 1c shows an Enzyme-linked immunosorbent assay (ELISA) for Mouse Insulin of in vitro transfected Human Keratinocyte cells. Keratinocytes were grown in EpiLife medium with Supplement S7 from Invitrogen until they reached a confluence of 50-70%. Cells were transfected with 0, 100, 250, 500, 1000, and 1500 ng mRNA complexed with RNAiMAX from Invitrogen. The RNA:RNAiMAX complex was formed by first incubating the RNA with Supplement-free EpiLife media in a 5× volumetric dilution for 10 minutes at room temperature. In a second vial, RNAiMAX reagent was incubated with Supplement-free EpiLife Media in a 10× volumetric dilution for 10 minutes at room temperature. The RNA vial was then mixed with the RNAiMAX vial and incubated for 20-30 at room temperature before being added to the cells in a drop-wise fashion. Secreted mu-Insulin concentration in the culture medium was measured at 6, 12, 24, and 36 hours post-transfection for each of the 6 concentrations. Secretion of Mouse Insulin from transfected human keratinocytes was quantified using an ELISA kit from Millipore following the manufacturers recommended instructions. Mouse Insulin shows a dose response, with 1500 ng mRNA showing the best response. Also, production peaked between 24 and 36 hours after transfection. These data show that mu-Insulin mRNA (SEQ ID NO: 3) is capable of being translated in Human Keratinocyte cells and that mu-Insulin is transported out of the cells and released into the extracellular environment.

Figure 3:
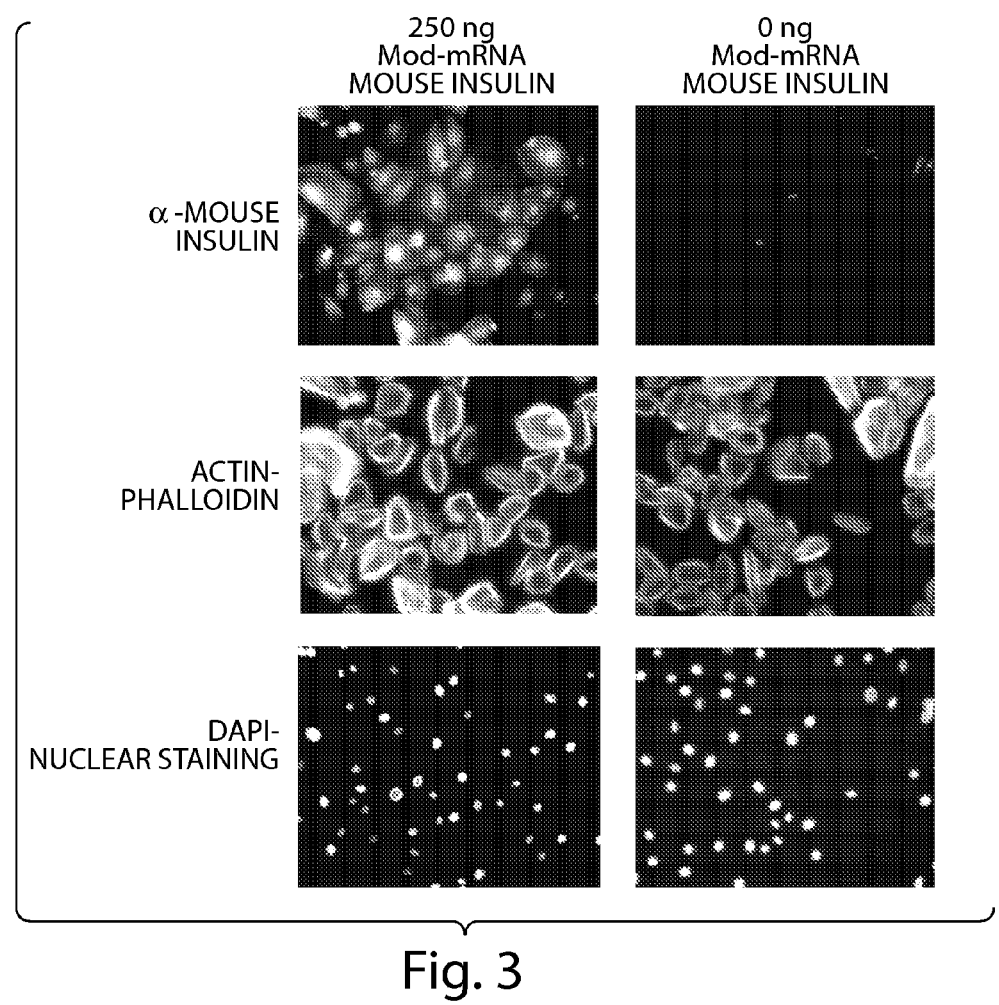
FIG. 3 depicts a photograph showing mouse insulin expression in human cells following transfection with modified mRNA as measured by immunofluorescence.
Figures 1, 4:
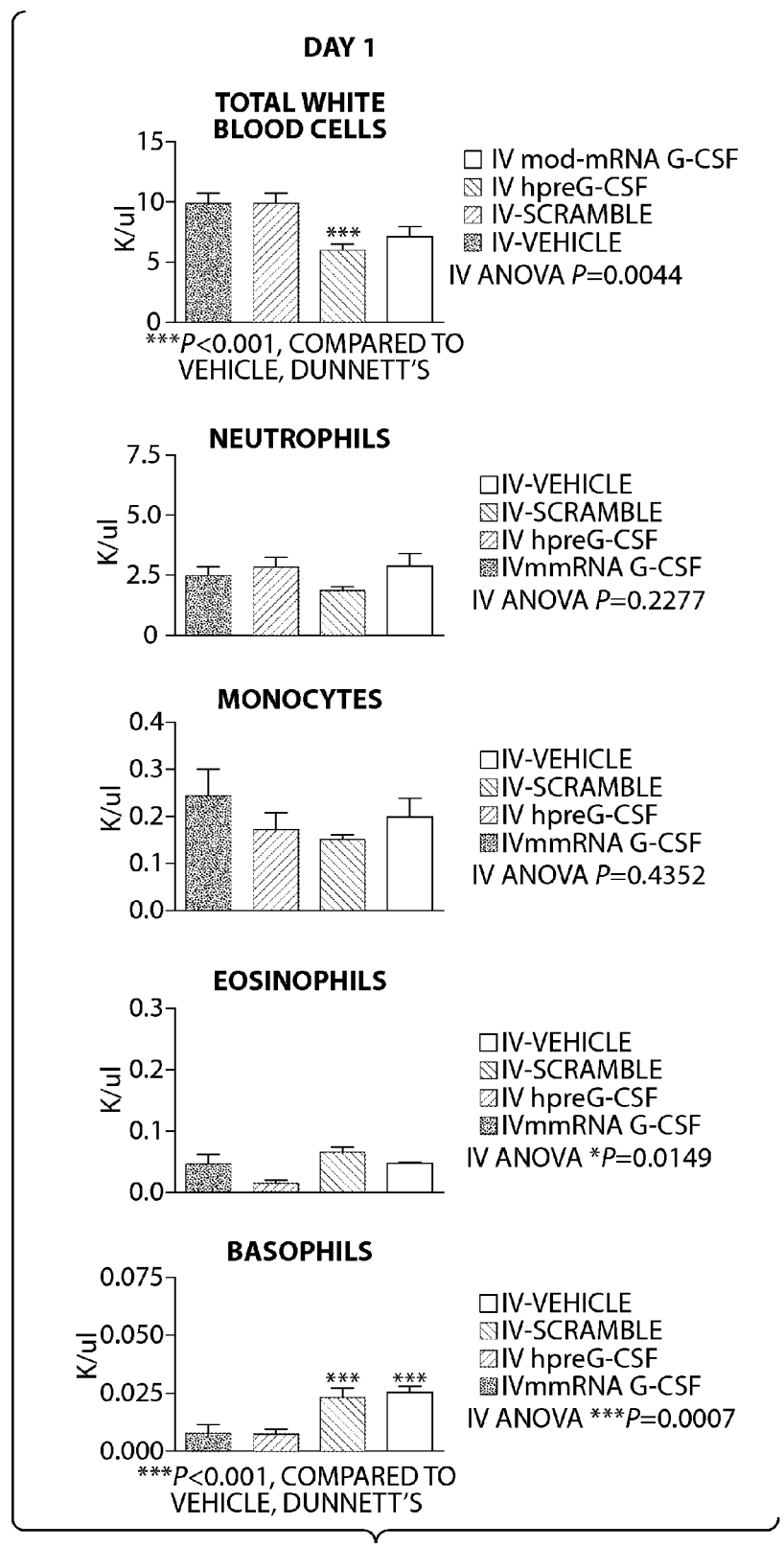
FIG. 4 depicts bar graphs of complete blood count and granulocyte lineage cell types of a mouse following intravenous injection of modified huG-CSF mRNA (FIGS. 4-1, 4-2, and 4-3).
Figures 2, 4:
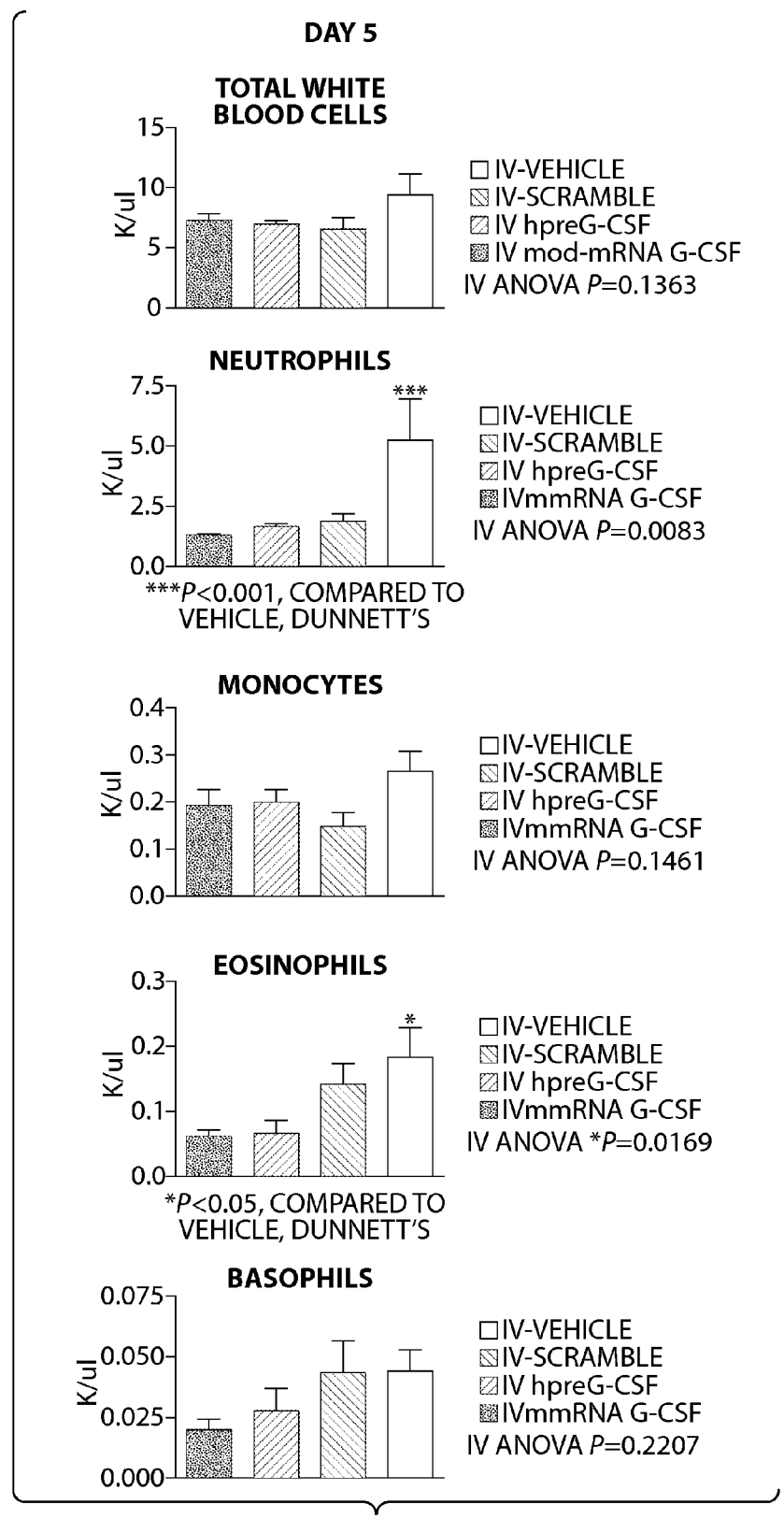
Figures 3, 4:
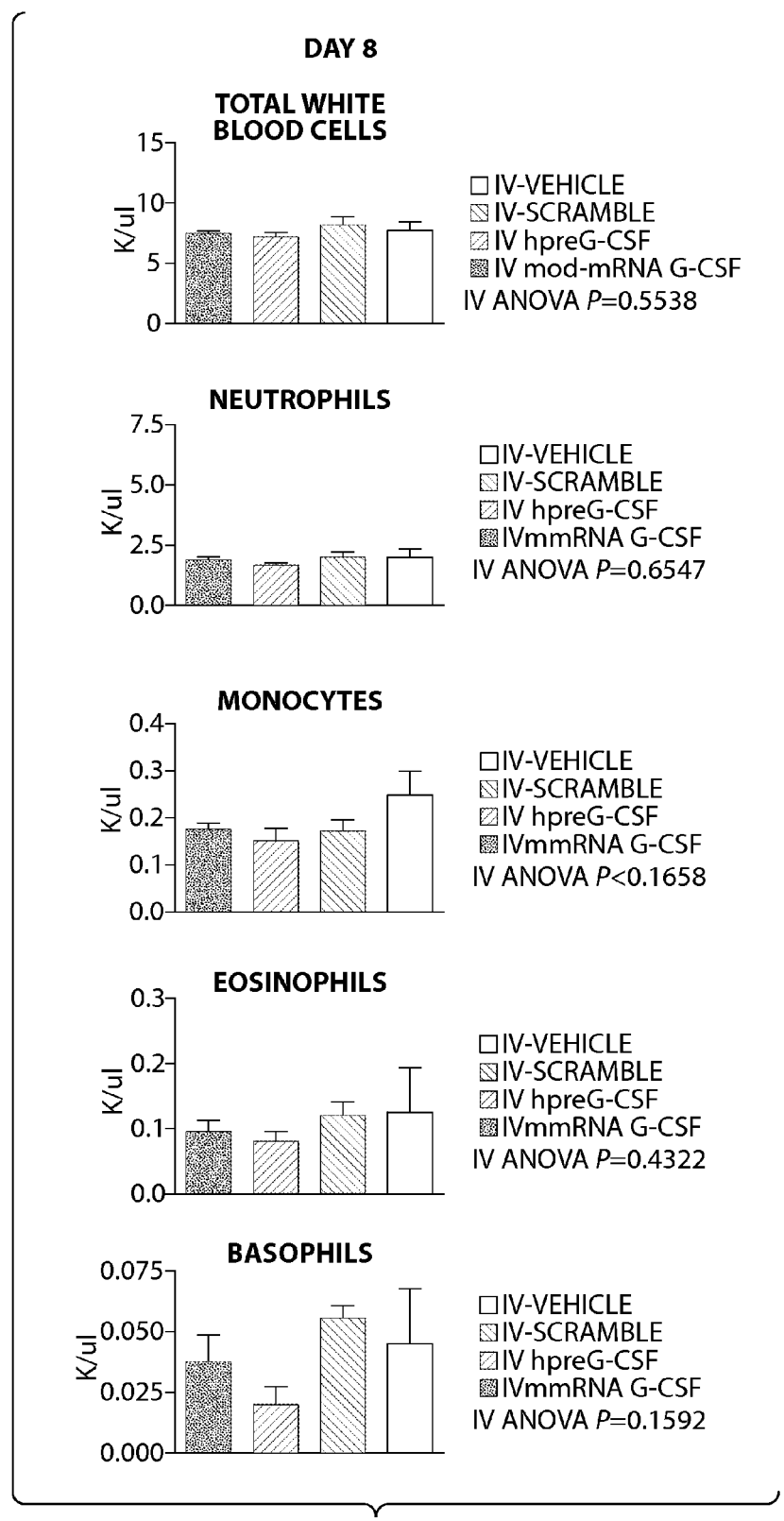

FIG. 3 shows human keratinocytes transfected with 0 or 250 ng of Mouse Insulin. Cells were grown in EpiLife Media with Supplement S7 from Invitrogen according to standard protocols in 24-well collagen-coated plates. Cells were fixed with 4% paraformaldehyde in PBS and permeabilized with 0.1% Triton X-100 in PBS for 5-10 minutes at room temperature. Cells were then washed 3× with room temperature PBS. Insulin protein staining was performed using Insulin mouse monoclonal antibody D6C4 (ab8304, abcam, Cambridge, Mass.) and goat polyclonal secondary antibody to mouse IgG conjugated to DyLight®594 (ab97017, abcam) according to the manufacturer's recommended dilutions. Nuclear DNA staining was performed with DAPI dye from Invitrogen. The cellular actin cytoskeleton was stained using AlexaFluor488-conjugated phalloidin from Invitrogen. Insulin protein is translated and localized to the cytoplasm upon Insulin mRNA transfection. The picture was taken 18 hours after transfection.

Mice (Streptozotocin-induced diabetic C57BL/6NTac mice, 10-12 weeks old, group housed, 96 total mice) are IV injected with mouse proinsulin or human proinsulin mRNA (SEQ ID NOs: 3 and 4) to analyze glucohomeostasis. Group Size: N=8 for each treatment group.

Experimental Design

| Treatment | Day | Dosing |
|---|---|---|
| Acute study with recovery | | |
| mmRNA hProinsulin | 1.8 | 50 μg |
| Dose 1 mmRNA mProinsulin | 1.8 | 0.5 μg |
| Dose 2 mmRNA mProinsulin | 1.8 | 5 μg |
| Dose 3 mmRNA mProinsulin | 1.8 | 50 μg |
| Dose 4 mmRNA mProinsulin | 1.8 | 100 μg |
| Control: unmodified mRNA mProinsulin | 1.8 | 50 μg |
| Control: scramble (yeast total mRNA) | 1.8 | 50 μg |
| Control: vehicle only | 1.8 | 50 μg |
| Sub-chronic study | | |
| Dose 1 mmRNA mProinsulin | 1-5 | 50 μg |
| Control: unmodified mRNA mProinsulin | 1-5 | 50 μg |
| Control: non-specific RNA (yeast total RNA) | 1-5 | 50 μg |
| Control: vehicle only | 1-5 | 50 μg |

Dosing Regimen:
Acute: IV in tail vein once, testing conducted 6 hours later
Sub-chronic: IV in tail vein once daily for 5 days, testing conducted 6 hours after final injection
Diet: Mice were given a high fat diet (HFD) (Research Diets D12492)
Assays:
Triglycerides
Whole blood is collected via the retro-orbital sinus and triglycerides are assessed on a hand held meter (CardioChek, PTS Inc. Indianapolis, Ind.) with test strips specific for triglyceride measurements, using approximately 20 μl of blood. Samples are tested in mice under three different conditions: fasted and freely fed on a regular diet, and fasted after 8 weeks of a high fat diet.
Oral Glucose Tolerance Test Procedure
Mice are tested before a high fat diet challenge and 8 weeks after a high fat diet challenge. Mice are fasted for 16 hours and transferred to a procedure room midway through the light phase of the light/dark cycle. Blood is obtained from a tail cut and blood glucose levels are measured by a glucometer (One-touch Ultra II) and additional blood is processed for plasma that is later used to determine the fasting insulin levels. The mice receive 2 g/kg body weight of glucose by oral gavage. 15, 30, 60, and 120 minutes after the administration of glucose, blood is collected to measure the glucose concentration and to prepare plasma samples for measuring insulin levels. All of the plasma samples are frozen after collection and assayed simultaneously by electrochemiluminscence (MA2400 Mouse/Rat insulin kit K152BZC, MesoScale Discovery) according to the manufacturer's recommendations.

APPENDIX

C-GSF (underlined) in pJ204 (SEQ ID NO: 5):

```
  1 ACCAATGCTT AATCAGTGAG GCACCTATCT CAGCGATCTG TCTATTTCGT TCATCCATAG TTGCCTGACT

71 CCCCGTCGTG TAGATAACTA CGATACGGGA GGGCTTACCA TCTGGCCCCA GCGCTGCGAT GATACCGCGA

141 GAACCACGCT CACCGGCTCC GGATTTATCA GCAATAAACC AGCCAGCCGG AAGGGCCGAG CGCAGAAGTG

211 GTCCTGCAAC TTTATCCGCC TCCATCCAGT CTATTAATTG TTGCCGGGAA GCTAGAGTAA GTAGTTCGCC

281 AGTTAATAGT TTGCGCAACG TTGTTGCCAT CGCTACAGGC ATCGTGGTGT CACGCTCGTC GTTTGGTATG

351 GCTTCATTCA GCTCCGGTTC CCAACGATCA AGGCGAGTTA CATGATCCCC CATGTTGTGC AAAAAAGCGG

421 TTAGCTCCTT CGGTCCTCCG ATCGTTGTCA GAAGTAAGTT GGCCGCAGTG TTATCACTCA TGGTTATGGC

491 AGCACTGCAT AATTCTCTTA CTGTCATGCC ATCCGTAAGA TGCTTTTCTG TGACTGGTGA GTACTCAACC

561 AAGTCATTCT GAGAATAGTG TATGCGGCGA CCGAGTTGCT CTTGCCCGGC GTCAATACGG GATAATACCG
```

APPENDIX-continued

```
 631 CGCCACATAG CAGAACTTTA AAAGTGCTCA TCATTGGAAA ACGTTCTTCG GGGCGAAAAC TCTCAAGGAT
 701 CTTACCGCTG TTGAGATCCA GTTCGATGTA ACCCACTCGT GCACCCAACT GATCTTCAGC ATCTTTTACT
 771 TTCACCAGCG TTTCTGGGTG AGCAAAAACA GGAAGGCAAA ATGCCGCAAA AAGGGAATA AGGGCGACAC
 841 GGAAATGTTG AATACTCATA TTCTTCCTTT TTCAATATTA TTGAAGCATT TATCAGGGTT ATTGTCTCAT
 911 GAGCGGATAC ATATTTGAAT GTATTTAGAA AAATAAACAA ATAGGGGTCA GTGTTACAAC CAATTAACCA
 981 ATTCTGAACA TTATCGCGAG CCCATTTATA CCTGAATATG GCTCATAACA CCCCTTGTTT GCCTGGCGGC
1051 AGTAGCGCGG TGGTCCCACC TGACCCCATG CCGAACTCAG AAGTGAAACG CCGTAGCGCC GATGGTAGTG
1121 TGGGGACTCC CCATGCGAGA GTAGGGAACT GCCAGGCATC AAATAAAACG AAAGGCTCAG TCGAAAGACT
1191 GGGCCTTTCG CCCGGGCTAA TTATGGGGTG TCGCCCTTTT GACGCGACTT CGAATAGGGC GAATTGGGCC
1261 CTCTAGATGC ATGCTCGAGC GGCCGCCTTC CTACTCAGGG TTTATTCAAA GACCAAGAGG TACAGGTGCA
1331 AGGGAGAGAA GAAGGGCATG GCCAGAAGGC AAGCCCCGCA GAAGGCAGCG CTTCACGGCT GCGCAAGATG
1401 TCTCAGCACC CGGTACGAGA CTTCCAAAAA TGATTGAAGG TGGCTCGCTA CGAGGACTCC ACCCGCCCTG
1471 CGCTGAAACG CGGACGCAAA GGCCGGCATT GCCCCCTGCG TGGGCTGCAG CGCGGGTGCC ATCCCCAGTT
1541 CCTCCATCTG CTGCCAGATG GTTGTTGCGA ATCCGCCAC GTCGAGCTGC AACGTGTCCA GCGTCGGGCC
1611 CAATTCTGGC GAGATTCCCT CAAGGGCTTG CAGCAGTCCC TGATACAAGA ACAAACCGGA GTGGAGCTGG
1681 GAAAGGCACC CTGCCAACTG CAAAGCCTGC GACGGACAGG ACGAGAGAGG AGCCCAGGGA ATCCCCAAGC
1751 TGTGCCCGAG CAGTACGAGC TCCTCGGGAT GGCAAAGTTT GTATGTCGCG CAGAGCTTCT CTTGGAGTGC
1821 GGCTCCATCG CCCTGAATCT TTCGCACCTG CTCCAGACAC TTCAAAAGGA ATGACTGCGG CAACGATGAG
1891 GCAGGTCCGA GAGGAGTCGC TTCTTGGACT GTCCAGAGGG CCGAGTGCCA AGCAGCAAC TGCAGGGCCA
1961 TAAGTTTCAT GGGGCTTTGG GTCGCGGGAC CGGCCATGGT GGCTCTTATA TTTCTTCTTA CTCTTCTTTT
2031 CTCTCTTATT TCCCTATAGT GAGTCGTATT AGCTTCTGTA CGAGGGTCCA AAAGCTTTCA GCGAAGGGCG
2101 ACACAAAATT TATTCTAAAT GCATAATAAA TACTGATAAC ATCTTATAGT TTGTATTATA TTTTGTATTA
2171 TCGTTGACAT GTATAATTTT GATATCAAAA ACTGATTTTC CCTTTATTAT TTTCGAGATT TATTTTCTTA
2241 ATTCTCTTTA ACAAACTAGA ATATTGTAT ATACAAAAAA TCATAAATAA TAGATGAATA GTTTAATTAT
2311 AGGTGTTCAT CAATCGAAAA AGCAACGTAT CTTATTTAAA GTGCGTTGCT TTTTTCTCAT TTATAAGGTT
2381 AAATAATTCT CATATATCAA GCAAAGTGAC AGGCGCCCTT AAATATTCTG ACAAATGCTC TTTCCCTAAA
2451 CTCCCCCCAT AAAAAAACCC GCCGAAGCGG GTTTTTACGT TATTTGCGGA TTAACGATTA CTCGTTATCA
2521 GAACCGCCCA GGGGGCCCGA GCTTAAGACT GGCCGTCGTT TTACAACACA GAAAGAGTTT GTAGAAACGC
2591 AAAAAGGCCA TCCGTCAGGG GCCTTCTGCT TAGTTTGATG CCTGGCAGTT CCCTACTCTC GCCTTCCGCT
2661 TCCTCGCTCA CTGACTCGCT GCGCTCGGTC GTTCGGCTGC GGCGAGCGGT ATCAGCTCAC TCAAAGGCGG
2731 TAATACGGTT ATCCACAGAA TCAGGGGATA ACGCAGGAAA GAACATGTGA GCAAAAGGCC AGCAAAAGGC
2801 CAGGAACCGT AAAAAGGCCG CGTTGCTGGC GTTTTTCCAT AGGCTCCGCC CCCTGACGA GCATCACAAA
2871 AATCGACGCT CAAGTCAGAG GTGGCGAAAC CCGACAGGAC TATAAAGATA CCAGGCGTTT CCCCCTGGAA
2941 GCTCCCTCGT GCGCTCTCCT GTTCCGACCC TGCCGCTTAC CGGATACCTG TCCGCCTTTC TCCCTTCGGG
3011 AAGCGTGGCG CTTTCTCATA GCTCACGCTG TAGGTATCTC AGTTCGGTGT AGGTCGTTCG CTCCAAGCTG
3081 GGCTGTGTGC ACGAACCCCC CGTTCAGCCC GACCGCTGCG CCTTATCCGG TAACTATCGT CTTGAGTCCA
3151 ACCCGGTAAG ACACGACTTA TCGCCACTGG CAGCAGCCAC TGGTAACAGG ATTAGCAGAG CGAGGTATGT
3221 AGGCGGTGCT ACAGAGTTCT TGAAGTGGTG GCCTAACTAC GGCTACACTA GAAGAACAGT ATTTGGTATC
3291 TGCGCTCTGC TGAAGCCAGT TACCTTCGGA AAAAGAGTTG GTAGCTCTTG ATCCGGCAAA CAAACCACCG
3361 CTGGTAGCGG TGGTTTTTTT GTTTGCAAGC AGCAGATTAC GCGCAGAAAA AAAGGATCTC AAGAAGATCC
```

```
3431 TTTGATCTTT TCTACGGGGT CTGACGCTCA GTGGAACGAC GCGCGCGTAA CTCACGTTAA GGGATTTTGG
3501 TCATGAGCTT GCGCCGTCCC GTCAAGTCAG CGTAATGCTC TGCTTTT
```

Human Insulin(underlined) in pJ204 (SEQ ID NO: 6):

```
   1 ACCAATGCTT AATCAGTGAG GCACCTATCT CAGCGATCTG TCTATTTCGT TCATCCATAG TTGCCTGACT
  71 CCCCGTCGTG TAGATAACTA CGATACGGGA GGGCTTACCA TCTGGCCCCA GCGCTGCGAT GATACCGCGA
 141 GAACCACGCT CACCGGCTCC GGATTTATCA GCAATAAACC AGCCAGCCGG AAGGGCCGAG CGCAGAAGTG
 211 GTCCTGCAAC TTTATCCGCC TCCATCCAGT CTATTAATTG TTGCCGGGAA GCTAGAGTAA GTAGTTCGCC
 281 AGTTAATAGT TTGCGCAACG TTGTTGCCAT CGCTACAGGC ATCGTGGTGT CACGCTCGTC GTTTGGTATG
 351 GCTTCATTCA GCTCCGGTTC CCAACGATCA AGGCGAGTTA CATGATCCCC CATGTTGTGC AAAAAAGCGG
 421 TTAGCTCCTT CGGTCCTCCG ATCGTTGTCA GAAGTAAGTT GGCCGCAGTG TTATCACTCA TGGTTATGGC
 491 AGCACTGCAT AATTCTCTTA CTGTCATGCC ATCCGTAAGA TGCTTTTCTG TGACTGGTGA GTACTCAACC
 561 AAGTCATTCT GAGAATAGTG TATGCGGCGA CCGAGTTGCT CTTGCCCGGC GTCAATACGG GATAATACCG
 631 CGCCACATAG CAGAACTTTA AAAGTGCTCA TCATTGGAAA ACGTTCTTCG GGGCGAAAAC TCTCAAGGAT
 701 CTTACCGCTG TTGAGATCCA GTTCGATGTA ACCCACTCGT GCACCCAACT GATCTTCAGC ATCTTTTACT
 771 TTCACCAGCG TTTCTGGGTG AGCAAAAACA GGAAGGCAAA ATGCCGCAAA AAAGGGAATA AGGGCGACAC
 841 GGAAATGTTG AATACTCATA TTCTTCCTTT TTCAATATTA TTGAAGCATT TATCAGGGTT ATTGTCTCAT
 911 GAGCGGATAC ATATTTGAAT GTATTTAGAA AAATAAACAA ATAGGGGTCA GTGTTACAAC CAATTAACCA
 981 ATTCTGAACA TTATCGCGAG CCCATTTATA CCTGAATATG GTCATAACA CCCCTTGTTT GCCTGGCGGC
1051 AGTAGCGCGG TGGTCCCACC TGACCCCATG CCGAACTCAG AAGTGAAACG CCGTAGCGCC GATGGTAGTG
1121 TGGGGACTCC CCATGCGAGA GTAGGGAACT GCCAGGCATC AAATAAAACG AAAGGCTCAG TCGAAAGACT
1191 GGGCCTTTCG CCCGGGCTAA TTATGGGGTG TCGCCCTTCG CTGAAAGCTT TTGGACCCTC GTACAGAAGC
1261 TAATACGACT CACTATAGGG AAATAAGAGA GAAAGAAGA GTAAGAAGAA ATATAAGAGC CACCATGGCT
1331 CTCTGGATGC GGCTTCTTCC ACTGCTCGCC CTCTTGGCGT TGTGGGGACC CGACCCTGCA GCAGCGTTTG
1401 TGAATCAGCA CCTCTGCGGG TCCCATCTGG TCGAAGCCCT TTACCTTGTG TGTGGCGAGC GCGGGTTCTT
1471 CTACACGCCC AAGACAAGGC GCGAGGCGGA GGATCTCCAA GTAGGGCAGG TGGAATTGGG AGGGGGACCG
1541 GGAGCCGGTT CACTCCAGCC CCTGGCGTTG GAGGGGTCGC TGCAGAAAAG AGGTATTGTC GAACAGTGTT
1611 GCACTAGCAT CTGCTCGCTG TATCAACTTG AGAACTATTG TAACTGAAGC GCTGCCTTCT GCGGGGCTTG
1681 CCTTCTGGCC ATGCCCTTCT TCTCTCCCTT GCACCTGTAC CTCTTGGTCT TTGAATAAAG CCTGAGTAGG
1751 AAGGCGGCCG CTCGAGCATG CATCTAGAGG GCCCAATTCG CCCTATTCGA AGCGTCAAAA GGGCGACACA
1821 AAATTTATTC TAAATGCATA ATAAATACTG ATAACATCTT ATAGTTTGTA TTATATTTTG TATTATCGTT
1891 GACATGTATA ATTTTGATAT CAAAAACTGA TTTTTCCCTTT ATTATTTTCG AGATTTATTT TCTTAATTCT
1961 CTTTAACAAA CTAGAAATAT TGTATATACA AAAAATCATA AATAATAGAT GAATAGTTTA ATTATAGGTG
2031 TTCATCAATC GAAAAAGCAA CGTATCTTAT TTAAAGTGCG TTGCTTTTTT CTCATTTATA AGGTTAAATA
2101 ATTCTCATAT ATCAAGCAAA GTGACAGGCG CCCTTAAATA TTCTGACAAA TGCTCTTTCC CTAAACTCCC
2171 CCCATAAAAA AACCCGCCGA AGCGGGTTTT TACGTTATTT GCGGATTAAC GATTACTCGT TATCAGAACC
2241 GCCCAGGGGG CCCGAGCTTA AGACTGGCCG TCGTTTTACA ACACAGAAAG AGTTTGTAGA AACGCAAAAA
2311 GGCCATCCGT CAGGGGCCTT CTGCTTAGTT TGATGCCTGG CAGTTCCCTA CTCTCGCCTT CCGCTTCCTC
2381 GCTCACTGAC TCGCTGCGCT CGGTCGTTCG GCTGCGGCGA GCGGTATCAG CTCACTCAAA GGCGGTAATA
2451 CGGTTATCCA CAGAATCAGG GGATAACGCA GGAAAGAACA TGTGAGCAAA AGGCCAGCAA AAGGCCAGGA
2521 ACCGTAAAAA GGCCGCGTTG CTGGCGTTTT TCCATAGGCT CCGCCCCCCT GACGAGCATC ACAAAAATCG
```

APPENDIX-continued

```
2591 ACGCTCAAGT CAGAGGTGGC GAAACCCGAC AGGACTATAA AGATACCAGG CGTTTCCCCC TGGAAGCTCC
2661 CTCGTGCGCT CTCCTGTTCC GACCCTGCCG CTTACCGGAT ACCTGTCCGC CTTTCTCCCT TCGGGAAGCG
2731 TGGCGCTTTC TCATAGCTCA CGCTGTAGGT ATCTCAGTTC GGTGTAGGTC GTTCGCTCCA AGCTGGGCTG
2801 TGTGCACGAA CCCCCCGTTC AGCCCGACCG CTGCGCCTTA TCCGGTAACT ATCGTCTTGA GTCCAACCCG
2871 GTAAGACACG ACTTATCGCC ACTGGCAGCA GCCACTGGTA ACAGGATTAG CAGAGCGAGG TATGTAGGCG
2941 GTGCTACAGA GTTCTTGAAG TGGTGGGCTA ACTACGGCTA CACTAGAAGA ACAGTATTTG GTATCTGCGC
3011 TCTGCTGAAG CCAGTTACCT TCGGAAAAAG AGTTGGTAGC TCTTGATCCG GCAAACAAAC CACCGCTGGT
3081 AGCGGTGGTT TTTTTGTTTG CAAGCAGCAG ATTACGCGCA GAAAAAAGG ATCTCAAGAA GATCCTTTGA
3151 TCTTTTCTAC GGGGTCTGAC GCTCAGTGGA ACGACGCGCG CGTAACTCAC GTTAAGGGAT TTTGGTCATG
3221 AGCTTGCGCC GTCCCGTCAA GTCAGCGTAA TGCTCTGCTT TT
```

Mouse Insulin (underlined) in pJ204 (SEQ ID NO: 7):

```
   1 ACCAATGCTT AATCAGTGAG GCACCTATCT CAGCGATCTG TCTATTTCGT TCATCCATAG TTGCCTGACT
  71 CCCCGTCGTG TAGATAACTA CGATACGGGA GGGCTTACCA TCTGGCCCCA GCGCTGCGAT GATACCGCGA
 141 GAACCACGCT CACCGGCTCC GGATTTATCA GCAATAAACC AGCCAGCCGG AAGGGCCGAG CGCAGAAGTG
 211 GTCCTGCAAC TTTATCCGCC TCCATCCAGT CTATTAATTG TTGCCGGGAA GCTAGAGTAA GTAGTTCGCC
 281 AGTTAATAGT TTGCGCAACG TTGTTGCCAT CGCTACAGGC ATCGTGGTGT CACGCTCGTC GTTTGGTATG
 351 GCTTCATTCA GCTCCGGTTC CCAACGATCA AGGCGAGTTA CATGATCCCC CATGTTGTGC AAAAAAGCGG
 421 TTAGCTCCTT CGGTCCTCCG ATCGTTGTCA GAAGTAAGTT GGCCGCAGTG TTATCACTCA TGGTTATGGC
 491 AGCACTGCAT AATTCTCTTA CTGTCATGCC ATCCGTAAGA TGCTTTTCTG TGACTGGTGA GTACTCAACC
 561 AAGTCATTCT GAGAATAGTG TATGCGGCGA CCGAGTTGCT CTTGCCCGGC GTCAATACGG GATAATACCG
 631 CGCCACATAG CAGAACTTTA AAAGTGCTCA TCATTGGAAA ACGTTCTTCG GGGCGAAAAC TCTCAAGGAT
 701 CTTACCGCTG TTGAGATCCA GTTCGATGTA ACCCACTCGT GCACCCAACT GATCTTCAGC ATCTTTTACT
 771 TTCACCAGCG TTTCTGGGTG AGCAAAAACA GGAAGGCAAA ATGCCGCAAA AAAGGGAATA AGGGCGACAC
 841 GGAAATGTTG AATACTCATA TTCTTCCTTT TTCAATATTA TTGAAGCATT TATCAGGGTT ATTGTCTCAT
 911 GAGCGGATAC ATATTTGAAT GTATTTAGAA AAATAAACAA ATAGGGGTCA GTGTTACAAC CAATTAACCA
 981 ATTCTGAACA TTATCGCGAG CCCATTTATA CCTGAATATG GCTCATAACA CCCCTTGTTT GCCTGGCGGC
1051 AGTAGCGCGG TGGTCCCACC TGACCCCATG CCGAACTCAG AAGTGAAACG CCGTAGCGCC GATGGTAGTG
1121 TGGGGACTCC CCATGCGAGA GTAGGGAACT GCCAGGCATC AAATAAAACG AAAGGCTCAG TCGAAAGACT
1191 GGGCCTTTCG CCCGGGCTAA TTATGGGGTG TCGCCCTTCG CTGAAAGCTT TTGGACCCTC GTACAGAAGC
1261 TAATACGACT CACTATAGGG AAATAAGAGA GAAAAGAAGA GTAAGAAGAA ATATAAGAGC CACCATGGCG
1331 CTCTGGATGA GGTTTCTGCC TTTGTTGGCC TTGCTGTTCC TCTGGGAGTC CCACCCCACA CAGGCGTTTG
1401 TGAAGCAGCA CTTGTGCGGG TCGCATCTGG TGGAGGCACT TTATCTCGTC TGCGGCGAGC GAGGATTCTT
1471 CTACACCCCG ATGAGCAGAC GCGAAGTGGA AGATCCGCAA GTCGCGCAGC TCGAACTTGG GGGTGGTCCC
1541 GGAGCCGGAG ACTTGCAAAC TCTCGCTCTC GAGGTAGCGC AGCAGAAACG GGTATCGTA GACCAGTGTT
1611 GCACGTCGAT CTGTTCACTT TATCAACTTG AGAACTACTG TAATTGAAGC GCTGCCTTCT GCGGGGCTTG
1681 CCTTCTGGCC ATGCCCTTCT TCTCTCCCTT GCACCTGTAC CTCTTGGTCT TGAATAAAG CCTGAGTAGG
1751 AAGGCGGCCG CTCGAGCATG CATCTAGAGG GCCCAATTCG CCCTATTCGC GTCAAAAGGG CGACACAAAA
1821 TTTATTCTAA ATGCATAATA AATACTGATA ACATCTTATA GTTTGTATTA TATTTTGTAT TATCGTTGAC
1891 ATGTATAATT TTGATATCAA AAACTGATTT TCCCTTTATT ATTTTCGAGA TTTATTTTCT TAATTCTCTT
1961 TAACAAACTA GAAATATTGT ATATACAAAA AATCATAAAT AATAGATGAA TAGTTTAATT ATAGGTGTTC
```

```
2031 ATCAATCGAA AAAGCAACGT ATCTTATTTA AAGTGCGTTG CTTTTTTCTC ATTTATAAGG TTAAATAATT
2101 CTCATATATC AAGCAAAGTG ACAGGCGCCC TTAAATATTC TGACAAATGC TCTTTCCCTA AACTCCCCCC
2171 ATAAAAAAAC CCGCCGAAGC GGGTTTTTAC GTTATTTGCG GATTAACGAT TACTCGTTAT CAGAACCGCC
2241 CAGGGGGCCC GAGCTTAAGA CTGGCCGTCG TTTTACAACA CAGAAAGAGT TTGTAGAAAC GCAAAAGGC
2311 CATCCGTCAG GGGCCTTCTG CTTAGTTTGA TGCCTGGCAG TTCCCTACTC TCGCCTTCCG CTTCCTCGCT
2381 CACTGACTCG CTGCGCTCGG TCGTTCGGCT GCGGCGAGCG GTATCAGCTC ACTCAAAGGC GGTAATACGG
2451 TTATCCACAG AATCAGGGGA TAACGCAGGA AGAACATGT GAGCAAAAGG CCAGCAAAAG GCCAGGAACC
2521 GTAAAAAGGC CGCGTTGCTG GCGTTTTTCC ATAGGCTCCG CCCCCCTGAC GAGCATCACA AAAATCGACG
2591 CTCAAGTCAG AGGTGGCGAA ACCCGACAGG ACTATAAAGA TACCAGGCGT TTCCCCCTGG AAGCTCCCTC
2661 GTGCGCTCTC CTGTTCCGAC CCTGCCGCTT ACCGGATACC TGTCCGCCTT CTCCCTTCG GGAAGCGTGG
2731 CGCTTTCTCA TAGCTCACGC TGTAGGTATC TCAGTTCGGT GTAGGTCGTT CGCTCCAAGC TGGGCTGTGT
2801 GCACGAACCC CCCGTTCAGC CCGACCGCTG CGCCTTATCC GGTAACTATC GTCTTGAGTC CAACCCGGTA
2871 AGACACGACT TATCGCCACT GGCAGCAGCC ACTGGTAACA GGATTAGCAG AGCGAGGTAT GTAGGCGGTG
2941 CTACAGAGTT CTTGAAGTGG TGGGCTAACT ACGGCTACAC TAGAAGAACA GTATTTGGTA TCTGCGCTCT
3011 GCTGAAGCCA GTTACCTTCG GAAAAAGAGT TGGTAGCTCT TGATCCGGCA ACAAACCAC CGCTGGTAGC
3081 GGTGGTTTTT TTGTTTGCAA GCAGCAGATT ACGCGCAGAA AAAAAGGATC TCAAGAAGAT CCTTTGATCT
3151 TTTCTACGGG GTCTGACGCT CAGTGGAACG ACGCGCGCGT AACTCACGTT AAGGGATTTT GGTCATGAGC
3221 TTGCGCCGTC CCGTCAAGTC AGCGTAATGC TCTGCTTTT
```

Human alpha-MSH (underlined) in pJ204 (SEQ ID NO: 8):

```
   1 TAGAAAAACT CATCGAGCAT CAAATGAAAC TGCAATTTAT TCATATCAGG ATTATCAATA CCATATTTTT
  71 GAAAAAGCCG TTTCTGTAAT GAAGGAGAAA ACTCACCGAG GCAGTTCCAT AGGATGGCAA GATCCTGGTA
 141 TCGGTCTGCG ATTCCGACTC GTCCAACATC AATACAACCT ATTAATTTCC CCTCGTCAAA AATAAGGTTA
 211 TCAAGTGAGA AATCACCATG AGTGACGACT GAATCCGGTG AGAATGGCAA AGTTTATGC ATTTCTTTCC
 281 AGACTTGTTC AACAGGCCAG CCATTACGCT CGTCATCAAA ATCACTCGCA TCAACCAAAC CGTTATTCAT
 351 TCGTGATTGC GCCTGAGCGA GGCGAAATAC GCGATCGCTG TTAAAAGGAC AATTACAAAC AGGAATCGAG
 421 TGCAACCGGC GCAGGAACAC TGCCAGCGCA TCAACAATAT TTTCACCTGA ATCAGGATAT TCTTCTAATA
 491 CCTGGAACGC TGTTTTTCCG GGGATCGCAG TGGTGAGTAA CCATGCATCA TCAGGAGTAC GGATAAAATG
 561 CTTGATGGTC GGAAGTGGCA TAAATTCCGT CAGCCAGTTT AGTCTGACCA TCTCATCTGT AACATCATTG
 631 GCAACGCTAC CTTTGCCATG TTTCAGAAAC AACTCTGGCG CATCGGGCTT CCCATACAAG CGATAGATTG
 701 TCGCACCTGA TTGCCCGACA TTATCGCGAG CCCATTTATA CCCATATAAA TCAGCATCCA TGTTGGAATT
 771 TAATCGCGGC CTCGACGTTT CCCGTTGAAT ATGGCTCATA TTCTTCCTTT TTCAATATTA TTGAAGCATT
 841 TATCAGGGTT ATTGTCTCAT GAGCGGATAC ATATTTGAAT GTATTTAGAA AATAAACAA ATAGGGGTCA
 911 GTGTTACAAC CAATTAACCA ATTCTGAACA TTATCGCGAG CCCATTTATA CCTGAATATG GCTCATAACA
 981 CCCCTTGTTT GCCTGGCGGC AGTAGCGCGG TGGTCCCACC TGACCCCATG CCGAACTCAG AAGTGAAACG
1051 CCGTAGCGCC GATGGTAGTG TGGGGACTCC CCATGCGAGA GTAGGGAACT GCCAGGCATC AAATAAAACG
1121 AAAGGCTCAG TCGAAAGACT GGGCCTTTCG CCCGGGCTAA TTAGGGGGTG TCGCCCTTCG CTGAATAAGC
1191 TTTTGGACCC TCGTACAGAA GCTAATACGA CTCACTATAG GGAAATAAGA GAGAAAAGAA GAGTAAGAAG
1261 AAATATAAGA GCCACCATGC CTAGATCATG TTGTTCACGA TCGGGAGCGT TGTTGCTGGC ACTCTTGCTC
1331 CAAGCCTCGA TGGAAGTGCG GGGATGGTGC CTTGAGAGCT CCCAGTGCCA GGACCTCACA ACGGAGTCGA
1401 ACCTTCTGGA ATGCATCCGC GCGTGTAAAC CGAGGGAAGG TAAAAGGTCC TACAGCATGG AGCACTTCAG
```

APPENDIX-continued

```
1471 ATGGGGGAAG CCCGTCGGGA AGAAGCGGTG AAGCGCTGCC TTCTGCGGGG CTTGCCTTCT GGCCATGCCC
1541 TTCTTCTCTC CCTTGCACCT GTACCTCTTG GTCTTTGAAT AAAGCCTGAG TAGGAAGGCG GCCGCTCGAG
1611 CATGCATCTA GAGCGTCAAA GGGCGACACA AAATTTATTC TAAATGCATA ATAAATACTG ATAACATCTT
1681 ATAGTTTGTA TTATATTTTG TATTATCGTT GACATGTATA ATTTTGATAT CAAAAACTGA TTTTCCCTTT
1751 ATTATTTTCG AGATTTATTT TCTTAATTCT CTTTAACAAA CTAGAAATAT TGTATATACA AAAATCATA
1821 AATAATAGAT GAATAGTTTA ATTATAGGTG TTCATCAATC GAAAAGCAA CGTATCTTAT TTAAAGTGCG
1891 TTGCTTTTTT CTCATTTATA AGGTTAAATA ATTCTCTATAT ATCAAGCAAA GTGACAGGCG CCCTTAAATA
1961 TTCTGACAAA TGCTCTTTCC CTAAACTCCC CCATAAAAA AACCCGCCGA AGCGGGTTTT TACGTTATTT
2031 GCGGATTAAC GATTACTCGT TATCAGAACC GCCCAGGGGG CCCGAGCTTA AGACTGGCCG TCGTTTTACA
2101 ACACAGAAAG AGTTTGTAGA AACGCAAAAA GGCCATCCGT CAGGGGCCTT CTGCTTAGTT TGATGCCTGG
2171 CAGTTCCCTA CTCTCGCCTT CCGCTTCCTC GCTCACTGAC TCGCTGCGCT CGGTCGTTCG GCTGCGGCGA
2241 GCGGTATCAG CTCACTCAAA GGCGGTAATA CGGTTATCCA CAGAATCAGG GGATAACGCA GGAAAGAACA
2311 TGTGAGCAAA AGGCCAGCAA AAGGCCAGGA ACCGTAAAAA GGCCGCGTTG CTGGCGTTTT TCCATAGGCT
2381 CCGCCCCCCT GACGAGCATC ACAAAAATCG ACGCTCAAGT CAGAGGTGGC GAAACCCGAC AGGACTATAA
2451 AGATACCAGG CGTTTCCCCC TGGAAGCTCC CTCGTGCGCT CTCCTGTTCC GACCCTGCCG CTTACCGGAT
2521 ACCTGTCCGC CTTTCTCCCT TCGGGAAGCG TGGCGCTTTC TCATAGCTCA CGCTGTAGGT ATCTCAGTTC
2591 GGTGTAGGTC GTTCGCTCCA AGCTGGGCTG TGTGCACGAA CCCCCCGTTC AGCCCGACCG CTGCGCCTTA
2661 TCCGGTAACT ATCGTCTTGA GTCCAACCCG GTAAGACACG ACTTATCGCC ACTGGCAGCA GCCACTGGTA
2731 ACAGGATTAG CAGAGCGAGG TATGTAGGCG GTGCTACAGA GTTCTTGAAG TGGTGGGCTA ACTACGGCTA
2801 CACTAGAAGA ACAGTATTTG GTATCTGCGC TCTGCTGAAG CCAGTTACCT TCGGAAAAAG AGTTGGTAGC
2871 TCTTGATCCG GCAAACAAAC CACCGCTGGT AGCGGTGGTT TTTTGTTTG CAAGCAGCAG ATTACGCGCA
2941 GAAAAAAAGG ATCTCAAGAA GATCCTTTGA TCTTTTCTAC GGGGTCTGAC GCTCAGTGGA ACGACGCGCG
3011 CGTAACTCAC GTTAAGGGAT TTTGGTCATG AGCTTGCGCC GTCCCGTCAA GTCAGCGTAA TGCTCTGCTT
3081 T
```

What is claimed is:

1. A pharmaceutical formulation comprising:
i) an effective amount of a mRNA sequence encoding a granulocyte colony-stimulating factor (G-CSF) polypeptide wherein the mRNA sequence is at least 95% identical to the sequence of SEQ ID NO: 17; and
ii) a pharmaceutically acceptable carrier, wherein the formulation is suitable for repeated intravenous administration to a mammalian subject in need thereof.

2. The pharmaceutical formulation of claim 1, further comprising a lipid-based transfection reagent.

3. A kit comprising the pharmaceutical formulation of claim 1 and AMD3100 (1,1'-[1,4-phenylene-bis(methylene)]-bis-1,4,8,11-tetraazacyclotetradecane), in one or more containers, and instructions for use thereof.

4. A pharmaceutical formulation consisting essentially of:
i) an effective amount of a mRNA sequence encoding a granulocyte colony-stimulating factor (G-CSF) polypeptide wherein the mRNA sequence is at least 95% identical to the sequence of SEQ ID NO: 17;
ii) a cell penetration agent; and
iii) a pharmaceutically acceptable carrier, wherein the formulation is suitable for repeated intravenous administration to a mammalian subject in need thereof.

* * * * *

UNITED STATES PATENT AND TRADEMARK OFFICE
CERTIFICATE OF CORRECTION

PATENT NO. : 8,822,663 B2  
APPLICATION NO. : 13/204609  
DATED : September 2, 2014  
INVENTOR(S) : Schrum et al.

Page 1 of 1

It is certified that error appears in the above-identified patent and that said Letters Patent is hereby corrected as shown below:

On the title page item (75), add --Kenechi Ejebe, Cambridge, MA (US)--

Signed and Sealed this
Nineteenth Day of July, 2016

Michelle K. Lee
*Director of the United States Patent and Trademark Office*

SEQUENCE LISTING

<160> NUMBER OF SEQ ID NOS: 24

<210> SEQ ID NO 1
<211> LENGTH: 852
<212> TYPE: DNA
<213> ORGANISM: Homo sapiens

<400> SEQUENCE: 1

```
agcttttgga ccctcgtaca gaagctaata cgactcacta tagggaaata agagagaaaa      60
gaagagtaag aagaaatata agagccacca tggccggtcc cgcgacccaa agccccatga     120
aacttatggc cctgcagttg ctgctttggc actcggccct ctggacagtc caagaagcga     180
ctcctctcgg acctgcctca tcgttgccgc agtcattcct tttgaagtgt ctggagcagg     240
tgcgaaagat tcaggcgat ggagccgcac tccaagagaa gctctgcgcg acatacaaac     300
tttgccatcc cgaggagctc gtactgctcg ggcacagctt ggggattccc tgggctcctc     360
tctcgtcctg tccgtcgcag gctttgcagt tggcagggtg cctttcccag ctccactccg     420
gtttgttctt gtatcaggga ctgctgcaag cccttgaggg aatctcgcca gaattgggcc     480
```

| | |
|---|---|
| cgacgctgga cacgttgcag ctcgacgtgg cggatttcgc aacaaccatc tggcagcaga | 540 |
| tggaggaact ggggatggca cccgcgctgc agcccacgca gggggcaatg ccggcctttg | 600 |
| cgtccgcgtt tcagcgcagg gcgggtggag tcctcgtagc gagccacctt caatcatttt | 660 |
| tggaagtctc gtaccgggtg ctgagacatc ttgcgcagcc gtgaagcgct gccttctgcg | 720 |
| gggcttgcct tctggccatg cccttcttct ctcccttgca cctgtacctc ttggtctttg | 780 |
| aataaagcct gagtaggaag gcggccgctc gagcatgcat ctagagggcc caattcgccc | 840 |
| tattcgaagt cg | 852 |

<210> SEQ ID NO 2
<211> LENGTH: 437
<212> TYPE: DNA
<213> ORGANISM: Homo sapiens

<400> SEQUENCE: 2

| | |
|---|---|
| aagcttttgg accctcgtac agaagctaat acgactcact atagggaaat aagagagaaa | 60 |
| agaagagtaa gaagaaatat aagagccacc atgcctagat catgttgttc acgatcggga | 120 |
| gcgttgttgc tggcactctt gctccaagcc tcgatggaag tgcggggatg gtgccttgag | 180 |
| agctcccagt gccaggacct cacaacggag tcgaaccttc tggaatgcat ccgcgcgtgt | 240 |
| aaaccgaggg aagtaaaag gtcctacagc atggagcact tcagatgggg gaagcccgtc | 300 |
| gggaagaagc ggtgaagcgc tgccttctgc ggggcttgcc ttctggccat gcccttcttc | 360 |
| tctcccttgc acctgtacct cttggtcttt gaataaagcc tgagtaggaa ggcggccgct | 420 |
| cgagcatgca tctagag | 437 |

<210> SEQ ID NO 3
<211> LENGTH: 563
<212> TYPE: DNA
<213> ORGANISM: Mus sp.

<400> SEQUENCE: 3

| | |
|---|---|
| agcttttgga ccctcgtaca gaagctaata cgactcacta tagggaaata agagagaaaa | 60 |
| gaagagtaag aagaaatata agagccacca tggcgctctg gtgaggtttc tgcctttgtt | 120 |
| ggccttgctg ttcctctggg agtcccaccc cacacaggcg tttgtgaagc agcacttgtg | 180 |
| cgggtcgcat ctggtggagg cactttatct cgtctgcggc gagcgaggat tcttctacac | 240 |
| cccgatgagc agacgcgaag tggaagatcc gcaagtcgcg cagctcgaac ttggggggtgg | 300 |
| tcccggagcc ggagacttgc aaactctcgc tctcgaggta gcgcagcaga aacggggtat | 360 |
| cgtagaccag tgttgcacgt cgatctgttc actttatcaa cttgagaact actgtaattg | 420 |
| aagcgctgcc ttctgcgggg cttgccttct ggccatgccc ttcttctctc ccttgcacct | 480 |
| gtacctcttg gtctttgaat aaagcctgag taggaaggcg gccgctcgag catgcatcta | 540 |
| gagggcccaa ttcgccctat tcg | 563 |

<210> SEQ ID NO 4
<211> LENGTH: 567
<212> TYPE: DNA
<213> ORGANISM: Homo sapiens

<400> SEQUENCE: 4

| | |
|---|---|
| agcttttgga ccctcgtaca gaagctaata cgactcacta tagggaaata agagagaaaa | 60 |
| gaagagtaag aagaaatata agagccacca tggctctctg gatgcggctt cttccactgc | 120 |

| | |
|---|---|
| tcgccctctt ggcgttgtgg ggacccgacc ctgcagcagc gtttgtgaat cagcacctct | 180 |
| gcgggtccca tctggtcgaa gccctttacc ttgtgtgtgg cgagcgcggg ttcttctaca | 240 |
| cgcccaagac aaggcgcgag gcggaggatc tccaagtagg gcaggtggaa ttgggagggg | 300 |
| gaccgggagc cggttcactc cagcccctgg cgttggaggg gtcgctgcag aaaagaggta | 360 |
| tgtcgaaca gtgttgcact agcatctgct cgctgtatca acttgagaac tattgtaact | 420 |
| gaagcgctgc cttctgcggg gcttgccttc tggccatgcc cttcttctct cccttgcacc | 480 |
| tgtacctctt ggtctttgaa taaagcctga gtaggaaggc ggccgctcga gcatgcatct | 540 |
| agagggccca attcgcccta ttcgaag | 567 |

<210> SEQ ID NO 5
<211> LENGTH: 3547
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

| | |
|---|---|
| accaatgctt aatcagtgag gcacctatct cagcgatctg tctatttcgt tcatccatag | 60 |
| ttgcctgact ccccgtcgtg tagataacta cgatacggga gggcttacca tctggcccca | 120 |
| gcgctgcgat gataccgcga gaaccacgct caccggctcc ggattatca gcaataaacc | 180 |
| agccagccgg aagggccgag cgcagaagtg gtcctgcaac tttatccgcc tccatccagt | 240 |
| ctattaattg ttgccgggaa gctagagtaa gtagttcgcc agttaatagt ttgcgcaacg | 300 |
| ttgttgccat cgctacaggc atcgtggtgt cacgctcgtc gtttggtatg gcttcattca | 360 |
| gctccggttc ccaacgatca aggcgagtta catgatcccc catgttgtgc aaaaaagcgg | 420 |
| ttagctcctt cggtcctccg atcgttgtca gaagtaagtt ggccgcagtg ttatcactca | 480 |
| tggttatggc agcactgcat aattctctta ctgtcatgcc atccgtaaga tgcttttctg | 540 |
| tgactggtga gtactcaacc aagtcattct gagaatagtg tatgcggcga ccgagttgct | 600 |
| cttgcccggc gtcaatacgg gataataccg cgccacatag cagaactta aaagtgctca | 660 |
| tcattggaaa acgttcttcg gggcgaaaac tctcaaggat cttaccgctg ttgagatcca | 720 |
| gttcgatgta acccactcgt gcacccaact gatcttcagc atcttttact ttcaccagcg | 780 |
| tttctgggtg agcaaaaaca ggaaggcaaa atgccgcaaa aaagggaata agggcgacac | 840 |
| ggaaatgttg aatactcata ttcttccttt ttcaatatta ttgaagcatt tatcagggtt | 900 |
| attgtctcat gagcggatac atatttgaat gtatttagaa aaataaacaa ataggggtca | 960 |
| gtgttacaac caattaacca attctgaaca ttatcgcgag cccatttata cctgaatatg | 1020 |
| gctcataaca ccccttgttt gcctggcggc agtagcgcgg tggtcccacc tgaccccatg | 1080 |
| ccgaactcag aagtgaaacg ccgtagcgcc gatggtagtg tggggactcc ccatgcgaga | 1140 |
| gtagggaact gccaggcatc aaataaaacg aaaggctcag tcgaaagact gggcctttcg | 1200 |
| cccgggctaa ttatggggtg tcgcccttt gacgcgactt cgaatagggc gaattgggcc | 1260 |
| ctctagatgc atgctcgagc ggccgccttc tactcaggc tttattcaaa gaccaagagg | 1320 |
| tacaggtgca aggagagaa gaagggcatg ccagaaggc aagccccgca gaaggcagcg | 1380 |
| cttcacggct gcgcaagatg tctcagcacc cggtacgaga cttccaaaaa tgattgaagg | 1440 |
| tggctcgcta cgaggactcc acccgccctg cgctgaaacg cggacgcaaa ggccggcatt | 1500 |
| gccccctgcg tgggctgcag cgcgggtgcc atccccagtt cctccatctg ctgccagatg | 1560 |

```
gttgttgcga aatccgccac gtcgagctgc aacgtgtcca gcgtcgggcc caattctggc   1620
gagattccct caagggcttg cagcagtccc tgatacaaga acaaaccgga gtggagctgg   1680
gaaaggcacc ctgccaactg caaagcctgc gacggacagg acgagagagg agcccaggga   1740
atccccaagc tgtgcccgag cagtacgagc tcctcgggat ggcaaagttt gtatgtcgcg   1800
cagagcttct cttggagtgc ggctccatcg ccctgaatct ttcgcacctg ctccagacac   1860
ttcaaaagga atgactgcgg caacgatgag gcaggtccga gaggagtcgc ttcttggact   1920
gtccagaggg ccgagtgcca agcagcaac tgcagggcca taagtttcat ggggctttgg   1980
gtcgcgggac cggccatggt ggctcttata tttcttctta ctcttctttt ctctcttatt   2040
tccctatagt gagtcgtatt agcttctgta cgagggtcca aaagctttca gcgaagggcg   2100
acacaaaatt tattctaaat gcataataaa tactgataac atcttatagt ttgtattata   2160
ttttgtatta tcgttgacat gtataatttt gatatcaaaa actgattttc cctttattat   2220
tttcgagatt tattttctta attctcttta acaaactaga aatattgtat atacaaaaaa   2280
tcataaataa tagatgaata gtttaattat aggtgttcat caatcgaaaa agcaacgtat   2340
cttatttaaa gtgcgttgct ttttctcat ttataaggtt aaataattct catatatcaa   2400
gcaaagtgac aggcgccctt aaatattctg acaaatgctc tttccctaaa ctcccccat   2460 aaaaaaccc gccgaagcgg gtttttacgt tatttgcgga ttaacgatta ctcgttatca   2520
gaaccgccca gggggcccga gcttaagact ggccgtcgtt ttacaacaca gaaagagttt   2580
gtagaaacgc aaaaggcca tccgtcaggg gccttctgct tagtttgatg cctggcagtt   2640
ccctactctc gccttccgct tcctcgctca ctgactcgct gcgctcggtc gttcggctgc   2700
ggcgagcggt atcagctcac tcaaaggcgg taatacggtt atccacagaa tcagggggata  2760 acgcaggaaa gaacatgtga gcaaaaggcc agcaaaaggc caggaaccgt aaaaaggccg   2820
cgttgctggc gtttttccat aggctccgcc ccctgacga gcatcacaaa aatcgacgct   2880
caagtcagag gtggcgaaac ccgacaggac tataaagata ccaggcgttt ccccctggaa   2940
gctccctcgt gcgctctcct gttccgaccc tgccgcttac cggatacctg tccgcctttc   3000
tcccttcggg aagcgtggcg ctttctcata gctcacgctg taggtatctc agttcggtgt   3060
aggtcgttcg ctccaagctg ggctgtgtgc acgaaccccc cgttcagccc gaccgctgcg   3120
ccttatccgg taactatcgt cttgagtcca acccggtaag acacgactta tcgccactgg   3180
cagcagccac tggtaacagg attagcagag cgaggtatgt aggcggtgct acagagttct   3240
tgaagtggtg gcctaactac ggctacacta agaacagt atttggtatc tgcgctctgc   3300
tgaagccagt taccttcgga aaaagagttg gtagctcttg atccggcaaa caaaccaccg   3360
ctggtagcgg tggttttttt gtttgcaagc agcagattac gcgcagaaaa aaggatctc   3420 aagaagatcc tttgatcttt tctacggggt ctgacgctca gtggaacgac gcgcgcgtaa   3480
ctcacgttaa gggattttgg tcatgagctt gcgccgtccc gtcaagtcag cgtaatgctc   3540
tgcttttt                                                           3547
```

<210> SEQ ID NO 6
<211> LENGTH: 3262
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
accaatgctt aatcagtgag gcacctatct cagcgatctg tctatttcgt tcatccatag    60
ttgcctgact ccccgtcgtg tagataacta cgatacggga gggcttacca tctggcccca   120
gcgctgcgat gataccgcga gaaccacgct caccggctcc ggatttatca gcaataaacc   180
agccagccgg aagggccgag cgcagaagtg gtcctgcaac tttatccgcc tccatccagt   240
ctattaattg ttgccgggaa gctagagtaa gtagttcgcc agttaatagt ttgcgcaacg   300
ttgttgccat cgctacaggc atcgtggtgt cacgctcgtc gtttggtatg gcttcattca   360
gctccggttc ccaacgatca aggcgagtta catgatcccc catgttgtgc aaaaaagcgg   420
ttagctcctt cggtcctccg atcgttgtca gaagtaagtt ggccgcagtg ttatcactca   480
tggttatggc agcactgcat aattctctta ctgtcatgcc atccgtaaga tgcttttctg   540
tgactggtga gtactcaacc aagtcattct gagaatagtg tatgcggcga ccgagttgct   600
cttgcccggc gtcaatacgg gataataccg cgccacatag cagaacttta aaagtgctca   660
tcattggaaa acgttcttcg ggcgaaaac tctcaaggat cttaccgctg ttgagatcca   720
gttcgatgta acccactcgt gcacccaact gatcttcagc atcttttact ttcaccagcg   780
tttctgggtg agcaaaaaca ggaaggcaaa atgccgcaaa aagggaata agggcgacac   840
ggaaatgttg aatactcata ttcttccttt tcaatatta ttgaagcatt tatcagggtt   900
attgtctcat gagcggatac atatttgaat gtatttagaa aaataaacaa ataggggtca   960
gtgttacaac caattaacca attctgaaca ttatcgcgag cccatttata cctgaatatg  1020
gctcataaca ccccttgttt gcctggcggc agtagcgcgg tggtcccacc tgaccccatg  1080
ccgaactcag aagtgaaacg ccgtagcgcc gatggtagtg tggggactcc ccatgcgaga  1140
gtagggaact gccaggcatc aaataaaacg aaaggctcag tcgaaagact gggcctttcg  1200
cccgggctaa ttatggggtg tcgccctcg ctgaaagctt ttggaccctc gtacagaagc  1260
taatacgact cactataggg aaataagaga gaaagaagaa gtaagaagaa atataagagc  1320
caccatggct ctctggatgc ggcttcttcc actgctcgcc ctcttggcgt tgtgggacc   1380
cgaccctgca gcagcgtttg tgaatcagca cctctgcggg tcccatctgg tcgaagccct  1440
ttaccttgtg tgtggcgagc gcgggttctt ctacacgccc aagacaaggc gcgaggcgga  1500
ggatctccaa gtagggcagg tggaattggg aggggggaccg ggagccggtt cactccagcc  1560
cctggcgttg gagggtcgc tgcagaaaag aggtattgtc gaacagtgtt gcactagcat  1620
ctgctcgctg tatcaacttg agaactattg taactgaagc gctgccttct gcgggggcttg  1680
ccttctggcc atgcccttct tctctcccct tgcacctgtac ctcttggtct ttgaataaag  1740
cctgagtagg aaggcggccg ctcgagcatg catctagagg gcccaattcg ccctattcga  1800
agcgtcaaaa gggcgacaca aaatttattc taaatgcata ataaatactg ataacatctt  1860
atagtttgta ttatattttg tattatcgtt gacatgtata attttgatat caaaaactga  1920
ttttccctt attattttcg agattttatt tcttaattct ctttaacaaa ctagaaatat  1980
tgtatataca aaaaatcata aataatagat gaatagttta attataggtg ttcatcaatc  2040
gaaaaagcaa cgtatcttat ttaaagtgcg ttgcttttt ctcatttata aggttaaata  2100
attctcatat atcaagcaaa gtgacaggcg cccttaaata ttctgacaaa tgctctttcc  2160
ctaaactccc cccataaaaa aacccgccga agcgggtttt tacgttattt gcggattaac  2220
gattactcgt tatcagaacc gcccaggggg cccgagctta agactggccg tcgttttaca  2280
acacagaaag agtttgtaga aacgcaaaaa ggccatccgt caggggcctt ctgcttagtt  2340
tgatgcctgg cagttcccta ctctcgcctt ccgcttcctc gctcactgac tcgctgcgct  2400
```

```
cggtcgttcg gctgcggcga gcggtatcag ctcactcaaa ggcggtaata cggttatcca    2460
cagaatcagg ggataacgca ggaaagaaca tgtgagcaaa aggccagcaa aaggccagga    2520
accgtaaaaa ggccgcgttg ctggcgtttt tccataggct ccgcccccct gacgagcatc    2580
acaaaaatcg acgctcaagt cagaggtggc gaaacccgac aggactataa agataccagg    2640
cgtttccccc tggaagctcc ctcgtgcgct ctcctgttcc gaccctgccg cttaccggat    2700
acctgtccgc ctttctccct tcgggaagcg tggcgctttc tcatagctca cgctgtaggt    2760
atctcagttc ggtgtaggtc gttcgctcca agctgggctg tgtgcacgaa ccccccgttc    2820
agcccgaccg ctgcgcctta tccggtaact atcgtcttga gtccaacccg gtaagacacg    2880
acttatcgcc actggcagca gccactggta acaggattag cagagcgagg tatgtaggcg    2940
gtgctacaga gttcttgaag tggtgggcta actacggcta cactagaaga acagtatttg    3000
gtatctgcgc tctgctgaag ccagttacct tcggaaaaag agttggtagc tcttgatccg    3060
gcaaacaaac caccgctggt agcggtggtt tttttgtttg caagcagcag attacgcgca    3120
gaaaaaaagg atctcaagaa gatcctttga tcttttctac ggggtctgac gctcagtgga    3180
acgacgcgcg cgtaactcac gttaagggat tttggtcatg agcttgcgcc gtcccgtcaa    3240
gtcagcgtaa tgctctgctt tt    3262

<210> SEQ ID NO 7
<211> LENGTH: 3259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
accaatgctt aatcagtgag gcacctatct cagcgatctg tctatttcgt tcatccatag      60
ttgcctgact ccccgtcgtg tagataacta cgatacggga gggcttacca tctgccccca     120
gcgctgcgat gataccgcga gaaccacgct caccggctcc ggatttatca gcaataaacc     180
agccagccgg aagggccgag cgcagaagtg gtcctgcaac tttatccgcc tccatccagt     240
ctattaattg ttgccgggaa gctagagtaa gtagttcgcc agttaatagt ttgcgcaacg     300
ttgttgccat cgctacaggc atcgtggtgt cacgctcgtc gtttggtatg gcttcattca     360
gctccggttc ccaacgatca aggcgagtta catgatcccc catgttgtgc aaaaaagcgg     420
ttagctcctt cggtcctccg atcgttgtca gaagtaagtt ggccgcagtg ttatcactca     480
tggttatggc agcactgcat aattctctta ctgtcatgcc atccgtaaga tgcttttctg     540
tgactggtga gtactcaacc aagtcattct gagaatagtg tatgcggcga ccgagttgct     600
cttgcccggc gtcaatacgg gataataccg cgccacatag cagaacttta aaagtgctca     660
tcattggaaa acgttcttcg gggcgaaaac tctcaaggat cttaccgctg ttgagatcca     720
gttcgatgta acccactcgt gcacccaact gatcttcagc atcttttact ttcaccagcg     780
tttctgggtg agcaaaaaca ggaaggcaaa atgccgcaaa aaagggaata agggcgacac     840
ggaaatgttg aatactcata ttcttccttt tcaatatta tgaagcatt tatcagggtt     900 attgtctcat gagcggatac atatttgaat gtatttagaa aaataaacaa ataggggtca     960
gtgttacaac caattaacca attctgaaca ttatcgcgag cccatttata cctgaatatg    1020
gctcataaca ccccttgttt gcctggcggc agtagcgcgg tggtcccacc tgaccccatg    1080
ccgaactcag aagtgaaacg ccgtagcgcc gatggtagtg tggggactcc ccatgcgaga    1140
```

```
gtagggaact gccaggcatc aaataaaacg aaaggctcag tcgaaagact gggcctttcg      1200
cccgggctaa ttatggggtg tcgcccttcg ctgaaagctt ttggaccctc gtacagaagc      1260
taatacgact cactataggg aaataagaga gaaagaagaa gtaagaagaa atataagagc      1320
caccatggcg ctctgatga ggtttctgcc tttgttggcc ttgctgttcc tctgggagtc       1380
ccaccccaca caggcgtttg tgaagcagca cttgtgcggg tcgcatctgg tggaggcact      1440
ttatctcgtc tgcggcgagc gaggattctt ctacaccccg atgagcagac gcaagtggaa      1500
agatccgcaa gtcgcgcagc tcgaacttgg gggtggtccc ggagccggag acttgcaaac      1560
tctcgctctc gaggtagcgc agcagaaacg gggtatcgta gaccagtgtt gcacgtcgat      1620
ctgttcactt tatcaacttg agaactactg taattgaagc gctgccttct gcgggcttg       1680 ccttctggcc atgcccttct tctctccctt gcacctgtac ctcttggtct ttgaataaag      1740
cctgagtagg aaggcggccg ctcgagcatg catctagagg gcccaattcg ccctattcgc      1800 gtcaaaggg cgacacaaaa tttattctaa atgcataata aatactgata acatcttata       1860
gtttgtatta tattttgtat tatcgttgac atgtataatt ttgatatcaa aaactgattt      1920
tccctttatt atttttcgaga tttattttct taattctctt taacaaacta gaaatattgt     1980
atatacaaaa aatcataaat aatagatgaa tagtttaatt ataggtgttc atcaatcgaa      2040
aaagcaacgt atcttattta aagtgcgttg cttttttctc atttataagg ttaaataatt      2100
ctcatatatc aagcaaagtg acaggcgccc ttaaatattc tgacaaatgc tctttccta      2160 aactcccccc ataaaaaaac ccgccgaagc gggtttttac gttatttgcg gattaacgat      2220
tactcgttat cagaaccgcc caggggggccc gagcttaaga ctggccgtcg ttttacaaca    2280
cagaaagagt ttgtagaaac gcaaaaaggc catccgtcag gggccttctg cttagtttga     2340
tgcctggcag ttccctactc tcgccttccg cttcctcgct cactgactcg ctgcgctcgg     2400

tcgttcggct gcggcgagcg gtatcagctc actcaaaggc ggtaatacgg ttatccacag     2460
aatcagggga taacgcagga agaacatgt gagcaaaagg ccagcaaaag gccaggaacc      2520
gtaaaaaggc cgcgttgctg gcgtttttcc ataggctccg cccccctgac gagcatcaca     2580
aaaatcgacg ctcaagtcag aggtggcgaa acccgacagg actataaaga taccaggcgt    2640

ttccccctgg aagctccctc gtgcgctctc ctgttccgac cctgccgctt accggatacc     2700

tgtccgcctt tctcccttcg ggaagcgtgg cgctttctca tagctcacgc tgtaggtatc     2760

tcagttcggt gtaggtcgtt cgctccaagc tgggctgtgt gcacgaaccc ccgttcagc      2820 ccgaccgctg cgccttatcc ggtaactatc gtcttgagtc caacccggta agacacgact    2880

tatcgccact ggcagcagcc actggtaaca ggattagcag agcgaggtat gtaggcggtg     2940 cтacagагтт cttgaagtgg tgggctaact acggctacac tagaagaaca gтaттgгтa     3000

tctgcgctct gctgaagcca gttaccttcg gaaaagagt tggtagctct tgatccggca    3060
aacaaaccac cgctggtagc ggtggtttt tgttttgcaa gcagcagaттт acgcgcagaa     3120 aaaaaggatc tcaagaagat ccттттgaтcт tttctacggg gtctgacgct cagtggaacg    3180
acgcgcgcgt aactcacgtt aagggatttt ggtcatgagc ttgcgccgtc ccgtcaagtc    3240
agcgtaatgc tctgctttt                                                  3259

<210> SEQ ID NO 8
<211> LENGTH: 3081
<212> TYPE: DNA
<213> ORGANISM: Artificial Sequence
<220> FEATURE:
```

<223> OTHER INFORMATION: Description of Artificial Sequence: Synthetic polynucleotide

<400> SEQUENCE: 8

```
tagaaaaact catcgagcat caaatgaaac tgcaatttat tcatatcagg attatcaata      60
ccatatttt gaaaaagccg tttctgtaat gaaggagaaa actcaccgag gcagttccat      120
aggatggcaa gatcctggta tcggtctgcg attccgactc gtccaacatc aatacaacct    180
attaatttcc cctcgtcaaa ataaggtta tcaagtgaga atcaccatg agtgacgact       240
gaatccggtg agaatggcaa aagtttatgc atttcttttcc agacttgttc aacaggccag    300
ccattacgct cgtcatcaaa atcactcgca tcaaccaaac cgttattcat tcgtgattgc     360
gcctgagcga ggcgaaatac gcgatcgctg ttaaaggac aattacaaac aggaatcgag      420
tgcaaccggc gcaggaacac tgccagcgca tcaacaatat tttcacctga atcaggatat    480
tcttctaata cctggaacgc tgttttccg gggatcgcag tggtgagtaa ccatgcatca     540
tcaggagtac ggataaaatg cttgatggtc ggaagtggca taaattccgt cagccagttt    600
agtctgacca tctcatctgt aacatcattg gcaacgctac ctttgccatg tttcagaaac   660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgacccatg ccgaactcag aagtgaaacg ccgtagcgcc gatggtagtg tggggactcc    1080
ccatgcgaga gtagggaact gccaggcatc aaataaaacg aaaggctcag tcgaaagact  1140
gggccttcg cccgggctaa ttaggggtg tcgcccttcg ctgaataagc ttttggaccc    1200
tcgtacagaa gctaatacga ctcactatag gaaataaga gagaaagaa gagtaagaag   1260
aaatataaga gccaccatgc ctagatcatg ttgttcacga tcgggagcgt tgttgctggc   1320
actcttgctc caagcctcga tggaagtgcg gggatggtgc cttgagagct cccagtgcca  1380
ggacctcaca acggagtcga accttctgga atgcatccgc gcgtgtaaac cgagggaagg  1440
taaaaggtcc tacagcatgg agcacttcag atggggaag cccgtcggga agaagcggtg    1500
aagcgctgcc ttctgcgggg cttgccttct ggccatgccc ttcttctctc ccttgcacct  1560
gtacctcttg gtctttgaat aaagcctgag taggaaggcg gccgctcgag catgcatcta  1620
gagcgtcaaa gggcgacaca aaatttattc taaatgcata ataaatactg ataacatctt  1680
atagtttgta ttatattttg tattatcgtt gacatgtata attttgatat caaaaactga  1740
ttttcccttt attattttcg agatttattt tcttaattct ctttaacaaa ctagaaatat  1800
tgtatataca aaaaatcata aataatagat gaatagttta attataggtg ttcatcaatc 1860
gaaaaagcaa cgtatcttat ttaaagtgcg ttgctttttt ctcatttata aggttaaata  1920
attctcatat atcaagcaaa gtgacaggcg cccttaaata ttctgacaaa tgctctttcc  1980
ctaaactccc cccataaaaa acccgccga agcgggtttt tacgttattt gcggattaac   2040
gattactcgt tatcagaacc gcccagggg cccgagctta agactggccg tcgttttaca   2100
acacagaaag agtttgtaga aacgcaaaaa ggccatccgt caggggcctt ctgcttagtt   2160
tgatgcctgg cagttcccta ctctcgcctt ccgcttcctc gctcactgac tcgctgcgct   2220
```

```
cggtcgttcg gctgcggcga gcggtatcag ctcactcaaa ggcggtaata cggttatcca    2280
cagaatcagg ggataacgca ggaaagaaca tgtgagcaaa aggccagcaa aaggccagga    2340
accgtaaaaa ggccgcgttg ctggcgtttt tccataggct ccgcccccct gacgagcatc    2400
acaaaaatcg acgctcaagt cagaggtggc gaaacccgac aggactataa agataccagg    2460
cgtttccccc tggaagctcc ctcgtgcgct ctcctgttcc gaccctgccg cttaccggat    2520
acctgtccgc ctttctccct tcgggaagcg tggcgctttc tcatagctca cgctgtaggt    2580
atctcagttc ggtgtaggtc gttcgctcca agctgggctg tgtgcacgaa ccccccgttc    2640
agcccgaccg ctgcgcctta tccggtaact atcgtcttga gtccaacccg gtaagacacg    2700
acttatcgcc actggcagca gccactggta acaggattag cagagcgagg tatgtaggcg    2760
gtgctacaga gttcttgaag tggtgggcta actacggcta cactagaaga acagtatttg    2820
gtatctgcgc tctgctgaag ccagttacct tcggaaaaag agttggtagc tcttgatccg    2880
gcaaacaaac caccgctggt agcggtggtt tttttgtttg caagcagcag attacgcgca    2940
gaaaaaaagg atctcaagaa gatcctttga tcttttctac ggggtctgac gctcagtgga    3000
acgacgcgcg cgtaactcac gttaagggat tttggtcatg agcttgcgcc gtcccgtcaa    3060
gtcagcgtaa tgctctgctt t                                              3081
```

<210> SEQ ID NO 9
<211> LENGTH: 17
<212> TYPE: PRT
<213> ORGANISM: Homo sapiens

<400> SEQUENCE: 9

Ser Tyr Ser Met Glu His Phe Arg Trp Gly Lys Pro Val Gly Lys Lys
1               5                   10                  15

Arg

<210> SEQ ID NO 10
<211> LENGTH: 13
<212> TYPE: PRT
<213> ORGANISM: Homo sapiens

<400> SEQUENCE: 10

Ser Tyr Ser Met Glu His Phe Arg Trp Gly Lys Pro Val
1               5                   10

<210> SEQ ID NO 11
<211> LENGTH: 22
<212> TYPE: PRT
<213> ORGANISM: Homo sapiens

<400> SEQUENCE: 11

Ala Glu Lys Lys Asp Glu Gly Pro Tyr Arg Met Glu His Phe Arg Trp
1               5                   10                  15

Gly Ser Pro Pro Lys Asp
            20

<210> SEQ ID NO 12
<211> LENGTH: 12
<212> TYPE: PRT
<213> ORGANISM: Homo sapiens

<400> SEQUENCE: 12

Tyr Val Met Gly His Phe Arg Trp Asp Arg Phe Gly
1               5                   10

<210> SEQ ID NO 13
<211> LENGTH: 207
<212> TYPE: PRT
<213> ORGANISM: Homo sapiens

<400> SEQUENCE: 13

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 14
<211> LENGTH: 175
<212> TYPE: PRT
<213> ORGANISM: Homo sapiens

<400> SEQUENCE: 14

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

```
Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 15
<211> LENGTH: 110
<212> TYPE: PRT
<213> ORGANISM: Mus sp.

<400> SEQUENCE: 15

Met Ala Leu Trp Met Arg Phe Leu Pro Leu Leu Ala Leu Leu Phe Leu
1               5                   10                  15

Trp Glu Ser His Pro Thr Gln Ala Phe Val Lys Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Met Ser Arg Arg Glu Val Glu Asp Pro Gln Val Ala
        50                  55                  60

Gln Leu Glu Leu Gly Gly Gly Pro Gly Ala Gly Asp Leu Gln Thr Leu
65                  70                  75                  80

Ala Leu Glu Val Ala Gln Gln Lys Arg Gly Ile Val Asp Gln Cys Cys
                85                  90                  95

Thr Ser Ile Cys Ser Leu Tyr Gln Leu Glu Asn Tyr Cys Asn
            100                 105                 110

<210> SEQ ID NO 16
<211> LENGTH: 110
<212> TYPE: PRT
<213> ORGANISM: Homo sapiens

<400> SEQUENCE: 16

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 17
<211> LENGTH: 852
<212> TYPE: RNA
<213> ORGANISM: Homo sapiens

<400> SEQUENCE: 17
agcuuuugga cccucguaca gaagcuaaua cgacucacua uagggaaaua agagagaaaa     60
gaagaguaag aagaaauaua agagccacca uggccgguuc cgcgacccaa agccccauga    120
```

```
aacuuauggc ccugcaguug cugcuuuggc acucggcccu cuggacaguc caagaagcga       180
cuccucucgg accugccuca ucguugccgc agucauuccu uuugaagugu cuggagcagg       240
ugcgaaagau ucagggcgau ggagccgcac uccaagagaa gcucugcgcg acauacaaac       300
uuugccaucc cgaggagcuc guacugcucg ggcacagcuu ggggauuccc ugggcuccuc       360
ucucguccug uccgucgcag gcuuugcagu uggcagggug ccuuucccag cuccacuccg       420
guuuguucuu guaucaggga cugcugcaag cccuugaggg aaucucgcca gaauugggcc       480
cgacgcugga cacguugcag cucgacgugg cggauuucgc aacaaccauc uggcagcaga       540
uggaggaacu ggggauggca cccgcgcugc agcccacgca gggggcaaug ccggccuuug       600
cguccgcguu ucagcgcagg gcggguggag uccucguagc gagccaccuu caaucauuuu       660
uggaagucuc guaccgggug cugagacauc uugcgcagcc gugaagcgcu gccuucugcg       720
gggcuugccu ucuggccaug cccuucuucu cucccuugca ccuguaccuc uuggucuuug       780
aauaaagccu gaguaggaag gcggccgcuc gagcaugcau cuagagggcc caauucgccc       840
uauucgaagu cg                                                          852
```

```
<210> SEQ ID NO 18
<211> LENGTH: 852
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: 5-methyl-cytidine
<220> FEATURE:
<221> NAME/KEY: modified_base
<222> LOCATION: (4)..(7)
<223> OTHER INFORMATION: Pseudouridine
<220> FEATURE:
<221> NAME/KEY: modified_base
<222> LOCATION: (11)..(13)
<223> OTHER INFORMATION: 5-methyl-cytidine
<220> FEATURE:
<221> NAME/KEY: modified_base
<222> LOCATION: (14)..(14)
<223> OTHER INFORMATION: Pseudouridine
<220> FEATURE:
<221> NAME/KEY: modified_base
<222> LOCATION: (15)..(15)
<223> OTHER INFORMATION: 5-methyl-cytidine
<220> FEATURE:
<221> NAME/KEY: modified_base
<222> LOCATION: (17)..(17)
<223> OTHER INFORMATION: Pseudouridine
<220> FEATURE:
<221> NAME/KEY: modified_base
<222> LOCATION: (19)..(19)
<223> OTHER INFORMATION: 5-methyl-cytidine
<220> FEATURE:
<221> NAME/KEY: modified_base
<222> LOCATION: (25)..(25)
<223> OTHER INFORMATION: 5-methyl-cytidine
<220> FEATURE:
<221> NAME/KEY: modified_base
<222> LOCATION: (26)..(26)
<223> OTHER INFORMATION: Pseudouridine
<220> FEATURE:
<221> NAME/KEY: modified_base
<222> LOCATION: (29)..(29)
<223> OTHER INFORMATION: Pseudouridine
<220> FEATURE:
<221> NAME/KEY: modified_base
<222> LOCATION: (31)..(31)
<223> OTHER INFORMATION: 5-methyl-cytidine
<220> FEATURE:
```

```
<221> NAME/KEY: modified_base
<222> LOCATION: (34)..(34)
<223> OTHER INFORMATION: 5-methyl-cytidine
<220> FEATURE:
<221> NAME/KEY: modified_base
<222> LOCATION: (35)..(35)
<223> OTHER INFORMATION: Pseudouridine
<220> FEATURE:
<221> NAME/KEY: modified_base
<222> LOCATION: (36)..(36)
<223> OTHER INFORMATION: 5-methyl-cytidine
<220> FEATURE:
<221> NAME/KEY: modified_base
<222> LOCATION: (38)..(38)
<223> OTHER INFORMATION: 5-methyl-cytidine
<220> FEATURE:
<221> NAME/KEY: modified_base
<222> LOCATION: (39)..(39)
<223> OTHER INFORMATION: Pseudouridine
<220> FEATURE:
<221> NAME/KEY: modified_base
<222> LOCATION: (41)..(41)
<223> OTHER INFORMATION: Pseudouridine
<220> FEATURE:
<221> NAME/KEY: modified_base
<222> LOCATION: (49)..(49)
<223> OTHER INFORMATION: Pseudouridine
<220> FEATURE:
<221> NAME/KEY: modified_base
<222> LOCATION: (67)..(67)
<223> OTHER INFORMATION: Pseudouridine
<220> FEATURE:
<221> NAME/KEY: modified_base
<222> LOCATION: (77)..(77)
<223> OTHER INFORMATION: Pseudouridine
<220> FEATURE:
<221> NAME/KEY: modified_base
<222> LOCATION: (79)..(79)
<223> OTHER INFORMATION: Pseudouridine
<220> FEATURE:
<221> NAME/KEY: modified_base
<222> LOCATION: (85)..(86)
<223> OTHER INFORMATION: 5-methyl-cytidine
<220> FEATURE:
<221> NAME/KEY: modified_base
<222> LOCATION: (88)..(89)
<223> OTHER INFORMATION: 5-methyl-cytidine
<220> FEATURE:
<221> NAME/KEY: modified_base
<222> LOCATION: (91)..(91)
<223> OTHER INFORMATION: Pseudouridine
<220> FEATURE:
<221> NAME/KEY: modified_base
<222> LOCATION: (94)..(95)
<223> OTHER INFORMATION: 5-methyl-cytidine
<220> FEATURE:
<221> NAME/KEY: modified_base
<222> LOCATION: (98)..(98)
<223> OTHER INFORMATION: Pseudouridine
<220> FEATURE:
<221> NAME/KEY: modified_base
<222> LOCATION: (99)..(101)
<223> OTHER INFORMATION: 5-methyl-cytidine
<220> FEATURE:
<221> NAME/KEY: modified_base
<222> LOCATION: (103)..(103)
<223> OTHER INFORMATION: 5-methyl-cytidine
<220> FEATURE:
<221> NAME/KEY: modified_base
<222> LOCATION: (106)..(108)
<223> OTHER INFORMATION: 5-methyl-cytidine
<220> FEATURE:
<221> NAME/KEY: modified_base
<222> LOCATION: (113)..(116)
<223> OTHER INFORMATION: 5-methyl-cytidine
<220> FEATURE:
<221> NAME/KEY: modified_base
<222> LOCATION: (118)..(118)
<223> OTHER INFORMATION: Pseudouridine
```

```
<220> FEATURE:
<221> NAME/KEY: modified_base
<222> LOCATION: (123)..(123)
<223> OTHER INFORMATION: 5-methyl-cytidine
<220> FEATURE:
<221> NAME/KEY: modified_base
<222> LOCATION: (124)..(125)
<223> OTHER INFORMATION: Pseudouridine
<220> FEATURE:
<221> NAME/KEY: modified_base
<222> LOCATION: (127)..(127)
<223> OTHER INFORMATION: Pseudouridine
<220> FEATURE:
<221> NAME/KEY: modified_base
<222> LOCATION: (130)..(132)
<223> OTHER INFORMATION: 5-methyl-cytidine
<220> FEATURE:
<221> NAME/KEY: modified_base
<222> LOCATION: (133)..(133)
<223> OTHER INFORMATION: Pseudouridine
<220> FEATURE:
<221> NAME/KEY: modified_base
<222> LOCATION: (135)..(135)
<223> OTHER INFORMATION: 5-methyl-cytidine
<220> FEATURE:
<221> NAME/KEY: modified_base
<222> LOCATION: (138)..(139)
<223> OTHER INFORMATION: Pseudouridine
<220> FEATURE:
<221> NAME/KEY: modified_base
<222> LOCATION: (141)..(141)
<223> OTHER INFORMATION: 5-methyl-cytidine
<220> FEATURE:
<221> NAME/KEY: modified_base
<222> LOCATION: (142)..(142)
<223> OTHER INFORMATION: Pseudouridine
<220> FEATURE:
<221> NAME/KEY: modified_base
<222> LOCATION: (144)..(144)
<223> OTHER INFORMATION: 5-methyl-cytidine
<220> FEATURE:
<221> NAME/KEY: modified_base
<222> LOCATION: (145)..(147)
<223> OTHER INFORMATION: Pseudouridine
<220> FEATURE:
<221> NAME/KEY: modified_base
<222> LOCATION: (150)..(150)
<223> OTHER INFORMATION: 5-methyl-cytidine
<220> FEATURE:
<221> NAME/KEY: modified_base
<222> LOCATION: (152)..(152)
<223> OTHER INFORMATION: 5-methyl-cytidine
<220> FEATURE:
<221> NAME/KEY: modified_base
<222> LOCATION: (153)..(153)
<223> OTHER INFORMATION: Pseudouridine
<220> FEATURE:
<221> NAME/KEY: modified_base
<222> LOCATION: (154)..(154)
<223> OTHER INFORMATION: 5-methyl-cytidine
<220> FEATURE:
<221> NAME/KEY: modified_base
<222> LOCATION: (157)..(159)
<223> OTHER INFORMATION: 5-methyl-cytidine
<220> FEATURE:
<221> NAME/KEY: modified_base
<222> LOCATION: (160)..(160)
<223> OTHER INFORMATION: Pseudouridine
<220> FEATURE:
<221> NAME/KEY: modified_base
<222> LOCATION: (161)..(161)
<223> OTHER INFORMATION: 5-methyl-cytidine
<220> FEATURE:
<221> NAME/KEY: modified_base
<222> LOCATION: (162)..(162)
<223> OTHER INFORMATION: Pseudouridine
<220> FEATURE:
<221> NAME/KEY: modified_base
<222> LOCATION: (166)..(166)
```

```
<223> OTHER INFORMATION: 5-methyl-cytidine
<220> FEATURE:
<221> NAME/KEY: modified_base
<222> LOCATION: (169)..(169)
<223> OTHER INFORMATION: Pseudouridine
<220> FEATURE:
<221> NAME/KEY: modified_base
<222> LOCATION: (170)..(171)
<223> OTHER INFORMATION: 5-methyl-cytidine
<220> FEATURE:
<221> NAME/KEY: modified_base
<222> LOCATION: (178)..(178)
<223> OTHER INFORMATION: 5-methyl-cytidine
<220> FEATURE:
<221> NAME/KEY: modified_base
<222> LOCATION: (181)..(181)
<223> OTHER INFORMATION: 5-methyl-cytidine
<220> FEATURE:
<221> NAME/KEY: modified_base
<222> LOCATION: (182)..(182)
<223> OTHER INFORMATION: Pseudouridine
<220> FEATURE:
<221> NAME/KEY: modified_base
<222> LOCATION: (183)..(184)
<223> OTHER INFORMATION: 5-methyl-cytidine
<220> FEATURE:
<221> NAME/KEY: modified_base
<222> LOCATION: (185)..(185)
<223> OTHER INFORMATION: Pseudouridine
<220> FEATURE:
<221> NAME/KEY: modified_base
<222> LOCATION: (186)..(186)
<223> OTHER INFORMATION: 5-methyl-cytidine
<220> FEATURE:
<221> NAME/KEY: modified_base
<222> LOCATION: (187)..(187)
<223> OTHER INFORMATION: Pseudouridine
<220> FEATURE:
<221> NAME/KEY: modified_base
<222> LOCATION: (188)..(188)
<223> OTHER INFORMATION: 5-methyl-cytidine
<220> FEATURE:
<221> NAME/KEY: modified_base
<222> LOCATION: (192)..(193)
<223> OTHER INFORMATION: 5-methyl-cytidine
<220> FEATURE:
<221> NAME/KEY: modified_base
<222> LOCATION: (194)..(194)
<223> OTHER INFORMATION: Pseudouridine
<220> FEATURE:
<221> NAME/KEY: modified_base
<222> LOCATION: (196)..(197)
<223> OTHER INFORMATION: 5-methyl-cytidine
<220> FEATURE:
<221> NAME/KEY: modified_base
<222> LOCATION: (198)..(198)
<223> OTHER INFORMATION: Pseudouridine
<220> FEATURE:
<221> NAME/KEY: modified_base
<222> LOCATION: (199)..(199)
<223> OTHER INFORMATION: 5-methyl-cytidine
<220> FEATURE:
<221> NAME/KEY: modified_base
<222> LOCATION: (201)..(201)
<223> OTHER INFORMATION: Pseudouridine
<220> FEATURE:
<221> NAME/KEY: modified_base
<222> LOCATION: (202)..(202)
<223> OTHER INFORMATION: 5-methyl-cytidine
<220> FEATURE:
<221> NAME/KEY: modified_base
<222> LOCATION: (204)..(205)
<223> OTHER INFORMATION: Pseudouridine
<220> FEATURE:
<221> NAME/KEY: modified_base
<222> LOCATION: (207)..(208)
<223> OTHER INFORMATION: 5-methyl-cytidine
<220> FEATURE:
<221> NAME/KEY: modified_base
```

```
<222> LOCATION: (210)..(210)
<223> OTHER INFORMATION: 5-methyl-cytidine
<220> FEATURE:
<221> NAME/KEY: modified_base
<222> LOCATION: (213)..(213)
<223> OTHER INFORMATION: Pseudouridine
<220> FEATURE:
<221> NAME/KEY: modified_base
<222> LOCATION: (214)..(214)
<223> OTHER INFORMATION: 5-methyl-cytidine
<220> FEATURE:
<221> NAME/KEY: modified_base
<222> LOCATION: (216)..(217)
<223> OTHER INFORMATION: Pseudouridine
<220> FEATURE:
<221> NAME/KEY: modified_base
<222> LOCATION: (218)..(219)
<223> OTHER INFORMATION: 5-methyl-cytidine
<220> FEATURE:
<221> NAME/KEY: modified_base
<222> LOCATION: (220)..(223)
<223> OTHER INFORMATION: Pseudouridine
<220> FEATURE:
<221> NAME/KEY: modified_base
<222> LOCATION: (228)..(228)
<223> OTHER INFORMATION: Pseudouridine
<220> FEATURE:
<221> NAME/KEY: modified_base
<222> LOCATION: (230)..(230)
<223> OTHER INFORMATION: Pseudouridine
<220> FEATURE:
<221> NAME/KEY: modified_base
<222> LOCATION: (231)..(231)
<223> OTHER INFORMATION: 5-methyl-cytidine
<220> FEATURE:
<221> NAME/KEY: modified_base
<222> LOCATION: (232)..(232)
<223> OTHER INFORMATION: Pseudouridine
<220> FEATURE:
<221> NAME/KEY: modified_base
<222> LOCATION: (237)..(237)
<223> OTHER INFORMATION: 5-methyl-cytidine
<220> FEATURE:
<221> NAME/KEY: modified_base
<222> LOCATION: (241)..(241)
<223> OTHER INFORMATION: Pseudouridine
<220> FEATURE:
<221> NAME/KEY: modified_base
<222> LOCATION: (243)..(243)
<223> OTHER INFORMATION: 5-methyl-cytidine
<220> FEATURE:
<221> NAME/KEY: modified_base
<222> LOCATION: (250)..(251)
<223> OTHER INFORMATION: Pseudouridine
<220> FEATURE:
<221> NAME/KEY: modified_base
<222> LOCATION: (252)..(252)
<223> OTHER INFORMATION: 5-methyl-cytidine
<220> FEATURE:
<221> NAME/KEY: modified_base
<222> LOCATION: (257)..(257)
<223> OTHER INFORMATION: 5-methyl-cytidine
<220> FEATURE:
<221> NAME/KEY: modified_base
<222> LOCATION: (260)..(260)
<223> OTHER INFORMATION: Pseudouridine
<220> FEATURE:
<221> NAME/KEY: modified_base
<222> LOCATION: (265)..(266)
<223> OTHER INFORMATION: 5-methyl-cytidine
<220> FEATURE:
<221> NAME/KEY: modified_base
<222> LOCATION: (268)..(268)
<223> OTHER INFORMATION: 5-methyl-cytidine
<220> FEATURE:
<221> NAME/KEY: modified_base
<222> LOCATION: (270)..(270)
<223> OTHER INFORMATION: 5-methyl-cytidine
<220> FEATURE:
```

```
<221> NAME/KEY: modified_base
<222> LOCATION: (271)..(271)
<223> OTHER INFORMATION: Pseudouridine
<220> FEATURE:
<221> NAME/KEY: modified_base
<222> LOCATION: (272)..(273)
<223> OTHER INFORMATION: 5-methyl-cytidine
<220> FEATURE:
<221> NAME/KEY: modified_base
<222> LOCATION: (282)..(282)
<223> OTHER INFORMATION: 5-methyl-cytidine
<220> FEATURE:
<221> NAME/KEY: modified_base
<222> LOCATION: (283)..(283)
<223> OTHER INFORMATION: Pseudouridine
<220> FEATURE:
<221> NAME/KEY: modified_base
<222> LOCATION: (284)..(284)
<223> OTHER INFORMATION: 5-methyl-cytidine
<220> FEATURE:
<221> NAME/KEY: modified_base
<222> LOCATION: (285)..(285)
<223> OTHER INFORMATION: Pseudouridine
<220> FEATURE:
<221> NAME/KEY: modified_base
<222> LOCATION: (287)..(287)
<223> OTHER INFORMATION: 5-methyl-cytidine
<220> FEATURE:
<221> NAME/KEY: modified_base
<222> LOCATION: (289)..(289)
<223> OTHER INFORMATION: 5-methyl-cytidine
<220> FEATURE:
<221> NAME/KEY: modified_base
<222> LOCATION: (292)..(292)
<223> OTHER INFORMATION: 5-methyl-cytidine
<220> FEATURE:
<221> NAME/KEY: modified_base
<222> LOCATION: (294)..(294)
<223> OTHER INFORMATION: Pseudouridine
<220> FEATURE:
<221> NAME/KEY: modified_base
<222> LOCATION: (296)..(296)
<223> OTHER INFORMATION: 5-methyl-cytidine
<220> FEATURE:
<221> NAME/KEY: modified_base
<222> LOCATION: (300)..(300)
<223> OTHER INFORMATION: 5-methyl-cytidine
<220> FEATURE:
<221> NAME/KEY: modified_base
<222> LOCATION: (301)..(303)
<223> OTHER INFORMATION: Pseudouridine
<220> FEATURE:
<221> NAME/KEY: modified_base
<222> LOCATION: (305)..(306)
<223> OTHER INFORMATION: 5-methyl-cytidine
<220> FEATURE:
<221> NAME/KEY: modified_base
<222> LOCATION: (308)..(308)
<223> OTHER INFORMATION: Pseudouridine
<220> FEATURE:
<221> NAME/KEY: modified_base
<222> LOCATION: (309)..(311)
<223> OTHER INFORMATION: 5-methyl-cytidine
<220> FEATURE:
<221> NAME/KEY: modified_base
<222> LOCATION: (318)..(318)
<223> OTHER INFORMATION: 5-methyl-cytidine
<220> FEATURE:
<221> NAME/KEY: modified_base
<222> LOCATION: (319)..(319)
<223> OTHER INFORMATION: Pseudouridine
<220> FEATURE:
<221> NAME/KEY: modified_base
<222> LOCATION: (320)..(320)
<223> OTHER INFORMATION: 5-methyl-cytidine
<220> FEATURE:
<221> NAME/KEY: modified_base
<222> LOCATION: (322)..(322)
<223> OTHER INFORMATION: Pseudouridine
```

-continued

```
<220> FEATURE:
<221> NAME/KEY: modified_base
<222> LOCATION: (324)..(324)
<223> OTHER INFORMATION: 5-methyl-cytidine
<220> FEATURE:
<221> NAME/KEY: modified_base
<222> LOCATION: (325)..(325)
<223> OTHER INFORMATION: Pseudouridine
<220> FEATURE:
<221> NAME/KEY: modified_base
<222> LOCATION: (327)..(327)
<223> OTHER INFORMATION: 5-methyl-cytidine
<220> FEATURE:
<221> NAME/KEY: modified_base
<222> LOCATION: (328)..(328)
<223> OTHER INFORMATION: Pseudouridine
<220> FEATURE:
<221> NAME/KEY: modified_base
<222> LOCATION: (329)..(329)
<223> OTHER INFORMATION: 5-methyl-cytidine
<220> FEATURE:
<221> NAME/KEY: modified_base
<222> LOCATION: (333)..(333)
<223> OTHER INFORMATION: 5-methyl-cytidine
<220> FEATURE:
<221> NAME/KEY: modified_base
<222> LOCATION: (335)..(335)
<223> OTHER INFORMATION: 5-methyl-cytidine
<220> FEATURE:
<221> NAME/KEY: modified_base
<222> LOCATION: (338)..(338)
<223> OTHER INFORMATION: 5-methyl-cytidine
<220> FEATURE:
<221> NAME/KEY: modified_base
<222> LOCATION: (339)..(340)
<223> OTHER INFORMATION: Pseudouridine
<220> FEATURE:
<221> NAME/KEY: modified_base
<222> LOCATION: (346)..(347)
<223> OTHER INFORMATION: Pseudouridine
<220> FEATURE:
<221> NAME/KEY: modified_base
<222> LOCATION: (348)..(350)
<223> OTHER INFORMATION: 5-methyl-cytidine
<220> FEATURE:
<221> NAME/KEY: modified_base
<222> LOCATION: (351)..(351)
<223> OTHER INFORMATION: Pseudouridine
<220> FEATURE:
<221> NAME/KEY: modified_base
<222> LOCATION: (355)..(355)
<223> OTHER INFORMATION: 5-methyl-cytidine
<220> FEATURE:
<221> NAME/KEY: modified_base
<222> LOCATION: (356)..(356)
<223> OTHER INFORMATION: Pseudouridine
<220> FEATURE:
<221> NAME/KEY: modified_base
<222> LOCATION: (357)..(358)
<223> OTHER INFORMATION: 5-methyl-cytidine
<220> FEATURE:
<221> NAME/KEY: modified_base
<222> LOCATION: (359)..(359)
<223> OTHER INFORMATION: Pseudouridine
<220> FEATURE:
<221> NAME/KEY: modified_base
<222> LOCATION: (360)..(360)
<223> OTHER INFORMATION: 5-methyl-cytidine
<220> FEATURE:
<221> NAME/KEY: modified_base
<222> LOCATION: (361)..(361)
<223> OTHER INFORMATION: Pseudouridine
<220> FEATURE:
<221> NAME/KEY: modified_base
<222> LOCATION: (362)..(362)
<223> OTHER INFORMATION: 5-methyl-cytidine
<220> FEATURE:
<221> NAME/KEY: modified_base
<222> LOCATION: (363)..(363)
```

-continued

```
<223> OTHER INFORMATION: Pseudouridine
<220> FEATURE:
<221> NAME/KEY: modified_base
<222> LOCATION: (364)..(364)
<223> OTHER INFORMATION: 5-methyl-cytidine
<220> FEATURE:
<221> NAME/KEY: modified_base
<222> LOCATION: (366)..(366)
<223> OTHER INFORMATION: Pseudouridine
<220> FEATURE:
<221> NAME/KEY: modified_base
<222> LOCATION: (367)..(368)
<223> OTHER INFORMATION: 5-methyl-cytidine
<220> FEATURE:
<221> NAME/KEY: modified_base
<222> LOCATION: (369)..(369)
<223> OTHER INFORMATION: Pseudouridine
<220> FEATURE:
<221> NAME/KEY: modified_base
<222> LOCATION: (371)..(371)
<223> OTHER INFORMATION: Pseudouridine
<220> FEATURE:
<221> NAME/KEY: modified_base
<222> LOCATION: (372)..(373)
<223> OTHER INFORMATION: 5-methyl-cytidine
<220> FEATURE:
<221> NAME/KEY: modified_base
<222> LOCATION: (375)..(375)
<223> OTHER INFORMATION: Pseudouridine
<220> FEATURE:
<221> NAME/KEY: modified_base
<222> LOCATION: (376)..(376)
<223> OTHER INFORMATION: 5-methyl-cytidine
<220> FEATURE:
<221> NAME/KEY: modified_base
<222> LOCATION: (378)..(378)
<223> OTHER INFORMATION: 5-methyl-cytidine
<220> FEATURE:
<221> NAME/KEY: modified_base
<222> LOCATION: (382)..(382)
<223> OTHER INFORMATION: 5-methyl-cytidine
<220> FEATURE:
<221> NAME/KEY: modified_base
<222> LOCATION: (383)..(385)
<223> OTHER INFORMATION: Pseudouridine
<220> FEATURE:
<221> NAME/KEY: modified_base
<222> LOCATION: (387)..(387)
<223> OTHER INFORMATION: 5-methyl-cytidine
<220> FEATURE:
<221> NAME/KEY: modified_base
<222> LOCATION: (390)..(391)
<223> OTHER INFORMATION: Pseudouridine
<220> FEATURE:
<221> NAME/KEY: modified_base
<222> LOCATION: (394)..(394)
<223> OTHER INFORMATION: 5-methyl-cytidine
<220> FEATURE:
<221> NAME/KEY: modified_base
<222> LOCATION: (399)..(399)
<223> OTHER INFORMATION: Pseudouridine
<220> FEATURE:
<221> NAME/KEY: modified_base
<222> LOCATION: (401)..(402)
<223> OTHER INFORMATION: 5-methyl-cytidine
<220> FEATURE:
<221> NAME/KEY: modified_base
<222> LOCATION: (403)..(405)
<223> OTHER INFORMATION: Pseudouridine
<220> FEATURE:
<221> NAME/KEY: modified_base
<222> LOCATION: (406)..(408)
<223> OTHER INFORMATION: 5-methyl-cytidine
<220> FEATURE:
<221> NAME/KEY: modified_base
<222> LOCATION: (411)..(411)
<223> OTHER INFORMATION: 5-methyl-cytidine
<220> FEATURE:
<221> NAME/KEY: modified_base
```

-continued

```
<222> LOCATION: (412)..(412)
<223> OTHER INFORMATION: Pseudouridine
<220> FEATURE:
<221> NAME/KEY: modified_base
<222> LOCATION: (413)..(414)
<223> OTHER INFORMATION: 5-methyl-cytidine
<220> FEATURE:
<221> NAME/KEY: modified_base
<222> LOCATION: (416)..(416)
<223> OTHER INFORMATION: 5-methyl-cytidine
<220> FEATURE:
<221> NAME/KEY: modified_base
<222> LOCATION: (417)..(417)
<223> OTHER INFORMATION: Pseudouridine
<220> FEATURE:
<221> NAME/KEY: modified_base
<222> LOCATION: (418)..(419)
<223> OTHER INFORMATION: 5-methyl-cytidine
<220> FEATURE:
<221> NAME/KEY: modified_base
<222> LOCATION: (422)..(424)
<223> OTHER INFORMATION: Pseudouridine
<220> FEATURE:
<221> NAME/KEY: modified_base
<222> LOCATION: (426)..(427)
<223> OTHER INFORMATION: Pseudouridine
<220> FEATURE:
<221> NAME/KEY: modified_base
<222> LOCATION: (428)..(428)
<223> OTHER INFORMATION: 5-methyl-cytidine
<220> FEATURE:
<221> NAME/KEY: modified_base
<222> LOCATION: (429)..(430)
<223> OTHER INFORMATION: Pseudouridine
<220> FEATURE:
<221> NAME/KEY: modified_base
<222> LOCATION: (432)..(432)
<223> OTHER INFORMATION: Pseudouridine
<220> FEATURE:
<221> NAME/KEY: modified_base
<222> LOCATION: (434)..(434)
<223> OTHER INFORMATION: Pseudouridine
<220> FEATURE:
<221> NAME/KEY: modified_base
<222> LOCATION: (435)..(435)
<223> OTHER INFORMATION: 5-methyl-cytidine
<220> FEATURE:
<221> NAME/KEY: modified_base
<222> LOCATION: (441)..(441)
<223> OTHER INFORMATION: 5-methyl-cytidine
<220> FEATURE:
<221> NAME/KEY: modified_base
<222> LOCATION: (442)..(442)
<223> OTHER INFORMATION: Pseudouridine
<220> FEATURE:
<221> NAME/KEY: modified_base
<222> LOCATION: (444)..(444)
<223> OTHER INFORMATION: 5-methyl-cytidine
<220> FEATURE:
<221> NAME/KEY: modified_base
<222> LOCATION: (445)..(445)
<223> OTHER INFORMATION: Pseudouridine
<220> FEATURE:
<221> NAME/KEY: modified_base
<222> LOCATION: (447)..(447)
<223> OTHER INFORMATION: 5-methyl-cytidine
<220> FEATURE:
<221> NAME/KEY: modified_base
<222> LOCATION: (451)..(453)
<223> OTHER INFORMATION: 5-methyl-cytidine
<220> FEATURE:
<221> NAME/KEY: modified_base
<222> LOCATION: (454)..(455)
<223> OTHER INFORMATION: Pseudouridine
<220> FEATURE:
<221> NAME/KEY: modified_base
<222> LOCATION: (463)..(463)
<223> OTHER INFORMATION: Pseudouridine
<220> FEATURE:
```

```
<221> NAME/KEY: modified_base
<222> LOCATION: (464)..(464)
<223> OTHER INFORMATION: 5-methyl-cytidine
<220> FEATURE:
<221> NAME/KEY: modified_base
<222> LOCATION: (465)..(465)
<223> OTHER INFORMATION: Pseudouridine
<220> FEATURE:
<221> NAME/KEY: modified_base
<222> LOCATION: (466)..(466)
<223> OTHER INFORMATION: 5-methyl-cytidine
<220> FEATURE:
<221> NAME/KEY: modified_base
<222> LOCATION: (468)..(469)
<223> OTHER INFORMATION: 5-methyl-cytidine
<220> FEATURE:
<221> NAME/KEY: modified_base
<222> LOCATION: (474)..(475)
<223> OTHER INFORMATION: Pseudouridine
<220> FEATURE:
<221> NAME/KEY: modified_base
<222> LOCATION: (479)..(481)
<223> OTHER INFORMATION: 5-methyl-cytidine
<220> FEATURE:
<221> NAME/KEY: modified_base
<222> LOCATION: (484)..(484)
<223> OTHER INFORMATION: 5-methyl-cytidine
<220> FEATURE:
<221> NAME/KEY: modified_base
<222> LOCATION: (486)..(486)
<223> OTHER INFORMATION: 5-methyl-cytidine
<220> FEATURE:
<221> NAME/KEY: modified_base
<222> LOCATION: (487)..(487)
<223> OTHER INFORMATION: Pseudouridine
<220> FEATURE:
<221> NAME/KEY: modified_base
<222> LOCATION: (491)..(491)
<223> OTHER INFORMATION: 5-methyl-cytidine
<220> FEATURE:
<221> NAME/KEY: modified_base
<222> LOCATION: (493)..(493)
<223> OTHER INFORMATION: 5-methyl-cytidine
<220> FEATURE:
<221> NAME/KEY: modified_base
<222> LOCATION: (495)..(496)
<223> OTHER INFORMATION: Pseudouridine
<220> FEATURE:
<221> NAME/KEY: modified_base
<222> LOCATION: (498)..(498)
<223> OTHER INFORMATION: 5-methyl-cytidine
<220> FEATURE:
<221> NAME/KEY: modified_base
<222> LOCATION: (501)..(501)
<223> OTHER INFORMATION: 5-methyl-cytidine
<220> FEATURE:
<221> NAME/KEY: modified_base
<222> LOCATION: (502)..(502)
<223> OTHER INFORMATION: Pseudouridine
<220> FEATURE:
<221> NAME/KEY: modified_base
<222> LOCATION: (503)..(503)
<223> OTHER INFORMATION: 5-methyl-cytidine
<220> FEATURE:
<221> NAME/KEY: modified_base
<222> LOCATION: (506)..(506)
<223> OTHER INFORMATION: 5-methyl-cytidine
<220> FEATURE:
<221> NAME/KEY: modified_base
<222> LOCATION: (508)..(508)
<223> OTHER INFORMATION: Pseudouridine
<220> FEATURE:
<221> NAME/KEY: modified_base
<222> LOCATION: (511)..(511)
<223> OTHER INFORMATION: 5-methyl-cytidine
<220> FEATURE:
<221> NAME/KEY: modified_base
<222> LOCATION: (515)..(517)
<223> OTHER INFORMATION: Pseudouridine
```

```
-continued

<220> FEATURE:
<221> NAME/KEY: modified_base
<222> LOCATION: (518)..(518)
<223> OTHER INFORMATION: 5-methyl-cytidine
<220> FEATURE:
<221> NAME/KEY: modified_base
<222> LOCATION: (520)..(520)
<223> OTHER INFORMATION: 5-methyl-cytidine
<220> FEATURE:
<221> NAME/KEY: modified_base
<222> LOCATION: (523)..(523)
<223> OTHER INFORMATION: 5-methyl-cytidine
<220> FEATURE:
<221> NAME/KEY: modified_base
<222> LOCATION: (526)..(527)
<223> OTHER INFORMATION: 5-methyl-cytidine
<220> FEATURE:
<221> NAME/KEY: modified_base
<222> LOCATION: (529)..(529)
<223> OTHER INFORMATION: Pseudouridine
<220> FEATURE:
<221> NAME/KEY: modified_base
<222> LOCATION: (530)..(530)
<223> OTHER INFORMATION: 5-methyl-cytidine
<220> FEATURE:
<221> NAME/KEY: modified_base
<222> LOCATION: (531)..(531)
<223> OTHER INFORMATION: Pseudouridine
<220> FEATURE:
<221> NAME/KEY: modified_base
<222> LOCATION: (534)..(534)
<223> OTHER INFORMATION: 5-methyl-cytidine
<220> FEATURE:
<221> NAME/KEY: modified_base
<222> LOCATION: (537)..(537)
<223> OTHER INFORMATION: 5-methyl-cytidine
<220> FEATURE:
<221> NAME/KEY: modified_base
<222> LOCATION: (541)..(541)
<223> OTHER INFORMATION: Pseudouridine
<220> FEATURE:
<221> NAME/KEY: modified_base
<222> LOCATION: (549)..(549)
<223> OTHER INFORMATION: 5-methyl-cytidine
<220> FEATURE:
<221> NAME/KEY: modified_base
<222> LOCATION: (550)..(550)
<223> OTHER INFORMATION: Pseudouridine
<220> FEATURE:
<221> NAME/KEY: modified_base
<222> LOCATION: (556)..(556)
<223> OTHER INFORMATION: Pseudouridine
<220> FEATURE:
<221> NAME/KEY: modified_base
<222> LOCATION: (559)..(559)
<223> OTHER INFORMATION: 5-methyl-cytidine
<220> FEATURE:
<221> NAME/KEY: modified_base
<222> LOCATION: (561)..(563)
<223> OTHER INFORMATION: 5-methyl-cytidine
<220> FEATURE:
<221> NAME/KEY: modified_base
<222> LOCATION: (565)..(565)
<223> OTHER INFORMATION: 5-methyl-cytidine
<220> FEATURE:
<221> NAME/KEY: modified_base
<222> LOCATION: (567)..(567)
<223> OTHER INFORMATION: 5-methyl-cytidine
<220> FEATURE:
<221> NAME/KEY: modified_base
<222> LOCATION: (568)..(568)
<223> OTHER INFORMATION: Pseudouridine
<220> FEATURE:
<221> NAME/KEY: modified_base
<222> LOCATION: (570)..(570)
<223> OTHER INFORMATION: 5-methyl-cytidine
<220> FEATURE:
<221> NAME/KEY: modified_base
<222> LOCATION: (573)..(575)
```

```
<223> OTHER INFORMATION: 5-methyl-cytidine
<220> FEATURE:
<221> NAME/KEY: modified_base
<222> LOCATION: (577)..(577)
<223> OTHER INFORMATION: 5-methyl-cytidine
<220> FEATURE:
<221> NAME/KEY: modified_base
<222> LOCATION: (579)..(579)
<223> OTHER INFORMATION: 5-methyl-cytidine
<220> FEATURE:
<221> NAME/KEY: modified_base
<222> LOCATION: (586)..(586)
<223> OTHER INFORMATION: 5-methyl-cytidine
<220> FEATURE:
<221> NAME/KEY: modified_base
<222> LOCATION: (589)..(589)
<223> OTHER INFORMATION: Pseudouridine
<220> FEATURE:
<221> NAME/KEY: modified_base
<222> LOCATION: (591)..(592)
<223> OTHER INFORMATION: 5-methyl-cytidine
<220> FEATURE:
<221> NAME/KEY: modified_base
<222> LOCATION: (595)..(596)
<223> OTHER INFORMATION: 5-methyl-cytidine
<220> FEATURE:
<221> NAME/KEY: modified_base
<222> LOCATION: (597)..(599)
<223> OTHER INFORMATION: Pseudouridine
<220> FEATURE:
<221> NAME/KEY: modified_base
<222> LOCATION: (601)..(601)
<223> OTHER INFORMATION: 5-methyl-cytidine
<220> FEATURE:
<221> NAME/KEY: modified_base
<222> LOCATION: (603)..(603)
<223> OTHER INFORMATION: Pseudouridine
<220> FEATURE:
<221> NAME/KEY: modified_base
<222> LOCATION: (604)..(605)
<223> OTHER INFORMATION: 5-methyl-cytidine
<220> FEATURE:
<221> NAME/KEY: modified_base
<222> LOCATION: (607)..(607)
<223> OTHER INFORMATION: 5-methyl-cytidine
<220> FEATURE:
<221> NAME/KEY: modified_base
<222> LOCATION: (609)..(611)
<223> OTHER INFORMATION: Pseudouridine
<220> FEATURE:
<221> NAME/KEY: modified_base
<222> LOCATION: (612)..(612)
<223> OTHER INFORMATION: 5-methyl-cytidine
<220> FEATURE:
<221> NAME/KEY: modified_base
<222> LOCATION: (615)..(615)
<223> OTHER INFORMATION: 5-methyl-cytidine
<220> FEATURE:
<221> NAME/KEY: modified_base
<222> LOCATION: (617)..(617)
<223> OTHER INFORMATION: 5-methyl-cytidine
<220> FEATURE:
<221> NAME/KEY: modified_base
<222> LOCATION: (622)..(622)
<223> OTHER INFORMATION: 5-methyl-cytidine
<220> FEATURE:
<221> NAME/KEY: modified_base
<222> LOCATION: (626)..(626)
<223> OTHER INFORMATION: Pseudouridine
<220> FEATURE:
<221> NAME/KEY: modified_base
<222> LOCATION: (631)..(631)
<223> OTHER INFORMATION: Pseudouridine
<220> FEATURE:
<221> NAME/KEY: modified_base
<222> LOCATION: (632)..(633)
<223> OTHER INFORMATION: 5-methyl-cytidine
<220> FEATURE:
<221> NAME/KEY: modified_base
```

```
<222> LOCATION: (634)..(634)
<223> OTHER INFORMATION: Pseudouridine
<220> FEATURE:
<221> NAME/KEY: modified_base
<222> LOCATION: (635)..(635)
<223> OTHER INFORMATION: 5-methyl-cytidine
<220> FEATURE:
<221> NAME/KEY: modified_base
<222> LOCATION: (637)..(637)
<223> OTHER INFORMATION: Pseudouridine
<220> FEATURE:
<221> NAME/KEY: modified_base
<222> LOCATION: (640)..(640)
<223> OTHER INFORMATION: 5-methyl-cytidine
<220> FEATURE:
<221> NAME/KEY: modified_base
<222> LOCATION: (644)..(645)
<223> OTHER INFORMATION: 5-methyl-cytidine
<220> FEATURE:
<221> NAME/KEY: modified_base
<222> LOCATION: (647)..(648)
<223> OTHER INFORMATION: 5-methyl-cytidine
<220> FEATURE:
<221> NAME/KEY: modified_base
<222> LOCATION: (649)..(650)
<223> OTHER INFORMATION: Pseudouridine
<220> FEATURE:
<221> NAME/KEY: modified_base
<222> LOCATION: (651)..(651)
<223> OTHER INFORMATION: 5-methyl-cytidine
<220> FEATURE:
<221> NAME/KEY: modified_base
<222> LOCATION: (654)..(654)
<223> OTHER INFORMATION: Pseudouridine
<220> FEATURE:
<221> NAME/KEY: modified_base
<222> LOCATION: (655)..(655)
<223> OTHER INFORMATION: 5-methyl-cytidine
<220> FEATURE:
<221> NAME/KEY: modified_base
<222> LOCATION: (657)..(661)
<223> OTHER INFORMATION: Pseudouridine
<220> FEATURE:
<221> NAME/KEY: modified_base
<222> LOCATION: (667)..(667)
<223> OTHER INFORMATION: Pseudouridine
<220> FEATURE:
<221> NAME/KEY: modified_base
<222> LOCATION: (668)..(668)
<223> OTHER INFORMATION: 5-methyl-cytidine
<220> FEATURE:
<221> NAME/KEY: modified_base
<222> LOCATION: (669)..(669)
<223> OTHER INFORMATION: Pseudouridine
<220> FEATURE:
<221> NAME/KEY: modified_base
<222> LOCATION: (670)..(670)
<223> OTHER INFORMATION: 5-methyl-cytidine
<220> FEATURE:
<221> NAME/KEY: modified_base
<222> LOCATION: (672)..(672)
<223> OTHER INFORMATION: Pseudouridine
<220> FEATURE:
<221> NAME/KEY: modified_base
<222> LOCATION: (674)..(675)
<223> OTHER INFORMATION: 5-methyl-cytidine
<220> FEATURE:
<221> NAME/KEY: modified_base
<222> LOCATION: (679)..(679)
<223> OTHER INFORMATION: Pseudouridine
<220> FEATURE:
<221> NAME/KEY: modified_base
<222> LOCATION: (681)..(681)
<223> OTHER INFORMATION: 5-methyl-cytidine
<220> FEATURE:
<221> NAME/KEY: modified_base
<222> LOCATION: (682)..(682)
<223> OTHER INFORMATION: Pseudouridine
<220> FEATURE:
```

```
<221> NAME/KEY: modified_base
<222> LOCATION: (687)..(687)
<223> OTHER INFORMATION: 5-methyl-cytidine
<220> FEATURE:
<221> NAME/KEY: modified_base
<222> LOCATION: (689)..(689)
<223> OTHER INFORMATION: Pseudouridine
<220> FEATURE:
<221> NAME/KEY: modified_base
<222> LOCATION: (690)..(690)
<223> OTHER INFORMATION: 5-methyl-cytidine
<220> FEATURE:
<221> NAME/KEY: modified_base
<222> LOCATION: (691)..(692)
<223> OTHER INFORMATION: Pseudouridine
<220> FEATURE:
<221> NAME/KEY: modified_base
<222> LOCATION: (694)..(694)
<223> OTHER INFORMATION: 5-methyl-cytidine
<220> FEATURE:
<221> NAME/KEY: modified_base
<222> LOCATION: (696)..(696)
<223> OTHER INFORMATION: 5-methyl-cytidine
<220> FEATURE:
<221> NAME/KEY: modified_base
<222> LOCATION: (699)..(700)
<223> OTHER INFORMATION: 5-methyl-cytidine
<220> FEATURE:
<221> NAME/KEY: modified_base
<222> LOCATION: (702)..(702)
<223> OTHER INFORMATION: Pseudouridine
<220> FEATURE:
<221> NAME/KEY: modified_base
<222> LOCATION: (707)..(707)
<223> OTHER INFORMATION: 5-methyl-cytidine
<220> FEATURE:
<221> NAME/KEY: modified_base
<222> LOCATION: (709)..(709)
<223> OTHER INFORMATION: 5-methyl-cytidine
<220> FEATURE:
<221> NAME/KEY: modified_base
<222> LOCATION: (710)..(710)
<223> OTHER INFORMATION: Pseudouridine
<220> FEATURE:
<221> NAME/KEY: modified_base
<222> LOCATION: (712)..(713)
<223> OTHER INFORMATION: 5-methyl-cytidine
<220> FEATURE:
<221> NAME/KEY: modified_base
<222> LOCATION: (714)..(715)
<223> OTHER INFORMATION: Pseudouridine
<220> FEATURE:
<221> NAME/KEY: modified_base
<222> LOCATION: (716)..(716)
<223> OTHER INFORMATION: 5-methyl-cytidine
<220> FEATURE:
<221> NAME/KEY: modified_base
<222> LOCATION: (717)..(717)
<223> OTHER INFORMATION: Pseudouridine
<220> FEATURE:
<221> NAME/KEY: modified_base
<222> LOCATION: (719)..(719)
<223> OTHER INFORMATION: 5-methyl-cytidine
<220> FEATURE:
<221> NAME/KEY: modified_base
<222> LOCATION: (724)..(724)
<223> OTHER INFORMATION: 5-methyl-cytidine
<220> FEATURE:
<221> NAME/KEY: modified_base
<222> LOCATION: (725)..(726)
<223> OTHER INFORMATION: Pseudouridine
<220> FEATURE:
<221> NAME/KEY: modified_base
<222> LOCATION: (728)..(729)
<223> OTHER INFORMATION: 5-methyl-cytidine
<220> FEATURE:
<221> NAME/KEY: modified_base
<222> LOCATION: (730)..(731)
<223> OTHER INFORMATION: Pseudouridine
```

```
<220> FEATURE:
<221> NAME/KEY: modified_base
<222> LOCATION: (732)..(732)
<223> OTHER INFORMATION: 5-methyl-cytidine
<220> FEATURE:
<221> NAME/KEY: modified_base
<222> LOCATION: (733)..(733)
<223> OTHER INFORMATION: Pseudouridine
<220> FEATURE:
<221> NAME/KEY: modified_base
<222> LOCATION: (736)..(737)
<223> OTHER INFORMATION: 5-methyl-cytidine
<220> FEATURE:
<221> NAME/KEY: modified_base
<222> LOCATION: (739)..(739)
<223> OTHER INFORMATION: Pseudouridine
<220> FEATURE:
<221> NAME/KEY: modified_base
<222> LOCATION: (741)..(743)
<223> OTHER INFORMATION: 5-methyl-cytidine
<220> FEATURE:
<221> NAME/KEY: modified_base
<222> LOCATION: (744)..(745)
<223> OTHER INFORMATION: Pseudouridine
<220> FEATURE:
<221> NAME/KEY: modified_base
<222> LOCATION: (746)..(746)
<223> OTHER INFORMATION: 5-methyl-cytidine
<220> FEATURE:
<221> NAME/KEY: modified_base
<222> LOCATION: (747)..(748)
<223> OTHER INFORMATION: Pseudouridine
<220> FEATURE:
<221> NAME/KEY: modified_base
<222> LOCATION: (749)..(749)
<223> OTHER INFORMATION: 5-methyl-cytidine
<220> FEATURE:
<221> NAME/KEY: modified_base
<222> LOCATION: (750)..(750)
<223> OTHER INFORMATION: Pseudouridine
<220> FEATURE:
<221> NAME/KEY: modified_base
<222> LOCATION: (751)..(751)
<223> OTHER INFORMATION: 5-methyl-cytidine
<220> FEATURE:
<221> NAME/KEY: modified_base
<222> LOCATION: (752)..(752)
<223> OTHER INFORMATION: Pseudouridine
<220> FEATURE:
<221> NAME/KEY: modified_base
<222> LOCATION: (753)..(755)
<223> OTHER INFORMATION: 5-methyl-cytidine
<220> FEATURE:
<221> NAME/KEY: modified_base
<222> LOCATION: (756)..(757)
<223> OTHER INFORMATION: Pseudouridine
<220> FEATURE:
<221> NAME/KEY: modified_base
<222> LOCATION: (759)..(759)
<223> OTHER INFORMATION: 5-methyl-cytidine
<220> FEATURE:
<221> NAME/KEY: modified_base
<222> LOCATION: (761)..(762)
<223> OTHER INFORMATION: 5-methyl-cytidine
<220> FEATURE:
<221> NAME/KEY: modified_base
<222> LOCATION: (763)..(763)
<223> OTHER INFORMATION: Pseudouridine
<220> FEATURE:
<221> NAME/KEY: modified_base
<222> LOCATION: (765)..(765)
<223> OTHER INFORMATION: Pseudouridine
<220> FEATURE:
<221> NAME/KEY: modified_base
<222> LOCATION: (767)..(768)
<223> OTHER INFORMATION: 5-methyl-cytidine
<220> FEATURE:
<221> NAME/KEY: modified_base
<222> LOCATION: (769)..(769)
```

```
<223> OTHER INFORMATION: Pseudouridine
<220> FEATURE:
<221> NAME/KEY: modified_base
<222> LOCATION: (770)..(770)
<223> OTHER INFORMATION: 5-methyl-cytidine
<220> FEATURE:
<221> NAME/KEY: modified_base
<222> LOCATION: (771)..(772)
<223> OTHER INFORMATION: Pseudouridine
<220> FEATURE:
<221> NAME/KEY: modified_base
<222> LOCATION: (775)..(775)
<223> OTHER INFORMATION: Pseudouridine
<220> FEATURE:
<221> NAME/KEY: modified_base
<222> LOCATION: (776)..(776)
<223> OTHER INFORMATION: 5-methyl-cytidine
<220> FEATURE:
<221> NAME/KEY: modified_base
<222> LOCATION: (777)..(779)
<223> OTHER INFORMATION: Pseudouridine
<220> FEATURE:
<221> NAME/KEY: modified_base
<222> LOCATION: (783)..(783)
<223> OTHER INFORMATION: Pseudouridine
<220> FEATURE:
<221> NAME/KEY: modified_base
<222> LOCATION: (788)..(789)
<223> OTHER INFORMATION: 5-methyl-cytidine
<220> FEATURE:
<221> NAME/KEY: modified_base
<222> LOCATION: (790)..(790)
<223> OTHER INFORMATION: Pseudouridine
<220> FEATURE:
<221> NAME/KEY: modified_base
<222> LOCATION: (794)..(794)
<223> OTHER INFORMATION: Pseudouridine
<220> FEATURE:
<221> NAME/KEY: modified_base
<222> LOCATION: (802)..(802)
<223> OTHER INFORMATION: 5-methyl-cytidine
<220> FEATURE:
<221> NAME/KEY: modified_base
<222> LOCATION: (805)..(806)
<223> OTHER INFORMATION: 5-methyl-cytidine
<220> FEATURE:
<221> NAME/KEY: modified_base
<222> LOCATION: (808)..(808)
<223> OTHER INFORMATION: 5-methyl-cytidine
<220> FEATURE:
<221> NAME/KEY: modified_base
<222> LOCATION: (809)..(809)
<223> OTHER INFORMATION: Pseudouridine
<220> FEATURE:
<221> NAME/KEY: modified_base
<222> LOCATION: (810)..(810)
<223> OTHER INFORMATION: 5-methyl-cytidine
<220> FEATURE:
<221> NAME/KEY: modified_base
<222> LOCATION: (814)..(814)
<223> OTHER INFORMATION: 5-methyl-cytidine
<220> FEATURE:
<221> NAME/KEY: modified_base
<222> LOCATION: (816)..(816)
<223> OTHER INFORMATION: Pseudouridine
<220> FEATURE:
<221> NAME/KEY: modified_base
<222> LOCATION: (818)..(818)
<223> OTHER INFORMATION: 5-methyl-cytidine
<220> FEATURE:
<221> NAME/KEY: modified_base
<222> LOCATION: (820)..(820)
<223> OTHER INFORMATION: Pseudouridine
<220> FEATURE:
<221> NAME/KEY: modified_base
<222> LOCATION: (821)..(821)
<223> OTHER INFORMATION: 5-methyl-cytidine
<220> FEATURE:
<221> NAME/KEY: modified_base
```

```
<222> LOCATION: (822)..(822)
<223> OTHER INFORMATION: Pseudouridine
<220> FEATURE:
<221> NAME/KEY: modified_base
<222> LOCATION: (829)..(831)
<223> OTHER INFORMATION: 5-methyl-cytidine
<220> FEATURE:
<221> NAME/KEY: modified_base
<222> LOCATION: (834)..(835)
<223> OTHER INFORMATION: Pseudouridine
<220> FEATURE:
<221> NAME/KEY: modified_base
<222> LOCATION: (836)..(836)
<223> OTHER INFORMATION: 5-methyl-cytidine
<220> FEATURE:
<221> NAME/KEY: modified_base
<222> LOCATION: (838)..(840)
<223> OTHER INFORMATION: 5-methyl-cytidine
<220> FEATURE:
<221> NAME/KEY: modified_base
<222> LOCATION: (841)..(841)
<223> OTHER INFORMATION: Pseudouridine
<220> FEATURE:
<221> NAME/KEY: modified_base
<222> LOCATION: (843)..(844)
<223> OTHER INFORMATION: Pseudouridine
<220> FEATURE:
<221> NAME/KEY: modified_base
<222> LOCATION: (845)..(845)
<223> OTHER INFORMATION: 5-methyl-cytidine
<220> FEATURE:
<221> NAME/KEY: modified_base
<222> LOCATION: (850)..(850)
<223> OTHER INFORMATION: Pseudouridine
<220> FEATURE:
<221> NAME/KEY: modified_base
<222> LOCATION: (851)..(851)
<223> OTHER INFORMATION: 5-methyl-cytidine

<400> SEQUENCE: 18
agcuuuugga cccucguaca gaagcuaaua cgacucacua uagggaaaua agagagaaaa      60
gaagaguaag aagaaauaua agagccacca uggccgqucc cgcgacccaa agccccauga     120
aacuuauggc ccugcaguug cugcuuuggc acucggcccu cuggacaguc caagaagcga     180
cuccucucgg accugccuca ucguugccgc agucauuccu uuugaagugu cuggagcagg     240
ugcgaaagau ucagggcgau ggagccgcac uccaagagaa gcucugcgcg acauacaaac     300
uuugccaucc cgaggagcuc guacugcucg ggcacagcuu ggggauuccc ugggcuccuc     360
ucucguccug uccgucgcag gcuuugcagu uggcagggug ccuuucccag cuccacuccg     420
guuuguucuu guaucaggga cugcugcaag cccuugaggg aaucucgcca gaauugggcc     480
cgacgcugga cacguugcag cucgacgugg cggauuucgc aacaaccauc uggcagcaga     540
uggaggaacu ggggauggca cccgcgcugc agcccacgca gggggcaaug ccggccuuug     600
cguccgcguu ucagcgcagg gcggguggag uccucguagc gagccaccuu caaucauuuu     660
uggaagucuc guaccggguy cugagacauc uugcgcagcc gugaagcgcu gccuucugcg     720
gggcuugccu ucuggccaug cccuucuucu cucccuugca ccuguaccuc uuggucuuug     780
aauaaagccu gaguaggaag gcggccgcuc gagcaugcau cuagagggcc caauucgccc     840
uauucgaagu cg                                                        852

<210> SEQ ID NO 19
<211> LENGTH: 437
<212> TYPE: RNA
<213> ORGANISM: Homo sapiens

<400> SEQUENCE: 19
```

```
aagcuuuugg acccucguac agaagcuaau acgacucacu auagggaaau aagagagaaa      60
agaagaguaa gaagaaauau aagagccacc augccuagau cauguuguuc acgaucggga     120
gcguuguugc uggcacucuu gcuccaagcc ucgauggaag ugcggggaug gugccuugag     180
agcucccagu gccaggaccu cacaacggag ucgaaccuuc uggaaugcau ccgcgcgugu     240
aaaccgaggg aagguaaaag guccuacagc auggagcacu ucagauggggg gaagcccguc   300 gggaagaagc ggugaagcgc ugccuucugc ggggcuugcc uucuggccau gcccuucuuc     360
ucucccuugc accuguaccu cuuggucuuu gaauaaagcc ugauaggaa ggcggccgcu     420 cgagcaugca ucuagag                                                    437
```

```
<210> SEQ ID NO 20
<211> LENGTH: 437
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(4)
<223> OTHER INFORMATION: 5-methyl-cytidine
<220> FEATURE:
<221> NAME/KEY: modified_base
<222> LOCATION: (5)..(8)
<223> OTHER INFORMATION: Pseudouridine
<220> FEATURE:
<221> NAME/KEY: modified_base
<222> LOCATION: (12)..(14)
<223> OTHER INFORMATION: 5-methyl-cytidine
<220> FEATURE:
<221> NAME/KEY: modified_base
<222> LOCATION: (15)..(15)
<223> OTHER INFORMATION: Pseudouridine
<220> FEATURE:
<221> NAME/KEY: modified_base
<222> LOCATION: (16)..(16)
<223> OTHER INFORMATION: 5-methyl-cytidine
<220> FEATURE:
<221> NAME/KEY: modified_base
<222> LOCATION: (18)..(18)
<223> OTHER INFORMATION: Pseudouridine
<220> FEATURE:
<221> NAME/KEY: modified_base
<222> LOCATION: (20)..(20)
<223> OTHER INFORMATION: 5-methyl-cytidine
<220> FEATURE:
<221> NAME/KEY: modified_base
<222> LOCATION: (26)..(26)
<223> OTHER INFORMATION: 5-methyl-cytidine
<220> FEATURE:
<221> NAME/KEY: modified_base
<222> LOCATION: (27)..(27)
<223> OTHER INFORMATION: Pseudouridine
<220> FEATURE:
<221> NAME/KEY: modified_base
<222> LOCATION: (30)..(30)
<223> OTHER INFORMATION: Pseudouridine
<220> FEATURE:
<221> NAME/KEY: modified_base
<222> LOCATION: (32)..(32)
<223> OTHER INFORMATION: 5-methyl-cytidine
<220> FEATURE:
<221> NAME/KEY: modified_base
<222> LOCATION: (35)..(35)
<223> OTHER INFORMATION: 5-methyl-cytidine
<220> FEATURE:
<221> NAME/KEY: modified_base
<222> LOCATION: (36)..(36)
<223> OTHER INFORMATION: Pseudouridine
<220> FEATURE:
<221> NAME/KEY: modified_base
<222> LOCATION: (37)..(37)
```

```
<223> OTHER INFORMATION: 5-methyl-cytidine
<220> FEATURE:
<221> NAME/KEY: modified_base
<222> LOCATION: (39)..(39)
<223> OTHER INFORMATION: 5-methyl-cytidine
<220> FEATURE:
<221> NAME/KEY: modified_base
<222> LOCATION: (40)..(40)
<223> OTHER INFORMATION: Pseudouridine
<220> FEATURE:
<221> NAME/KEY: modified_base
<222> LOCATION: (42)..(42)
<223> OTHER INFORMATION: Pseudouridine
<220> FEATURE:
<221> NAME/KEY: modified_base
<222> LOCATION: (50)..(50)
<223> OTHER INFORMATION: Pseudouridine
<220> FEATURE:
<221> NAME/KEY: modified_base
<222> LOCATION: (68)..(68)
<223> OTHER INFORMATION: Pseudouridine
<220> FEATURE:
<221> NAME/KEY: modified_base
<222> LOCATION: (78)..(78)
<223> OTHER INFORMATION: Pseudouridine
<220> FEATURE:
<221> NAME/KEY: modified_base
<222> LOCATION: (80)..(80)
<223> OTHER INFORMATION: Pseudouridine
<220> FEATURE:
<221> NAME/KEY: modified_base
<222> LOCATION: (86)..(87)
<223> OTHER INFORMATION: 5-methyl-cytidine
<220> FEATURE:
<221> NAME/KEY: modified_base
<222> LOCATION: (89)..(90)
<223> OTHER INFORMATION: 5-methyl-cytidine
<220> FEATURE:
<221> NAME/KEY: modified_base
<222> LOCATION: (92)..(92)
<223> OTHER INFORMATION: Pseudouridine
<220> FEATURE:
<221> NAME/KEY: modified_base
<222> LOCATION: (94)..(95)
<223> OTHER INFORMATION: 5-methyl-cytidine
<220> FEATURE:
<221> NAME/KEY: modified_base
<222> LOCATION: (96)..(96)
<223> OTHER INFORMATION: Pseudouridine
<220> FEATURE:
<221> NAME/KEY: modified_base
<222> LOCATION: (100)..(100)
<223> OTHER INFORMATION: Pseudouridine
<220> FEATURE:
<221> NAME/KEY: modified_base
<222> LOCATION: (101)..(101)
<223> OTHER INFORMATION: 5-methyl-cytidine
<220> FEATURE:
<221> NAME/KEY: modified_base
<222> LOCATION: (103)..(103)
<223> OTHER INFORMATION: Pseudouridine
<220> FEATURE:
<221> NAME/KEY: modified_base
<222> LOCATION: (105)..(106)
<223> OTHER INFORMATION: Pseudouridine
<220> FEATURE:
<221> NAME/KEY: modified_base
<222> LOCATION: (108)..(109)
<223> OTHER INFORMATION: Pseudouridine
<220> FEATURE:
<221> NAME/KEY: modified_base
<222> LOCATION: (110)..(110)
<223> OTHER INFORMATION: 5-methyl-cytidine
<220> FEATURE:
<221> NAME/KEY: modified_base
<222> LOCATION: (112)..(112)
<223> OTHER INFORMATION: 5-methyl-cytidine
<220> FEATURE:
<221> NAME/KEY: modified_base
```

```
<222> LOCATION: (115)..(115)
<223> OTHER INFORMATION: Pseudouridine
<220> FEATURE:
<221> NAME/KEY: modified_base
<222> LOCATION: (116)..(116)
<223> OTHER INFORMATION: 5-methyl-cytidine
<220> FEATURE:
<221> NAME/KEY: modified_base
<222> LOCATION: (122)..(122)
<223> OTHER INFORMATION: 5-methyl-cytidine
<220> FEATURE:
<221> NAME/KEY: modified_base
<222> LOCATION: (124)..(125)
<223> OTHER INFORMATION: Pseudouridine
<220> FEATURE:
<221> NAME/KEY: modified_base
<222> LOCATION: (127)..(128)
<223> OTHER INFORMATION: Pseudouridine
<220> FEATURE:
<221> NAME/KEY: modified_base
<222> LOCATION: (130)..(130)
<223> OTHER INFORMATION: 5-methyl-cytidine
<220> FEATURE:
<221> NAME/KEY: modified_base
<222> LOCATION: (131)..(131)
<223> OTHER INFORMATION: Pseudouridine
<220> FEATURE:
<221> NAME/KEY: modified_base
<222> LOCATION: (134)..(134)
<223> OTHER INFORMATION: 5-methyl-cytidine
<220> FEATURE:
<221> NAME/KEY: modified_base
<222> LOCATION: (136)..(136)
<223> OTHER INFORMATION: 5-methyl-cytidine
<220> FEATURE:
<221> NAME/KEY: modified_base
<222> LOCATION: (137)..(137)
<223> OTHER INFORMATION: Pseudouridine
<220> FEATURE:
<221> NAME/KEY: modified_base
<222> LOCATION: (138)..(138)
<223> OTHER INFORMATION: 5-methyl-cytidine
<220> FEATURE:
<221> NAME/KEY: modified_base
<222> LOCATION: (139)..(140)
<223> OTHER INFORMATION: Pseudouridine
<220> FEATURE:
<221> NAME/KEY: modified_base
<222> LOCATION: (142)..(142)
<223> OTHER INFORMATION: 5-methyl-cytidine
<220> FEATURE:
<221> NAME/KEY: modified_base
<222> LOCATION: (143)..(143)
<223> OTHER INFORMATION: Pseudouridine
<220> FEATURE:
<221> NAME/KEY: modified_base
<222> LOCATION: (144)..(145)
<223> OTHER INFORMATION: 5-methyl-cytidine
<220> FEATURE:
<221> NAME/KEY: modified_base
<222> LOCATION: (149)..(150)
<223> OTHER INFORMATION: 5-methyl-cytidine
<220> FEATURE:
<221> NAME/KEY: modified_base
<222> LOCATION: (151)..(151)
<223> OTHER INFORMATION: Pseudouridine
<220> FEATURE:
<221> NAME/KEY: modified_base
<222> LOCATION: (152)..(152)
<223> OTHER INFORMATION: 5-methyl-cytidine
<220> FEATURE:
<221> NAME/KEY: modified_base
<222> LOCATION: (155)..(155)
<223> OTHER INFORMATION: Pseudouridine
<220> FEATURE:
<221> NAME/KEY: modified_base
<222> LOCATION: (161)..(161)
<223> OTHER INFORMATION: Pseudouridine
<220> FEATURE:
```

```
<221> NAME/KEY: modified_base
<222> LOCATION: (163)..(163)
<223> OTHER INFORMATION: 5-methyl-cytidine
<220> FEATURE:
<221> NAME/KEY: modified_base
<222> LOCATION: (169)..(169)
<223> OTHER INFORMATION: Pseudouridine
<220> FEATURE:
<221> NAME/KEY: modified_base
<222> LOCATION: (172)..(172)
<223> OTHER INFORMATION: Pseudouridine
<220> FEATURE:
<221> NAME/KEY: modified_base
<222> LOCATION: (174)..(175)
<223> OTHER INFORMATION: 5-methyl-cytidine
<220> FEATURE:
<221> NAME/KEY: modified_base
<222> LOCATION: (176)..(177)
<223> OTHER INFORMATION: Pseudouridine
<220> FEATURE:
<221> NAME/KEY: modified_base
<222> LOCATION: (183)..(183)
<223> OTHER INFORMATION: 5-methyl-cytidine
<220> FEATURE:
<221> NAME/KEY: modified_base
<222> LOCATION: (184)..(184)
<223> OTHER INFORMATION: Pseudouridine
<220> FEATURE:
<221> NAME/KEY: modified_base
<222> LOCATION: (185)..(187)
<223> OTHER INFORMATION: 5-methyl-cytidine
<220> FEATURE:
<221> NAME/KEY: modified_base
<222> LOCATION: (190)..(190)
<223> OTHER INFORMATION: Pseudouridine
<220> FEATURE:
<221> NAME/KEY: modified_base
<222> LOCATION: (192)..(193)
<223> OTHER INFORMATION: 5-methyl-cytidine
<220> FEATURE:
<221> NAME/KEY: modified_base
<222> LOCATION: (198)..(199)
<223> OTHER INFORMATION: 5-methyl-cytidine
<220> FEATURE:
<221> NAME/KEY: modified_base
<222> LOCATION: (200)..(200)
<223> OTHER INFORMATION: Pseudouridine
<220> FEATURE:
<221> NAME/KEY: modified_base
<222> LOCATION: (201)..(201)
<223> OTHER INFORMATION: 5-methyl-cytidine
<220> FEATURE:
<221> NAME/KEY: modified_base
<222> LOCATION: (203)..(203)
<223> OTHER INFORMATION: 5-methyl-cytidine
<220> FEATURE:
<221> NAME/KEY: modified_base
<222> LOCATION: (206)..(206)
<223> OTHER INFORMATION: 5-methyl-cytidine
<220> FEATURE:
<221> NAME/KEY: modified_base
<222> LOCATION: (211)..(211)
<223> OTHER INFORMATION: Pseudouridine
<220> FEATURE:
<221> NAME/KEY: modified_base
<222> LOCATION: (212)..(212)
<223> OTHER INFORMATION: 5-methyl-cytidine
<220> FEATURE:
<221> NAME/KEY: modified_base
<222> LOCATION: (216)..(217)
<223> OTHER INFORMATION: 5-methyl-cytidine
<220> FEATURE:
<221> NAME/KEY: modified_base
<222> LOCATION: (218)..(219)
<223> OTHER INFORMATION: Pseudouridine
<220> FEATURE:
<221> NAME/KEY: modified_base
<222> LOCATION: (220)..(220)
<223> OTHER INFORMATION: 5-methyl-cytidine
```

-continued

```
<220> FEATURE:
<221> NAME/KEY: modified_base
<222> LOCATION: (221)..(221)
<223> OTHER INFORMATION: Pseudouridine
<220> FEATURE:
<221> NAME/KEY: modified_base
<222> LOCATION: (226)..(226)
<223> OTHER INFORMATION: Pseudouridine
<220> FEATURE:
<221> NAME/KEY: modified_base
<222> LOCATION: (228)..(228)
<223> OTHER INFORMATION: 5-methyl-cytidine
<220> FEATURE:
<221> NAME/KEY: modified_base
<222> LOCATION: (230)..(230)
<223> OTHER INFORMATION: Pseudouridine
<220> FEATURE:
<221> NAME/KEY: modified_base
<222> LOCATION: (231)..(232)
<223> OTHER INFORMATION: 5-methyl-cytidine
<220> FEATURE:
<221> NAME/KEY: modified_base
<222> LOCATION: (234)..(234)
<223> OTHER INFORMATION: 5-methyl-cytidine
<220> FEATURE:
<221> NAME/KEY: modified_base
<222> LOCATION: (236)..(236)
<223> OTHER INFORMATION: 5-methyl-cytidine
<220> FEATURE:
<221> NAME/KEY: modified_base
<222> LOCATION: (238)..(238)
<223> OTHER INFORMATION: Pseudouridine
<220> FEATURE:
<221> NAME/KEY: modified_base
<222> LOCATION: (240)..(240)
<223> OTHER INFORMATION: Pseudouridine
<220> FEATURE:
<221> NAME/KEY: modified_base
<222> LOCATION: (244)..(245)
<223> OTHER INFORMATION: 5-methyl-cytidine
<220> FEATURE:
<221> NAME/KEY: modified_base
<222> LOCATION: (255)..(255)
<223> OTHER INFORMATION: Pseudouridine
<220> FEATURE:
<221> NAME/KEY: modified_base
<222> LOCATION: (262)..(262)
<223> OTHER INFORMATION: Pseudouridine
<220> FEATURE:
<221> NAME/KEY: modified_base
<222> LOCATION: (263)..(264)
<223> OTHER INFORMATION: 5-methyl-cytidine
<220> FEATURE:
<221> NAME/KEY: modified_base
<222> LOCATION: (265)..(265)
<223> OTHER INFORMATION: Pseudouridine
<220> FEATURE:
<221> NAME/KEY: modified_base
<222> LOCATION: (267)..(267)
<223> OTHER INFORMATION: 5-methyl-cytidine
<220> FEATURE:
<221> NAME/KEY: modified_base
<222> LOCATION: (270)..(270)
<223> OTHER INFORMATION: 5-methyl-cytidine
<220> FEATURE:
<221> NAME/KEY: modified_base
<222> LOCATION: (272)..(272)
<223> OTHER INFORMATION: Pseudouridine
<220> FEATURE:
<221> NAME/KEY: modified_base
<222> LOCATION: (277)..(277)
<223> OTHER INFORMATION: 5-methyl-cytidine
<220> FEATURE:
<221> NAME/KEY: modified_base
<222> LOCATION: (279)..(279)
<223> OTHER INFORMATION: 5-methyl-cytidine
<220> FEATURE:
<221> NAME/KEY: modified_base
<222> LOCATION: (280)..(281)
```

```
<223> OTHER INFORMATION: Pseudouridine
<220> FEATURE:
<221> NAME/KEY: modified_base
<222> LOCATION: (282)..(282)
<223> OTHER INFORMATION: 5-methyl-cytidine
<220> FEATURE:
<221> NAME/KEY: modified_base
<222> LOCATION: (286)..(286)
<223> OTHER INFORMATION: Pseudouridine
<220> FEATURE:
<221> NAME/KEY: modified_base
<222> LOCATION: (295)..(297)
<223> OTHER INFORMATION: 5-methyl-cytidine
<220> FEATURE:
<221> NAME/KEY: modified_base
<222> LOCATION: (299)..(299)
<223> OTHER INFORMATION: Pseudouridine
<220> FEATURE:
<221> NAME/KEY: modified_base
<222> LOCATION: (300)..(300)
<223> OTHER INFORMATION: 5-methyl-cytidine
<220> FEATURE:
<221> NAME/KEY: modified_base
<222> LOCATION: (310)..(310)
<223> OTHER INFORMATION: 5-methyl-cytidine
<220> FEATURE:
<221> NAME/KEY: modified_base
<222> LOCATION: (313)..(313)
<223> OTHER INFORMATION: Pseudouridine
<220> FEATURE:
<221> NAME/KEY: modified_base
<222> LOCATION: (318)..(318)
<223> OTHER INFORMATION: 5-methyl-cytidine
<220> FEATURE:
<221> NAME/KEY: modified_base
<222> LOCATION: (320)..(320)
<223> OTHER INFORMATION: 5-methyl-cytidine
<220> FEATURE:
<221> NAME/KEY: modified_base
<222> LOCATION: (321)..(321)
<223> OTHER INFORMATION: Pseudouridine
<220> FEATURE:
<221> NAME/KEY: modified_base
<222> LOCATION: (323)..(324)
<223> OTHER INFORMATION: 5-methyl-cytidine
<220> FEATURE:
<221> NAME/KEY: modified_base
<222> LOCATION: (325)..(326)
<223> OTHER INFORMATION: Pseudouridine
<220> FEATURE:
<221> NAME/KEY: modified_base
<222> LOCATION: (327)..(327)
<223> OTHER INFORMATION: 5-methyl-cytidine
<220> FEATURE:
<221> NAME/KEY: modified_base
<222> LOCATION: (328)..(328)
<223> OTHER INFORMATION: Pseudouridine
<220> FEATURE:
<221> NAME/KEY: modified_base
<222> LOCATION: (330)..(330)
<223> OTHER INFORMATION: 5-methyl-cytidine
<220> FEATURE:
<221> NAME/KEY: modified_base
<222> LOCATION: (335)..(335)
<223> OTHER INFORMATION: 5-methyl-cytidine
<220> FEATURE:
<221> NAME/KEY: modified_base
<222> LOCATION: (336)..(337)
<223> OTHER INFORMATION: Pseudouridine
<220> FEATURE:
<221> NAME/KEY: modified_base
<222> LOCATION: (339)..(340)
<223> OTHER INFORMATION: 5-methyl-cytidine
<220> FEATURE:
<221> NAME/KEY: modified_base
<222> LOCATION: (341)..(342)
<223> OTHER INFORMATION: Pseudouridine
<220> FEATURE:
<221> NAME/KEY: modified_base
```

```
<222> LOCATION: (343)..(343)
<223> OTHER INFORMATION: 5-methyl-cytidine
<220> FEATURE:
<221> NAME/KEY: modified_base
<222> LOCATION: (344)..(344)
<223> OTHER INFORMATION: Pseudouridine
<220> FEATURE:
<221> NAME/KEY: modified_base
<222> LOCATION: (347)..(348)
<223> OTHER INFORMATION: 5-methyl-cytidine
<220> FEATURE:
<221> NAME/KEY: modified_base
<222> LOCATION: (350)..(350)
<223> OTHER INFORMATION: Pseudouridine
<220> FEATURE:
<221> NAME/KEY: modified_base
<222> LOCATION: (352)..(354)
<223> OTHER INFORMATION: 5-methyl-cytidine
<220> FEATURE:
<221> NAME/KEY: modified_base
<222> LOCATION: (355)..(356)
<223> OTHER INFORMATION: Pseudouridine
<220> FEATURE:
<221> NAME/KEY: modified_base
<222> LOCATION: (357)..(357)
<223> OTHER INFORMATION: 5-methyl-cytidine
<220> FEATURE:
<221> NAME/KEY: modified_base
<222> LOCATION: (358)..(359)
<223> OTHER INFORMATION: Pseudouridine
<220> FEATURE:
<221> NAME/KEY: modified_base
<222> LOCATION: (360)..(360)
<223> OTHER INFORMATION: 5-methyl-cytidine
<220> FEATURE:
<221> NAME/KEY: modified_base
<222> LOCATION: (361)..(361)
<223> OTHER INFORMATION: Pseudouridine
<220> FEATURE:
<221> NAME/KEY: modified_base
<222> LOCATION: (362)..(362)
<223> OTHER INFORMATION: 5-methyl-cytidine
<220> FEATURE:
<221> NAME/KEY: modified_base
<222> LOCATION: (363)..(363)
<223> OTHER INFORMATION: Pseudouridine
<220> FEATURE:
<221> NAME/KEY: modified_base
<222> LOCATION: (364)..(366)
<223> OTHER INFORMATION: 5-methyl-cytidine
<220> FEATURE:
<221> NAME/KEY: modified_base
<222> LOCATION: (367)..(368)
<223> OTHER INFORMATION: Pseudouridine
<220> FEATURE:
<221> NAME/KEY: modified_base
<222> LOCATION: (370)..(370)
<223> OTHER INFORMATION: 5-methyl-cytidine
<220> FEATURE:
<221> NAME/KEY: modified_base
<222> LOCATION: (372)..(373)
<223> OTHER INFORMATION: 5-methyl-cytidine
<220> FEATURE:
<221> NAME/KEY: modified_base
<222> LOCATION: (374)..(374)
<223> OTHER INFORMATION: Pseudouridine
<220> FEATURE:
<221> NAME/KEY: modified_base
<222> LOCATION: (376)..(376)
<223> OTHER INFORMATION: Pseudouridine
<220> FEATURE:
<221> NAME/KEY: modified_base
<222> LOCATION: (378)..(379)
<223> OTHER INFORMATION: 5-methyl-cytidine
<220> FEATURE:
<221> NAME/KEY: modified_base
<222> LOCATION: (380)..(380)
<223> OTHER INFORMATION: Pseudouridine
<220> FEATURE:
```

```
<221> NAME/KEY: modified_base
<222> LOCATION: (381)..(381)
<223> OTHER INFORMATION: 5-methyl-cytidine
<220> FEATURE:
<221> NAME/KEY: modified_base
<222> LOCATION: (382)..(383)
<223> OTHER INFORMATION: Pseudouridine
<220> FEATURE:
<221> NAME/KEY: modified_base
<222> LOCATION: (386)..(386)
<223> OTHER INFORMATION: Pseudouridine
<220> FEATURE:
<221> NAME/KEY: modified_base
<222> LOCATION: (387)..(387)
<223> OTHER INFORMATION: 5-methyl-cytidine
<220> FEATURE:
<221> NAME/KEY: modified_base
<222> LOCATION: (388)..(390)
<223> OTHER INFORMATION: Pseudouridine
<220> FEATURE:
<221> NAME/KEY: modified_base
<222> LOCATION: (394)..(394)
<223> OTHER INFORMATION: Pseudouridine
<220> FEATURE:
<221> NAME/KEY: modified_base
<222> LOCATION: (399)..(400)
<223> OTHER INFORMATION: 5-methyl-cytidine
<220> FEATURE:
<221> NAME/KEY: modified_base
<222> LOCATION: (401)..(401)
<223> OTHER INFORMATION: Pseudouridine
<220> FEATURE:
<221> NAME/KEY: modified_base
<222> LOCATION: (405)..(405)
<223> OTHER INFORMATION: Pseudouridine
<220> FEATURE:
<221> NAME/KEY: modified_base
<222> LOCATION: (413)..(413)
<223> OTHER INFORMATION: 5-methyl-cytidine
<220> FEATURE:
<221> NAME/KEY: modified_base
<222> LOCATION: (416)..(417)
<223> OTHER INFORMATION: 5-methyl-cytidine
<220> FEATURE:
<221> NAME/KEY: modified_base
<222> LOCATION: (419)..(419)
<223> OTHER INFORMATION: 5-methyl-cytidine
<220> FEATURE:
<221> NAME/KEY: modified_base
<222> LOCATION: (420)..(420)
<223> OTHER INFORMATION: Pseudouridine
<220> FEATURE:
<221> NAME/KEY: modified_base
<222> LOCATION: (421)..(421)
<223> OTHER INFORMATION: 5-methyl-cytidine
<220> FEATURE:
<221> NAME/KEY: modified_base
<222> LOCATION: (425)..(425)
<223> OTHER INFORMATION: 5-methyl-cytidine
<220> FEATURE:
<221> NAME/KEY: modified_base
<222> LOCATION: (427)..(427)
<223> OTHER INFORMATION: Pseudouridine
<220> FEATURE:
<221> NAME/KEY: modified_base
<222> LOCATION: (429)..(429)
<223> OTHER INFORMATION: 5-methyl-cytidine
<220> FEATURE:
<221> NAME/KEY: modified_base
<222> LOCATION: (431)..(431)
<223> OTHER INFORMATION: Pseudouridine
<220> FEATURE:
<221> NAME/KEY: modified_base
<222> LOCATION: (432)..(432)
<223> OTHER INFORMATION: 5-methyl-cytidine
<220> FEATURE:
<221> NAME/KEY: modified_base
<222> LOCATION: (433)..(433)
<223> OTHER INFORMATION: Pseudouridine
```

-continued

<400> SEQUENCE: 20
aagcuuuugg acccucguac agaagcuaau acgacucacu auagggaaau aagagagaaa      60
agaagaguaa gaagaaauau aagagccacc augccuagau caguguuuc acgaucggga     120 gcguuguugc uggcacucuu gcuccaagcc ucgauggaag ugcggggaug gugccuugag     180
agcucccagu gccaggaccu cacaacggag ucgaaccuuc uggaaugcau ccgcgcgugu     240
aaaccgaggg aagguaaaag guccuacagc auggagcacu ucagauggg gaagcccguc     300 gggaagaagc ggugaagcgc ugccuucugc ggggcuugcc uucuggccau gcccuucuuc     360
ucucccuugc accuguaccu cuuggucuuu gaauaaagcc ugaguaggaa ggcggccgcu     420
cgagcaugca ucuagag                                                   437

<210> SEQ ID NO 21
<211> LENGTH: 563
<212> TYPE: RNA
<213> ORGANISM: Mus sp.

<400> SEQUENCE: 21
agcuuuugga cccucguaca gaagcuaaua cgacucacua uagggaaaua agagagaaaa      60
gaagaguaag aagaaauaua agagccacca uggcgcucug gugagguuuc ugccuuuguu     120
ggccuugcug uuccucuggg aguccaccc cacacaggcg uuugaagc agcacuugug        180 cgggucgcau cuggguggagg cacuuuaucu cgucugcggc gagcgaggau ucuucuacac    240
cccgaugagc agacgcgaag uggaagaucc gcaagucgcg cagcucgaac uugggggugg    300
ucccggagcc ggagacuugc aaacucucgc ucucgaggua gcgcagcaga acgggguau     360 cguagaccag uguugcacgu cgaucuguuc acuuuaucaa cuugaaacu acuguaauug     420 aagcgcugcc uucgcgggg cuugccuucu ggccaugccc uucuucucuc ccuugcaccu    480
guaccucuug gucuuugaau aaagccugag uaggaaggcg ccgcucgag caugcaucua    540 gagggcccaa uucgcccuau ucg                                           563

<210> SEQ ID NO 22
<211> LENGTH: 563
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: 5-methyl-cytidine
<220> FEATURE:
<221> NAME/KEY: modified_base
<222> LOCATION: (4)..(7)
<223> OTHER INFORMATION: Pseudouridine
<220> FEATURE:
<221> NAME/KEY: modified_base
<222> LOCATION: (11)..(13)
<223> OTHER INFORMATION: 5-methyl-cytidine
<220> FEATURE:
<221> NAME/KEY: modified_base
<222> LOCATION: (14)..(14)
<223> OTHER INFORMATION: Pseudouridine
<220> FEATURE:
<221> NAME/KEY: modified_base
<222> LOCATION: (15)..(15)
<223> OTHER INFORMATION: 5-methyl-cytidine
<220> FEATURE:
<221> NAME/KEY: modified_base
<222> LOCATION: (17)..(17)
<223> OTHER INFORMATION: Pseudouridine -continued

```
<220> FEATURE:
<221> NAME/KEY: modified_base
<222> LOCATION: (19)..(19)
<223> OTHER INFORMATION: 5-methyl-cytidine
<220> FEATURE:
<221> NAME/KEY: modified_base
<222> LOCATION: (25)..(25)
<223> OTHER INFORMATION: 5-methyl-cytidine
<220> FEATURE:
<221> NAME/KEY: modified_base
<222> LOCATION: (26)..(26)
<223> OTHER INFORMATION: Pseudouridine
<220> FEATURE:
<221> NAME/KEY: modified_base
<222> LOCATION: (29)..(29)
<223> OTHER INFORMATION: Pseudouridine
<220> FEATURE:
<221> NAME/KEY: modified_base
<222> LOCATION: (31)..(31)
<223> OTHER INFORMATION: 5-methyl-cytidine
<220> FEATURE:
<221> NAME/KEY: modified_base
<222> LOCATION: (34)..(34)
<223> OTHER INFORMATION: 5-methyl-cytidine
<220> FEATURE:
<221> NAME/KEY: modified_base
<222> LOCATION: (35)..(35)
<223> OTHER INFORMATION: Pseudouridine
<220> FEATURE:
<221> NAME/KEY: modified_base
<222> LOCATION: (36)..(36)
<223> OTHER INFORMATION: 5-methyl-cytidine
<220> FEATURE:
<221> NAME/KEY: modified_base
<222> LOCATION: (38)..(38)
<223> OTHER INFORMATION: 5-methyl-cytidine
<220> FEATURE:
<221> NAME/KEY: modified_base
<222> LOCATION: (39)..(39)
<223> OTHER INFORMATION: Pseudouridine
<220> FEATURE:
<221> NAME/KEY: modified_base
<222> LOCATION: (41)..(41)
<223> OTHER INFORMATION: Pseudouridine
<220> FEATURE:
<221> NAME/KEY: modified_base
<222> LOCATION: (49)..(49)
<223> OTHER INFORMATION: Pseudouridine
<220> FEATURE:
<221> NAME/KEY: modified_base
<222> LOCATION: (67)..(67)
<223> OTHER INFORMATION: Pseudouridine
<220> FEATURE:
<221> NAME/KEY: modified_base
<222> LOCATION: (77)..(77)
<223> OTHER INFORMATION: Pseudouridine
<220> FEATURE:
<221> NAME/KEY: modified_base
<222> LOCATION: (79)..(79)
<223> OTHER INFORMATION: Pseudouridine
<220> FEATURE:
<221> NAME/KEY: modified_base
<222> LOCATION: (85)..(86)
<223> OTHER INFORMATION: 5-methyl-cytidine
<220> FEATURE:
<221> NAME/KEY: modified_base
<222> LOCATION: (88)..(89)
<223> OTHER INFORMATION: 5-methyl-cytidine
<220> FEATURE:
<221> NAME/KEY: modified_base
<222> LOCATION: (91)..(91)
<223> OTHER INFORMATION: Pseudouridine
<220> FEATURE:
<221> NAME/KEY: modified_base
<222> LOCATION: (94)..(94)
<223> OTHER INFORMATION: 5-methyl-cytidine
<220> FEATURE:
<221> NAME/KEY: modified_base
<222> LOCATION: (96)..(96)
```

```
<223> OTHER INFORMATION: 5-methyl-cytidine
<220> FEATURE:
<221> NAME/KEY: modified_base
<222> LOCATION: (97)..(97)
<223> OTHER INFORMATION: Pseudouridine
<220> FEATURE:
<221> NAME/KEY: modified_base
<222> LOCATION: (98)..(98)
<223> OTHER INFORMATION: 5-methyl-cytidine
<220> FEATURE:
<221> NAME/KEY: modified_base
<222> LOCATION: (99)..(99)
<223> OTHER INFORMATION: Pseudouridine
<220> FEATURE:
<221> NAME/KEY: modified_base
<222> LOCATION: (102)..(102)
<223> OTHER INFORMATION: Pseudouridine
<220> FEATURE:
<221> NAME/KEY: modified_base
<222> LOCATION: (107)..(109)
<223> OTHER INFORMATION: Pseudouridine
<220> FEATURE:
<221> NAME/KEY: modified_base
<222> LOCATION: (110)..(110)
<223> OTHER INFORMATION: 5-methyl-cytidine
<220> FEATURE:
<221> NAME/KEY: modified_base
<222> LOCATION: (111)..(111)
<223> OTHER INFORMATION: Pseudouridine
<220> FEATURE:
<221> NAME/KEY: modified_base
<222> LOCATION: (113)..(114)
<223> OTHER INFORMATION: 5-methyl-cytidine
<220> FEATURE:
<221> NAME/KEY: modified_base
<222> LOCATION: (115)..(117)
<223> OTHER INFORMATION: Pseudouridine
<220> FEATURE:
<221> NAME/KEY: modified_base
<222> LOCATION: (119)..(120)
<223> OTHER INFORMATION: Pseudouridine
<220> FEATURE:
<221> NAME/KEY: modified_base
<222> LOCATION: (123)..(124)
<223> OTHER INFORMATION: 5-methyl-cytidine
<220> FEATURE:
<221> NAME/KEY: modified_base
<222> LOCATION: (125)..(126)
<223> OTHER INFORMATION: Pseudouridine
<220> FEATURE:
<221> NAME/KEY: modified_base
<222> LOCATION: (128)..(128)
<223> OTHER INFORMATION: 5-methyl-cytidine
<220> FEATURE:
<221> NAME/KEY: modified_base
<222> LOCATION: (129)..(129)
<223> OTHER INFORMATION: Pseudouridine
<220> FEATURE:
<221> NAME/KEY: modified_base
<222> LOCATION: (131)..(132)
<223> OTHER INFORMATION: Pseudouridine
<220> FEATURE:
<221> NAME/KEY: modified_base
<222> LOCATION: (133)..(134)
<223> OTHER INFORMATION: 5-methyl-cytidine
<220> FEATURE:
<221> NAME/KEY: modified_base
<222> LOCATION: (135)..(135)
<223> OTHER INFORMATION: Pseudouridine
<220> FEATURE:
<221> NAME/KEY: modified_base
<222> LOCATION: (136)..(136)
<223> OTHER INFORMATION: 5-methyl-cytidine
<220> FEATURE:
<221> NAME/KEY: modified_base
<222> LOCATION: (137)..(137)
<223> OTHER INFORMATION: Pseudouridine
<220> FEATURE:
<221> NAME/KEY: modified_base
```

```
<222> LOCATION: (143)..(143)
<223> OTHER INFORMATION: Pseudouridine
<220> FEATURE:
<221> NAME/KEY: modified_base
<222> LOCATION: (144)..(146)
<223> OTHER INFORMATION: 5-methyl-cytidine
<220> FEATURE:
<221> NAME/KEY: modified_base
<222> LOCATION: (148)..(151)
<223> OTHER INFORMATION: 5-methyl-cytidine
<220> FEATURE:
<221> NAME/KEY: modified_base
<222> LOCATION: (153)..(153)
<223> OTHER INFORMATION: 5-methyl-cytidine
<220> FEATURE:
<221> NAME/KEY: modified_base
<222> LOCATION: (155)..(155)
<223> OTHER INFORMATION: 5-methyl-cytidine
<220> FEATURE:
<221> NAME/KEY: modified_base
<222> LOCATION: (159)..(159)
<223> OTHER INFORMATION: 5-methyl-cytidine
<220> FEATURE:
<221> NAME/KEY: modified_base
<222> LOCATION: (161)..(163)
<223> OTHER INFORMATION: Pseudouridine
<220> FEATURE:
<221> NAME/KEY: modified_base
<222> LOCATION: (165)..(165)
<223> OTHER INFORMATION: Pseudouridine
<220> FEATURE:
<221> NAME/KEY: modified_base
<222> LOCATION: (170)..(170)
<223> OTHER INFORMATION: 5-methyl-cytidine
<220> FEATURE:
<221> NAME/KEY: modified_base
<222> LOCATION: (173)..(173)
<223> OTHER INFORMATION: 5-methyl-cytidine
<220> FEATURE:
<221> NAME/KEY: modified_base
<222> LOCATION: (175)..(175)
<223> OTHER INFORMATION: 5-methyl-cytidine
<220> FEATURE:
<221> NAME/KEY: modified_base
<222> LOCATION: (176)..(177)
<223> OTHER INFORMATION: Pseudouridine
<220> FEATURE:
<221> NAME/KEY: modified_base
<222> LOCATION: (179)..(179)
<223> OTHER INFORMATION: Pseudouridine
<220> FEATURE:
<221> NAME/KEY: modified_base
<222> LOCATION: (181)..(181)
<223> OTHER INFORMATION: 5-methyl-cytidine
<220> FEATURE:
<221> NAME/KEY: modified_base
<222> LOCATION: (185)..(185)
<223> OTHER INFORMATION: Pseudouridine
<220> FEATURE:
<221> NAME/KEY: modified_base
<222> LOCATION: (186)..(186)
<223> OTHER INFORMATION: 5-methyl-cytidine
<220> FEATURE:
<221> NAME/KEY: modified_base
<222> LOCATION: (188)..(188)
<223> OTHER INFORMATION: 5-methyl-cytidine
<220> FEATURE:
<221> NAME/KEY: modified_base
<222> LOCATION: (190)..(190)
<223> OTHER INFORMATION: Pseudouridine
<220> FEATURE:
<221> NAME/KEY: modified_base
<222> LOCATION: (191)..(191)
<223> OTHER INFORMATION: 5-methyl-cytidine
<220> FEATURE:
<221> NAME/KEY: modified_base
<222> LOCATION: (192)..(192)
<223> OTHER INFORMATION: Pseudouridine
<220> FEATURE:
```

```
<221> NAME/KEY: modified_base
<222> LOCATION: (195)..(195)
<223> OTHER INFORMATION: Pseudouridine
<220> FEATURE:
<221> NAME/KEY: modified_base
<222> LOCATION: (201)..(201)
<223> OTHER INFORMATION: 5-methyl-cytidine
<220> FEATURE:
<221> NAME/KEY: modified_base
<222> LOCATION: (203)..(203)
<223> OTHER INFORMATION: 5-methyl-cytidine
<220> FEATURE:
<221> NAME/KEY: modified_base
<222> LOCATION: (204)..(206)
<223> OTHER INFORMATION: Pseudouridine
<220> FEATURE:
<221> NAME/KEY: modified_base
<222> LOCATION: (208)..(208)
<223> OTHER INFORMATION: Pseudouridine
<220> FEATURE:
<221> NAME/KEY: modified_base
<222> LOCATION: (209)..(209)
<223> OTHER INFORMATION: 5-methyl-cytidine
<220> FEATURE:
<221> NAME/KEY: modified_base
<222> LOCATION: (210)..(210)
<223> OTHER INFORMATION: Pseudouridine
<220> FEATURE:
<221> NAME/KEY: modified_base
<222> LOCATION: (211)..(211)
<223> OTHER INFORMATION: 5-methyl-cytidine
<220> FEATURE:
<221> NAME/KEY: modified_base
<222> LOCATION: (213)..(213)
<223> OTHER INFORMATION: Pseudouridine
<220> FEATURE:
<221> NAME/KEY: modified_base
<222> LOCATION: (214)..(214)
<223> OTHER INFORMATION: 5-methyl-cytidine
<220> FEATURE:
<221> NAME/KEY: modified_base
<222> LOCATION: (215)..(215)
<223> OTHER INFORMATION: Pseudouridine
<220> FEATURE:
<221> NAME/KEY: modified_base
<222> LOCATION: (217)..(217)
<223> OTHER INFORMATION: 5-methyl-cytidine
<220> FEATURE:
<221> NAME/KEY: modified_base
<222> LOCATION: (220)..(220)
<223> OTHER INFORMATION: 5-methyl-cytidine
<220> FEATURE:
<221> NAME/KEY: modified_base
<222> LOCATION: (224)..(224)
<223> OTHER INFORMATION: 5-methyl-cytidine
<220> FEATURE:
<221> NAME/KEY: modified_base
<222> LOCATION: (230)..(231)
<223> OTHER INFORMATION: Pseudouridine
<220> FEATURE:
<221> NAME/KEY: modified_base
<222> LOCATION: (232)..(232)
<223> OTHER INFORMATION: 5-methyl-cytidine
<220> FEATURE:
<221> NAME/KEY: modified_base
<222> LOCATION: (233)..(234)
<223> OTHER INFORMATION: Pseudouridine
<220> FEATURE:
<221> NAME/KEY: modified_base
<222> LOCATION: (235)..(235)
<223> OTHER INFORMATION: 5-methyl-cytidine
<220> FEATURE:
<221> NAME/KEY: modified_base
<222> LOCATION: (236)..(236)
<223> OTHER INFORMATION: Pseudouridine
<220> FEATURE:
<221> NAME/KEY: modified_base
<222> LOCATION: (238)..(238)
<223> OTHER INFORMATION: 5-methyl-cytidine
```

```
<220> FEATURE:
<221> NAME/KEY: modified_base
<222> LOCATION: (240)..(243)
<223> OTHER INFORMATION: 5-methyl-cytidine
<220> FEATURE:
<221> NAME/KEY: modified_base
<222> LOCATION: (246)..(246)
<223> OTHER INFORMATION: Pseudouridine
<220> FEATURE:
<221> NAME/KEY: modified_base
<222> LOCATION: (250)..(250)
<223> OTHER INFORMATION: 5-methyl-cytidine
<220> FEATURE:
<221> NAME/KEY: modified_base
<222> LOCATION: (254)..(254)
<223> OTHER INFORMATION: 5-methyl-cytidine
<220> FEATURE:
<221> NAME/KEY: modified_base
<222> LOCATION: (256)..(256)
<223> OTHER INFORMATION: 5-methyl-cytidine
<220> FEATURE:
<221> NAME/KEY: modified_base
<222> LOCATION: (261)..(261)
<223> OTHER INFORMATION: Pseudouridine
<220> FEATURE:
<221> NAME/KEY: modified_base
<222> LOCATION: (268)..(268)
<223> OTHER INFORMATION: Pseudouridine
<220> FEATURE:
<221> NAME/KEY: modified_base
<222> LOCATION: (269)..(270)
<223> OTHER INFORMATION: 5-methyl-cytidine
<220> FEATURE:
<221> NAME/KEY: modified_base
<222> LOCATION: (272)..(272)
<223> OTHER INFORMATION: 5-methyl-cytidine
<220> FEATURE:
<221> NAME/KEY: modified_base
<222> LOCATION: (276)..(276)
<223> OTHER INFORMATION: Pseudouridine
<220> FEATURE:
<221> NAME/KEY: modified_base
<222> LOCATION: (277)..(277)
<223> OTHER INFORMATION: 5-methyl-cytidine
<220> FEATURE:
<221> NAME/KEY: modified_base
<222> LOCATION: (279)..(279)
<223> OTHER INFORMATION: 5-methyl-cytidine
<220> FEATURE:
<221> NAME/KEY: modified_base
<222> LOCATION: (281)..(281)
<223> OTHER INFORMATION: 5-methyl-cytidine
<220> FEATURE:
<221> NAME/KEY: modified_base
<222> LOCATION: (284)..(284)
<223> OTHER INFORMATION: 5-methyl-cytidine
<220> FEATURE:
<221> NAME/KEY: modified_base
<222> LOCATION: (285)..(285)
<223> OTHER INFORMATION: Pseudouridine
<220> FEATURE:
<221> NAME/KEY: modified_base
<222> LOCATION: (286)..(286)
<223> OTHER INFORMATION: 5-methyl-cytidine
<220> FEATURE:
<221> NAME/KEY: modified_base
<222> LOCATION: (290)..(290)
<223> OTHER INFORMATION: 5-methyl-cytidine
<220> FEATURE:
<221> NAME/KEY: modified_base
<222> LOCATION: (291)..(292)
<223> OTHER INFORMATION: Pseudouridine
<220> FEATURE:
<221> NAME/KEY: modified_base
<222> LOCATION: (298)..(298)
<223> OTHER INFORMATION: Pseudouridine
<220> FEATURE:
<221> NAME/KEY: modified_base
<222> LOCATION: (301)..(301)
```

```
<223> OTHER INFORMATION: Pseudouridine
<220> FEATURE:
<221> NAME/KEY: modified_base
<222> LOCATION: (302)..(304)
<223> OTHER INFORMATION: 5-methyl-cytidine
<220> FEATURE:
<221> NAME/KEY: modified_base
<222> LOCATION: (309)..(310)
<223> OTHER INFORMATION: 5-methyl-cytidine
<220> FEATURE:
<221> NAME/KEY: modified_base
<222> LOCATION: (316)..(316)
<223> OTHER INFORMATION: 5-methyl-cytidine
<220> FEATURE:
<221> NAME/KEY: modified_base
<222> LOCATION: (317)..(318)
<223> OTHER INFORMATION: Pseudouridine
<220> FEATURE:
<221> NAME/KEY: modified_base
<222> LOCATION: (320)..(320)
<223> OTHER INFORMATION: 5-methyl-cytidine
<220> FEATURE:
<221> NAME/KEY: modified_base
<222> LOCATION: (324)..(324)
<223> OTHER INFORMATION: 5-methyl-cytidine
<220> FEATURE:
<221> NAME/KEY: modified_base
<222> LOCATION: (325)..(325)
<223> OTHER INFORMATION: Pseudouridine
<220> FEATURE:
<221> NAME/KEY: modified_base
<222> LOCATION: (326)..(326)
<223> OTHER INFORMATION: 5-methyl-cytidine
<220> FEATURE:
<221> NAME/KEY: modified_base
<222> LOCATION: (327)..(327)
<223> OTHER INFORMATION: Pseudouridine
<220> FEATURE:
<221> NAME/KEY: modified_base
<222> LOCATION: (328)..(328)
<223> OTHER INFORMATION: 5-methyl-cytidine
<220> FEATURE:
<221> NAME/KEY: modified_base
<222> LOCATION: (330)..(330)
<223> OTHER INFORMATION: 5-methyl-cytidine
<220> FEATURE:
<221> NAME/KEY: modified_base
<222> LOCATION: (331)..(331)
<223> OTHER INFORMATION: Pseudouridine
<220> FEATURE:
<221> NAME/KEY: modified_base
<222> LOCATION: (332)..(332)
<223> OTHER INFORMATION: 5-methyl-cytidine
<220> FEATURE:
<221> NAME/KEY: modified_base
<222> LOCATION: (333)..(333)
<223> OTHER INFORMATION: Pseudouridine
<220> FEATURE:
<221> NAME/KEY: modified_base
<222> LOCATION: (334)..(334)
<223> OTHER INFORMATION: 5-methyl-cytidine
<220> FEATURE:
<221> NAME/KEY: modified_base
<222> LOCATION: (339)..(339)
<223> OTHER INFORMATION: Pseudouridine
<220> FEATURE:
<221> NAME/KEY: modified_base
<222> LOCATION: (342)..(342)
<223> OTHER INFORMATION: 5-methyl-cytidine
<220> FEATURE:
<221> NAME/KEY: modified_base
<222> LOCATION: (344)..(344)
<223> OTHER INFORMATION: 5-methyl-cytidine
<220> FEATURE:
<221> NAME/KEY: modified_base
<222> LOCATION: (347)..(347)
<223> OTHER INFORMATION: 5-methyl-cytidine
<220> FEATURE:
<221> NAME/KEY: modified_base
```

```
<222> LOCATION: (353)..(353)
<223> OTHER INFORMATION: 5-methyl-cytidine
<220> FEATURE:
<221> NAME/KEY: modified_base
<222> LOCATION: (358)..(358)
<223> OTHER INFORMATION: Pseudouridine
<220> FEATURE:
<221> NAME/KEY: modified_base
<222> LOCATION: (360)..(360)
<223> OTHER INFORMATION: Pseudouridine
<220> FEATURE:
<221> NAME/KEY: modified_base
<222> LOCATION: (361)..(361)
<223> OTHER INFORMATION: 5-methyl-cytidine
<220> FEATURE:
<221> NAME/KEY: modified_base
<222> LOCATION: (363)..(363)
<223> OTHER INFORMATION: Pseudouridine
<220> FEATURE:
<221> NAME/KEY: modified_base
<222> LOCATION: (367)..(368)
<223> OTHER INFORMATION: 5-methyl-cytidine
<220> FEATURE:
<221> NAME/KEY: modified_base
<222> LOCATION: (371)..(371)
<223> OTHER INFORMATION: Pseudouridine
<220> FEATURE:
<221> NAME/KEY: modified_base
<222> LOCATION: (373)..(374)
<223> OTHER INFORMATION: Pseudouridine
<220> FEATURE:
<221> NAME/KEY: modified_base
<222> LOCATION: (376)..(376)
<223> OTHER INFORMATION: 5-methyl-cytidine
<220> FEATURE:
<221> NAME/KEY: modified_base
<222> LOCATION: (378)..(378)
<223> OTHER INFORMATION: 5-methyl-cytidine
<220> FEATURE:
<221> NAME/KEY: modified_base
<222> LOCATION: (380)..(380)
<223> OTHER INFORMATION: Pseudouridine
<220> FEATURE:
<221> NAME/KEY: modified_base
<222> LOCATION: (381)..(381)
<223> OTHER INFORMATION: 5-methyl-cytidine
<220> FEATURE:
<221> NAME/KEY: modified_base
<222> LOCATION: (384)..(384)
<223> OTHER INFORMATION: Pseudouridine
<220> FEATURE:
<221> NAME/KEY: modified_base
<222> LOCATION: (385)..(385)
<223> OTHER INFORMATION: 5-methyl-cytidine
<220> FEATURE:
<221> NAME/KEY: modified_base
<222> LOCATION: (386)..(386)
<223> OTHER INFORMATION: Pseudouridine
<220> FEATURE:
<221> NAME/KEY: modified_base
<222> LOCATION: (388)..(389)
<223> OTHER INFORMATION: Pseudouridine
<220> FEATURE:
<221> NAME/KEY: modified_base
<222> LOCATION: (390)..(390)
<223> OTHER INFORMATION: 5-methyl-cytidine
<220> FEATURE:
<221> NAME/KEY: modified_base
<222> LOCATION: (392)..(392)
<223> OTHER INFORMATION: 5-methyl-cytidine
<220> FEATURE:
<221> NAME/KEY: modified_base
<222> LOCATION: (393)..(395)
<223> OTHER INFORMATION: Pseudouridine
<220> FEATURE:
<221> NAME/KEY: modified_base
<222> LOCATION: (397)..(397)
<223> OTHER INFORMATION: Pseudouridine
<220> FEATURE:
```

```
<221> NAME/KEY: modified_base
<222> LOCATION: (398)..(398)
<223> OTHER INFORMATION: 5-methyl-cytidine
<220> FEATURE:
<221> NAME/KEY: modified_base
<222> LOCATION: (401)..(401)
<223> OTHER INFORMATION: 5-methyl-cytidine
<220> FEATURE:
<221> NAME/KEY: modified_base
<222> LOCATION: (402)..(403)
<223> OTHER INFORMATION: Pseudouridine
<220> FEATURE:
<221> NAME/KEY: modified_base
<222> LOCATION: (409)..(409)
<223> OTHER INFORMATION: 5-methyl-cytidine
<220> FEATURE:
<221> NAME/KEY: modified_base
<222> LOCATION: (410)..(410)
<223> OTHER INFORMATION: Pseudouridine
<220> FEATURE:
<221> NAME/KEY: modified_base
<222> LOCATION: (412)..(412)
<223> OTHER INFORMATION: 5-methyl-cytidine
<220> FEATURE:
<221> NAME/KEY: modified_base
<222> LOCATION: (413)..(413)
<223> OTHER INFORMATION: Pseudouridine
<220> FEATURE:
<221> NAME/KEY: modified_base
<222> LOCATION: (415)..(415)
<223> OTHER INFORMATION: Pseudouridine
<220> FEATURE:
<221> NAME/KEY: modified_base
<222> LOCATION: (418)..(419)
<223> OTHER INFORMATION: Pseudouridine
<220> FEATURE:
<221> NAME/KEY: modified_base
<222> LOCATION: (424)..(424)
<223> OTHER INFORMATION: 5-methyl-cytidine
<220> FEATURE:
<221> NAME/KEY: modified_base
<222> LOCATION: (426)..(426)
<223> OTHER INFORMATION: 5-methyl-cytidine
<220> FEATURE:
<221> NAME/KEY: modified_base
<222> LOCATION: (427)..(427)
<223> OTHER INFORMATION: Pseudouridine
<220> FEATURE:
<221> NAME/KEY: modified_base
<222> LOCATION: (429)..(430)
<223> OTHER INFORMATION: 5-methyl-cytidine
<220> FEATURE:
<221> NAME/KEY: modified_base
<222> LOCATION: (431)..(432)
<223> OTHER INFORMATION: Pseudouridine
<220> FEATURE:
<221> NAME/KEY: modified_base
<222> LOCATION: (433)..(433)
<223> OTHER INFORMATION: 5-methyl-cytidine
<220> FEATURE:
<221> NAME/KEY: modified_base
<222> LOCATION: (434)..(434)
<223> OTHER INFORMATION: Pseudouridine
<220> FEATURE:
<221> NAME/KEY: modified_base
<222> LOCATION: (436)..(436)
<223> OTHER INFORMATION: 5-methyl-cytidine
<220> FEATURE:
<221> NAME/KEY: modified_base
<222> LOCATION: (441)..(441)
<223> OTHER INFORMATION: 5-methyl-cytidine
<220> FEATURE:
<221> NAME/KEY: modified_base
<222> LOCATION: (442)..(443)
<223> OTHER INFORMATION: Pseudouridine
<220> FEATURE:
<221> NAME/KEY: modified_base
<222> LOCATION: (445)..(446)
<223> OTHER INFORMATION: 5-methyl-cytidine
```

```
<220> FEATURE:
<221> NAME/KEY: modified_base
<222> LOCATION: (447)..(448)
<223> OTHER INFORMATION: Pseudouridine
<220> FEATURE:
<221> NAME/KEY: modified_base
<222> LOCATION: (449)..(449)
<223> OTHER INFORMATION: 5-methyl-cytidine
<220> FEATURE:
<221> NAME/KEY: modified_base
<222> LOCATION: (450)..(450)
<223> OTHER INFORMATION: Pseudouridine
<220> FEATURE:
<221> NAME/KEY: modified_base
<222> LOCATION: (453)..(454)
<223> OTHER INFORMATION: 5-methyl-cytidine
<220> FEATURE:
<221> NAME/KEY: modified_base
<222> LOCATION: (456)..(456)
<223> OTHER INFORMATION: Pseudouridine
<220> FEATURE:
<221> NAME/KEY: modified_base
<222> LOCATION: (458)..(460)
<223> OTHER INFORMATION: 5-methyl-cytidine
<220> FEATURE:
<221> NAME/KEY: modified_base
<222> LOCATION: (461)..(462)
<223> OTHER INFORMATION: Pseudouridine
<220> FEATURE:
<221> NAME/KEY: modified_base
<222> LOCATION: (463)..(463)
<223> OTHER INFORMATION: 5-methyl-cytidine
<220> FEATURE:
<221> NAME/KEY: modified_base
<222> LOCATION: (464)..(465)
<223> OTHER INFORMATION: Pseudouridine
<220> FEATURE:
<221> NAME/KEY: modified_base
<222> LOCATION: (466)..(466)
<223> OTHER INFORMATION: 5-methyl-cytidine
<220> FEATURE:
<221> NAME/KEY: modified_base
<222> LOCATION: (467)..(467)
<223> OTHER INFORMATION: Pseudouridine
<220> FEATURE:
<221> NAME/KEY: modified_base
<222> LOCATION: (468)..(468)
<223> OTHER INFORMATION: 5-methyl-cytidine
<220> FEATURE:
<221> NAME/KEY: modified_base
<222> LOCATION: (469)..(469)
<223> OTHER INFORMATION: Pseudouridine
<220> FEATURE:
<221> NAME/KEY: modified_base
<222> LOCATION: (470)..(472)
<223> OTHER INFORMATION: 5-methyl-cytidine
<220> FEATURE:
<221> NAME/KEY: modified_base
<222> LOCATION: (473)..(474)
<223> OTHER INFORMATION: Pseudouridine
<220> FEATURE:
<221> NAME/KEY: modified_base
<222> LOCATION: (476)..(476)
<223> OTHER INFORMATION: 5-methyl-cytidine
<220> FEATURE:
<221> NAME/KEY: modified_base
<222> LOCATION: (478)..(479)
<223> OTHER INFORMATION: 5-methyl-cytidine
<220> FEATURE:
<221> NAME/KEY: modified_base
<222> LOCATION: (480)..(480)
<223> OTHER INFORMATION: Pseudouridine
<220> FEATURE:
<221> NAME/KEY: modified_base
<222> LOCATION: (482)..(482)
<223> OTHER INFORMATION: Pseudouridine
<220> FEATURE:
<221> NAME/KEY: modified_base
<222> LOCATION: (484)..(485)
```

```
<223> OTHER INFORMATION: 5-methyl-cytidine
<220> FEATURE:
<221> NAME/KEY: modified_base
<222> LOCATION: (486)..(486)
<223> OTHER INFORMATION: Pseudouridine
<220> FEATURE:
<221> NAME/KEY: modified_base
<222> LOCATION: (487)..(487)
<223> OTHER INFORMATION: 5-methyl-cytidine
<220> FEATURE:
<221> NAME/KEY: modified_base
<222> LOCATION: (488)..(489)
<223> OTHER INFORMATION: Pseudouridine
<220> FEATURE:
<221> NAME/KEY: modified_base
<222> LOCATION: (492)..(492)
<223> OTHER INFORMATION: Pseudouridine
<220> FEATURE:
<221> NAME/KEY: modified_base
<222> LOCATION: (493)..(493)
<223> OTHER INFORMATION: 5-methyl-cytidine
<220> FEATURE:
<221> NAME/KEY: modified_base
<222> LOCATION: (494)..(496)
<223> OTHER INFORMATION: Pseudouridine
<220> FEATURE:
<221> NAME/KEY: modified_base
<222> LOCATION: (500)..(500)
<223> OTHER INFORMATION: Pseudouridine
<220> FEATURE:
<221> NAME/KEY: modified_base
<222> LOCATION: (505)..(506)
<223> OTHER INFORMATION: 5-methyl-cytidine
<220> FEATURE:
<221> NAME/KEY: modified_base
<222> LOCATION: (507)..(507)
<223> OTHER INFORMATION: Pseudouridine
<220> FEATURE:
<221> NAME/KEY: modified_base
<222> LOCATION: (511)..(511)
<223> OTHER INFORMATION: Pseudouridine
<220> FEATURE:
<221> NAME/KEY: modified_base
<222> LOCATION: (519)..(519)
<223> OTHER INFORMATION: 5-methyl-cytidine
<220> FEATURE:
<221> NAME/KEY: modified_base
<222> LOCATION: (522)..(523)
<223> OTHER INFORMATION: 5-methyl-cytidine
<220> FEATURE:
<221> NAME/KEY: modified_base
<222> LOCATION: (525)..(525)
<223> OTHER INFORMATION: 5-methyl-cytidine
<220> FEATURE:
<221> NAME/KEY: modified_base
<222> LOCATION: (526)..(526)
<223> OTHER INFORMATION: Pseudouridine
<220> FEATURE:
<221> NAME/KEY: modified_base
<222> LOCATION: (527)..(527)
<223> OTHER INFORMATION: 5-methyl-cytidine
<220> FEATURE:
<221> NAME/KEY: modified_base
<222> LOCATION: (531)..(531)
<223> OTHER INFORMATION: 5-methyl-cytidine
<220> FEATURE:
<221> NAME/KEY: modified_base
<222> LOCATION: (533)..(533)
<223> OTHER INFORMATION: Pseudouridine
<220> FEATURE:
<221> NAME/KEY: modified_base
<222> LOCATION: (535)..(535)
<223> OTHER INFORMATION: 5-methyl-cytidine
<220> FEATURE:
<221> NAME/KEY: modified_base
<222> LOCATION: (537)..(537)
<223> OTHER INFORMATION: Pseudouridine
<220> FEATURE:
<221> NAME/KEY: modified_base
```

```
<222> LOCATION: (538)..(538)
<223> OTHER INFORMATION: 5-methyl-cytidine
<220> FEATURE:
<221> NAME/KEY: modified_base
<222> LOCATION: (539)..(539)
<223> OTHER INFORMATION: Pseudouridine
<220> FEATURE:
<221> NAME/KEY: modified_base
<222> LOCATION: (546)..(548)
<223> OTHER INFORMATION: 5-methyl-cytidine
<220> FEATURE:
<221> NAME/KEY: modified_base
<222> LOCATION: (551)..(552)
<223> OTHER INFORMATION: Pseudouridine
<220> FEATURE:
<221> NAME/KEY: modified_base
<222> LOCATION: (553)..(553)
<223> OTHER INFORMATION: 5-methyl-cytidine
<220> FEATURE:
<221> NAME/KEY: modified_base
<222> LOCATION: (555)..(557)
<223> OTHER INFORMATION: 5-methyl-cytidine
<220> FEATURE:
<221> NAME/KEY: modified_base
<222> LOCATION: (558)..(558)
<223> OTHER INFORMATION: Pseudouridine
<220> FEATURE:
<221> NAME/KEY: modified_base
<222> LOCATION: (560)..(561)
<223> OTHER INFORMATION: Pseudouridine
<220> FEATURE:
<221> NAME/KEY: modified_base
<222> LOCATION: (562)..(562)
<223> OTHER INFORMATION: 5-methyl-cytidine

<400> SEQUENCE: 22
agcuuuugga cccucguaca gaagcuaaua cgacucacua uagggaaaua agagagaaaa        60
gaagaguaag aagaaauaua agagccacca uggcgcucug gugagguuuc ugccuuuguu       120
ggccuugcug uuccucuggg aguoccaccc cacacaggcg uuugugaagc agcacuugug       180
cgggucgcau cugguggagg cacuuuaucu cgucugcggc gagcgaggau ucuucuacac       240
cccgaugagc agacgcgaag uggaagaucc gcaagucgcg cagcucgaac uuggggugg       300 ucccggagcc ggagacuugc aaacucucgc ucucgaggua gcgcagcaga aacgggguau       360
cguagaccag uguugcacgu cgaucuguuc acuuuaucaa cuugagaacu acuguaauug       420
aagcgcugcc uucugcgggg cuugccucu ggccaugccc ucuucucuc ccuugccu        480 guaccucuug gucuuugaau aaagccgag uaggaaggcg ccgcucgag caugcaucua       540 gagggcccaa uucgcccuau ucg                                              563

<210> SEQ ID NO 23
<211> LENGTH: 567
<212> TYPE: RNA
<213> ORGANISM: Homo sapiens

<400> SEQUENCE: 23
agcuuuugga cccucguaca gaagcuaaua cgacucacua uagggaaaua agagagaaaa        60
gaagaguaag aagaaauaua agagccacca uggcucucug gaugcggcuu cuuccacugc       120
ucgcccucuu ggcguugugg ggacccgacc cugcagcagc guuugugaau cagcaccucu       180 gcgguucccca ucuggucgaa gcccuuuacc uugugugug cgagcgcggg uucuucuaca       240
cgcccaagac aaggcgcgag gcggaggauc uccaaguagg gcaggggaa uggggagggg       300 gaccgggagc cgguucacuc cagccccugg cguuggaggg gucgcugcag aaagagugga       360
uugucgaaca guguugcacu agcaucugcu cgcuguauca acuugagaac uauuuguaacu       420
```

```
gaagcgcugc cuucugcggg gcuugccuuc uggccaugcc cuucuucucu cccuugcacc    480
uguaccucuu ggucuuugaa uaaagccuga guaggaaggc ggccgcucga gcaugcaucu    540
agagggccca auucgcccua uucgaag                                       567
```

<210> SEQ ID NO 24
<211> LENGTH: 567
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: 5-methyl-cytidine
<220> FEATURE:
<221> NAME/KEY: modified_base
<222> LOCATION: (4)..(7)
<223> OTHER INFORMATION: Pseudouridine
<220> FEATURE:
<221> NAME/KEY: modified_base
<222> LOCATION: (11)..(13)
<223> OTHER INFORMATION: 5-methyl-cytidine
<220> FEATURE:
<221> NAME/KEY: modified_base
<222> LOCATION: (14)..(14)
<223> OTHER INFORMATION: Pseudouridine
<220> FEATURE:
<221> NAME/KEY: modified_base
<222> LOCATION: (15)..(15)
<223> OTHER INFORMATION: 5-methyl-cytidine
<220> FEATURE:
<221> NAME/KEY: modified_base
<222> LOCATION: (17)..(17)
<223> OTHER INFORMATION: Pseudouridine
<220> FEATURE:
<221> NAME/KEY: modified_base
<222> LOCATION: (19)..(19)
<223> OTHER INFORMATION: 5-methyl-cytidine
<220> FEATURE:
<221> NAME/KEY: modified_base
<222> LOCATION: (25)..(25)
<223> OTHER INFORMATION: 5-methyl-cytidine
<220> FEATURE:
<221> NAME/KEY: modified_base
<222> LOCATION: (26)..(26)
<223> OTHER INFORMATION: Pseudouridine
<220> FEATURE:
<221> NAME/KEY: modified_base
<222> LOCATION: (29)..(29)
<223> OTHER INFORMATION: Pseudouridine
<220> FEATURE:
<221> NAME/KEY: modified_base
<222> LOCATION: (31)..(31)
<223> OTHER INFORMATION: 5-methyl-cytidine
<220> FEATURE:
<221> NAME/KEY: modified_base
<222> LOCATION: (34)..(34)
<223> OTHER INFORMATION: 5-methyl-cytidine
<220> FEATURE:
<221> NAME/KEY: modified_base
<222> LOCATION: (35)..(35)
<223> OTHER INFORMATION: Pseudouridine
<220> FEATURE:
<221> NAME/KEY: modified_base
<222> LOCATION: (36)..(36)
<223> OTHER INFORMATION: 5-methyl-cytidine
<220> FEATURE:
<221> NAME/KEY: modified_base
<222> LOCATION: (38)..(38)
<223> OTHER INFORMATION: 5-methyl-cytidine
<220> FEATURE:
<221> NAME/KEY: modified_base
<222> LOCATION: (39)..(39)
<223> OTHER INFORMATION: Pseudouridine
<220> FEATURE:

```
<221> NAME/KEY: modified_base
<222> LOCATION: (41)..(41)
<223> OTHER INFORMATION: Pseudouridine
<220> FEATURE:
<221> NAME/KEY: modified_base
<222> LOCATION: (49)..(49)
<223> OTHER INFORMATION: Pseudouridine
<220> FEATURE:
<221> NAME/KEY: modified_base
<222> LOCATION: (67)..(67)
<223> OTHER INFORMATION: Pseudouridine
<220> FEATURE:
<221> NAME/KEY: modified_base
<222> LOCATION: (77)..(77)
<223> OTHER INFORMATION: Pseudouridine
<220> FEATURE:
<221> NAME/KEY: modified_base
<222> LOCATION: (79)..(79)
<223> OTHER INFORMATION: Pseudouridine
<220> FEATURE:
<221> NAME/KEY: modified_base
<222> LOCATION: (85)..(86)
<223> OTHER INFORMATION: 5-methyl-cytidine
<220> FEATURE:
<221> NAME/KEY: modified_base
<222> LOCATION: (88)..(89)
<223> OTHER INFORMATION: 5-methyl-cytidine
<220> FEATURE:
<221> NAME/KEY: modified_base
<222> LOCATION: (91)..(91)
<223> OTHER INFORMATION: Pseudouridine
<220> FEATURE:
<221> NAME/KEY: modified_base
<222> LOCATION: (94)..(94)
<223> OTHER INFORMATION: 5-methyl-cytidine
<220> FEATURE:
<221> NAME/KEY: modified_base
<222> LOCATION: (95)..(95)
<223> OTHER INFORMATION: Pseudouridine
<220> FEATURE:
<221> NAME/KEY: modified_base
<222> LOCATION: (96)..(96)
<223> OTHER INFORMATION: 5-methyl-cytidine
<220> FEATURE:
<221> NAME/KEY: modified_base
<222> LOCATION: (97)..(97)
<223> OTHER INFORMATION: Pseudouridine
<220> FEATURE:
<221> NAME/KEY: modified_base
<222> LOCATION: (98)..(98)
<223> OTHER INFORMATION: 5-methyl-cytidine
<220> FEATURE:
<221> NAME/KEY: modified_base
<222> LOCATION: (99)..(99)
<223> OTHER INFORMATION: Pseudouridine
<220> FEATURE:
<221> NAME/KEY: modified_base
<222> LOCATION: (103)..(103)
<223> OTHER INFORMATION: Pseudouridine
<220> FEATURE:
<221> NAME/KEY: modified_base
<222> LOCATION: (105)..(105)
<223> OTHER INFORMATION: 5-methyl-cytidine
<220> FEATURE:
<221> NAME/KEY: modified_base
<222> LOCATION: (108)..(108)
<223> OTHER INFORMATION: 5-methyl-cytidine
<220> FEATURE:
<221> NAME/KEY: modified_base
<222> LOCATION: (109)..(110)
<223> OTHER INFORMATION: Pseudouridine
<220> FEATURE:
<221> NAME/KEY: modified_base
<222> LOCATION: (111)..(111)
<223> OTHER INFORMATION: 5-methyl-cytidine
<220> FEATURE:
<221> NAME/KEY: modified_base
<222> LOCATION: (112)..(113)
<223> OTHER INFORMATION: Pseudouridine
```

-continued

```
<220> FEATURE:
<221> NAME/KEY: modified_base
<222> LOCATION: (114)..(115)
<223> OTHER INFORMATION: 5-methyl-cytidine
<220> FEATURE:
<221> NAME/KEY: modified_base
<222> LOCATION: (117)..(117)
<223> OTHER INFORMATION: 5-methyl-cytidine
<220> FEATURE:
<221> NAME/KEY: modified_base
<222> LOCATION: (118)..(118)
<223> OTHER INFORMATION: Pseudouridine
<220> FEATURE:
<221> NAME/KEY: modified_base
<222> LOCATION: (120)..(120)
<223> OTHER INFORMATION: 5-methyl-cytidine
<220> FEATURE:
<221> NAME/KEY: modified_base
<222> LOCATION: (121)..(121)
<223> OTHER INFORMATION: Pseudouridine
<220> FEATURE:
<221> NAME/KEY: modified_base
<222> LOCATION: (122)..(122)
<223> OTHER INFORMATION: 5-methyl-cytidine
<220> FEATURE:
<221> NAME/KEY: modified_base
<222> LOCATION: (124)..(126)
<223> OTHER INFORMATION: 5-methyl-cytidine
<220> FEATURE:
<221> NAME/KEY: modified_base
<222> LOCATION: (127)..(127)
<223> OTHER INFORMATION: Pseudouridine
<220> FEATURE:
<221> NAME/KEY: modified_base
<222> LOCATION: (128)..(128)
<223> OTHER INFORMATION: 5-methyl-cytidine
<220> FEATURE:
<221> NAME/KEY: modified_base
<222> LOCATION: (129)..(130)
<223> OTHER INFORMATION: Pseudouridine
<220> FEATURE:
<221> NAME/KEY: modified_base
<222> LOCATION: (133)..(133)
<223> OTHER INFORMATION: 5-methyl-cytidine
<220> FEATURE:
<221> NAME/KEY: modified_base
<222> LOCATION: (135)..(136)
<223> OTHER INFORMATION: Pseudouridine
<220> FEATURE:
<221> NAME/KEY: modified_base
<222> LOCATION: (138)..(138)
<223> OTHER INFORMATION: Pseudouridine
<220> FEATURE:
<221> NAME/KEY: modified_base
<222> LOCATION: (144)..(146)
<223> OTHER INFORMATION: 5-methyl-cytidine
<220> FEATURE:
<221> NAME/KEY: modified_base
<222> LOCATION: (149)..(151)
<223> OTHER INFORMATION: 5-methyl-cytidine
<220> FEATURE:
<221> NAME/KEY: modified_base
<222> LOCATION: (152)..(152)
<223> OTHER INFORMATION: Pseudouridine
<220> FEATURE:
<221> NAME/KEY: modified_base
<222> LOCATION: (154)..(154)
<223> OTHER INFORMATION: 5-methyl-cytidine
<220> FEATURE:
<221> NAME/KEY: modified_base
<222> LOCATION: (157)..(157)
<223> OTHER INFORMATION: 5-methyl-cytidine
<220> FEATURE:
<221> NAME/KEY: modified_base
<222> LOCATION: (160)..(160)
<223> OTHER INFORMATION: 5-methyl-cytidine
<220> FEATURE:
<221> NAME/KEY: modified_base
<222> LOCATION: (162)..(164)
```

```
<223> OTHER INFORMATION: Pseudouridine
<220> FEATURE:
<221> NAME/KEY: modified_base
<222> LOCATION: (166)..(166)
<223> OTHER INFORMATION: Pseudouridine
<220> FEATURE:
<221> NAME/KEY: modified_base
<222> LOCATION: (170)..(170)
<223> OTHER INFORMATION: Pseudouridine
<220> FEATURE:
<221> NAME/KEY: modified_base
<222> LOCATION: (171)..(171)
<223> OTHER INFORMATION: 5-methyl-cytidine
<220> FEATURE:
<221> NAME/KEY: modified_base
<222> LOCATION: (174)..(174)
<223> OTHER INFORMATION: 5-methyl-cytidine
<220> FEATURE:
<221> NAME/KEY: modified_base
<222> LOCATION: (176)..(177)
<223> OTHER INFORMATION: 5-methyl-cytidine
<220> FEATURE:
<221> NAME/KEY: modified_base
<222> LOCATION: (178)..(178)
<223> OTHER INFORMATION: Pseudouridine
<220> FEATURE:
<221> NAME/KEY: modified_base
<222> LOCATION: (179)..(179)
<223> OTHER INFORMATION: 5-methyl-cytidine
<220> FEATURE:
<221> NAME/KEY: modified_base
<222> LOCATION: (180)..(180)
<223> OTHER INFORMATION: Pseudouridine
<220> FEATURE:
<221> NAME/KEY: modified_base
<222> LOCATION: (182)..(182)
<223> OTHER INFORMATION: 5-methyl-cytidine
<220> FEATURE:
<221> NAME/KEY: modified_base
<222> LOCATION: (186)..(186)
<223> OTHER INFORMATION: Pseudouridine
<220> FEATURE:
<221> NAME/KEY: modified_base
<222> LOCATION: (187)..(189)
<223> OTHER INFORMATION: 5-methyl-cytidine
<220> FEATURE:
<221> NAME/KEY: modified_base
<222> LOCATION: (191)..(191)
<223> OTHER INFORMATION: Pseudouridine
<220> FEATURE:
<221> NAME/KEY: modified_base
<222> LOCATION: (192)..(192)
<223> OTHER INFORMATION: 5-methyl-cytidine
<220> FEATURE:
<221> NAME/KEY: modified_base
<222> LOCATION: (193)..(193)
<223> OTHER INFORMATION: Pseudouridine
<220> FEATURE:
<221> NAME/KEY: modified_base
<222> LOCATION: (196)..(196)
<223> OTHER INFORMATION: Pseudouridine
<220> FEATURE:
<221> NAME/KEY: modified_base
<222> LOCATION: (197)..(197)
<223> OTHER INFORMATION: 5-methyl-cytidine
<220> FEATURE:
<221> NAME/KEY: modified_base
<222> LOCATION: (202)..(204)
<223> OTHER INFORMATION: 5-methyl-cytidine
<220> FEATURE:
<221> NAME/KEY: modified_base
<222> LOCATION: (205)..(207)
<223> OTHER INFORMATION: Pseudouridine
<220> FEATURE:
<221> NAME/KEY: modified_base
<222> LOCATION: (209)..(210)
<223> OTHER INFORMATION: 5-methyl-cytidine
<220> FEATURE:
<221> NAME/KEY: modified_base
```

```
<222> LOCATION: (211)..(212)
<223> OTHER INFORMATION: Pseudouridine
<220> FEATURE:
<221> NAME/KEY: modified_base
<222> LOCATION: (214)..(214)
<223> OTHER INFORMATION: Pseudouridine
<220> FEATURE:
<221> NAME/KEY: modified_base
<222> LOCATION: (216)..(216)
<223> OTHER INFORMATION: Pseudouridine
<220> FEATURE:
<221> NAME/KEY: modified_base
<222> LOCATION: (218)..(218)
<223> OTHER INFORMATION: Pseudouridine
<220> FEATURE:
<221> NAME/KEY: modified_base
<222> LOCATION: (221)..(221)
<223> OTHER INFORMATION: 5-methyl-cytidine
<220> FEATURE:
<221> NAME/KEY: modified_base
<222> LOCATION: (225)..(225)
<223> OTHER INFORMATION: 5-methyl-cytidine
<220> FEATURE:
<221> NAME/KEY: modified_base
<222> LOCATION: (227)..(227)
<223> OTHER INFORMATION: 5-methyl-cytidine
<220> FEATURE:
<221> NAME/KEY: modified_base
<222> LOCATION: (231)..(232)
<223> OTHER INFORMATION: Pseudouridine
<220> FEATURE:
<221> NAME/KEY: modified_base
<222> LOCATION: (233)..(233)
<223> OTHER INFORMATION: 5-methyl-cytidine
<220> FEATURE:
<221> NAME/KEY: modified_base
<222> LOCATION: (234)..(235)
<223> OTHER INFORMATION: Pseudouridine
<220> FEATURE:
<221> NAME/KEY: modified_base
<222> LOCATION: (236)..(236)
<223> OTHER INFORMATION: 5-methyl-cytidine
<220> FEATURE:
<221> NAME/KEY: modified_base
<222> LOCATION: (237)..(237)
<223> OTHER INFORMATION: Pseudouridine
<220> FEATURE:
<221> NAME/KEY: modified_base
<222> LOCATION: (239)..(239)
<223> OTHER INFORMATION: 5-methyl-cytidine
<220> FEATURE:
<221> NAME/KEY: modified_base
<222> LOCATION: (241)..(241)
<223> OTHER INFORMATION: 5-methyl-cytidine
<220> FEATURE:
<221> NAME/KEY: modified_base
<222> LOCATION: (243)..(245)
<223> OTHER INFORMATION: 5-methyl-cytidine
<220> FEATURE:
<221> NAME/KEY: modified_base
<222> LOCATION: (250)..(250)
<223> OTHER INFORMATION: 5-methyl-cytidine
<220> FEATURE:
<221> NAME/KEY: modified_base
<222> LOCATION: (255)..(255)
<223> OTHER INFORMATION: 5-methyl-cytidine
<220> FEATURE:
<221> NAME/KEY: modified_base
<222> LOCATION: (257)..(257)
<223> OTHER INFORMATION: 5-methyl-cytidine
<220> FEATURE:
<221> NAME/KEY: modified_base
<222> LOCATION: (262)..(262)
<223> OTHER INFORMATION: 5-methyl-cytidine
<220> FEATURE:
<221> NAME/KEY: modified_base
<222> LOCATION: (269)..(269)
<223> OTHER INFORMATION: Pseudouridine
<220> FEATURE:
```

```
-continued

<221> NAME/KEY: modified_base
<222> LOCATION: (270)..(270)
<223> OTHER INFORMATION: 5-methyl-cytidine
<220> FEATURE:
<221> NAME/KEY: modified_base
<222> LOCATION: (271)..(271)
<223> OTHER INFORMATION: Pseudouridine
<220> FEATURE:
<221> NAME/KEY: modified_base
<222> LOCATION: (272)..(273)
<223> OTHER INFORMATION: 5-methyl-cytidine
<220> FEATURE:
<221> NAME/KEY: modified_base
<222> LOCATION: (277)..(277)
<223> OTHER INFORMATION: Pseudouridine
<220> FEATURE:
<221> NAME/KEY: modified_base
<222> LOCATION: (282)..(282)
<223> OTHER INFORMATION: 5-methyl-cytidine
<220> FEATURE:
<221> NAME/KEY: modified_base
<222> LOCATION: (286)..(286)
<223> OTHER INFORMATION: Pseudouridine
<220> FEATURE:
<221> NAME/KEY: modified_base
<222> LOCATION: (291)..(292)
<223> OTHER INFORMATION: Pseudouridine
<220> FEATURE:
<221> NAME/KEY: modified_base
<222> LOCATION: (303)..(304)
<223> OTHER INFORMATION: 5-methyl-cytidine
<220> FEATURE:
<221> NAME/KEY: modified_base
<222> LOCATION: (310)..(311)
<223> OTHER INFORMATION: 5-methyl-cytidine
<220> FEATURE:
<221> NAME/KEY: modified_base
<222> LOCATION: (314)..(315)
<223> OTHER INFORMATION: Pseudouridine
<220> FEATURE:
<221> NAME/KEY: modified_base
<222> LOCATION: (316)..(316)
<223> OTHER INFORMATION: 5-methyl-cytidine
<220> FEATURE:
<221> NAME/KEY: modified_base
<222> LOCATION: (318)..(318)
<223> OTHER INFORMATION: 5-methyl-cytidine
<220> FEATURE:
<221> NAME/KEY: modified_base
<222> LOCATION: (319)..(319)
<223> OTHER INFORMATION: Pseudouridine
<220> FEATURE:
<221> NAME/KEY: modified_base
<222> LOCATION: (320)..(321)
<223> OTHER INFORMATION: 5-methyl-cytidine
<220> FEATURE:
<221> NAME/KEY: modified_base
<222> LOCATION: (324)..(327)
<223> OTHER INFORMATION: 5-methyl-cytidine
<220> FEATURE:
<221> NAME/KEY: modified_base
<222> LOCATION: (328)..(328)
<223> OTHER INFORMATION: Pseudouridine
<220> FEATURE:
<221> NAME/KEY: modified_base
<222> LOCATION: (331)..(331)
<223> OTHER INFORMATION: 5-methyl-cytidine
<220> FEATURE:
<221> NAME/KEY: modified_base
<222> LOCATION: (333)..(334)
<223> OTHER INFORMATION: Pseudouridine
<220> FEATURE:
<221> NAME/KEY: modified_base
<222> LOCATION: (342)..(342)
<223> OTHER INFORMATION: Pseudouridine
<220> FEATURE:
<221> NAME/KEY: modified_base
<222> LOCATION: (343)..(343)
<223> OTHER INFORMATION: 5-methyl-cytidine
```

-continued

```
<220> FEATURE:
<221> NAME/KEY: modified_base
<222> LOCATION: (345)..(345)
<223> OTHER INFORMATION: 5-methyl-cytidine
<220> FEATURE:
<221> NAME/KEY: modified_base
<222> LOCATION: (346)..(346)
<223> OTHER INFORMATION: Pseudouridine
<220> FEATURE:
<221> NAME/KEY: modified_base
<222> LOCATION: (348)..(348)
<223> OTHER INFORMATION: 5-methyl-cytidine
<220> FEATURE:
<221> NAME/KEY: modified_base
<222> LOCATION: (359)..(359)
<223> OTHER INFORMATION: Pseudouridine
<220> FEATURE:
<221> NAME/KEY: modified_base
<222> LOCATION: (361)..(362)
<223> OTHER INFORMATION: Pseudouridine
<220> FEATURE:
<221> NAME/KEY: modified_base
<222> LOCATION: (364)..(364)
<223> OTHER INFORMATION: Pseudouridine
<220> FEATURE:
<221> NAME/KEY: modified_base
<222> LOCATION: (365)..(365)
<223> OTHER INFORMATION: 5-methyl-cytidine
<220> FEATURE:
<221> NAME/KEY: modified_base
<222> LOCATION: (369)..(369)
<223> OTHER INFORMATION: 5-methyl-cytidine
<220> FEATURE:
<221> NAME/KEY: modified_base
<222> LOCATION: (372)..(372)
<223> OTHER INFORMATION: Pseudouridine
<220> FEATURE:
<221> NAME/KEY: modified_base
<222> LOCATION: (374)..(375)
<223> OTHER INFORMATION: Pseudouridine
<220> FEATURE:
<221> NAME/KEY: modified_base
<222> LOCATION: (377)..(377)
<223> OTHER INFORMATION: 5-methyl-cytidine
<220> FEATURE:
<221> NAME/KEY: modified_base
<222> LOCATION: (379)..(379)
<223> OTHER INFORMATION: 5-methyl-cytidine
<220> FEATURE:
<221> NAME/KEY: modified_base
<222> LOCATION: (380)..(380)
<223> OTHER INFORMATION: Pseudouridine
<220> FEATURE:
<221> NAME/KEY: modified_base
<222> LOCATION: (383)..(383)
<223> OTHER INFORMATION: 5-methyl-cytidine
<220> FEATURE:
<221> NAME/KEY: modified_base
<222> LOCATION: (385)..(385)
<223> OTHER INFORMATION: Pseudouridine
<220> FEATURE:
<221> NAME/KEY: modified_base
<222> LOCATION: (386)..(386)
<223> OTHER INFORMATION: 5-methyl-cytidine
<220> FEATURE:
<221> NAME/KEY: modified_base
<222> LOCATION: (387)..(387)
<223> OTHER INFORMATION: Pseudouridine
<220> FEATURE:
<221> NAME/KEY: modified_base
<222> LOCATION: (389)..(389)
<223> OTHER INFORMATION: 5-methyl-cytidine
<220> FEATURE:
<221> NAME/KEY: modified_base
<222> LOCATION: (390)..(390)
<223> OTHER INFORMATION: Pseudouridine
<220> FEATURE:
<221> NAME/KEY: modified_base
<222> LOCATION: (391)..(391)
```

```
<223> OTHER INFORMATION: 5-methyl-cytidine
<220> FEATURE:
<221> NAME/KEY: modified_base
<222> LOCATION: (393)..(393)
<223> OTHER INFORMATION: 5-methyl-cytidine
<220> FEATURE:
<221> NAME/KEY: modified_base
<222> LOCATION: (394)..(394)
<223> OTHER INFORMATION: Pseudouridine
<220> FEATURE:
<221> NAME/KEY: modified_base
<222> LOCATION: (396)..(396)
<223> OTHER INFORMATION: Pseudouridine
<220> FEATURE:
<221> NAME/KEY: modified_base
<222> LOCATION: (398)..(398)
<223> OTHER INFORMATION: Pseudouridine
<220> FEATURE:
<221> NAME/KEY: modified_base
<222> LOCATION: (399)..(399)
<223> OTHER INFORMATION: 5-methyl-cytidine
<220> FEATURE:
<221> NAME/KEY: modified_base
<222> LOCATION: (402)..(402)
<223> OTHER INFORMATION: 5-methyl-cytidine
<220> FEATURE:
<221> NAME/KEY: modified_base
<222> LOCATION: (403)..(404)
<223> OTHER INFORMATION: Pseudouridine
<220> FEATURE:
<221> NAME/KEY: modified_base
<222> LOCATION: (410)..(410)
<223> OTHER INFORMATION: 5-methyl-cytidine
<220> FEATURE:
<221> NAME/KEY: modified_base
<222> LOCATION: (411)..(411)
<223> OTHER INFORMATION: Pseudouridine
<220> FEATURE:
<221> NAME/KEY: modified_base
<222> LOCATION: (413)..(414)
<223> OTHER INFORMATION: Pseudouridine
<220> FEATURE:
<221> NAME/KEY: modified_base
<222> LOCATION: (416)..(416)
<223> OTHER INFORMATION: Pseudouridine
<220> FEATURE:
<221> NAME/KEY: modified_base
<222> LOCATION: (419)..(419)
<223> OTHER INFORMATION: 5-methyl-cytidine
<220> FEATURE:
<221> NAME/KEY: modified_base
<222> LOCATION: (420)..(420)
<223> OTHER INFORMATION: Pseudouridine
<220> FEATURE:
<221> NAME/KEY: modified_base
<222> LOCATION: (425)..(425)
<223> OTHER INFORMATION: 5-methyl-cytidine
<220> FEATURE:
<221> NAME/KEY: modified_base
<222> LOCATION: (427)..(427)
<223> OTHER INFORMATION: 5-methyl-cytidine
<220> FEATURE:
<221> NAME/KEY: modified_base
<222> LOCATION: (428)..(428)
<223> OTHER INFORMATION: Pseudouridine
<220> FEATURE:
<221> NAME/KEY: modified_base
<222> LOCATION: (430)..(431)
<223> OTHER INFORMATION: 5-methyl-cytidine
<220> FEATURE:
<221> NAME/KEY: modified_base
<222> LOCATION: (432)..(433)
<223> OTHER INFORMATION: Pseudouridine
<220> FEATURE:
<221> NAME/KEY: modified_base
<222> LOCATION: (434)..(434)
<223> OTHER INFORMATION: 5-methyl-cytidine
<220> FEATURE:
<221> NAME/KEY: modified_base
```

```
<222> LOCATION: (435)..(435)
<223> OTHER INFORMATION: Pseudouridine
<220> FEATURE:
<221> NAME/KEY: modified_base
<222> LOCATION: (437)..(437)
<223> OTHER INFORMATION: 5-methyl-cytidine
<220> FEATURE:
<221> NAME/KEY: modified_base
<222> LOCATION: (442)..(442)
<223> OTHER INFORMATION: 5-methyl-cytidine
<220> FEATURE:
<221> NAME/KEY: modified_base
<222> LOCATION: (443)..(444)
<223> OTHER INFORMATION: Pseudouridine
<220> FEATURE:
<221> NAME/KEY: modified_base
<222> LOCATION: (446)..(447)
<223> OTHER INFORMATION: 5-methyl-cytidine
<220> FEATURE:
<221> NAME/KEY: modified_base
<222> LOCATION: (448)..(449)
<223> OTHER INFORMATION: Pseudouridine
<220> FEATURE:
<221> NAME/KEY: modified_base
<222> LOCATION: (450)..(450)
<223> OTHER INFORMATION: 5-methyl-cytidine
<220> FEATURE:
<221> NAME/KEY: modified_base
<222> LOCATION: (451)..(451)
<223> OTHER INFORMATION: Pseudouridine
<220> FEATURE:
<221> NAME/KEY: modified_base
<222> LOCATION: (454)..(455)
<223> OTHER INFORMATION: 5-methyl-cytidine
<220> FEATURE:
<221> NAME/KEY: modified_base
<222> LOCATION: (457)..(457)
<223> OTHER INFORMATION: Pseudouridine
<220> FEATURE:
<221> NAME/KEY: modified_base
<222> LOCATION: (459)..(461)
<223> OTHER INFORMATION: 5-methyl-cytidine
<220> FEATURE:
<221> NAME/KEY: modified_base
<222> LOCATION: (462)..(463)
<223> OTHER INFORMATION: Pseudouridine
<220> FEATURE:
<221> NAME/KEY: modified_base
<222> LOCATION: (464)..(464)
<223> OTHER INFORMATION: 5-methyl-cytidine
<220> FEATURE:
<221> NAME/KEY: modified_base
<222> LOCATION: (465)..(466)
<223> OTHER INFORMATION: Pseudouridine
<220> FEATURE:
<221> NAME/KEY: modified_base
<222> LOCATION: (467)..(467)
<223> OTHER INFORMATION: 5-methyl-cytidine
<220> FEATURE:
<221> NAME/KEY: modified_base
<222> LOCATION: (468)..(468)
<223> OTHER INFORMATION: Pseudouridine
<220> FEATURE:
<221> NAME/KEY: modified_base
<222> LOCATION: (469)..(469)
<223> OTHER INFORMATION: 5-methyl-cytidine
<220> FEATURE:
<221> NAME/KEY: modified_base
<222> LOCATION: (470)..(470)
<223> OTHER INFORMATION: Pseudouridine
<220> FEATURE:
<221> NAME/KEY: modified_base
<222> LOCATION: (471)..(473)
<223> OTHER INFORMATION: 5-methyl-cytidine
<220> FEATURE:
<221> NAME/KEY: modified_base
<222> LOCATION: (474)..(475)
<223> OTHER INFORMATION: Pseudouridine
<220> FEATURE:
```

```
<221> NAME/KEY: modified_base
<222> LOCATION: (477)..(477)
<223> OTHER INFORMATION: 5-methyl-cytidine
<220> FEATURE:
<221> NAME/KEY: modified_base
<222> LOCATION: (479)..(480)
<223> OTHER INFORMATION: 5-methyl-cytidine
<220> FEATURE:
<221> NAME/KEY: modified_base
<222> LOCATION: (481)..(481)
<223> OTHER INFORMATION: Pseudouridine
<220> FEATURE:
<221> NAME/KEY: modified_base
<222> LOCATION: (483)..(483)
<223> OTHER INFORMATION: Pseudouridine
<220> FEATURE:
<221> NAME/KEY: modified_base
<222> LOCATION: (485)..(486)
<223> OTHER INFORMATION: 5-methyl-cytidine
<220> FEATURE:
<221> NAME/KEY: modified_base
<222> LOCATION: (487)..(487)
<223> OTHER INFORMATION: Pseudouridine
<220> FEATURE:
<221> NAME/KEY: modified_base
<222> LOCATION: (488)..(488)
<223> OTHER INFORMATION: 5-methyl-cytidine
<220> FEATURE:
<221> NAME/KEY: modified_base
<222> LOCATION: (489)..(490)
<223> OTHER INFORMATION: Pseudouridine
<220> FEATURE:
<221> NAME/KEY: modified_base
<222> LOCATION: (493)..(493)
<223> OTHER INFORMATION: Pseudouridine
<220> FEATURE:
<221> NAME/KEY: modified_base
<222> LOCATION: (494)..(494)
<223> OTHER INFORMATION: 5-methyl-cytidine
<220> FEATURE:
<221> NAME/KEY: modified_base
<222> LOCATION: (495)..(497)
<223> OTHER INFORMATION: Pseudouridine
<220> FEATURE:
<221> NAME/KEY: modified_base
<222> LOCATION: (501)..(501)
<223> OTHER INFORMATION: Pseudouridine
<220> FEATURE:
<221> NAME/KEY: modified_base
<222> LOCATION: (506)..(507)
<223> OTHER INFORMATION: 5-methyl-cytidine
<220> FEATURE:
<221> NAME/KEY: modified_base
<222> LOCATION: (508)..(508)
<223> OTHER INFORMATION: Pseudouridine
<220> FEATURE:
<221> NAME/KEY: modified_base
<222> LOCATION: (512)..(512)
<223> OTHER INFORMATION: Pseudouridine
<220> FEATURE:
<221> NAME/KEY: modified_base
<222> LOCATION: (520)..(520)
<223> OTHER INFORMATION: 5-methyl-cytidine
<220> FEATURE:
<221> NAME/KEY: modified_base
<222> LOCATION: (523)..(524)
<223> OTHER INFORMATION: 5-methyl-cytidine
<220> FEATURE:
<221> NAME/KEY: modified_base
<222> LOCATION: (526)..(526)
<223> OTHER INFORMATION: 5-methyl-cytidine
<220> FEATURE:
<221> NAME/KEY: modified_base
<222> LOCATION: (527)..(527)
<223> OTHER INFORMATION: Pseudouridine
<220> FEATURE:
<221> NAME/KEY: modified_base
<222> LOCATION: (528)..(528)
<223> OTHER INFORMATION: 5-methyl-cytidine
```

```
<220> FEATURE:
<221> NAME/KEY: modified_base
<222> LOCATION: (532)..(532)
<223> OTHER INFORMATION: 5-methyl-cytidine
<220> FEATURE:
<221> NAME/KEY: modified_base
<222> LOCATION: (534)..(534)
<223> OTHER INFORMATION: Pseudouridine
<220> FEATURE:
<221> NAME/KEY: modified_base
<222> LOCATION: (536)..(536)
<223> OTHER INFORMATION: 5-methyl-cytidine
<220> FEATURE:
<221> NAME/KEY: modified_base
<222> LOCATION: (538)..(538)
<223> OTHER INFORMATION: Pseudouridine
<220> FEATURE:
<221> NAME/KEY: modified_base
<222> LOCATION: (539)..(539)
<223> OTHER INFORMATION: 5-methyl-cytidine
<220> FEATURE:
<221> NAME/KEY: modified_base
<222> LOCATION: (540)..(540)
<223> OTHER INFORMATION: Pseudouridine
<220> FEATURE:
<221> NAME/KEY: modified_base
<222> LOCATION: (547)..(549)
<223> OTHER INFORMATION: 5-methyl-cytidine
<220> FEATURE:
<221> NAME/KEY: modified_base
<222> LOCATION: (552)..(553)
<223> OTHER INFORMATION: Pseudouridine
<220> FEATURE:
<221> NAME/KEY: modified_base
<222> LOCATION: (554)..(554)
<223> OTHER INFORMATION: 5-methyl-cytidine
<220> FEATURE:
<221> NAME/KEY: modified_base
<222> LOCATION: (556)..(558)
<223> OTHER INFORMATION: 5-methyl-cytidine
<220> FEATURE:
<221> NAME/KEY: modified_base
<222> LOCATION: (559)..(559)
<223> OTHER INFORMATION: Pseudouridine
<220> FEATURE:
<221> NAME/KEY: modified_base
<222> LOCATION: (561)..(562)
<223> OTHER INFORMATION: Pseudouridine
<220> FEATURE:
<221> NAME/KEY: modified_base
<222> LOCATION: (563)..(563)
<223> OTHER INFORMATION: 5-methyl-cytidine

<400> SEQUENCE: 24
agcuuuugga cccucguaca gaagcuaaua cgacucacua uagggaaaua agagagaaaa      60
gaagaguaag aagaaauaua agagccacca uggcucucug gaugcggcuu cuuccacugc     120
ucgcccucuu ggcguugugg ggacccgacc cugcagcagc guuugugaau cagcaccucu     180
gcggguccca ucuggucgaa gcccuuuacc uguguguguu cgagcgcggg uucuucuaca     240
cgcccaagac aaggcgcgag gcggaggauc uccaaguagg gcagguggaa uugggagggg     300
gaccgggagc cgguucacuc cagccccugg cguuggaggg gucgcugcag aaaagaggua     360
uugucgaaca guguugcacu agcaucugcu cgcuguauca acuugagaac uauuguaacu     420
gaagcgcugc cuucugcggg gcuugccuuc uggccaugcc cuucuucucu cccuugcacc     480
uguaccucuu ggucuuugaa uaaagccuga guaggaaggc ggccgcucga gcaugcaucu     540
agagggccca auucgcccua uucgaag                                        567
```